US010533011B2

(12) United States Patent
Mao et al.

(10) Patent No.: US 10,533,011 B2
(45) Date of Patent: Jan. 14, 2020

(54) PHARMACEUTICAL SALTS, PHYSICAL FORMS, AND COMPOSITIONS OF PYRROLOPYRIMIDINE KINASE INHIBITORS, AND METHODS OF MAKING SAME

(71) Applicant: ACEA THERAPEUTICS, INC., San Diego, CA (US)

(72) Inventors: Long Mao, San Diego, CA (US); Jia Liu, San Diego, CA (US); Yile Chen, Zhejiang (CN); Yuning Hua, Zhejiang (CN); Kongen Dai, Zhejiang (CN); Yimei Bao, Zhejiang (CN); Bojie Weng, Zhejiang (CN); Xiaopeng Mo, Zhejiang (CN); Jian Wu, Zhejiang (CN); Xiao Xu, San Diego, CA (US); Wanhong Xu, Zhejiang (CN); Xiaobo Wang, San Diego, CA (US)

(73) Assignee: ACEA THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 15/766,736

(22) PCT Filed: Jun. 30, 2016

(86) PCT No.: PCT/CN2016/087857
§ 371 (c)(1),
(2) Date: Apr. 6, 2018

(87) PCT Pub. No.: WO2017/059702
PCT Pub. Date: Apr. 13, 2017

(65) Prior Publication Data
US 2018/0312510 A1 Nov. 1, 2018

(30) Foreign Application Priority Data
Oct. 9, 2015 (WO) ................ PCT/CN2015/091536

(51) Int. Cl.
C07D 487/04 (2006.01)
A61K 9/48 (2006.01)
A61K 9/20 (2006.01)

(52) U.S. Cl.
CPC .......... C07D 487/04 (2013.01); A61K 9/2013 (2013.01); A61K 9/2054 (2013.01); A61K 9/4858 (2013.01); A61K 9/4866 (2013.01); C07B 2200/13 (2013.01)

(58) Field of Classification Search
CPC .............. C07D 487/02; C07B 2200/13; A61K 9/2054; A61K 9/2013; A61K 9/4858
See application file for complete search history.

(56) References Cited

U.S. PATENT DOCUMENTS

| 3,974,277 | A | 8/1976 | Horn et al. | |
|---|---|---|---|---|
| 7,192,752 | B2 | 3/2007 | Xu et al. | |
| 7,459,303 | B2 | 12/2008 | Wang et al. | |
| 7,468,255 | B2 | 12/2008 | Xu et al. | |
| 7,470,533 | B2 | 12/2008 | Xu et al. | |
| 7,560,269 | B2 | 7/2009 | Wang et al. | |
| 7,732,127 | B2 | 6/2010 | Wang et al. | |
| 8,685,988 | B2* | 4/2014 | Xu ...................... | A61K 31/519 514/265.1 |
| 8,685,998 | B2 | 4/2014 | Gordon et al. | |
| 8,975,249 | B2 | 3/2015 | Lee et al. | |
| 9,034,885 | B2* | 5/2015 | Xu ...................... | A61K 31/519 514/265.1 |
| 9,464,089 | B2 | 10/2016 | Xu et al. | |
| 9,586,965 | B2* | 3/2017 | Xu ........................ | A61K 45/06 |
| 9,763,949 | B2 | 9/2017 | Xu et al. | |
| 9,925,188 | B2* | 3/2018 | Charifson ............ | C07D 401/14 |
| 2004/0116422 | A1 | 6/2004 | Kitano et al. | |
| 2008/0318950 | A1 | 12/2008 | Ahn et al. | |
| 2009/0076037 | A1 | 3/2009 | Connolly et al. | |
| 2010/0016296 | A1 | 1/2010 | Singh et al. | |
| 2010/0029610 | A1 | 2/2010 | Singh et al. | |
| 2010/0239631 | A1 | 9/2010 | Bourke et al. | |
| 2010/0249092 | A1 | 9/2010 | Singh et al. | |
| 2011/0207736 | A1 | 8/2011 | Gray et al. | |
| 2012/0094999 | A1 | 4/2012 | Gray et al. | |

(Continued)

FOREIGN PATENT DOCUMENTS

CN 102083800 A 6/2011
CN 102482277 A 5/2012

(Continued)

OTHER PUBLICATIONS

WIPO, International Search Report and Written Opinion for Int'l Application No. PCT/CN2016/087857, dated Sep. 29, 2016
Berge, Stephen M., et al., "Pharmaceutical Salts," Journal of Pharmaceutical Sciences, vol. 66, No. 1, Jan. 1977, pp. 1-19.
CN, Response to 5th Office Action for CN patent application 2013800132790, dated Feb. 13, 2019, 10 pages.
CN, Official filing receipt for CN patent application 2013800132790, dated Feb. 13, 2019, 1 page.
CN, Notification of Granting Patent Right for CN patent application 2013800132790, dated Mar. 5, 2019, 1 page with additional 2 pages of an English language equivalent or summary. .

(Continued)

Primary Examiner — Alexander R Pagano
Assistant Examiner — Ebenezer O Sackey
(74) Attorney, Agent, or Firm — Rimon, P.C.

(57) ABSTRACT

Provided are methods of making certain pyrrolopyrimidine derivatives, which are useful in the treatment of proliferation disorders and other diseases related to the dysregulation of kinase (such as, but not limited to, EGFR (including HER), Alk, PDGFR, BLK, BMX/ETK, BTK, FLT3 (D835Y), ITK, JAK1, JAK2, JAK3, TEC and TXK) and/or the respective pathways, salts, polymorphs, and amorphous forms of said compounds, synthetic intermediates for preparing said compounds, and pharmaceutical compositions comprising said compounds and methods for making such compositions.

25 Claims, 58 Drawing Sheets

(56) References Cited

U.S. PATENT DOCUMENTS

| | | | |
|---|---|---|---|
| 2013/0190320 A1 | 7/2013 | Xu et al. | |
| 2015/0133457 A1 | 5/2015 | Xu et al. | |
| 2018/0008607 A1* | 1/2018 | Xu ........................ | A61K 31/519 |
| 2018/0312510 A1 | 11/2018 | Mao et al. | |
| 2018/0312513 A1 | 11/2018 | Mao et al. | |

FOREIGN PATENT DOCUMENTS

| | | |
|---|---|---|
| CN | 103748096 A | 4/2014 |
| CN | 104306348 A | 1/2015 |
| EP | 2802568 A0 | 7/2013 |
| EP | 3019496 A2 | 5/2016 |
| EP | 3170825 B1 | 4/2019 |
| JP | 45-24146 B1 | 8/1970 |
| JP | 2011-526299 A | 10/2011 |
| JP | 2012-526113 A | 10/2012 |
| JP | 2013-515786 A | 5/2013 |
| JP | 2015503625 A | 2/2015 |
| JP | 6215938 B2 | 10/2017 |
| JP | 6353788 B2 | 6/2018 |
| JP | 6353788 B2 | 7/2018 |
| RU | 2645672 C2 | 2/2018 |
| WO | 01/32632 A2 | 5/2001 |
| WO | 02/083653 A1 | 10/2002 |
| WO | 03/026664 A1 | 4/2003 |
| WO | 2004/021979 A2 | 3/2004 |
| WO | 2004/045624 A1 | 6/2004 |
| WO | 2004045624 A1 | 6/2004 |
| WO | 2005/062795 A2 | 7/2005 |
| WO | 2005/065156 A1 | 7/2005 |
| WO | 2005/084401 A2 | 9/2005 |
| WO | 2006/009755 A2 | 1/2006 |
| WO | 2006/014325 A2 | 2/2006 |
| WO | 2007/039404 A1 | 4/2007 |
| WO | 2007/042298 A1 | 4/2007 |
| WO | 2007/055514 A1 | 5/2007 |
| WO | 2007/071393 A2 | 6/2007 |
| WO | 2007/103233 A2 | 9/2007 |
| WO | 2007/126841 A2 | 11/2007 |
| WO | 2008/073687 A2 | 6/2008 |
| WO | 2008/094737 A2 | 8/2008 |
| WO | 2008/150118 A2 | 12/2008 |
| WO | 2009/017838 A2 | 2/2009 |
| WO | 2009/020990 A1 | 2/2009 |
| WO | 2009/032694 A1 | 3/2009 |
| WO | 2009/032703 A1 | 3/2009 |
| WO | 2009/051822 A1 | 4/2009 |
| WO | 2009/131687 A2 | 10/2009 |
| WO | 2009/143389 A1 | 11/2009 |
| WO | 2009/158571 A1 | 12/2009 |
| WO | 2010/045451 A1 | 4/2010 |
| WO | 2010/090764 A1 | 8/2010 |
| WO | 2010/129053 A2 | 11/2010 |
| WO | 2010129053 * | 11/2010 |
| WO | 2011/079231 A1 | 6/2011 |
| WO | 2011/090760 A1 | 7/2011 |
| WO | 2011090760 A1 | 7/2011 |
| WO | 2011/140338 A1 | 11/2011 |
| WO | 2011/162515 A2 | 12/2011 |
| WO | 2012/061299 A1 | 5/2012 |
| WO | 2012/061303 A1 | 5/2012 |
| WO | 2012/064706 A1 | 5/2012 |
| WO | 2012094999 A1 | 7/2012 |
| WO | 2012/120048 A1 | 9/2012 |
| WO | 2012/135801 A1 | 10/2012 |
| WO | 2012/151561 A1 | 11/2012 |
| WO | 2012/156437 A1 | 11/2012 |
| WO | 2013/106792 A1 | 7/2013 |
| WO | 2014/925486 A1 | 2/2014 |
| WO | 2014025486 A1 | 2/2014 |
| WO | 2015/006754 A2 | 1/2015 |
| WO | 2015/006754 A3 | 1/2015 |
| WO | 2015006754 A2 | 1/2015 |
| WO | 2017/059792 A1 | 4/2017 |
| WO | 2017059702 A1 | 4/2017 |
| WO | 2018/184206 A1 | 10/2018 |

OTHER PUBLICATIONS

CN, Notification of Patent Registration for CN patent application 2013800132790, dated Mar. 5, 2019, 1 page with additional 1 page of an English language equivalent or summary.
U.S., Non-Final Office Action for U.S. Appl. No. 15/435,722, dated Feb. 25, 2019, 27 pages.
CA, Notice of Abandonment for CA patent application 2861010, dated Jan. 11, 2019, 1 page.
EP, Decision of Grant for European patent application EP16202341, dated Mar. 18, 2019, 2 pages.
IL, Patent Certificate for Israel patent application 237923, dated Dec. 21, 2018, 2 pages.
CN, Response to Office Action for CN patent application 2017102293087, dated Jan. 21, 2019, 17 pages.
HK, Filing Certificate for HK patent application 17112259, dated Apr. 15, 2019, 1 page.
U.S., Response to Restriction Requirement for U.S. Appl. No. 15/882,924, dated Feb. 5, 2019, 9 pages.
U.S., Non-Final Office Action for U.S. Appl. No. 15/882,924, dated Feb. 19, 2019, 44 pages.
AU, Standard Patent Certificate for Australia patent application 2014287016, dated Feb. 14, 2019, 1 page.
CN, Decision of Rejection for CN patent application 201480049793, dated Mar. 14, 2019, 6 pages with additional 10 pages of an English language equivalent or summary.
EP, Office Action for European patent application EP147483515, dated Feb. 8, 2019, 233 pages.
JP, Notice of Grounds of Rejection for Japanese patent application JP 2016-525833, dated Mar. 12, 2019, 4 pages with additional 6 pages of an English language equivalent or summary.
MX, 2nd Office Action for Mexico patent application MX/a/2016/000261, dated Dec. 3, 2016, 6 pages.
MX, Response to 2nd Office Action for Mexico patent application MX/a/2016/000261, dated Feb. 5, 2019, 14 pages.
NZ, Response to Examination Report for New Zealand patent application 715687, dated Feb. 18, 2019, 6 pages.
NZ, Response to Office Action for New Zealand patent application 715687, dated Mar. 29, 2019, 272 pages.
NZ, Patent Notice of Acceptance for New Zealand patent application NZ715687, dated Apr. 3, 2019, 1 page.
NZ, Examination Report with issues for New Zealand patent application NZ715687, dated Mar. 18, 2019, 2 pages.
U.S., First Preliminary Amendment for U.S. Appl. No. 15/766,736, dated Apr. 6, 2018, 10 pages.
U.S., Non-Final Office Action for U.S. Appl. No. 15/766,736, dated Dec. 12, 2018, 7 pages.
WO, Written Opinion for international patent application PCT/CN2016/087857, dated Sep. 18, 2016, 6 pages.
WO, International Search Report for international patent application PCT/CN2016/087857, dated Sep. 29, 2016, 4 pages.
WO, International Preliminary Report on Patentability for international patent application PCT/CN2016/087857, dated Jan. 23, 2018, 45 pages.
EP, Partial Search Report for European patent application 168530095, dated Mar. 25, 2019, 17 pages.
EP, Communication pursuant to Rules 161(2) and 162 EPC for international patent application European phase application EP 168530095, dated May 17, 2018, 3 pages.
EP, Response to Office Action for international patent application European phase application EP 168530095, dated Nov. 8, 2018, 23 pages.
EP, Search Report for European patent application 168530095, dated Mar. 21, 2019, 15 pages.
MX, Formality Office Action for Mexico patent application MX/a/2018/004332, dated Aug. 15, 2018, 2 pages.
MX, Response to Formality Office Action for Mexico patent application MX/a/2018/004332, dated Dec. 19, 2018, 2 pages.

(56) References Cited

OTHER PUBLICATIONS

WO, Written Opinion for international patent application PCT/CN2017/079724, dated Jan. 2, 2018, 7 pages.
WO, International Search Report for international patent application PCT/CN2017/079724, dated Jan. 5, 2018, 6 pages.
WO, Notification Concerning Availability of the Publication of the International Application for international patent application PCT/CN2017/079724, dated Oct. 11, 2018, 1 page.
Mino R. Caira, "Crystalline Polymorphism of Organic Compounds," Topics in Current Chemistry, vol. 198 @ Springer Verlag Berlin Heidelberg 1998, p. 163-208.
Bouaziz et al., "Regulatory B cells as inhibitors of immune responses and inflammation," Immunological Reviews, 2008, vol. 224:201-214.
Honigberg. et al., "The Bruton tyrosine kinase inhibitor PCI-32765 blocks B-cell activation and is efficacious in models of autoimmune disease and B-cell malignancy," PNAS. Jul. 20, 2010, vol. 107, No. 29, p. 13075-13080.
Shripad S. Bhagwat, "Kinase inhibitors for the treatment of inflammatory and autoimmune disorders," Purinergic Signalling (2009) 5:107-115 DOI 10.1007/s11302-008-9117-z.
IN, Office Action for Indian Patent application 201617004306, dated Apr. 30, 2019, 7 pages.
EP, Extended European Search Report for European patent application 168530095, dated May 8, 2019, 17 pages.
JP, RN 1348622-25-2 Registry,Database Registry [Online] Retrieved from STN, Dec. 4, 2011, Search Date: Jun. 27, 2018, (cited by JP exminater in Office Action dated Mar. 12, 2019 for JP patent application 2016-525833), 1 page.
Notice of Acceptance for AU patent application 2013300106, dated Nov. 21, 2017, 3 pages.
Request for Continued Examination for U.S. Appl. No. 13/740,182, filed May 23, 2017, 21 pages.
Response to the communication pursuant to Article 94(3) EPC for EP 14 748 351.5, filed Jun. 13, 2017, 13 pages.
Examination Report No. 3 for AU 2013207712, dated Jun. 19, 2017, 11 pages.
Response to Official Action for RU 2015107831, filed Jun. 30, 2017, 6 pages.
Office Action for U.S. Appl. No. 15/435,722, dated Jul. 3, 2017, 48 pages.
Communication pursuant to Article 94(3) EPC for EP 14 748 351.5, dated Jul. 13, 2017, 6 pages.
Notice of Grounds for Rejection (translation) for JP 2014-552357, dated Aug. 1, 2017, 6 pages.
Office Action for JP 2017-005935, dated Aug. 3, 2017, 2 pages.
Official Action (translation) for RU 2015107831, dated Aug. 11, 2017, 3 pages.
Response to examination report for AU 2013207712, filed Aug. 15, 2017, 28 pages.
Notice of acceptance for AU 2013207712, dated Aug. 22, 2017, 3 pages.
Notice of Allowance for JP 2015-526540, dated Sep. 4, 2017, 3 pages.
Notification of Reexamination (translation) for CN 201380013279.0, dated Sep. 8, 2017, 1 page.
Restriction Requirement for U.S. Appl. No. 14/420,341, dated Feb. 22, 2016, 8 pages.
Response to Restriction Requirement for U.S. Appl. No. 14/420,341, filed Apr. 22, 2016, 12 pages.
Patent Examination Report No. 1 for AU 2013300106, dated Nov. 23, 2016, 3 pages.
Response to Communication pursuant to Art 94(3) for EP 13 701 326.4, dated Dec. 2, 2016, 25 pages.
Response to Non-final Rejection for U.S. Appl. No. 13/740,182, dated Dec. 1, 2016, 17 pages.
Response to Second Office Action for CN 201380001359.4, dated Nov. 25, 2016.
Notice of Reasons for Rejection for JP 2015-526540, dated Apr. 25, 2017, 5 pages.

Response to Communication pursuant to Art 94(3) for EP 13 701 326.4, dated Jun. 29, 2017, 21 pages.
Response to JPOA 2014552357, dated Oct. 26, 2017, 7 pages.
Notice of Allowance for U.S. Appl. No. 15/271,124, dated Jul. 10, 2017, 7 pages.
Request for Continued Examination for U.S. Appl. No. 15/271,124, dated Oct. 10, 2017, 3 pages.
Notice of Allowance for U.S. Appl. No. 15/271,124, dated Oct. 25, 2017, 7 pages.
Response to Non-final Rejection for U.S. Appl. No. 15/271,124, dated Oct. 26, 2017, 41 pages.
U.S., Patent issue Notification for U.S. Appl. No. 13/843,554, date May 19, 2015, 1 page.
U.S., First Preliminary amendment for U.S. Appl. No. 14/712,794, dated May 14, 2015, 6 pages.
U.S., Second Preliminary amendment for U.S. Appl. No. 14/712,794, dated May 28, 2015, 17 pages.
U.S., Response to non-final office action for U.S. Appl. No. 14/712,794, dated Jul. 8, 2016, 27 pages.
U.S., Response to final office action for U.S. Appl. No. 14/712,794, dated Oct. 6, 2016, 24 pages.
U.S., Final Office action for U.S. Appl. No. 15/435,722, dated Feb. 7, 2018, 15 pages.
U.S., Response to Final office action for U.S. Appl. No. 15/435,722, dated Jun. 7, 2018, 10 pages.
U.S., Notice of allowance for U.S. Appl. No. 15/435,722, dated Nov. 1, 2018, 7 pages.
U.S., Response to Final Office action for U.S. Appl. No. 14/420,341, dated Oct. 5, 2016, 9 pages.
CN, Response to First Office action for CN patent application 201380001359.4, dated May 19, 2016, 44 pages. (English).
CN, Response to Third Office action for CN patent application 201380001359.4, dated Apr. 6, 2017, 11 pages (English).
CN, Notice of patent issued for CN patent application 201380001359.4, patent No. ZL201380001359.4, dated Oct. 24, 2017, 4 pages.
CN, Allowed claim for CN patent application 201380001359.4, dated Aug. 7, 2018, 3 pages (English).
BR, Request for Examination for Brazil patent application 1120150027091, dated Apr. 14, 2016, 1 page.
CA, Request for Examination for Canadian patent application 2881275 (PCT/US2013/050163), dated Jul. 11, 2018, 1 page.
IN, Response to First Examination report or Indian patent application 914/DELNP/2015, dated Jul. 16, 2018, 22 pages.
IL, Response to Office action for Isreal patent application 237023, dated Apr. 27, 2017, 46 pages.
IL, Second Office action for Isreal patent application 237023, dated Nov. 14, 2017, 2 pages.
IL, Response to Second Office action for Isreal patent application 237023, dated Nov. 29, 2017, 2 pages.
IL, Official notification Prior to acceptance for Isreal patent application 237023, dated May 31, 2018, 2 pages.
JP, First Examination report for Japan patent application 2015-526540, dated Oct. 17, 2016, 6 pages (English).
JP, First Examination report ffor Japan patent application 2015-526540, dated Oct. 17, 2016, 6 pages.
JP, Response to First Office action (claims) for Japan patent application 2015-526540, dated Jan. 17, 2017, 17 pages (English).
JP, Response to First Office action (instruction) for Japan patent application 2015-526540, dated Jan. 17, 2017, 47 pages (English).
JP, Second Examination report for Japan patent application 2015-526540, dated Apr. 25, 2017, 5 pages (English).
JP, Response to Second Examination report for Japan patent application 2015-526540, dated Jun. 26, 2017, 42 pages (English).
JP, Notice of allowance for JP patent application 2015-526540, dated Aug. 31, 2017, 3 pages.
KR, Written Request for Examination for KR patent application 10-2015-7006007, dated Apr. 9, 2018, 2 pages.
NZ, First Examination report for New Zealand patent application 629807, dated Aug. 26, 2015, 2 pages.
NZ, Further Examination report for New Zealand patent application 629807, dated Dec. 13, 2016, 2 pages.
NZ, Notice of Acceptance of further examination report for New Zealand patent application 629807, dated Apr. 4, 2017, 1 page.

(56) References Cited

OTHER PUBLICATIONS

RU, Response to Office action for RU patent application 2015107831/04, dated Jun. 30, 2017, 6 pages.
RU, Response to Office action for RU patent application 2015107831/04, dated Jun. 30, 2017, 3 pages (English).
ZA, Accepted claims for South African patent application 2015/00762, dated Oct. 14, 2016, 14 pages.
MX, Notice of allowance for MX patent application MX/a/2015/001715, dated Oct. 30, 2018, 1 page.
EP, Extended search report for European patent application 16202341.0, dated Feb. 22, 2017, 7 pages.
CN, First Examination report for CN patent application 2017102293087, dated Sep. 30, 2018, 6 pages (English).
CN, First Examination report for CN patent application 2017102293087, dated Sep. 30, 2018, 6 pages.
CN, Office Action for CN patent application 2013800013594.4, dated Jan. 25, 2017, 15 pages (English).
IL, Office Action for Israel patent application 237023, dated Jan. 4, 2017, 2 pages (English).
NZ, Response to Examination Report for New Zealand patent application 629807, dated Mar. 8, 2017, 71 pages.
SG, Office Action,Search Report and Written Opinion for Singapore patent application 11201500872S, dated Dec. 22, 2015, 9 pages.
WO, Notification,International Search Report and Written Opinion for international patent application PCT/US2013/050163, dated Sep. 4, 2013, 10 pages.
U.S., Notice of the Office communication for U.S. Appl. No. 15/882,924, dated Aug. 6, 2018, 10 pages.
U.S., Office communication for U.S. Appl. No. 14/420,341, dated Nov. 2, 2016, 3 pages.
Australian, Examination report No. 1 for standard patent application 2014287016, dated Nov. 15, 2017, 6 pages.
Australian, Notice of grant for patent for 2013300106, dated Mar. 15, 2018, 1 pages.
Australian, Response to office action for application 2016334141, dated May 16, 2018, 4 pages.
Australian, Response to APO for application 2014287016, dated Sep. 11, 2018, 48 pages.
CA, Notice of requisition for PCT/US 2013021338, dated May 25, 2018, 4 pages.
CN, Response to 1st office action for 201480049793.4, dated May 2, 2018, 50 pages.
CN, 4th office action for application 201380013279.0, dated Jun. 1, 2018, 3 pages, including extra 4 pages English translation.
CN, Response to 4th office action for application 2013800132790, dated Jul. 23, 2018,10 pages.
CN, Search report for application 201710229308.7, dated Aug. 28, 2018, 2 pages, including extra 2 pages English translation.
CN, 2nd office action for 201480049793.4, dated Aug. 30, 2018, 5 pages, including extra 3 pages English translation.
CN, 1st office action for application 201710229306.7, dated Sep. 5, 2018, 5 pages ( extra 6 pages for English translation).
EP, Communication pursuant to Article 94(3) ERC for application 14 748 351.5-1462, dated Dec. 20, 2017, 4 pages.
EP, Communication pursuant to Article 94(3) EPC for application 16202341.0-1116, dated May 8, 2018, 5 Pages.
EP, Communication pursuant to Rules 161(2) and 162 EPC for application 16853009.5-1109, dated May 23, 2018, 3 pages.
EP, Response to Notice of Omitted Item(s) for U.S. Appl. No. 15/882,924, dated May 24, 2018, 4 pages.
EP, Communication pursuant to Article 94(3) EPC for application 14748351.5-1116, dated May 24, 2018, 4 pages.
EP, Communication pursuant to Article 94(3) EPC for application 13701326.4-1114, dated Jul. 13, 2018, 8 pages.
EP, Communication of European publication number and information on the application of Article 67(3) EPC for application 16853009.5-1109 / 3359159 PCT/CN2016087857, dated Jul. 18, 2018, 1 page.
EP, Response to the Communication pursuant to Art. 94(3) EPC for application 16 202 341.0, dated Sep. 10, 2018, 34 pages.

India, First examination report for application 914/DELNP/2015 (PCT/US2013050163), dated Jun. 26, 2018, 6 pages.
Israel; Response to Notification of defects in patent application 243420, dated May 15, 2018, 2 pages with 4 page s of Englist translation.
Israel, Response to office action for application 243420, dated Aug. 23, 2018, 16 pages.
Israel, Response to office action for application 243420, dated Sep. 13, 2018, 2 pages (translation).
JP, Notice of the reasons of rejection for application 2014-552357, dated Feb. 6, 2018, 2 pages, including extra 2 pages English translation.
JP, Written opinion for application 2014-552357, dated Apr. 23, 2018, 2 pages.
JP, Amendment for application 2014-552357, dated Apr. 23, 2018, 5 pages.
JP, Patent granted for application 2014-552357, dated May 15, 2018, 3 pages.
JP, Notice of grounds of rejection for application 2016-525833, dated Jul. 31, 2018, 6 pages, including extra 8 pages of English translation.
Korea, Written request for examination for 10-2016-7002970, dated Aug. 6, 2018, 2 pages.
Korea, Amendment for 10-2016-7002970, dated Aug. 6, 2018, 33 pages.
Mexico, 1st requisition for application MXA2015001715, dated Aug. 15, 2018, 3 pages.
Mexico, Response to 1st requisition for application MX/a/2016/000261, dated Sep. 3, 2018, 7 pages.
NZ, First examination report for application 715687, dated Aug. 22, 2018, 6 pages.
RU, Search report for 2016104388, dated Apr. 25, 2018, 3 pages, including extra 4 pages of English translation.
RU, Official action for application 2016104388/04(006925), dated Apr. 27, 2018, 13 pages, including extra 10 pages of English translation.
RU, Response to office action for application 2016104388, dated Jul. 27, 2018 4 pages.
RU, Office action for application 2016104388/04(006925), dated Aug. 16, 2018, 6 pages, including extra 4 pages of English translation.
Cortot, Alexis B.; et al., Resistance to Irreversible EGF Receptor Tyrosine Kinase Inhibitors through a Multistep Mechanism Involving the IGF1R Pathway. Cancer Research, 2013, 73(2), 834-843 (English).
Zhou et al. "Novel mutant-selective EGFR kinase inhibitors against EGFR T790M", NATURE, val. 462, No. 7276, Dec. 24, 2009, p. 1070-1074, XP005505337 4; ISSN: 0028-0836, DOI: 10.1 038/nature08622.
Abbot et al., "Synthesis of heteroarly-fused pyrazoles as P38 kinase inhibitors," Heterocycles (2009) 78)11):2811-2826.
Andries et al., "TMC125, a novel next-generation nonnucleoside reverse transcriptase inhibitor active against nonnucleoside reverse transcriptase inhibitor-resistant human immunodeficiency virus type 1," Antimicrobial Agents and Chemotherapy (2004) 48(12):4680-4686.
Avizienyte et al.,"Comparison of the EGFR resistance mutation profiles generated by EGFR-targeted tyrosine kinase inhibitors and the impact of drug combinations," Biochem. J. (2008) 415:197-206.
Bagshawe, "Antibody-directed enzyme prodrug therapy: A review," Drug Dev. Res. (1995) 34(2):220-230.
Baselga et al., "Critical Update and Emerging Trends in Epidermal Growth Factor Receptor Targeting in Cancer," Journal of Clinical Oncology (2005) 23(11):2445-2459.
Bean et al., "Acquired Resistance to Epidermal Growth Factor Receptor Kinase Inhibitors Associated with a Novel T854A Mutation in a Patient with EGFR-Mutant Lung Adenocarcinoma," Clin. Cancer Res. (2008) 14(22):7519-7525.
Berge et al., "Pharmaceutical Salts," J. Pharm. Sci. (1977) 66:1-19.
Bertolini et al., "A new rational hypothesis for the pharmacophore of the active metabolite of leflunomide, a potent immunosuppressive drug," J. Med. Chem. (1997) 40(13):2011-2016.

(56) References Cited

OTHER PUBLICATIONS

Blair et al., "Structure-guided development of affinity probes for tyrosine kinases using chemical agents," Nature Chemical Biology (2007) 3(4):229-238.
Bodor, "Novel approaches to the design of safer drugs: soft drugs and site-specific chemical delivery systems," Adv. Drug. Res. (1984) 13:255-331.
Carter et al., "Inhibition of drug-resistant mutants of ABL, KIT, and EGF receptor kinases," Proc. Natl. Acad. Sci. 2005, 102(31), 11011-11016.
Chamberlain et al., "Discovery of 4,6-bis-anilino-1H-pyrrolo[2,3-d]pyrimidines: Potent inhibitors of the IGF-1R receptor tyrosine kinase," Bioorganic & Medicinal Chemistry Letters (2009) 19:469-473.
Chamberlain et al., "Optimization of 4,6-bis-anilino-1H-pyrrolo[2,3-d]pyrimidine IGF-1R tyrosine kinase inhibitors. towards JNK selectivity," Bioorganic & Medicinal Chemistry Letters (2009) 19:360-364.
Chamberlain et al., "Optimization of a series of 4,6-bis-anilino-1H-pyrrolo[2,3-d]pyrimidine inhibitors of IGF-1R: Elimination of an acid-mediated decomposition pathway," Bioorganic & Medicinal Chemistry Letters (2009) 19:373-377.
Frenkel et al., "Concentration and pH Dependent Aggregation of Hydrophobic Drug Molecules and Relevance to Oral Bioavailability," J. Med. Chem. (2005) 48:1974-1983.
Fry et al., "Specific, irreversible inactivation of the epidermal growth factor receptor and erbB2, by a new class of tyrosine kinase inhibitor," PNAS USA (1998) 95:12022-12027.
Ghosh et al., "2,4-bis(aryloxy)pyrimidines as antimicrobial agents," J. Med. Chem. (1968) 11(6):1237-1238.
Han et al., "Novel Hybrids of (Phenylsulfonyl)furoxan and Anilinopyrimidine as Potent and Selective Epidermal Growth Factor Receptor Inhibitors for Intervention of Non-Small-Cell Lung Cancer," Journal of Medicinal Chemistry (2013) 56:4738-4748.
Johnson et al., "Relationships between drug activity in NCI preclinical in vitro and in vivo models and early clinical trials," British Journal of Cancer, 2001, 84, 1424-1431.
Kato et al., "Ketene and its derivatives. XVII. Reaction of diketene with imidates," Chemical and Pharmaceutical Bulletin (1967) 15(9):1334-1338.
Kumar et al., "Structure and Clinical Relevance of the Epidermal Growth Factor Receptor in Human Cancer," J. Clin. Oncol. 2008, 26(10), 1742-1751 (Apr. 2008).
Ludovici et al., "Evolution of Anti-HIV Drug Candidates. Part 3: Diarylpyrimidine (DAPY) Analogues," Bioorganic & Medicinal Chemistry Letters (2001) 11:2235-2239.
Mellinghoff, "Why Do Cancer Cells Become "Addicted" to Oncogenic Epidermal Growth Factor Receptor?" PLoS Medicine (2007) 4(10):e321:1620-1622.
Modjtahedi et al., "Epidermal growth factor receptor inhibitors in cancer treatment: advances, challenges and opportunities," Anti-Cancer Drugs (2009) 220(10):851-855. (Abstract).
Patani et al., "Bioisosterism: A Rational Approach in Drug Design," Chem. Rev. (1996) 96:3147-3176.
Petter et al., A novel small-molecule drug platform to silence cancer targets—Application to the pan-ErbB kinases, Poster from AACR 2009, Denver, CO—Abstr. 3746 (presented on Apr. 18-22, 2009).
Profft et al., "Uber in 2- und 6-Stellung substituierte 4-Methylpyrimidine," Archiv der Pharmazie (1962) 295 (9):649-662.
Raymond et al., "Epidermal growth factor receptor tyrosine kinase as a target for anticancer therapy," Drugs (2000) 60(Suppl 1):15-23.
Roili et al., "Diarylpyrimidine-Dihydrobenzyloxopyrimidine Hybrids: New, Wide-Spectrum Anti-HIV-1 Agents Active at (Sub)-Nanomolar Level," J. Med. Chem. (2011) 54(8):3091-3096.
Shan et al., "Prodrug strategies based on intramolecular cyclization reactions," J. Pharm. Sci. (1997) 86(7):765-767.
Slichenmeyer et al., "CI-1033, a pan-erbB tyrosine kinase inhibitor," Semin. Oncol. (2001) 28(5 Suppl. 16):80-85.
Smaill et al., "Tyrosine Kinase Inhibitors. 17. Irreversible Inhibitors of the Epidermal Growth Factor Receptor: 4-(Phenylamino)quinazoline- and 4-(Phenylamino)pyrido[3,2-d]pyrimidine-6-acrylamides Bearing Additional Solubilizing Functions," J. Med. Chem. (2000) 43:1380-1397.
Xu et al., "AC0010, an irreversible EGFR inhibitor selectively targeting mutated EGFR and overcoming T790M-induced resistance in animal models and lung cancer patients," Molecular Cancer Therapeutics, Published Online Aug. 29, 2016, DOI: 10.1158/1535-7163.MCT-16-0281, 32 pages.
Zhou et al., "Discovery of selective irreversible inhibitors for EGFR-T790M," Bioorganic & Medicinal Chemistry Letters (2011) 21:638-643.
Zhou et al., "Novel mutant-selective EGFR kinase inhibitors against EGFR T790M," Nature (2009) 462 (24/31):1070-1074.
CI-1033 (Canertinib, PD183805), Selleck Chemicals, retrieved from the Internet Aug. 15, 2013, 5 pages.
Li et al., "BIBW2992, an irreversible EGFR/HER2 inhibitor highly effective in preclinical lung cancer models," Oncogene (2008) 27(34):4702-4711.
U.S., Restriction Requirement for U.S. Appl. No. 14/329,890, dated Jun. 3, 2015, 9 pages.
U.S., Response to Restriction Requirement for U.S. Appl. No. 14/329,890, filed Aug. 3, 2015, 12 pages.
U.S., Office Action for U.S. Appl. No. 14/329,890, dated Sep. 23, 2015, 16 pages.
U.S., Response to Office Action for U.S. Appl. No. 14/329,890, filed Dec. 21, 2015, 14 pages.
U.S., Final Office Action for U.S. Appl. No. 14/329,890 dated Mar. 3, 2016, 5 pages.
U.S., Request for Continued Examination for U.S. Appl. No. 14/329,890, filed May 3, 2016, 14 pages.
U.S., Notice of Allowance for U.S. Appl. No. 14/329,890, dated May 27, 2016, 7 pages.
U.S., Corrected Notice of Allowance for U.S. Appl. No. 14/329,890, dated Jun. 20, 2016, 4 pages.
U.S., Amendment after Notice of Allowance for U.S. Appl. No. 14/329,890, dated Aug. 8, 2016, 3 pages.
U.S., Non-final Rejection for U.S. Appl. No. 15/271,124, dated Jan. 17, 2017, 6 pages.
U.S., Response for Non-final Rejection for U.S. Appl. No. 15/271,124, dated Apr. 17, 2017, 15 pages.
Invitation to Pay Additional Fees for PCT/US2014/046442, dated Oct. 7, 2014, 6 pages.
International Search Report and Written Opinion for PCT/US2014/046442, dated Jan. 5, 2015, 22 pages.
Response to Written Opinion with Chapter II Demand and Article 34 Amendments for PCT/US2014/046442, filed May 11, 2015, 62 pages.
International Preliminary Report on Patentability for PCT/US14/46442, dated Jul. 28, 2015, 5 pages.
EP, Communication pursuant to Article 94(3) EPC for EP 14 748 351.5, dated Apr. 3, 2017, 3 pages.
CN, Request for re-examination for Chinese patent application 201480049793.4, dated Jun. 11, 2019, 29 pages.
JP, Response to the office action for Japanese patent application No. 2016-525833, dated Jun. 7, 2019, 16 pages.
Extended European Search Report for EP 16202341.0, dated Feb. 22, 2017, 5 pages.
Claims of U.S. Appl. No. 61/076,450, filed Jun. 27, 2008, 23 pages.
Gura et al., "Systems for identifying new drugs are often faulty," Science 1997, 278, 1041-1042.
U.S., Response to final Office Action for U.S. Appl. No. 13/740,182, dated Dec. 17, 2015, 19 pages.
U.S., First preliminary amendment for U.S. Appl. No. 15/271,124, dated Sep. 20, 2016, 12 pages.
U.S., Non Office Action U.S. Appl. No. 15/271,124, dated Feb. 14, 2018, 4 pages.
AU, Notice of acceptance for patent application for Australian patent application 2014287016, dated Oct. 8, 2018, 3 pages.
CN, Response to Office Action for CN patent application 2013800132790, dated Mar. 15, 2017, 128 pages.

(56) References Cited

OTHER PUBLICATIONS

CN, Response to Second Office Action for CN patent application 2013800132790, dated Feb. 22, 2016, 26 pages.
CN, First Office Action for CN patent application 201480049793.4, dated Dec. 18, 2017, 7 pages.
CN, First Office Action for CN patent application 201480049793.4, dated Dec. 18, 2017, 3 pages (English).
CN, Response to First Office Action for CN patent application 201480049793.4, dated May 2, 2018, 46 pages.
CN, Second Office Action for CN patent application 201480049793.4, dated Aug. 30, 2018, 3 pages (English).
CN, Response to Second Office Action for CN patent application 201480049793.4, dated Nov. 13, 2018, 5 pages.
EP, Office Action for European patent application 137013264, dated May 24, 2016, 5 pages.
EP, Office Action of Communication pursuant to Article 94(3) EPC for for European patent application 137013264, dated Oct. 27, 2017, 5 pages.
EP, Office Action of Communication pursuant to Rules 161(1) and 162 EPC for European patent application 147483515, dated Mar. 2, 2016, 2 pages.
EP, Office Action of Communication pursuant to Article 94(3) EPC for European patent application 147483515, dated Apr. 3, 2017, 3 pages.
EP, Response to Office Action for European patent application 147483515, dated Jun. 13, 2017, 13 pages.
EP, Office Action for European patent application 147483515, dated Jul. 13, 2017, 6 pages.
EP, Response to Office Action for European patent application 147483515, dated Nov. 14, 2017, 15 pages.
EP, Response to Office Action of Communication pursuant to Article 94(3) EPC for European patent application 147483515, dated Apr. 27, 2018, 14 pages.
EP, Office Action for European patent application 168530095, dated May 17, 2018, 3 pages.
EP, Response to Office Action for European patent application 168530095, dated Nov. 8, 2018, 23 pages.
JP, Office Action for JP patent application 2014552357, dated Aug. 1, 2017, 6 pages.
JP, Office Action for JP patent application 2016525833, dated Aug. 9, 2018, 8 pages (English).
JP, Office Action for JP patent application 2016525833, dated Aug. 9, 2018, 6 pages.
JP, Response to Office Action for JP patent application 2016525833, dated Oct. 1, 2016, 27 pages (English).
JP, Response to Office Action for JP patent application 2016525833, dated Oct. 25, 2018, 12 pages.
MX, First Office Action for Mexico patent application MX/a/2016000261, dated Oct. 3, 2018, 6 pages (English).
MX, First Office Action for Mexico patent application MX/a/2016000261, dated Oct. 3, 2018, 7 pages.
MX, Response to First Office Action for Mexico patent application MX/a/2016000261, dated Nov. 13, 2018, 18 pages.
MX, Office Action for Mexico patent application 2018004332, dated Aug. 15, 2018, 2 pages.
RU, Office Action for Russia patent application 2016104388, dated Jun. 2, 2016, 2 pages (English).
RU, Office Action for Russia patent application 2016104388, dated Jun. 2, 2016, 2 pages.
RU, Response to Office Action for Russia patent application 2016104388, dated Sep. 28, 2016, 44 pages (English).
RU, Response to Office Action for Russia patent application 2016104388, dated Sep. 28, 2016, 33 pages.
RU, Response to Office Action for Russia patent application 2016104388, dated Dec. 10, 2018, 12 pages.
RU, Response to Office Action (Amended claims) for Russia patent application 2016104388, dated Dec. 10, 2018, 7 pages (English).
RU, Decision to Grant for Russia patent application 2016104388, dated Dec. 17, 2018, 12 pages.
RU, Decision to Grant for Russia patent application 2016104388, dated Dec. 17, 2018, 12 pages (English).
SG, Notice of Eligibility for Grant for Singapore patent application 11201600062R, dated Jun. 11, 2018, 5 pages.
WO, International Search Report for international patent application WO2018184206, PCT/CN2017/079724, dated Jan. 5, 2018, 4 pages.
WO, Written Opinion for international patent application WO2018184206, PCT/CN2017/079724, dated Jan. 5, 2018, 7 pages.
WO, International Publication for international patent application WO2018184206, PCT/CN2017/079724, dated Oct. 11, 2018, 182 pages.
WO, Written Opinion for international patent application WO2017059702, dated Sep. 18, 2016, 6 pages.
WO, International Search Report for international patent application WO2017059702, dated Sep. 29, 2016, 4 pages.
WO, International Publication for international patent application WO2017059702, dated Apr. 13, 2017, 148 pages.
WO, International preliminary report on patentability for international patent application WO2017059702, dated Jan. 23, 2018, 45 pages.
Response to Notification of Reexamination (translation) for CN 201380013279.0, dated Oct. 20, 2017, 12 pages.
Response to Notice of Grounds for Rejection for JP 2014-552357, dated Oct. 26, 2017, 14 pages.
Response to Examination Report for AU 2013300106, dated Oct. 26, 2017, 38 pages.
Examination Report for AU 2013300106, dated Oct. 27, 2017, 3 pages.
Response to Examination Report for AU 2013300106, dated Nov. 10, 2017, 34 pages.
Notice of Acceptance for AU 2013300106, dated Nov. 21, 2017, 3 pages.
Response to Official Action for RU 2015107831, filed Nov. 13, 2017, 28 pages.
Decision on grant of patent for invention for RU 2015107831, dated Nov. 24, 2017, 37 pages (Including English translation).
Notification of Defects in Patent Application IL No. 237023, dated Nov. 14, 2017, 2 pages (English translation).
Response to Communication pursuant to Article 94(3) EPC for EP 14 748 351.5, dated Nov. 14, 2017, 15 pages.
Communication pursuant to Article 94(3) EPC for EP 13 701 326.4, dated Oct. 27, 2017, 5 pages.
Examination Report No. 1 for AU 2014287016, dated Nov. 15, 2017, 6 pages.
International Search Report and Written Opinion for PCT/CN2016/087857, dated Sep. 29, 2016, 10 pages.
Non-final Rejection for U.S. Appl. No. 13/740,182, dated Oct. 18, 2017, 17 pages.
First Office Action for CN 2017121302212480, dated Dec. 18, 2017, 10 pages.
Communication pursuant to Article 94(3) EPC for EP 14 748 351.5, dated Dec. 20, 2017, 4 pages.
Notice of Grant for Patent for AU 20132077120, dated Dec. 18, 2017, 144 pages.
Voluntary amendment for CN 201380013279.0, dated Jan. 11, 2018, 14 pages.
Response to Non-Final Rejection for U.S. Appl. No. 13/740,182, dated Jan. 18, 2018, 14 pages.
Non-Final Office Action for U.S. Appl. No. 15/708,024, dated Feb. 9, 2018, 13 pages.
Final Rejection for U.S. Appl. No. 13/740,182, dated Jun. 1, 2018, 28 pages.
Office Action Response for JP patent application 2014-552357, dated Apr. 23, 2018, part one 5 pages (in Japanese) and part two 2 pages (in English).
Response to the Communication pursuant for Article 94(3) EPC for European Patent Application 14 748 351.5, dated Apr. 27, 2018, 14 pages.
U.S., Response to Notice for U.S. Appl. No. 13/740,182, dated Apr. 3, 2013, 4 pages.
U.S., Response to Non-Final Office Action for U.S. Appl. No. 13/740,182, dated Mar. 12, 2015, 21 pages.

(56) References Cited

OTHER PUBLICATIONS

U.S., Non-Final Rejection for U.S. Appl. No. 13/740,182, dated Oct. 18, 2017, 19 pages.
U.S., Response to Non-Final Office Action for U.S. Appl. No. 13/740,182, dated Jan. 18, 2018, 14 pages.
U.S., Final Office Action for U.S. Appl. No. 13/740,182, dated Jun. 1, 2018, 28 pages.
U.S., Response to Non-Final Office Action for U.S. Appl. No. 13/740,182, dated Nov. 30, 2018, 10 pages.
WO, Communication relating to the results of the partial international search for international patent application PCT/US2013/021338, dated Aug. 3, 2012, 9 pages.
WO, International search report and written opinion for international patent application PCT/US2013/021338, dated Jun. 12, 2013, 25 pages.
WO, Written opinion of the International searching authority for international patent application PCT/US2013/021338, dated Jul. 15, 2014, 15 pages.
CA, Notice of a requisition in accordance with subsection 30(2) of the patent rules for Canadian patent application 2,861,010, PCT/US2013/021338, dated May 25, 2018, 4 pages.
CN, 5th Office Action for Chinese patent application 201380013279.0, dated Dec. 5, 2018, 3 pages with extra 3 pages of English translation.
EP, Communication of European publication number and Information on the application of Article 67(3) EPC for European patent application 13701326.4, dated Oct. 22, 2014, 1 page.
EP, Communication pursuant to Article 94(3) EPC for European patent application 13701326.4, dated Oct. 27, 2017, 2 pages.
EP, Request to grant an extension of the term for European patent application 13701326.4, dated Nov. 20, 2018, 2 pages.
EP, Extension of time limit pursuant to Rule 132(2) EPC for European patent application 13701326.4, dated Nov. 26, 2018, 2 pages.
EP, Response to the Communication pursuant to Art. 94(3) EPC, dated Mar. 5, 2018, 7 pages.
CN, Response to 2nd Office Action for CN patent application 2014800497934, dated Nov. 2, 2018, 39 pages (English).
CN, Response to 1st Examination Report for CN patent application 2017102293087, dated Jan. 7, 2019, 18 pages.
EP, Response to Office Action 94(3) EPC for European patent application 147483515, dated Sep. 28, 2018, 80 pages.
EP, Intent to Grant for European patent application 162023410, dated Oct. 25, 2018, 160 pages.
EP, Response to Office Action for European patent application 137013264, dated Jan. 21, 2019, 28 pages.
IN, Response to 1st Examination Report for Indian patent application IN914DELNP2014, dated Jan. 21, 2019, 7 pages.
MX, Response to 1st Office Action for Mexican patent application MXa2016000261, dated Oct. 25, 2018, 23 pages (English).
MX, 2nd Office Action for Mexican patent application MXa2016000261, dated Nov. 23, 2018, pages, including extra 6 pages of English translation.
MX, Response to Formality Office Action for Mexican patent application MXa2018004332, dated Dec. 19, 2018, 2 pages.
AU, Response to 2nd Examination Report for Australia patent application 2013207712, dated Jun. 1, 2017, 27 pages.
EP, Opinion Examining Division for EP patent application 137013264, dated May 9, 2019, 5 pages.
EP, Summons to attend oral proceedings R115(1) EPC for EP patent application 137013264, dated May 7, 2019, 2 pages.
U.S., Notice of Allowance for U.S. Appl. No. 15/708,024, dated Jun. 3, 2019, 15 pages.
EP, Pending claims for EP patent application 3170825, dated May 18, 2018, 5 pages.
EP, Patent Certificate for EP patent application 3170825, dated Apr. 10, 2019, 4 pages.
CN, The Second Office Action for CN patent application 201710229308.7, dated Apr. 24, 2019, 3 pages with additional 4 pages of English translation for Office Action and another additional 3 pages for Office Action Form.
IL, Office Action for Israel patent application 243420, dated May 27, 2019, 3 pages with additional 2 pages of English translation.
IN, The First Examination Report for Indian patent application 201617004306, dated Apr. 30, 2019, 7 pages.
MX, The Third Office Action for Mexican patent application MX/a/2016/000261, dated Apr. 30, 6 pages with 4 pages of an English language equivalent or summary.
EP, Communication Pursuant to Rules 70(2) and 70a (2) EPC for EP patent application 16853009.5, dated May 23, 2019, 1 page.
EP, Partial European Search Report for EP patent application 16853009.5, dated Mar. 6, 2019, 3 pages.
EP, Supplementary European Search Report for EP patent application 16853009.5, dated Apr. 26, 2019, 4 pages.
EP, European Search Report for for EP patent application 16853009.5, dated May 6, 2019, 10 pages.
International Search Report for international patent application PCT/CN2016/087857, dated Sep. 29, 2016, 4 pages.
International Preliminary Report on Patentability for International patent application PCT/CN2016/087857, dated Jan. 23, 2018, 45 pages.
Written Opinion of the International Search Authority for International patent application PCT/CN2016/087857, dated Sep. 29, 2016, 6 pages.
U.S., Response to Non-Final Office Action under 37 C.F.R. 1.111 for U.S. Appl. No. 15/435,722, dated Oct. 26, 2017, 41 pages.
U.S., 1st Preliminary Amendment for U.S. Appl. No. 15/708,024, dated Sep. 24, 2017, 3 pages.
U.S., 2nd Preliminary Amendment for U.S. Appl. No. 15/708,024, dated Dec. 4, 2017, 7 pages.
U.S., Non-final Office Action for U.S. Appl. No. 15/708,024, dated Feb. 9, 2018, 13 pages.
U.S., Response to Non-final Office Action for U.S. Appl. No. 15/708,024, dated Aug. 9, 2018, 8 pages.
U.S., Notice of Allowance for U.S. Appl. No. 15/708,024, dated Oct. 3, 2018, 7 pages.
Claims as amended under PCT article 34 (clean version) for international application PCT/CN2016/087857, dated Aug. 7, 2017, 17 pages.
Chapter II Demand with Response to Written Opinion and Article 34 Amendments for international application PCT/CN2016/087857, dated Aug. 7, 2017 , 4 pages.
Claim Amendments under PCT Article 34 for international application PCT/CN2016/087857, dated Aug. 7, 2017, 17 pages.
First request for change under Rule 92 bis for international patent application PCT/CN2016/087857, dated Nov. 16, 2016, 5 pages.
Second request for change under Rule 92 bis for international patent application PCT/CN2016/087857, dated Aug. 10, 2016, 8 pages.
Examination Request Form for Chinese patent application CN2016800217716, dated Sep. 27, 2018, 1 page.
Official Filing receipt for Chinese patent application CN2016800217716, dated Sep. 27, 2018, 1 page.
Opinion Statement for Chinese patent application CN2016800217716, dated Sep. 27, 2018, 1 page.
Chapter I request form for international patent application PCT/CN2016087857, dated Aug. 7, 2017, 4 pages.
RN 1348622-25-2 Registry Reference by examiner for JP patent application 2016525833, dated Jul. 31, 2018, 1 page.
U.S., Restriction Requirement for U.S. Appl. No. 13/740,182, dated Apr. 11, 2014, 13 pages.
U.S., Response to Office Action for U.S. Appl. No. 13/740,182, filed Aug. 15, 2014, 16 pages.
U.S., Office Action for U.S. Appl. No. 13/740,182, dated Dec. 12, 2014, 17 pages.
U.S., Final Office Action for U.S. Appl. No. 13/740,182, dated Jun. 30, 2015, 28 pages.
U.S., Response to Final Office Action for U.S. Appl. No. 13/740,182 dated Dec. 17, 2015, 17 pages.

(56) References Cited

OTHER PUBLICATIONS

U.S., Request for Continued Examination and Amendment after final action for U.S. Appl. No. 13/740,182, dated Dec. 17, 2015, 22 pages.
U.S., Supplemental response for U.S. Appl. No. 13/740,182, dated Feb. 9, 2016, 16 pages.
U.S., Non-final Rejection for U.S. Appl. No. 13/740,182, dated Sep. 1, 2016, 20 pages.
U.S., Request for Continued Examination for U.S. Appl. No. 13/740,182, filed May 23, 2017, 21 pages.
U.S., Final Rejection for U.S. Appl. No. 13/740,182, dated Mar. 23, 2017, 26 pages.
International Search Report and Written Opinion for PCT/US2013/021338, dated Jun. 12, 2013, 25 pages.
International Preliminary Report on Patentability for PCT/US2013/021338, dated Jul. 15, 2014, 15 pages.
AU, Patent Examination Report No. 1 for AU 2013207712, dated Sep. 19, 2016, 4 pages.
AU, Response to Examination Report No. 1 for AU 2013207712, filed Mar. 23, 2017, 35 pages.
AU, Examination Report No. 2 for AU 2013207712, dated Apr. 3, 2017, 6 pages.
CN, The First Office Action (translation) for CN 201380013279.0, dated Apr. 29, 2015, 3 pages.
CN, Response to the First Office Action for CN 201380013279.0, filed Sep. 14, 2015, 30 pages.
CN, Second Office Action for CN 201380013279.0, dated Dec. 3, 2015, 3 pages.
CN, Response to the Second Office Action for CN 201380013279.0, filed Feb. 22, 2016, 26 pages.
CN, The Third Office Action (translation) for CN 201380013279.0, dated May 17, 2016, 3 pages.
CN, Response to the Third Office Action for CN 201380013279.0, filed Aug. 1, 2016, 24 pages.
CN, Decision of Rejection for CN 201380013279.0, dated Dec. 2, 2016, 9 pages.
CN, Request for re-examination for CN 201380013279.0, dated Mar. 15, 2017, 256 pages.
EP, Response to Communication pursuant to Rules 161(1) and 162 EPC for EP 13 701 326.4, filed Feb. 26, 2015, 11 pages.
EP, Communication pursuant to Article 94(3) EPC for EP 13701326.4, dated Aug. 10, 2015, 5 pages.
EP, Response to Communication pursuant to Article 94(3) EPC for EP 13701326.4, dated Feb. 22, 2016, 66 pages.
EP, Communication pursuant to Article 94(3) EPC for EP 13 701 326.4, dated May 24, 2016, 5 pages.
EP, Response to Communication pursuant to Art 94(3) for EP 13 701 326.4, dated Dec. 2, 2016, 25 pages.
EP, Communication pursuant to Art 94(3) for EP 13 701 326.4, dated Feb. 1, 2017, 5 pages.
JP, Notice of grounds of rejection for JP 2014-552357, dated Nov. 4, 2016, 13 pages.
JP, Response to Notice of grounds of rejection for JP 2014-552357, dated Feb. 3, 2017, 20 pages.
U.S., Restriction Requirement for U.S. Appl. No. 13/843,554, dated Jun. 30, 2014, 8 pages.
U.S., Response to Restriction Requirement for U.S. Appl. No. 13/843,554, filed Aug. 5, 2014, 3 pages.
U.S., Office Action for U.S. Appl. No. 13/843,554, dated Aug. 19, 2014, 7 pages.
U.S., Response to Non-Final Office Action for U.S. Appl. No. 13/843,554, filed Dec. 19, 2014, 19 pages.
U.S., Notice of Allowance for U.S. Appl. No. 13/843,554, dated Jan. 13, 2015, 8 pages.
U.S., Restriction Requirement for U.S. Appl. No. 13/917,514, dated Sep. 10, 2013, 8 pages.
U.S., Response to Restriction Requirement for U.S. Appl. No. 13/917,514, filed Oct. 9, 2013, 13 pages.
U.S., Notice of Allowance for U.S. Appl. No. 13/917,514, dated Nov. 14, 2013, 10 pages.
U.S., Office Action for U.S. Appl. No. 14/712,794 dated Mar. 8, 2016, 20 pages.
U.S., Response to Office Action for U.S. Appl. No. 14/712,794, filed Jul. 8, 2016, 27 pages.
U.S., Final Office Action for U.S. Appl. No. 14/712,794, dated Jul. 22, 2016, 6 pages.
U.S., Request for Continued Examination for U.S. Appl. No. 14/712,794, filed Oct. 6, 2016, 24 pages.
U.S., Notice of Allowance for U.S. Appl. No. 14/712,794, dated Dec. 2, 2016, 7 pages.
U.S., Notice of Allowance for U.S. Appl. No. 14/712,794, dated Apr. 24, 2017, 4 pages.
U.S., Office Action for U.S. Appl. No. 14/420,341, dated Jun. 3, 2016, 7 pages.
U.S., Response to Office Action for U.S. Appl. No. 14/420,341, filed Sep. 1, 2016, 12 pages.
U.S., Final Office Action for U.S. Appl. No. 14/420,341, dated Sep. 22, 2016, 8 pages.
U.S., Notice of Allowance for U.S. Appl. No. 14/420,341, dated Oct. 18, 2016, 16 pages.
International Search Report and Written Opinion for PCT Appln. No. PCT/US2013/050163, dated Sep. 4, 2013, 10 pages.
International Preliminary Report on Patentability for PCT/US2013/050163, dated Feb. 10, 2015, 5 pages.
CN, First Office Action (translation) for CN 201380001359.4, dated Jan. 13, 2016, 9 pages.
CN, Response to Office Action for CN 201380001359.4, filed May 30, 2016, 31 pages.
CN, Second Office Action for CN 201380001359.4, dated Jul. 11, 2016, 11 pages.
CN, Third Office Action for CN 201380001359.4, dated Jan. 25, 2017, 15 pages.
CN, Response to Third Office Action for CN 201380001359.4, filed Apr. 10, 2017, 24 pages.
EP, Communication pursuant to Rules 161(1) and 162 EPC for EP 13745491.4, dated Mar. 17, 2015, 2 pages.
EP, Response to Communication pursuant to Rules 161(1) and 162 EPC for EP 13 745 491.4, dated Sep. 25, 2015, 4 pages.
EP, Communication pursuant to Article 94(3) EPC for EP 13 745 491.4, dated Jan. 25, 2016, 3 pages.
EP, Response to Communication pursuant to Article 94(3) EPC for EP 13 745 491.4, filed May 16, 2016, 27 pages.
EP, Communication under Rule 71(3) EPC for EP 13 745 491.4, dated Jun. 20, 2016, 7 pages.
EP, Decision to Grant for EP 13745491.4, dated Nov. 10, 2016, 2 pages.
JP, Notice of Reason for Rejection for JP 2015-526540, dated Oct. 17, 2016, 6 pages.
JP, Response to Notice of Reason for Rejection for JP 2015-526540, dated Jan. 17, 2017, 35 pages.
JP, Notice of Reasons for Rejection for JP 2015-526540, dated Apr. 25, 2017, 5 pages.
IL, Notification of Defects in IL 237023, dated Jan. 4, 2017, 2 pages.
NZ, First Examination Report for NZ 629807, dated Aug. 26, 2015, 2 pages.
NZ, Further Examination Report for NZ 629807, dated Dec. 13, 2016, 2 pages.
NZ, Response to Examination Report for NZ 629807, dated Nov. 24, 2016, 163 pages.
NZ, Response to Further Examination Report for NZ 629807, dated Mar. 8, 2017, 168 pages.
NZ, Further Examination Report Acceptance for NZ 629807, dated Apr. 4, 2017, 1 page.
RU, Office Action for RU 2015107831, dated Apr. 5, 2017, 14 pages.
SG, Written Opinion and Search Report for SG 11201500872S dated Dec. 22, 2015, 9 pages.
SG, Response to Written Opinion for SG 11201500872S, filed May 12, 2016, 22 pages.
SG, Invitation to Respond to Written Opinion for SG 11201500872S, dated Aug. 1, 2016, 7 pages.
SG, Response to Written Opinion for SG 11201500872s, dated Dec. 23, 2016, 25 pages.

(56) References Cited

OTHER PUBLICATIONS

SG, Notice of Eligibility to Grant for SG 11201500872s, dated Feb. 1, 2017, 6 pages.
Certificate of Invention Patent for Chinese patent application CN201380013279.0, patent No. ZL 2013 8 0013279.0, dated Jun. 11, 2019, 1 page with extra 1 page of an English language equivalent or summary.
Granted Pamphlet for Chinese patent application CN201380013279.0, dated Jun. 11, 2019, 96 pages.
Office Action for Canadian patent application CA2,881,275, dated Jun. 27, 2019, 5 pages.
Office Action for Canadian patent application CA2,917,364, dated Jun. 5, 2019, 8 pages.
Notification of Acceptance of Request for Reexamination for Chinese patent application CN201480049793.4, dated Jun. 21, 2019, 2 pages.
Notice of Grant for Japanese patent application JP2016-525833, dated Jul. 2, 2019, 4 pages.
Patent Certificated for Russian patent application RU2016104388, dated May 30, 2019, 1 page.
Notice of Acceptance for Chinese patent application CN2014800497934, dated Jun. 11, 2019, 1 page.
Noline Filing Notification for Japanese patent application JP2018-537705, dated Jun. 7, 2019, 1 page.

\* cited by examiner

PHARMACEUTICAL SALTS, PHYSICAL FORMS, AND COMPOSITIONS OF PYRROLOPYRIMIDINE KINASE INHIBITORS, AND METHODS OF MAKING SAME

CROSS-REFERENCE TO RELATED APPLICATIONS

This application is a U.S. National Phase filing of International Patent Application Serial No. PCT/CN2016/087857, entitled "Pharmaceutical Salts, Physical Forms, and Compositions of Pyrrolopyrimidine Kinase Inhibitors, and Methods of Making Same," having an international filing date of Jun. 30, 2016, which claims priority to International Patent Application Serial No. PCT/CN2015/091536, filed Oct. 9, 2015: the contents of each of these applications are incorporated herein by reference in their entireties for all purposes.

TECHNICAL FIELD

Described herein are methods for the preparation of certain pyrrolopyrimidine compounds that are useful for the treatment of proliferation disorders and other diseases related to the dysregulation of kinase (such as, but not limited to, EGFR (including HER), Alk, PDGFR, BLK, BMX/ETK, BTK, FLT3(D835Y), ITK, JAK1, JAK2, JAK3, TEC, and TXK) and/or the respective pathways. Also described herein are certain salt forms and physical forms of said pyrrolopyrimidine compounds, stabilized pharmaceutical compositions comprising said pyrrolopyrimidine compounds and processes for preparing such compositions, and intermediates useful in the preparation of the pyrrolopyrimidine compounds.

BACKGROUND ART

Certain pyrrolopyrimidine compounds are modulators of protein kinases and are therefore useful in protein kinase-mediated diseases, including cancer and chronic inflammation. A particular kinase of interest is epidermal growth factor receptor (EGFR; ErbB-1; HER1 in humans). This kinase is a member of the ErbB family of receptors, a subfamily of four closely related receptor tyrosine kinases: EGFR (ErbB-1), HER2/c-neu (ErbB-2), Her 3 (ErbB-3) and Her 4 (ErbB-4). EGFR is reportedly deregulated in most solid tumor types, such as lung cancer, breast cancer, and brain tumors. Resistance to known therapies develops due to the presence of a mutation of T790M, which is the gatekeeper of EGFR. Certain pyrrolopyrimidine compounds show selective inhibition of the T790M-mutated EGFR inhibitor relative to the wild type EGFR. It is desirable to develop a more efficient EGFR inhibitor that will target substantially the mutated EGFR over the wild type protein. Other protein kinases that are useful targets for small molecule pharmaceuticals include B lymphoid tyrosine kinase (BLK), janus kinase 1 (JAK1), bone marrow kinase on the X chromosome (BMX/ETK), Bruton's tyrosine kinase (BTK), janus kinase 2 (JAK2), janus kinase 3 (JAK3), tyrosine kinase expressed in hepatocellular carcinoma (TEC), resting lymphocyte kinase (TXK, also known as RLK), FMS-like tyrosine kinase 3 (FLT3), and FLT3 (D835Y). Such compounds are described in PCT Publ. No. WO2014/025486.

An efficient method of making such pyrrolopyrimidine kinase inhibitors is needed to allow for clinical testing and commercial use. Such methods, and intermediates useful for the preparation of such compounds, are described herein. Certain salt forms and polymorphs of said compounds are also described.

Certain pyrrolopyrimidine compounds, including N-(3-((2-((3-fluoro-4-(4-methylpiperazin-1-yl)phenyl)amino)-7H-pyrrolo[2,3-d]pyrimidin-4-yl)oxy)phenyl)acrylamide and pharmaceutically acceptable salts thereof, are useful in treating tumors and related diseases related to the dysregulation of kinases such as those described herein (including, but not limited to, EGFR (including HER), Alk, and PDGFR pathways). See, e.g., U.S. Pat. No. 8,685,998 B2.

In general, drug stability is an important consideration in the design, manufacture, and storage of pharmaceutical compositions. Drug products that lack stability can form degradation products that can cause undesirable side effects or, in some cases, can cause a decrease in the efficacy and bioavailability of the drug substance itself, making it difficult for physicians to prescribe consistent and effective doses. Therefore, pharmaceutical compositions containing active therapeutic agents, such as those described herein, including N-(3-((2-((3-fluoro-4-(4-methylpiperazin-1-yl) phenyl)amino)-7H-pyrrolo[2,3-d]pyrimidin-4-yl)oxy)phenyl)acrylamide and pharmaceutically acceptable salts thereof, that have quick release characteristics, excellent stability, extensive adaptability, and medicinal significance are needed. Described herein are such pharmaceutical compositions.

SUMMARY

The present invention is directed to methods of preparing certain pyrrolopyrimidine derivatives and intermediates useful in their preparation. Also described herein are certain salt forms, polymorphs, and amorphous forms of said compounds.

The present disclosure provides a method of making a compound of Formula (I):

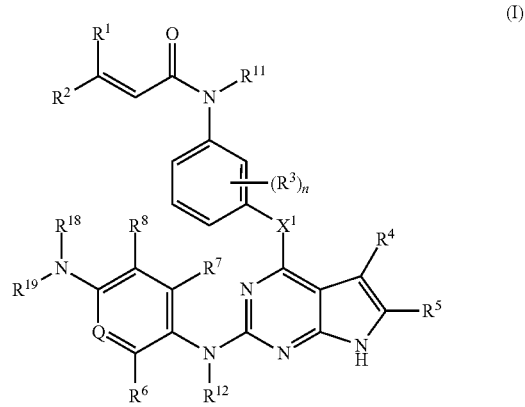

wherein
$X^1$ is O, NH, or S;
$R^1$ and $R^2$ are each independently hydrogen, halo, $C_{1-6}$alkyl, or $C_{1-6}$haloalkyl;
$R^3$ is halo, hydroxyl, $C_{1-6}$alkyl, $C_{1-6}$alkoxy, cyano, or nitro;
n is 0, 1, 2, 3, or 4;
$R^4$ is hydrogen, $C_{1-6}$alkyl, $C_{3-7}$cycloalkyl, or —$NR^{22}R^{23}$;
  wherein the alkyl and cycloalkyl are unsubstituted or substituted with hydroxyl or amino; and $R^{22}$ and $R^{23}$ are each independently hydrogen or $C_{1-6}$alkyl; or $R^{22}$ and $R^{23}$ taken together with the nitrogen to which they are attached form a 3- to 10-membered heterocycloalkyl ring;

$R^5$ is hydrogen or $C_{1-6}$alkyl;

$R^6$ and $R^7$ are each independently hydrogen, halo, $C_{1-6}$alkyl, $C_{1-6}$haloalkyl, $C_{2-6}$alkoxy, $C_{1-6}$haloalkoxy, hydroxyl, cyano, or nitro;

$R^8$ is hydrogen, halo, $C_{1-6}$alkyl, $C_{1-6}$haloalkyl, $C_{1-6}$alkoxy, $C_{1-6}$haloalkoxy, hydroxyl, cyano, or nitro;

$R^{11}$ and $R^{12}$ are each independently hydrogen or $C_{1-6}$alkyl;

Q is $CR^9$ or N;

where $R^9$ is hydrogen, halo, $C_{1-6}$alkyl, $C_{1-6}$haloalkyl, $C_{1-6}$alkoxy, $C_{1-6}$haloalkoxy, hydroxyl, cyano, or nitro;

—$NR^{18}R^{19}$ is:

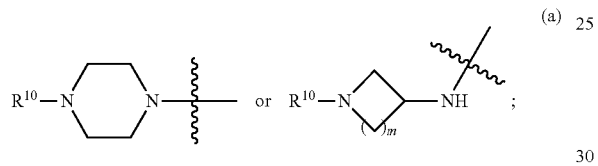

(a)

where $R^{10}$ is selected from hydrogen and $C_{1-6}$ alkyl;

$R^{15}$ is unsubstituted methyl, or is $C_{2-4}$alkyl unsubstituted or substituted with hydroxy, methoxy, or halo; and m is 1 or 2; or (b) $R^{19}$ and $R^9$ are taken together with the atoms to which they are attached to form a 5- or 6-membered heteroaryl ring optionally substituted with $C_{1-6}$alkyl, wherein the alkyl is unsubstituted or substituted with amino, hydroxyl, halo, or an N-linked heterocycloalkyl; and $R^{18}$ is hydrogen or $C_{1-6}$alkyl, where the alkyl is unsubstituted or substituted with amino, or $R^{18}$ is absent to satisfy valency of the heteroaryl ring;

or a pharmaceutically acceptable salt thereof.

The present disclosure is directed to a method of making a compound of Formula (I) or a pharmaceutically acceptable salt thereof, comprising one or more of the following steps:

(a) reacting a compound of Formula (X):

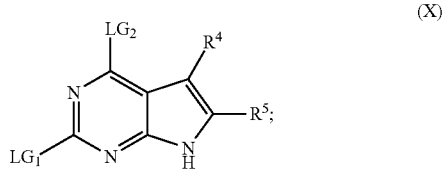

(X)

wherein $LG_1$ and $LG_2$ are each a leaving group; and $R^4$ and $R^5$ are each as defined for Formula (I);

with chloromethyl pivalate to form a compound of Formula (XI);

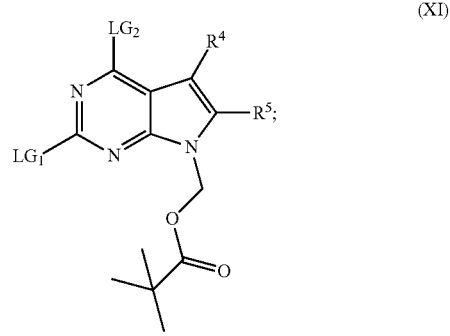

(XI)

(b) reacting a compound of Formula (XI) with a compound of Formula (XII):

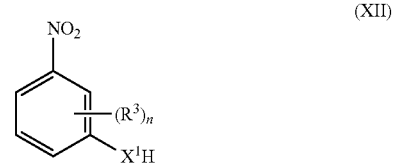

(XII)

wherein $X^1$, n, and $R^3$ are each as defined for Formula (I); to form a compound of Formula (XIII):

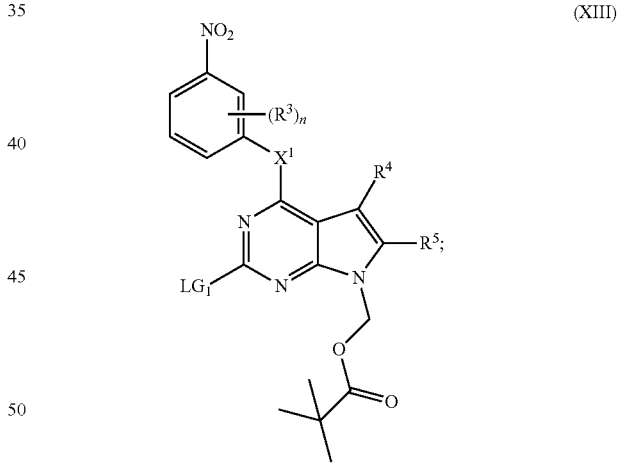

(XIII)

(c) coupling a compound of Formula (XIII) with a compound of Formula (XIV):

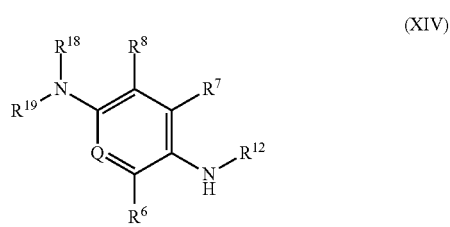

(XIV)

where $R^6$, $R^7$, $R^8$, $R^{12}$, $R^{18}$, $R^{19}$, and Q are each as defined for Formula (I);

to form a compound of Formula (XV):

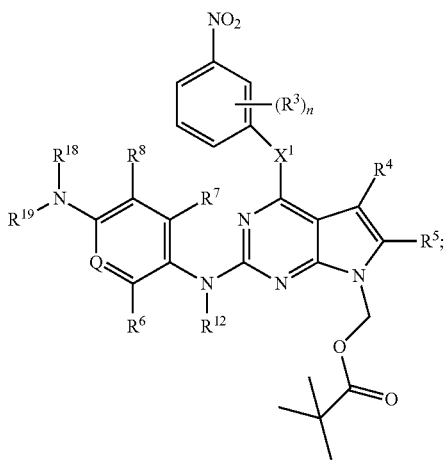

(XV)

(d) deprotecting the compound of Formula (XV) to form a compound of Formula (XVI):

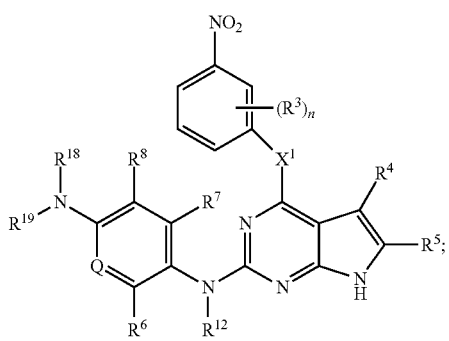

(XVI)

(e) reducing the compound of Formula (XVI) to form a compound of Formula (XVII):

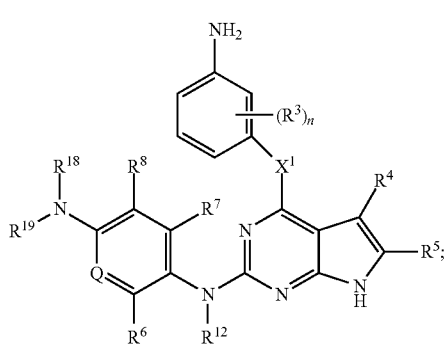

(XVII)

and (f) reacting the compound of Formula (XVII) with acryloyl chloride to form the compound of Formula (I).

The methods described herein may further comprise the step of reacting a compound of Formula (I) with a pharmaceutically acceptable acid to form a pharmaceutically acceptable salt of a compound of Formula (I).

Also contemplated are compounds of Formulae (X), (XI), (XII), (XIII), (XIV), (XV), (XVI), and (XVII), or salts thereof, which are useful as synthetic intermediates in the described methods.

Also contemplated are pharmaceutically acceptable salt forms of compounds described herein, such as compounds of Formula (I), and polymorphs or amorphous forms of such salts.

Also contemplated are pharmaceutical compositions comprising Compound 1:

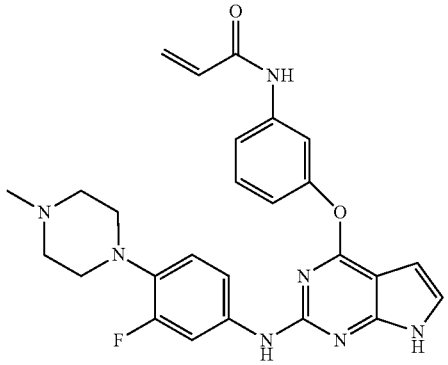

(1)

(chemical name: N-(3-((2-((3-fluoro-4-(4-methylpiperazin-1-yl)phenyl)amino)-7H-pyrrolo[2,3-d]pyrimidin-4-yl)oxy) phenyl)acrylamide) or a pharmaceutically acceptable salt thereof.

In another aspect are described methods of making and methods of manufacturing such pharmaceutical compositions into a dosage form, e.g., a solid oral formulation.

Additional embodiments, features, and advantages of the invention will be apparent from the following detailed description and through practice of the invention.

For the sake of brevity, the disclosures of the publications cited in this specification, including patents, are herein incorporated by reference.

DETAILED DESCRIPTION

Figure 1:
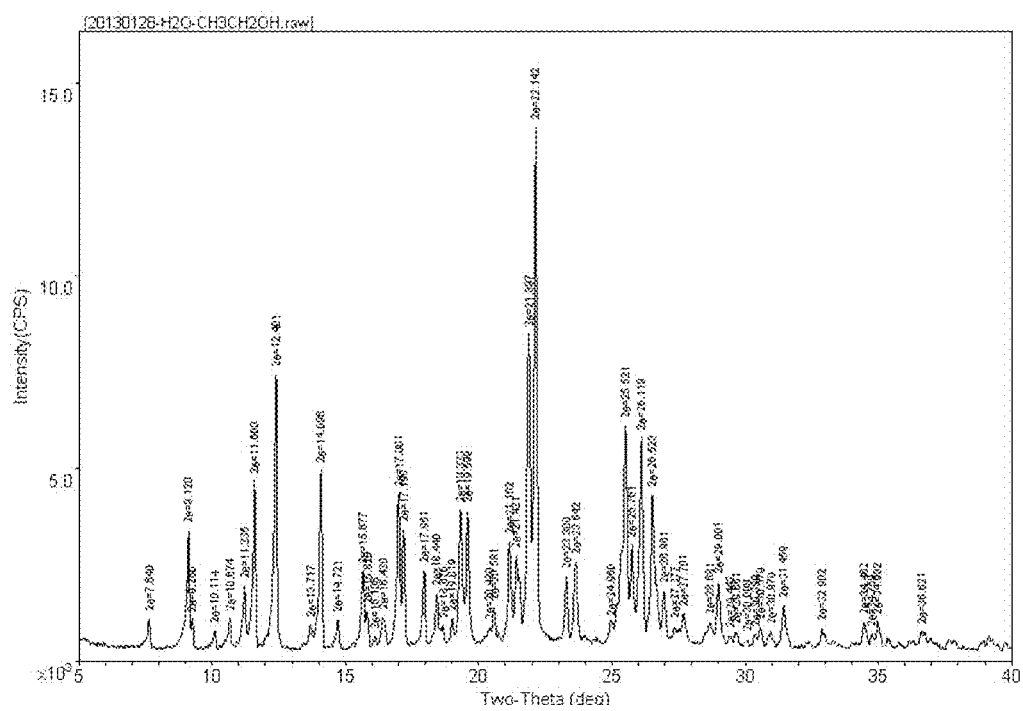
FIG. 1 is an X-ray powder diffractogram of polymorph Form I maleate salt obtained from 1:1 ethanol/H$_2$O.

The present invention is directed to methods of making certain pyrrolopyrimidine derivatives, which are useful in pharmaceutical compositions and in methods of treating proliferation disorders. The compounds as described herein exhibit anti-tumor, anticancer, anti-inflammation, anti-infectious, and anti-proliferation activity. Biological activity of these compounds is described, for example, in PCT Publ. No. WO2014/025486.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. This nomenclature has generally been derived using the commercially-available AutoNom software (MDL, San Leandro, Calif.).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

Chemical Terms

The term "alkyl" refers to a straight- or branched-chain alkyl group having from 1 to 12 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "alkoxy" refers to an alkyl group as defined above, bonded to an oxygen atom. The alkoxy group is connected to the parent structure via the oxygen atom.

The term "amino" refers to an —$NH_2$ group, or a mono- or dialkylamino group.

The term "cycloalkyl" refers to a saturated or partially saturated, monocyclic, fused polycyclic, bridged polycyclic, or spiro polycyclic carbocycle having from 3 to 12 ring atoms per carbocycle. Illustrative examples of cycloalkyl groups include the following entities, in the form of properly bonded moieties:

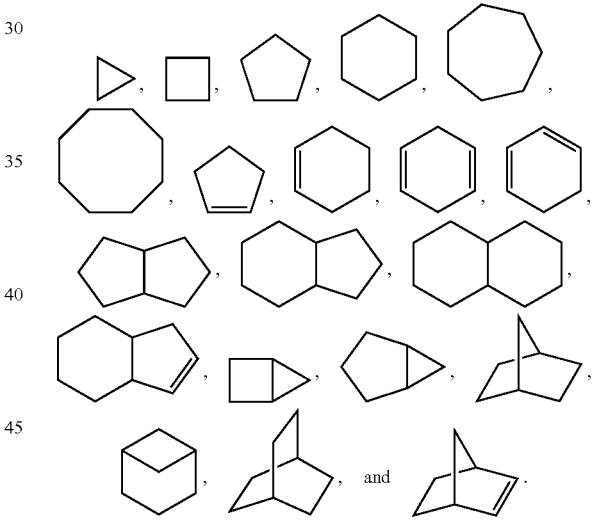

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

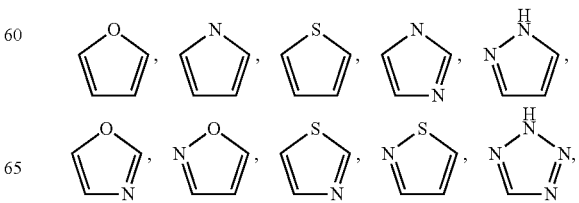

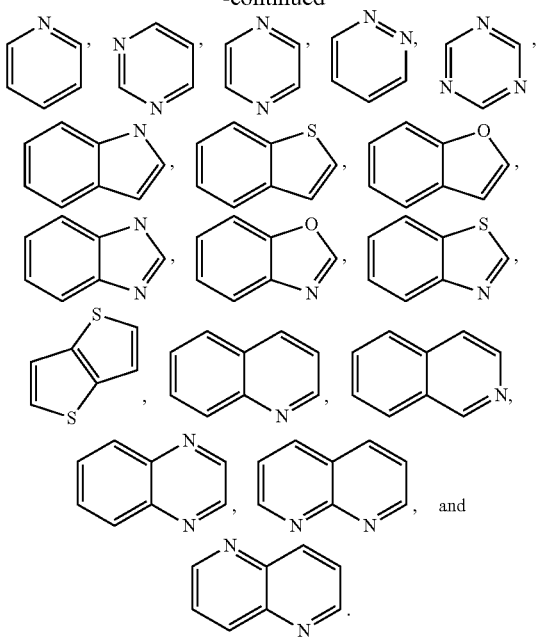

The term "halogen" represents chlorine, fluorine, bromine, or iodine. The term "halo" represents chloro, fluoro, bromo, or iodo. The term "haloalkyl" means an alkyl as defined above, substituted with one or more halogen atoms. The term "haloalkoxy" means an alkoxy as defined above, substituted with one or more halogen atoms.

The term "acyl" refers to a group R—C(O)— where R is from 1 to 10 carbon atoms ($C_{1-10}$) of a straight, branched, or cyclic configuration or a combination thereof, attached to the parent structure through carbonyl functionality. Such R group may be saturated or unsaturated, and aliphatic or aromatic.

The term "cyano" refers to the group —CN.
The term "nitro" refers to the group —$NO_2$.
The term "hydroxyl" refers to the group —OH.

Those skilled in the art will recognize that the species listed or illustrated above are not exhaustive, and that additional species within the scope of these defined terms may also be selected.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the embodiments include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically-labelled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically-labeled compounds of the embodiments and prodrugs thereof can generally be prepared by carrying out the procedures disclosed in the schemes or in the examples and preparations described below by substituting a readily available isotopically-labeled reagent for a non-isotopically-labeled reagent.

The nomenclature "$C_{i-j}$" with j>i, when applied herein to a class of substituents, is meant to refer to embodiments for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates.

For a compound described herein that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology. In certain embodiments, the pharmaceutically acceptable salt is the HCl salt, maleic acid salt, HBr salt, hydroxybutanedioic acid salt, fumaric acid salt, lactic acid salt, tartaric acid salt, or methanesulfonic acid salt.

Representative Embodiments

Formula (I)

In some embodiments of Formula (I), $X^1$ is O, NH, or S. In other embodiments, $X^1$ is O. In other embodiments, $X^1$ is NH. In other embodiments, $X^1$ is S.

In some embodiments, $R^1$ and $R^2$ are each independently hydrogen, halo, $C_{1-6}$alkyl, or $C_{1-6}$haloalkyl. In certain instances, $R^1$ is hydrogen. In certain instances, $R^1$ is $C_{1-6}$alkyl. In certain instances, $R^1$ is methyl or ethyl. In certain instances, $R^2$ is hydrogen. In certain instances, $R^2$ is $C_{1-6}$alkyl. In certain instances, $R^2$ is methyl or ethyl. In certain instances, $R^1$ and $R^2$ are each hydrogen.

In Formula (I), n is 0, 1, 2, 3, or 4. In certain instances, n is zero. In certain instances, n is 1. In certain instances, n is 2. In certain instances, n is 3. In certain instances, n is 4.

In Formula (I), $R^3$ is halo, hydroxyl, $C_{1-6}$alkyl, $C_{1-6}$alkoxy, cyano, or nitro. In certain instances, $R^3$ is halo. In certain instances, $R^3$ is hydroxyl. In certain instances, $R^3$ is $C_{1-6}$alkyl. In certain instances, $R^3$ is $C_{1-6}$alkoxy. In certain instances, $R^3$ is cyano. In certain instances, $R^3$ is nitro.

In Formula (I), $R^4$ is hydrogen, $C_{1-6}$alkyl, $C_{3-7}$cycloalkyl, or —$NR^{22}R^{23}$; wherein the alkyl and cycloalkyl are unsubstituted or substituted with hydroxyl or amino; and wherein $R^{22}$ and $R^{23}$ are each independently hydrogen or $C_{1-6}$ alkyl; or $R^{22}$ and $R^{23}$ taken together with the nitrogen to which they are attached form a 3- to 10-membered heterocycloalkyl ring. In certain instances, $R^4$ is hydrogen. In certain instances, $R^4$ is $C_{1-6}$alkyl. In certain instances, $R^4$ is $C_{3-7}$cycloalkyl. In certain instances, $R^4$ is —$NR^{22}R^{23}$.

In certain instances, $R^4$ is unsubstituted $C_{1-6}$alkyl. In certain instances, $R^4$ is $C_{1-6}$alkyl that is substituted with hydroxyl. In certain instances, $R^4$ is $C_{1-3}$alkyl that is substituted with hydroxyl. In certain instances, $R^4$ is $C_{1-6}$alkyl that is substituted with amino. In certain instances, $R^4$ is $C_{1-6}$alkyl that is substituted with —$NH_2$. In certain instances, $R^4$ is $C_{1-6}$alkyl that is substituted with —$N(CH_3)_2$.

In certain instances, $R^4$ is $C_{1-3}$alkyl that is substituted with —$NH_2$. In certain instances, $R^4$ is $C_{1-3}$alkyl that is substituted with —$N(CH_3)_2$.

In certain instances, $R^4$ is unsubstituted $C_{3-7}$cycloalkyl. In certain instances, $R^4$ is unsubstituted $C_3$cycloalkyl. In certain instances, $R^4$ is unsubstituted $C_4$cycloalkyl. In certain instances, $R^4$ is unsubstituted $C_{5-6}$cycloalkyl. In certain instances, $R^4$ is unsubstituted $C_7$cycloalkyl.

In certain instances, $R^4$ is —$NR^{22}R^{23}$, wherein $R^{22}$ and $R^{23}$ are each independently hydrogen or $C_{1-6}$ alkyl; or $R^{22}$ and $R^{23}$ taken together with the nitrogen to which they are attached form a 3- to 10-membered heterocycloalkyl ring. In certain instances, $R^{22}$ and $R^{23}$ are each hydrogen. In certain instances, $R^{22}$ and $R^{23}$ are each $C_{1-6}$alkyl. In certain instances, $R^{22}$ and $R^{23}$ are each $C_{1-3}$alkyl. In certain instances, $R^{22}$ and $R^{23}$ are each methyl.

In certain instances, $R^{22}$ and $R^{23}$ are taken together with the nitrogen to which they are attached to form a 3- to 10-membered heterocycloalkyl ring, such that $R^4$ is

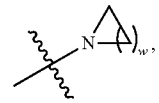

where w is a number from 1 to 8. In certain instances, $R^{22}$ and $R^{23}$ are taken together with the nitrogen to which they are attached to form a 3-, 4-, 5-, or 6-membered ring.

In Formula (I), $R^5$ is hydrogen or $C_{1-6}$-alkyl. In certain instances, $R^5$ is hydrogen. In certain instances, $R^5$ is $C_{1-6}$alkyl. In certain instances, $R^5$ is methyl. In certain instances, $R^5$ is ethyl. In certain instances, $R^5$ is $C_{1-3}$alkyl. In certain instances, $R^5$ is $C_{4-6}$alkyl.

In Formula (I), $R^6$ and $R^7$ are each independently hydrogen, halo, $C_{1-6}$ alkyl, $C_{1-6}$ haloalkyl, $C_{2-6}$ alkoxy, $C_{1-6}$ haloalkoxy, hydroxyl, cyano, or nitro. In certain instances, $R^6$ is hydrogen. In certain instances, $R^6$ is halo. In certain instances, $R^6$ is fluoro. In certain instances, $R^6$ is chloro. In certain instances, $R^6$ is bromo. In certain instances, $R^6$ is $C_{1-6}$alkyl. In certain instances, $R^6$ is $C_{1-6}$haloalkyl. In certain instances, $R^6$ is $C_{2-6}$alkoxy. In certain instances, $R^6$ is $C_{1-6}$haloalkoxy. In certain instances, $R^6$ is hydroxyl. In certain instances, $R^6$ is cyano. In certain instances, $R^6$ is nitro. In certain instances, $R^7$ is hydrogen. In certain instances, $R^7$ is halo. In certain instances, $R^7$ is fluoro. In certain instances, $R^7$ is chloro. In certain instances, $R^7$ is bromo. In certain instances, $R^7$ is $C_{1-6}$alkyl. In certain instances, $R^7$ is $C_{1-6}$haloalkyl. In certain instances, $R^7$ is $C_{2-6}$alkoxy. In certain instances, $R^7$ is $C_{1-6}$haloalkoxy. In certain instances, $R^7$ is hydroxyl. In certain instances, $R^7$ is cyano. In certain instances, $R^7$ is nitro.

In Formula (I), $R^8$ is hydrogen, halo, $C_{1-6}$ alkyl, $C_{1-6}$ haloalkyl, $C_{1-6}$ alkoxy, $C_{1-6}$ haloalkoxy, hydroxyl, cyano, or nitro. In certain instances, $R^8$ is hydrogen. In certain instances, $R^8$ is halo. In certain instances, $R^8$ is fluoro. In certain instances, $R^8$ is chloro. In certain instances, $R^8$ is bromo. In certain instances, $R^8$ is $C_{1-6}$alkyl. In certain instances, $R^8$ is $C_{1-6}$haloalkyl. In certain instances, $R^8$ is $C_{1-6}$alkoxy. In certain instances, $R^8$ is $C_{1-6}$haloalkoxy. In certain instances, $R^8$ is hydroxyl. In certain instances, $R^8$ is cyano. In certain instances, $R^8$ is nitro.

In Formula (I), $R^{11}$ is selected from hydrogen and $C_{1-6}$ alkyl. In certain instances, $R^{11}$ is hydrogen. In certain instances, $R^{11}$ is $C_{1-6}$ alkyl. In certain instances, $R^{11}$ is methyl. In certain instances, $R^{11}$ is ethyl. In certain instances, $R^{11}$ is $C_{1-3}$ alkyl. In certain instances, $R^{11}$ is $C_{4-6}$ alkyl.

In Formula (I), $R^{12}$ is selected from hydrogen and $C_{1-6}$ alkyl. In certain instances, $R^{12}$ is hydrogen. In certain instances, $R^{12}$ is $C_{1-6}$ alkyl. In certain instances, $R^{12}$ is methyl. In certain instances, $R^{12}$ is ethyl. In certain instances, $R^{12}$ is $C_{1-3}$ alkyl. In certain instances, $R^{12}$ is $C_{4-6}$ alkyl.

In Formula (I), Q is $CR^9$ or N. In certain instances, Q is $CR^9$. In certain instances, Q is N.

In Formula (I), $R^9$ is hydrogen, halo, $C_{1-6}$alkyl, $C_{1-6}$haloalkyl, $C_{1-6}$alkoxy, $C_{1-6}$haloalkoxy, hydroxyl, cyano, or nitro. In certain instances, $R^9$ is hydrogen. In certain instances, $R^9$ is halo. In certain instances, $R^9$ is fluoro. In certain instances, $R^9$ is chloro. In certain instances, $R^9$ is bromo. In certain instances, $R^9$ is $C_{1-6}$alkyl. In certain instances, $R^9$ is $C_{1-6}$haloalkyl. In certain instances, $R^9$ is $C_{1-6}$alkoxy. In certain instances, $R^9$ is $C_{1-6}$haloalkoxy. In certain instances, $R^9$ is hydroxyl. In certain instances, $R^9$ is cyano. In certain instances, $R^9$ is nitro. In certain instances, $R^9$ is hydrogen or fluoro.

In Formula (I), $-NR^{18}R^{19}$ is:

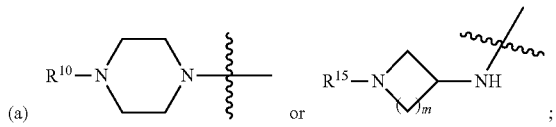

(a)    or    ;

wherein $R^{10}$ is selected from hydrogen and $C_{1-6}$ alkyl;

$R^{15}$ is unsubstituted methyl, or is $C_{2-4}$alkyl unsubstituted or substituted with hydroxy, methoxy, or halo; and m is 1 or 2; or (b) $R^{19}$ and $R^9$ are taken together with the atoms to which they are attached to form a 5- or 6-membered heteroaryl ring optionally substituted with $C_{1-6}$alkyl, wherein the alkyl is unsubstituted or substituted with amino, hydroxyl, halo, or an N-linked heterocycloalkyl; and $R^{18}$ is hydrogen or $C_{1-6}$alkyl, where the alkyl is unsubstituted or substituted with amino, or $R^{18}$ is absent to satisfy valency of the heteroaryl ring.

In certain instances, $-NR^{18}R^{19}$ is:

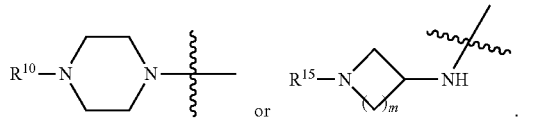

or    .

In certain instances, $-NR^{18}R^{19}$ is

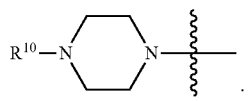

.

In certain instances, $-NR^{18}R^{19}$ is

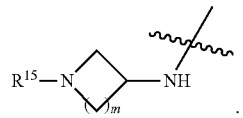

.

In Formula (I), $R^{10}$ is hydrogen or $C_{1-6}$alkyl. In certain instances, $R^{10}$ is hydrogen. In certain instances, $R^{10}$ is $C_{1-6}$alkyl. In certain instances, $R^{10}$ is methyl. In certain instances, $R^{10}$ is ethyl. In certain instances, $R^{10}$ is $C_{1-3}$alkyl. In certain instances, $R^{10}$ is $C_{4-6}$ alkyl.

In certain instances, $R^{15}$ is methyl, hydroxyethyl, methoxyethyl, or fluoroethyl. In other embodiments, $R^{15}$ is fluoroethyl. In some embodiments, m is 1. In other embodiments, m is 2.

In Formula (I), $-NR^{18}R^{19}$ is defined as follows: $R^{19}$ and $R^9$ are taken together with the atoms to which they are attached to form a 5- or 6-membered heteroaryl ring optionally substituted with $C_{1-6}$alkyl, wherein the alkyl is unsubstituted or substituted with amino, hydroxyl, halo, or an N-linked heterocycloalkyl, or the alkyl is substituted with amino; and $R^{18}$ is hydrogen or $C_{1-6}$alkyl, where the alkyl is unsubstituted or substituted with amino, or $R^{18}$ is absent to satisfy valency of the heteroaryl ring. In some embodiments, the heteroaryl ring is substituted with dimethylaminomethyl or piperidinylmethyl. In other embodiments, $R^9$ and $R^{19}$ taken together form optionally substituted pyrrole or pyridine. In some instances, $R^{18}$ is dimethylaminoethyl.

In certain instances, $R^6$, $R^7$, $R^8$, and $R^9$ are hydrogen. In certain instances, $R^6$, $R^7$, and $R^8$ are hydrogen and $R^9$ is halo. In certain instances, $R^6$, $R^7$, and $R^8$ are hydrogen and $R^9$ is fluoro.

In certain instances, $R^6$, $R^7$, $R^8$, and $R^9$ are hydrogen and $R^{10}$ is methyl. In certain instances, $R^6$, $R^7$, $R^8$ are hydrogen; $R^9$ is halo; and $R^{10}$ is methyl. In certain instances, $R^6$, $R^7$, $R^8$ are hydrogen; $R^9$ is fluoro; and $R^{10}$ is methyl.

In certain instances, $R^6$, $R^7$, $R^8$, and $R^9$ are hydrogen and $R^{13}$ is hydrogen. In certain instances, $R^6$, $R^7$, and $R^8$ are hydrogen; $R^9$ is halo; and $R^{13}$ is hydrogen. In certain instances, $R^6$, $R^7$, and $R^8$ are hydrogen; $R^9$ is fluoro; and $R^{13}$ is hydrogen.

In certain instances, $R^6$, $R^7$, $R^8$, and $R^9$ are hydrogen and $R^{13}$ is $-CH_2OH$. In certain instances, $R^6$, $R^7$, and $R^8$ are hydrogen; $R^9$ is halo; and $R^{13}$ is $-CH_2OH$. In certain instances, $R^6$, $R^7$, and $R^8$ are hydrogen; $R^9$ is fluoro; and $R^{13}$ is $-CH_2OH$.

In certain instances, $R^6$, $R^7$, $R^8$, and $R^9$ are hydrogen and $R^{13}$ is $-(CH_2)_mF$, wherein m is a number from one to 3. In certain instances, $R^6$, $R^7$, and $R^8$ are hydrogen; $R^9$ is halo; and $R^{13}$ is $-(CH_2)_mF$, wherein m is a number from one to 3. In certain instances, $R^6$, $R^7$, and $R^8$ are hydrogen; $R^9$ is fluoro; and $R^{13}$ is $-(CH_2)_mF$, wherein m is a number from one to 3.

Formula (II)

The present disclosure is directed to methods of making a compound of Formula (II):

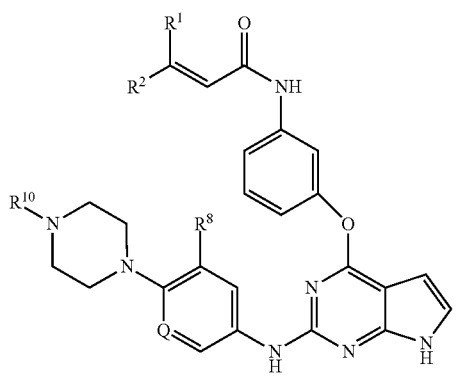

(II)

wherein

R$^1$ and R$^2$ are each independently hydrogen, halo, C$_{1-6}$alkyl, or C$_{1-6}$haloalkyl;

R$^8$ is hydrogen, halo, C$_{1-6}$alkyl, C$_{1-6}$haloalkyl, C$_{1-6}$alkoxy, C$_{1-6}$haloalkoxy, hydroxyl, cyano, or nitro;

Q is CR$^9$ or N;

where R$^9$ is hydrogen, halo, C$_{1-6}$-alkyl, C$_{1-6}$haloalkyl, C$_{1-6}$alkoxy, C$_{1-6}$haloalkoxy, hydroxyl, cyano, or nitro; and R$^{10}$ is hydrogen or C$_{1-6}$alkyl;

or a pharmaceutically acceptable salt thereof.

In some embodiments of Formula (II), R$^1$ and R$^2$ are each hydrogen. In other embodiments, R$^8$ is halo, methyl, methoxy, or cyano. In still other embodiments, R$^8$ is halo. In still other embodiments, R$^8$ is fluoro. In some embodiments, R$^{10}$ is methyl, ethyl, or isopropyl. In other embodiments, R$^{10}$ is methyl.

Formula (III)

The present disclosure provides methods of making a compound of Formula (III):

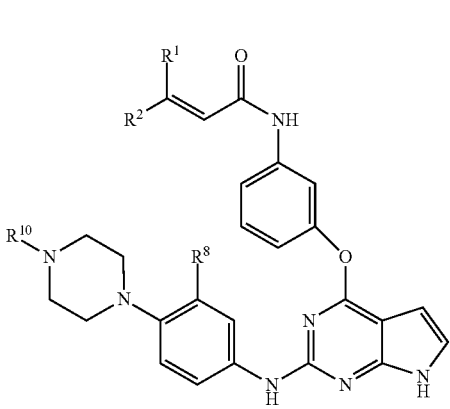

(III)

wherein

R$^1$ and R$^2$ are each independently hydrogen, halo, C$_{1-6}$alkyl, or C$_{1-6}$haloalkyl;

R$^8$ is halo, C$_{1-6}$alkyl, C$_{1-6}$haloalkyl, C$_{1-6}$alkoxy, C$_{1-6}$haloalkoxy, hydroxyl, cyano, or nitro; and R$^{10}$ is C$_{1-6}$alkyl;

or a pharmaceutically acceptable salt thereof.

In some embodiments of Formula (III), R$^1$ and R$^2$ are each hydrogen. In other embodiments, R$^8$ is halo, methyl, methoxy, or cyano. In still other embodiments, R$^8$ is halo. In still other embodiments, R$^8$ is fluoro. In some embodiments, R$^{10}$ is methyl, ethyl, or isopropyl. In other embodiments, R$^{10}$ is methyl.

In some embodiments of compounds of Formula (I), R$^6$ and R$^7$ may also be methoxy. In other embodiments, R$^6$ and R$^7$ may also be methoxy, provided that neither R$^6$ nor R$^7$ is methoxy when R$^{10}$ is methyl. In some embodiments, R$^6$ is methoxy. In other embodiments, R$^7$ is methoxy. In certain instances, R$^7$ is hydrogen or methoxy.

In other embodiments of Formula (II) or (III), the

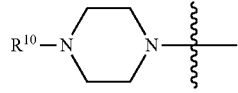

group is replaced with

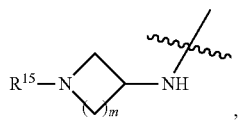

where m and R$^{15}$ are as defined herein.

In certain embodiments, the present disclosure is directed to methods of making a compound selected from the compounds in Table 1, and pharmaceutically acceptable salts thereof.

TABLE 1

| Compound | Structure | Chemical Name |
|---|---|---|
| 1 | 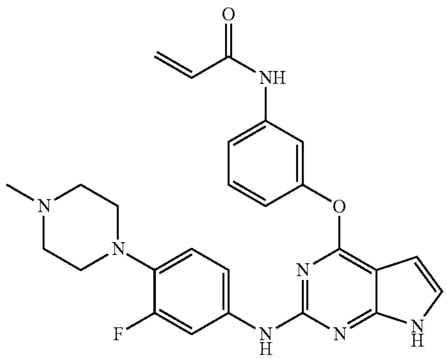 [SMILES: C=CC(=O)Nc1cccc(Oc2nc(Nc3ccc(N4CCN(C)CC4)c(F)c3)nc3[nH]ccc23)c1] | N-(3-((2-((3-fluoro-4-(4-methylpiperazin-1-yl)phenyl)amino)-7H-pyrrolo[2,3-d]pyrimidin-4-yl)oxy)phenyl)acrylamide |
| 2 | 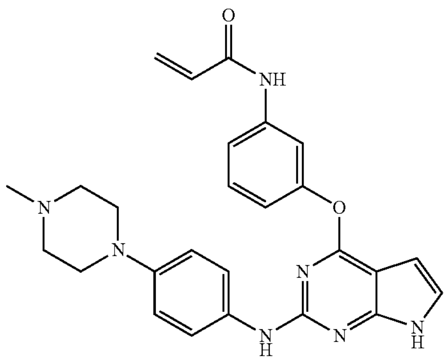 [SMILES: C=CC(=O)Nc1cccc(Oc2nc(Nc3ccc(N4CCN(C)CC4)cc3)nc3[nH]ccc23)c1] | N-(3-((2-((4-(4-methylpiperazin-1-yl)phenyl)amino)-7H-pyrrolo[2,3-d]pyrimidin-4-yl)oxy)phenyl)acrylamide |
| 3 | 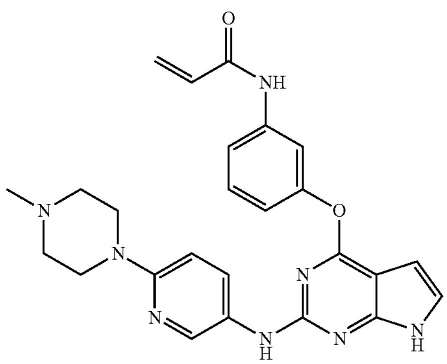 [SMILES: C=CC(=O)Nc1cccc(Oc2nc(Nc3ccc(N4CCN(C)CC4)nc3)nc3[nH]ccc23)c1] | N-(3-((2-((6-(4-methylpiperazin-1-yl)pyridin-3-yl)amino)-7H-pyrrolo[2,3-d]pyrimidin-4-yl)oxy)phenyl)acrylamide |
| 4 | 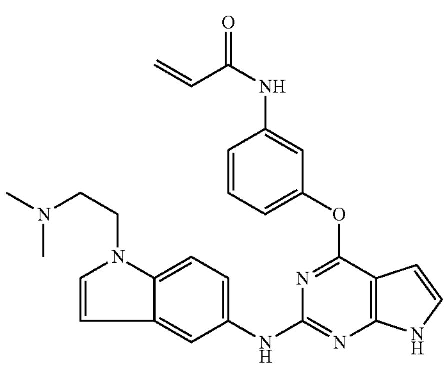 [SMILES: C=CC(=O)Nc1cccc(Oc2nc(Nc3ccc4c(ccn4CCN(C)C)c3)nc3[nH]ccc23)c1] | N-(3-((2-((1-(2-(dimethylamino)ethyl)-1H-indol-5-yl)amino)-7H-pyrrolo[2,3-d]pyrimidin-4-yl)oxy)phenyl)acrylamide |

TABLE 1-continued

| Compound | Structure | Chemical Name |
|---|---|---|
| 5 | 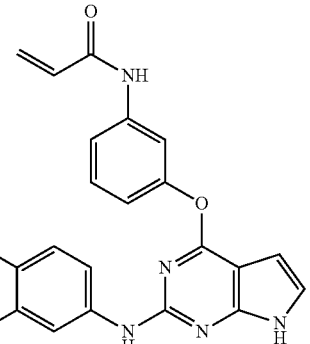 | N-(3-((2-((2-((dimethylamino)methyl)quinolin-6-yl)amino)-7H-pyrrolo[2,3-d]pyrimidin-4-yl)oxy)phenyl)acrylamide |
| 6 | 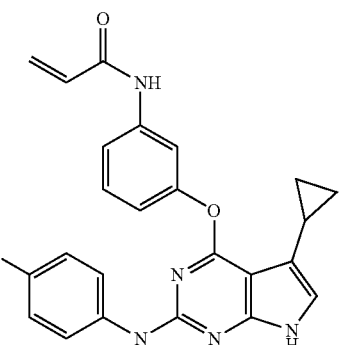 | N-(3-((5-cyclopropyl-2-((4-(4-methylpiperazin-1-yl)phenyl)amino)-7H-pyrrolo[2,3-d]pyrimidin-4-yl)oxy)phenyl)acrylamide |
| 7 | 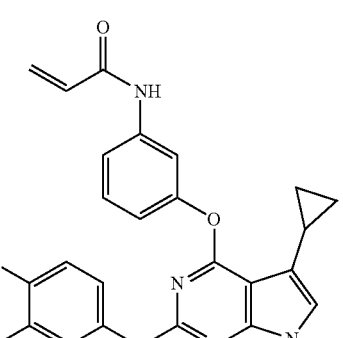 | N-(3-((5-cyclopropyl-2-((3-fluoro-4-(4-methylpiperazin-1-yl)phenyl)amino)-7H-pyrrolo[2,3-d]pyrimidin-4-yl)oxy)phenyl)acrylamide |
| 8 | 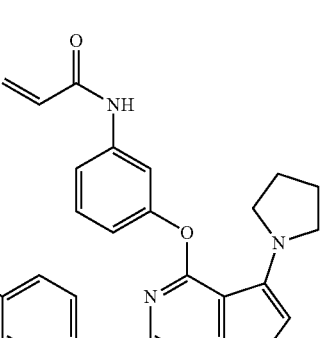 | N-(3-((2-((4-(4-methylpiperazin-1-yl)phenyl)amino)-5-(pyrrolidin-1-yl)-7H-pyrrolo[2,3-d]pyrimidin-4-yl)oxy)phenyl)acrylamide |

TABLE 1-continued

| Compound | Structure | Chemical Name |
| --- | --- | --- |
| 9 | 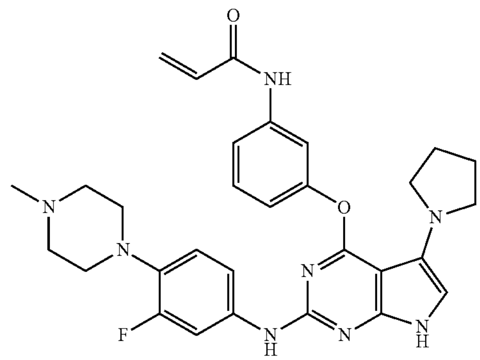 [SMILES: C=CC(=O)Nc1cccc(Oc2nc(Nc3ccc(N4CCN(C)CC4)c(F)c3)nc3[nH]cc(N4CCCC4)c23)c1] | N-(3-((2-((3-fluoro-4-(4-methylpiperazin-1-yl)phenyl)amino)-5-(pyrrolidin-1-yl)-7H-pyrrolo[2,3-d]pyrimidin-4-yl)oxy)phenyl)acrylamide |
| 10 | 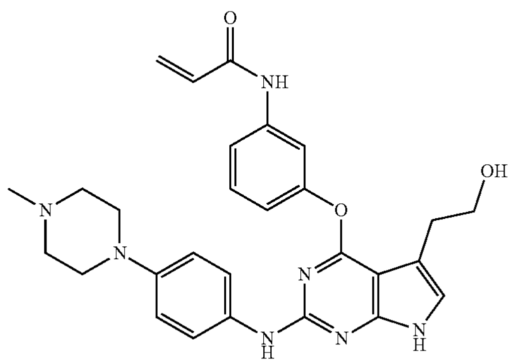 [SMILES: C=CC(=O)Nc1cccc(Oc2nc(Nc3ccc(N4CCN(C)CC4)cc3)nc3[nH]cc(CCO)c23)c1] | N-(3-((5-(2-hydroxyethyl)-2-((4-(4-methylpiperazin-1-yl)phenyl)amino)pyrrolo[2,3-d]pyrimidin-4-yl)oxy)phenyl)acrylamide |
| 11 | 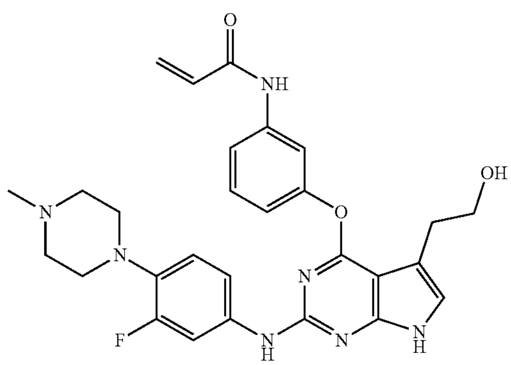 [SMILES: C=CC(=O)Nc1cccc(Oc2nc(Nc3ccc(N4CCN(C)CC4)c(F)c3)nc3[nH]cc(CCO)c23)c1] | N-(3-((2-((3-fluoro-4-(4-methylpiperazin-1-yl)phenyl)amino)-5-(2-hydroxyethyl)-7H-pyrrolo[2,3-d]pyrimidin-4-yl)oxy)phenyl)acrylamide |
| 12 | 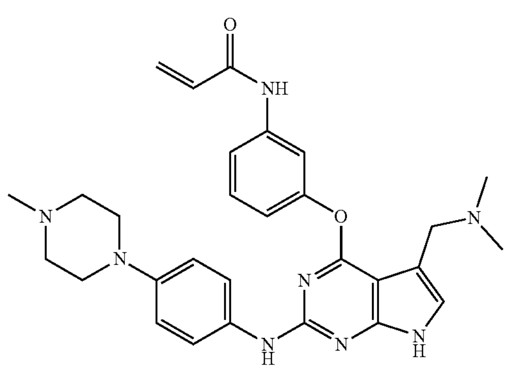 | N-(3-((5-((dimethylamino)methyl)-2-((4-(4-methylpiperazin-1-yl)phenyl)amino)-7H-pyrrolo[2,3-d]pyrimidin-4-yl)oxy)phenyl)acrylamide |

TABLE 1-continued

| Compound | Structure | Chemical Name |
|---|---|---|
| 13 | 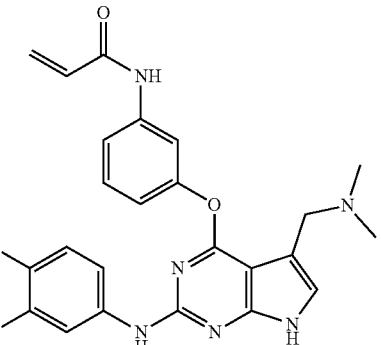 | N-(3-((5-((dimethylamino)methyl)-2-((3-fluoro-4-(4-methylpiperazin-1-yl)phenyl)amino)-7H-pyrrolo[2,3-d]pyrimidin-4-yl)oxy)phenyl)acrylamide |
| 14 | 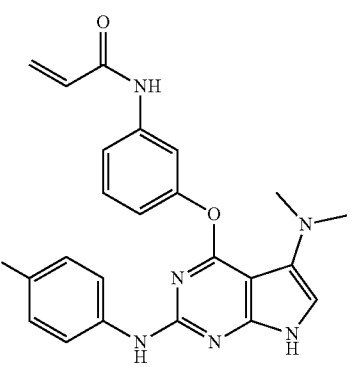 | N-(3-((5-(dimethylamino)-2-((4-(4-methylpiperazin-1-yl)phenyl)amino)-7H-pyrrolo[2,3-d]pyrimidin-4-yl)oxy)phenyl)acrylamide |
| 15 | 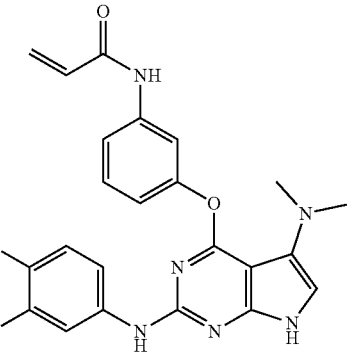 | N-(3-((5-(dimethylamino)-2-((3-fluoro-4-(4-methylpiperazin-1-yl)phenyl)amino)-7H-pyrrolo[2,3-d]pyrimidin-4-yl)oxy)phenyl)acrylamide |
| 16 | 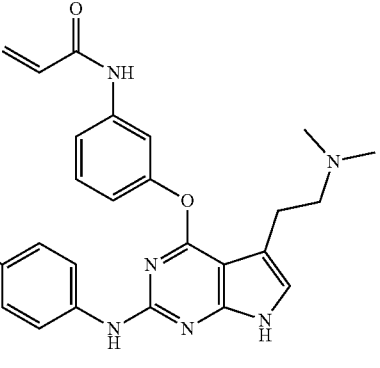 | N-(3-((5-(2-(dimethylamino)ethyl)-2-((4-(4-methylpiperazin-1-yl)phenyl)amino)-7H-pyrrolo[2,3-d]pyrimidin-4-yl)oxy)phenyl)acrylamide |

TABLE 1-continued

| Compound | Structure | Chemical Name |
|---|---|---|
| 17 | 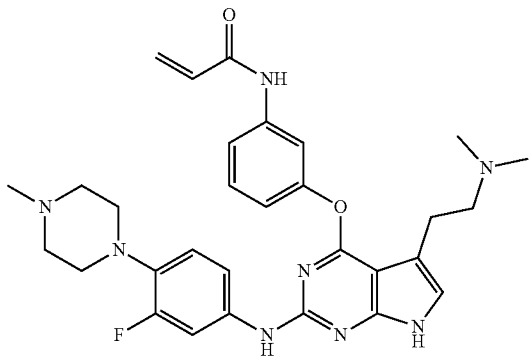 | N-(3-((5-(2-(dimethylamino)ethyl)-2-((3-fluoro-4-(4-methylpiperazin-1-yl)phenyl)amino)-7H-pyrrolo[2,3-d]pyrimidin-4-yl)oxy)phenyl)acrylamide |
| 18 | 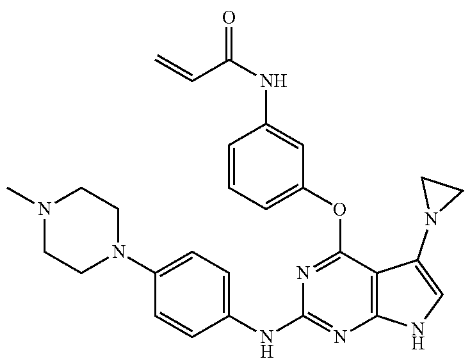 | N-(3-((5-(aziridin-1-yl)-2-((4-(4-methylpiperazin-1-yl)phenyl)amino)-7H-pyrrolo[2,3-d]pyrimidin-4-yl)oxy)phenyl)acrylamide |
| 19 | 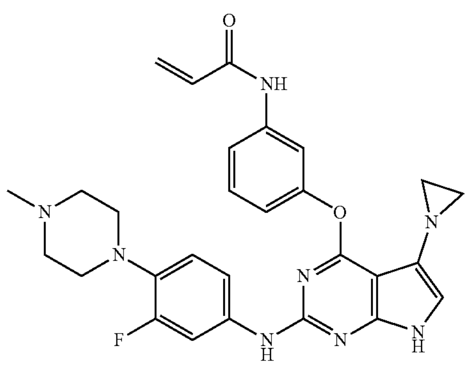 [SMILES: C=CC(=O)Nc1cccc(Oc2nc(Nc3ccc(N4CCN(C)CC4)c(F)c3)nc3[nH]cc(N4CC4)c23)c1] | N-(3-((5-(aziridin-1-yl)-2-((3-fluoro-4-(4-methylpiperazin-1-yl)phenyl)amino)-7H-pyrrolo[2,3-d]pyrimidin-4-yl)oxy)phenyl)acrylamide |
| 20 | 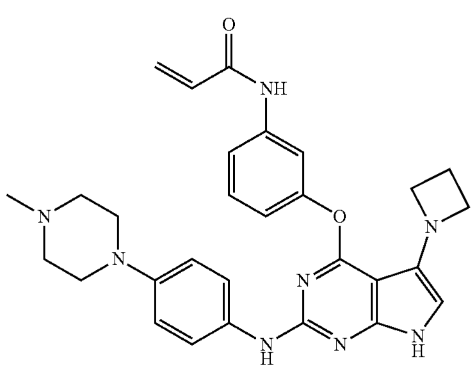 [SMILES: C=CC(=O)Nc1cccc(Oc2nc(Nc3ccc(N4CCN(C)CC4)cc3)nc3[nH]cc(N4CCC4)c23)c1] | N-(3-((5-(azetidin-1-yl)-2-((4-(4-methylpiperazin-1-yl)phenyl)amino)-7H-pyrrolo[2,3-d]pyrimidin-4-yl)oxy)phenyl)acrylamide |

TABLE 1-continued

| Compound | Structure | Chemical Name |
| --- | --- | --- |
| 21 | 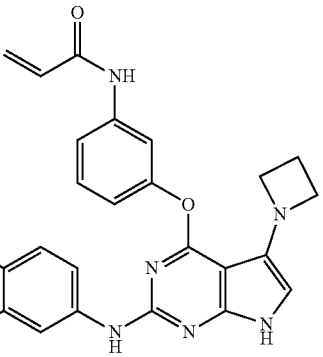 | N-(3-((5-(azetidin-1-yl)-2-((3-fluoro-4-(4-methylpiperazin-1-yl)phenyl)amino)-7H-pyrrolo[2,3-d]pyrimidin-4-yl)oxy)phenyl)acrylamide |
| 22 | 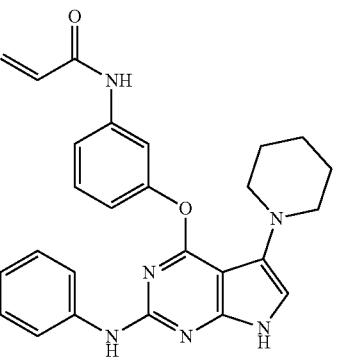 | N-(3-((2-((4-(4-methylpiperazin-1-yl)phenyl)amino)-5-(piperidin-1-yl)-7H-pyrrolo[2,3-d]pyrimidin-4-yl)oxy)phenyl)acrylamide |
| 23 | 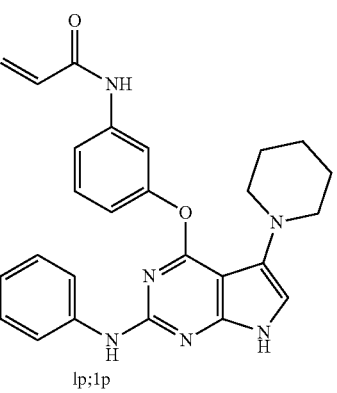 lp;1p | N-(3-((2-((3-fluoro-4-(4-methylpiperazin-1-yl)phenyl)amino)-5-(piperidin-1-yl)-7H-pyrrolo[2,3-d]pyrimidin-4-yl)oxy)phenyl)acrylamide |
| 24 | 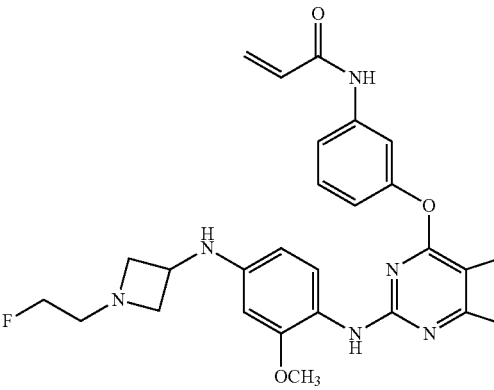 | N-(3-(2-(4-(1-(2-fluoroethyl)azetidin-3-ylamino)-2-methoxyphenylamino)-7H-pyrrolo[2,3-d]pyrimidin-4-yloxy)phenyl)acrylamide |

TABLE 1-continued

| Compound | Structure | Chemical Name |
|---|---|---|
| 25 | 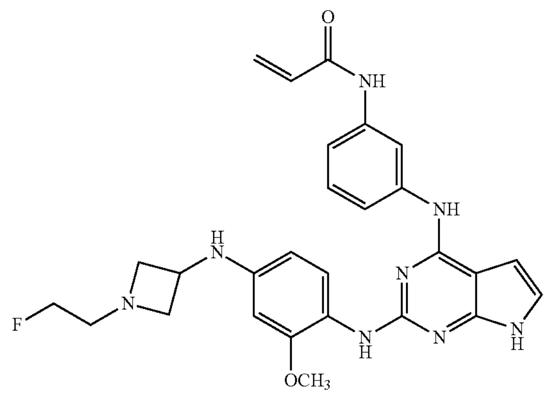 [SMILES: C=CC(=O)Nc1cccc(Nc2nc(Nc3ccc(NC4CN(CCF)C4)cc3OC)nc3[nH]ccc23)c1] | N-(3-(2-(4-(1-(2-fluoroethyl)azetidin-3-ylamino)-2-methoxyphenylamino)-7H-pyrrolo[2,3-d]pyrimidin-4-ylamino)phenyl)acrylamide and |
| 26 | | N-(3-((2-((2-(piperidin-1-ylmethyl)quinolin-6-yl)amino)-7H-pyrrolo[2,3-d]pyrimidin-4-yl)oxy)phenyl)acrylamide | and pharmaceutically acceptable salts thereof.

Chemical Embodiments

In some embodiments of step (a), $LG_1$ and $LG_2$ are each a leaving group. In some embodiments, $LG_1$ and $LG_2$ are each independently halo or trifluorosulfonate (triflate). In some embodiments, $LG_1$ and $LG_2$ are the same leaving group; in other embodiments, they are different leaving groups. In some embodiments, $LG_1$ and $LG_2$ are each halo, or are each Cl, Br, or I, or are each Cl.

In some embodiments, $R^4$ and $R^5$ are each as defined in any of the various permutations described herein.

In some embodiments of step (a), the reacting is performed in the presence of chloromethyl pivalate and an ionic base such as $K_2CO_3$, $Na_2CO_3$, $Cs_2CO_3$, NaOH, or KOH, or an amine base such as a trialkylamine, for example, $Et_3N$ or $iPr_2NEt$. In some embodiments, the reacting is performed in the presence of an ionic base. In some embodiments, the ionic base is $K_2CO_3$. In some embodiments, the solvent for step (a) is a polar solvent such as THF, DMF, or water, or a mixture thereof. In some embodiments, the solvent is a mixture of THF and water.

In some embodiments of step (b), $X^1$, n, and $R^3$ are each as defined in any of the various permutations described herein. In some embodiments of step (b), the reacting is performed in the presence of an ionic base such as $K_2CO_3$, $Na_2CO_3$, $Cs_2CO_3$, NaOH, or KOH, or an amine base such as a trialkylamine, for example, $Et_3N$ or $iPr_2NEt$. In some embodiments, the reacting is performed in the presence of an ionic base. In some embodiments, the ionic base is $K_2CO_3$. In some embodiments, the solvent for step (b) is a polar solvent such as THF, DMF, or water, or a mixture thereof. In some embodiments, the solvent is DMF.

In some embodiments of step (c), $R^6$, $R^7$, $R^8$, $R^{12}$, $R^{18}$, $R^{19}$, and Q are each as defined in any one of the various permutations described herein. In some embodiments, the coupling is a Buchwald-Hartwig cross-coupling reaction or a nucleophilic aromatic substitution. In other embodiments, the coupling is performed in the presence of a palladium catalyst and optionally in the presence of a separate phosphine ligand reagent. In some embodiments, the palladium catalyst is a palladium (0) catalyst. In other embodiments, the palladium catalyst is a palladium (II) catalyst. In other embodiments, the palladium catalyst is $Pd_2(dba)_3$, $Pd(OAc)_2$, $Pd(PPh_3)_4$, $PdCl_2(P(o-tolyl)_3)_2$, or $PdCl_2(PPh_3)_2$. In some embodiments, the phosphine ligand is $PPh_3$, a trialkyl phosphine, dppf, $P(o-tolyl)_3$, $P(t-Bu)_3$, BINAP, a dialkylbiarylphosphine, XPhos, XantPhos, or SpanPhos, or the like. In some embodiments, the palladium catalyst is $Pd_2(dba)_3$. In some embodiments, the coupling is done in the presence of a base such as a hydroxide, carbonate, alkoxide, silylamide, or phosphate base. In some embodiments, the base is $K_2CO_3$, $Cs_2CO_3$, NaOtBu, or KOH. In other embodiments, the base is $K_2CO_3$. In some embodiments of step (c), the coupling is done in a polar solvent, such as t-BuOH, THF, DMF, or water, or a mixture thereof. In other embodiments, the solvent is t-BuOH.

In some embodiments of step (d), the deprotecting is done in the presence of a aqueous hydroxide base in an alcohol solvent. In some embodiments, the hydroxide base is aqueous NaOH or aqueous KOH. In some embodiments, the base is aqueous NaOH, and the solvent is methanol.

In some embodiments of step (e), the reducing step is a catalytic hydrogenation with hydrogen gas (at atmospheric pressure or at above atmospheric pressure) and a palladium, platinum, iron, or nickel catalyst. In some embodiments, the metal catalyst is Pd/C. In some embodiments, the hydrogen gas pressure is about 1 MPa.

In some embodiments, steps (d) and (e) are combined into a single step (d/e), whereby the compound of Formula (XV) is deprotected and reduced in one step to form the compound of Formula (XVII). In this instance, the reaction is performed in the presence of hydrazine hydrate and methanol.

In some embodiments of step (f), the reaction is done in the presence of an amine or ionic base. In some embodiments, the base is an amine base. In other embodiments, the base is iPr$_2$NEt.

In some embodiments, the compound of Formula (I) is converted to a pharmaceutically acceptable salt by reaction with a pharmaceutically acceptable acid. In some embodiments, the compound of Formula (I) is treated with maleic acid. In other embodiments, the acid is maleic acid, HCl, or HBr.

In some embodiments, the methods described herein are used to make a compound of Formula (II) or a pharmaceutically acceptable salt thereof, or to make a compound of Formula (III) or a pharmaceutically acceptable salt thereof.

In some embodiments, the method of making comprises step (f). In other embodiments, the method comprises steps (e) and (f). In other embodiments, the method comprises steps (d), (e), and (f). In other embodiments, the method comprises steps (c), (d), (e), and (f). In other embodiments, the method comprises steps (b), (c), (d), (e), and (f). In other embodiments, the method comprises steps (a)-(f). In other embodiments, the method comprises step (d/e) in place of steps (d) and (e).

In some embodiments of the compounds of Formula (X) and (XI):

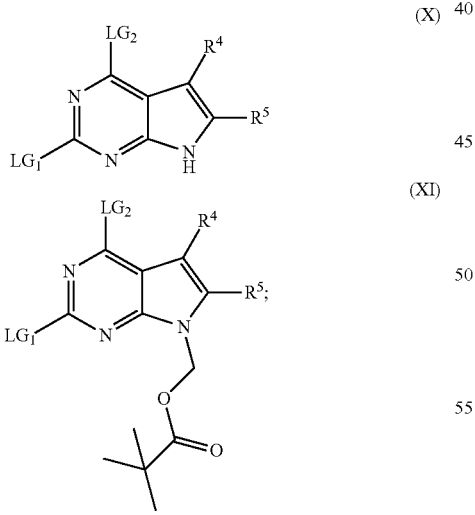

LG$_1$ and LG$_2$ are each a leaving group; and R$^4$ and R$^5$ are each as defined for Formula (I). In some embodiments, LG$_1$ and LG$_2$ are each independently halo or trifluorosulfonate (triflate). In some embodiments, LG$_1$ and LG$_2$ are the same leaving group; in other embodiments, they are different leaving groups. In some embodiments, LG$_1$ and LG$_2$ are each halo, or are each Cl, Br, or I, or are each Cl.

In some embodiments of Formulae (X), (XIII), (XV), (XVI), and (XVII):

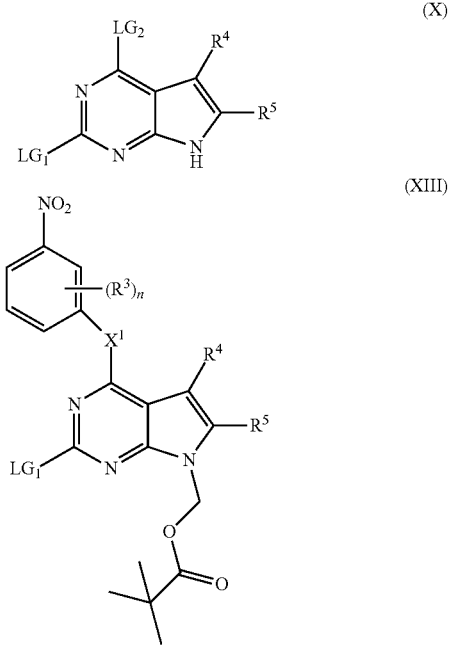

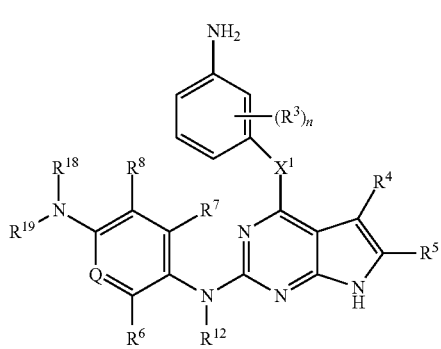
(XVII)

$R^4$ is hydrogen, $C_{1-6}$alkyl, $C_{3-7}$cycloalkyl, or —$NR^{22}R^{23}$; wherein the alkyl and cycloalkyl are unsubstituted or substituted with hydroxyl or amino; and wherein $R^{22}$ and $R^{23}$ are each independently hydrogen or $C_{1-6}$ alkyl; or $R^{22}$ and $R^{23}$ taken together with the nitrogen to which they are attached form a 3- to 10-membered heterocycloalkyl ring. In certain instances, $R^4$ is hydrogen. In certain instances, $R^4$ is $C_{1-6}$alkyl. In certain instances, $R^4$ is $C_{3-7}$cycloalkyl. In certain instances, $R^4$ is —$NR^{22}R^{23}$. In certain instances, $R^4$ is unsubstituted $C_{1-6}$alkyl. In certain instances, $R^4$ is $C_{1-6}$alkyl that is substituted with hydroxyl. In certain instances, $R^4$ is $C_{1-3}$alkyl that is substituted with hydroxyl. In certain instances, $R^4$ is $C_{1-6}$alkyl that is substituted with amino. In certain instances, $R^4$ is $C_{1-6}$alkyl that is substituted with —$NH_2$. In certain instances, $R^4$ is $C_{1-6}$alkyl that is substituted with —$N(CH_3)_2$. In certain instances, $R^4$ is $C_{1-3}$alkyl that is substituted with —$NH_2$. In certain instances, $R^4$ is $C_{1-3}$alkyl that is substituted with —$N(CH_3)_2$. In certain instances, $R^4$ is unsubstituted $C_{3-7}$cycloalkyl. In certain instances, $R^4$ is unsubstituted $C_3$cycloalkyl. In certain instances, $R^4$ is unsubstituted $C_4$cycloalkyl. In certain instances, $R^4$ is unsubstituted $C_{5-6}$cycloalkyl. In certain instances, $R^4$ is unsubstituted $C_7$cycloalkyl. In certain instances, $R^4$ is —$NR^{22}R^{23}$, wherein $R^{22}$ and $R^{23}$ are each independently hydrogen or $C_{1-6}$ alkyl; or $R^{22}$ and $R^{23}$ taken together with the nitrogen to which they are attached form a 3- to 10-membered heterocycloalkyl ring. In certain instances, $R^{22}$ and $R^{23}$ are each hydrogen. In certain instances, $R^{22}$ and $R^{23}$ are each $C_{1-6}$alkyl. In certain instances, $R^{22}$ and $R^{23}$ are each $C_{1-3}$alkyl. In certain instances, $R^{22}$ and $R^{23}$ are each methyl. In certain instances, $R^{22}$ and $R^{23}$ are taken together with the nitrogen to which they are attached to form a 3- to 10-membered heterocycloalkyl ring, such that $R^4$ is

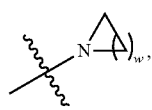

where w is a number from 1 to 8. In certain instances, $R^{22}$ and $R^{23}$ are taken together with the nitrogen to which they are attached to form a 3-, 4-, 5-, or 6-membered ring.

In some embodiments of Formulae (X), (XIII), (XV), (XVI), and (XVII), $R^5$ is hydrogen or $C_{1-6}$alkyl. In certain instances, $R^5$ is hydrogen. In certain instances, $R^5$ is $C_{1-6}$alkyl. In certain instances, $R^5$ is methyl. In certain instances, $R^5$ is ethyl. In certain instances, $R^5$ is $C_{1-3}$alkyl. In certain instances, $R^5$ is $C_{4-6}$alkyl.

In some embodiments of Formulae (XII), (XIII), (XV), (XVI), and (XVII):

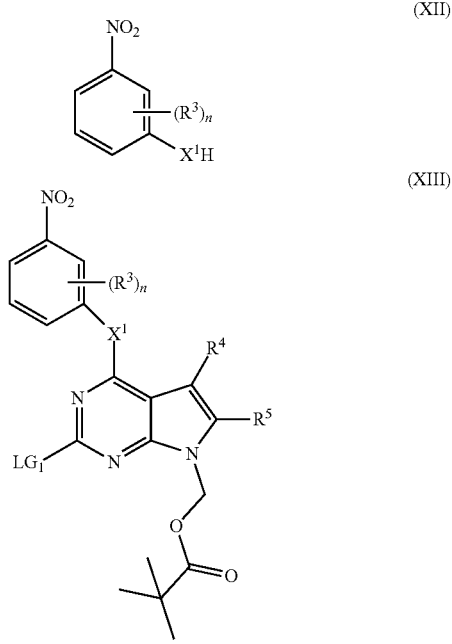
(XII)

(XIII)

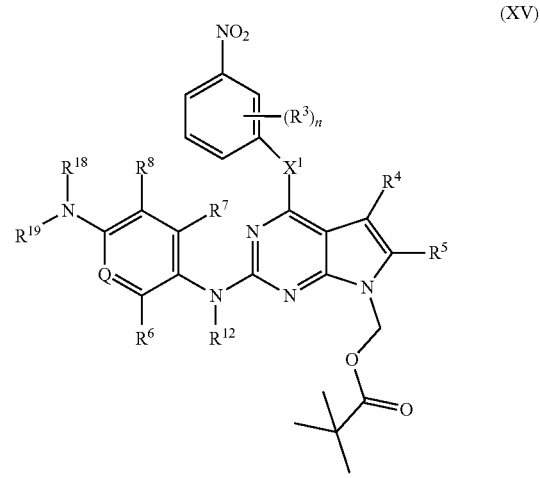
(XV)

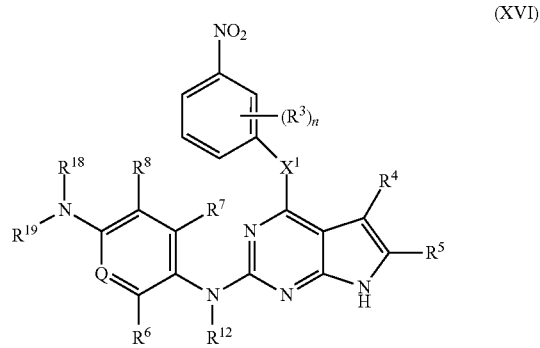
(XVI)

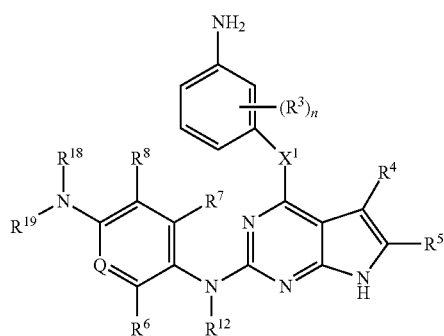

(XVII)

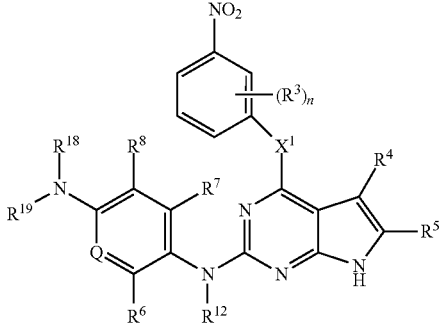

(XVI)

$R^3$ is halo, hydroxyl, $C_{1-6}$alkyl, $C_{1-6}$alkoxy, cyano, or nitro. In certain instances, $R^3$ is halo. In certain instances, $R^3$ is hydroxyl. In certain instances, $R^3$ is $C_{1-6}$-alkyl. In certain instances, $R^3$ is $C_{1-6}$alkoxy. In certain instances, $R^3$ is cyano. In certain instances, $R^3$ is nitro. In some embodiments, n is 0, 1, 2, 3, or 4. In certain instances, n is zero. In certain instances, n is 1. In certain instances, n is 2. In certain instances, n is 3. In certain instances, n is 4. In certain instances, $X^1$ is O, NH, or S. In other embodiments, $X^1$ is O. In other embodiments, $X^1$ is NH. In other embodiments, $X^1$ is S.

In some embodiments of Formulae (XIV), (XV), (XVI), and (XVII):

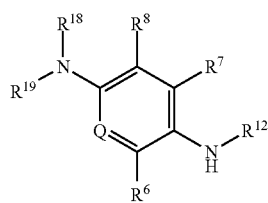

(XIV)

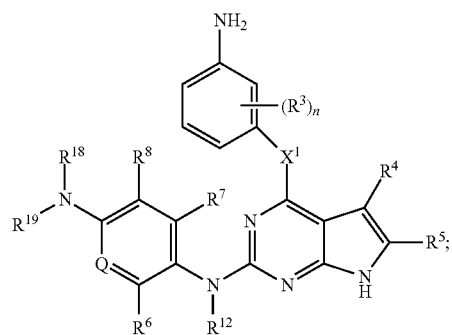

(XVII)

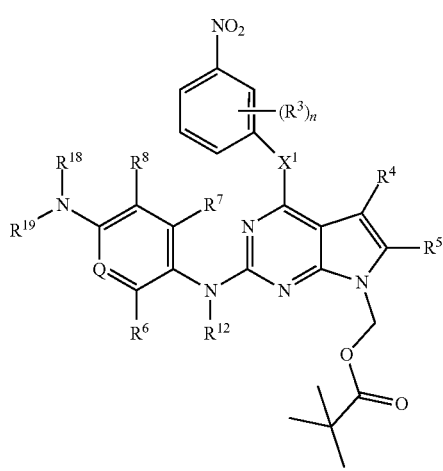

(XV)

$R^6$, $R^7$, $R^8$, $R^{12}$, $R^{18}$, $R^{19}$, and Q are each as defined for Formula (I);

In certain instances of compounds of Formulae (XIV), (XV), (XVI), and (XVII), $R^6$ and $R^7$ are each independently hydrogen, halo, $C_{1-6}$ alkyl, $C_{1-6}$ haloalkyl, $C_{2-6}$ alkoxy, $C_{1-6}$ haloalkoxy, hydroxyl, cyano, or nitro. In certain instances, $R^6$ is hydrogen. In certain instances, $R^6$ is halo. In certain instances, $R^6$ is fluoro. In certain instances, $R^6$ is chloro. In certain instances, $R^6$ is bromo. In certain instances, $R^6$ is $C_{1-6}$alkyl. In certain instances, $R^6$ is $C_{1-6}$haloalkyl. In certain instances, $R^6$ is $C_{2-6}$alkoxy. In certain instances, $R^6$ is $C_{1-6}$haloalkoxy. In certain instances, $R^6$ is hydroxyl. In certain instances, $R^6$ is cyano. In certain instances, $R^6$ is nitro. In certain instances, $R^7$ is hydrogen. In certain instances, $R^7$ is halo. In certain instances, $R^7$ is fluoro. In certain instances, $R^7$ is chloro. In certain instances, $R^7$ is bromo. In certain instances, $R^7$ is $C_{1-6}$alkyl. In certain instances, $R^7$ is $C_{1-6}$haloalkyl. In certain instances, $R^7$ is $C_{2-6}$alkoxy. In certain instances, $R^7$ is $C_{1-6}$haloalkoxy. In certain instances, $R^7$ is hydroxyl. In certain instances, $R^7$ is cyano. In certain instances, $R^7$ is nitro.

In certain instances of compounds of Formulae (XIV), (XV), (XVI), and (XVII), $R^8$ is hydrogen, halo, $C_{1-6}$ alkyl, $C_{1-6}$ haloalkyl, $C_{1-6}$ alkoxy, $C_{1-6}$ haloalkoxy, hydroxyl, cyano, or nitro. In certain instances, $R^8$ is hydrogen. In certain instances, $R^8$ is halo. In certain instances, $R^8$ is fluoro. In certain instances, $R^8$ is chloro. In certain instances, $R^8$ is bromo. In certain instances, $R^8$ is $C_{1-6}$alkyl. In certain instances, $R^8$ is $C_{1-6}$haloalkyl. In certain instances, $R^8$ is $C_{1-6}$alkoxy. In certain instances, $R^8$ is $C_{1-6}$haloalkoxy. In certain instances, $R^8$ is hydroxyl. In certain instances, $R^8$ is cyano. In certain instances, $R^8$ is nitro.

In certain instances of compounds of Formulae (XIV), (XV), (XVI), and (XVII), $R^{12}$ is hydrogen or $C_{1-6}$alkyl. In certain instances, $R^{12}$ is hydrogen. In certain instances, $R^{12}$ is $C_{1-6}$alkyl. In certain instances, $R^{12}$ is methyl. In certain instances, $R^{12}$ is ethyl. In certain instances, $R^{12}$ is $C_{1-3}$alkyl. In certain instances, $R^{12}$ is $C_{4-6}$alkyl.

In certain instances of compounds of Formulae (XIV), (XV), (XVI), and (XVII), Q is $CR^9$ or N. In certain instances, Q is $CR^9$. In certain instances, Q is N.

In certain instances of compounds of Formulae (XIV), (XV), (XVI), and (XVII), $R^9$ is hydrogen, halo, $C_{1-6}$alkyl, $C_{1-6}$haloalkyl, $C_{1-6}$alkoxy, $C_{1-6}$haloalkoxy, hydroxyl, cyano, or nitro. In certain instances, $R^9$ is hydrogen. In certain instances, $R^9$ is halo. In certain instances, $R^9$ is fluoro. In certain instances, $R^9$ is chloro. In certain instances, $R^9$ is bromo. In certain instances, $R^9$ is $C_{1-6}$alkyl. In certain instances, $R^9$ is $C_{1-6}$haloalkyl. In certain instances, $R^9$ is $C_{1-6}$alkoxy. In certain instances, $R^9$ is $C_{1-6}$haloalkoxy. In certain instances, $R^9$ is hydroxyl. In certain instances, $R^9$ is cyano. In certain instances, $R^9$ is nitro. In certain instances, $R^9$ is hydrogen or fluoro.

In certain instances of compounds of Formulae (XIV), (XV), (XVI), and (XVII), $-NR^{18}R^{19}$ is:

(a)

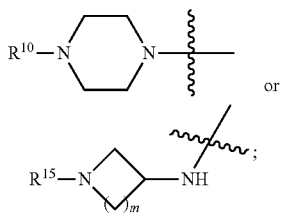

or wherein $R^{10}$ is selected from hydrogen and $C_{1-6}$ alkyl;
$R^{15}$ is unsubstituted methyl, or is $C_{2-4}$alkyl unsubstituted or substituted with hydroxy, methoxy, or halo; and
m is 1 or 2; or (b) $R^{19}$ and $R^9$ are taken together with the atoms to which they are attached to form a 5- or 6-membered heteroaryl ring optionally substituted with $C_{1-6}$alkyl, wherein the alkyl is unsubstituted or substituted with amino, hydroxyl, halo, or an N-linked heterocycloalkyl; and $R^{18}$ is hydrogen or $C_{1-6}$alkyl, where the alkyl is unsubstituted or substituted with amino, or $R^{18}$ is absent to satisfy valency of the heteroaryl ring.

In certain instances of compounds of Formulae (XIV), (XV), (XVI), and (XVII), $-NR^{18}R^{19}$ is:

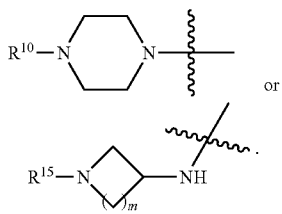

certain instances, $-NR^{18}R^{19}$ is

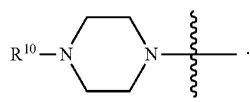

In certain instances, $-NR^{18}R^{19}$ is

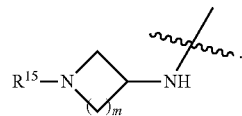

In certain instances of compounds of Formulae (XIV), (XV), (XVI), and (XVII), $R^{10}$ is hydrogen or $C_{1-6}$alkyl. In certain instances, $R^{10}$ is hydrogen. In certain instances, $R^{10}$ is $C_{1-6}$alkyl. In certain instances, $R^{10}$ is methyl. In certain instances, $R^{10}$ is ethyl. In certain instances, $R^{10}$ is $C_{1-3}$alkyl. In certain instances, $R^{10}$ is $C_{4-6}$ alkyl.

In certain instances of compounds of Formulae (XIV), (XV), (XVI), and (XVII), $R^{15}$ is methyl, hydroxyethyl, methoxyethyl, or fluoroethyl. In other embodiments, $R^{15}$ is fluoroethyl. In some embodiments, m is 1. In other embodiments, m is 2.

In certain instances of compounds of Formulae (XIV), (XV), (XVI), and (XVII), $-NR^{18}R^{19}$ is defined as follows: $R^{19}$ and $R^9$ are taken together with the atoms to which they are attached to form a 5- or 6-membered heteroaryl ring optionally substituted with $C_{1-6}$alkyl, wherein the alkyl is unsubstituted or substituted with amino, hydroxyl, halo, or an N-linked heterocycloalkyl, or the alkyl is substituted with amino; and $R^{18}$ is hydrogen or $C_{1-6}$alkyl, where the alkyl is unsubstituted or substituted with amino, or $R^{18}$ is absent to satisfy valency of the heteroaryl ring. In some embodiments, the heteroaryl ring is substituted with dimethylaminomethyl or piperidinylmethyl. In other embodiments, $R^9$ and $R^{19}$ taken together form optionally substituted pyrrole or pyridine. In some instances, $R^{18}$ is dimethylaminoethyl.

In certain instances of the intermediates described herein, $R^6$, $R^7$, $R^8$, and $R^9$ are hydrogen. In certain instances, $R^6$, $R^7$, and $R^8$ are hydrogen and $R^9$ is halo. In certain instances, $R^6$, $R^7$, and $R^8$ are hydrogen and $R^9$ is fluoro. In certain instances, $R^6$, $R^7$, $R^8$, and $R^9$ are hydrogen and $R^{10}$ is methyl. In certain instances, $R^6$, $R^7$, $R^8$ are hydrogen; $R^9$ is halo; and $R^{10}$ is methyl. In certain instances, $R^6$, $R^7$, $R^8$ are hydrogen; $R^9$ is fluoro; and $R^{10}$ is methyl. In certain instances, $R^6$, $R^7$, $R^8$, and $R^9$ are hydrogen and $R^{13}$ is hydrogen. In certain instances, $R^6$, $R^7$, and $R^8$ are hydrogen; $R^9$ is halo; and $R^{13}$ is hydrogen. In certain instances, $R^6$, $R^7$, and $R^8$ are hydrogen; $R^9$ is fluoro; and $R^{13}$ is hydrogen. In certain instances, $R^6$, $R^7$, $R^8$, and $R^9$ are hydrogen and $R^{13}$ is $-CH_2OH$. In certain instances, $R^6$, $R^7$, and $R^8$ are hydrogen; $R^9$ is halo; and $R^{13}$ is $-CH_2OH$. In certain instances, $R^6$, $R^7$, and $R^8$ are hydrogen; $R^9$ is fluoro; and $R^{13}$ is $-CH_2OH$. In certain instances, $R^6$, $R^7$, $R^8$, and $R^9$ are hydrogen and $R^{13}$ is $-(CH_2)_mF$, wherein m is a number from one to 3. In certain instances, $R^6$, $R^7$, and $R^8$ are hydrogen; $R^9$ is halo; and $R^{13}$ is $-(CH_2)_mF$, wherein m is a number from one to 3. In certain instances, $R^6$, $R^7$, and $R^8$ are hydrogen; $R^9$ is fluoro; and $R^{13}$ is $-(CH_2)_mF$, wherein m is a number from one to 3.

The present disclosure is directed to methods of making a compound of Formula (II):

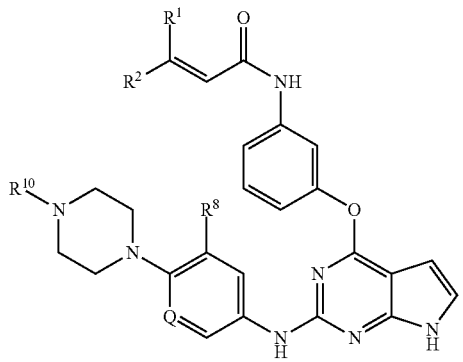

wherein
$R^1$ and $R^2$ are each independently hydrogen, halo, $C_{1-6}$alkyl, or $C_{1-6}$haloalkyl;
$R^8$ is hydrogen, halo, $C_{1-6}$alkyl, $C_{1-6}$haloalkyl, $C_{1-6}$alkoxy, $C_{1-6}$haloalkoxy, hydroxyl, cyano, or nitro;
Q is $CR^9$ or N;
where $R^9$ is hydrogen, halo, $C_{1-6}$alkyl, $C_{1-6}$haloalkyl, $C_{1-6}$alkoxy, $C_{1-6}$haloalkoxy, hydroxyl, cyano, or nitro; and
$R^{10}$ is hydrogen or $C_{1-6}$alkyl;
or a pharmaceutically acceptable salt thereof.

The methods of making compounds of Formula (II) comprise one or more of steps (a)-(f), where $R^1$, $R^2$, $R^8$, Q, and $R^{10}$ are each defined consistently with Formula (II) or the embodiments of Formula (II) described herein. Said methods further optionally comprise converting a compound of Formula (II) into a pharmaceutically acceptable salt thereof as described herein.

Formula (III)

The present disclosure provides methods of making a compound of Formula (III):

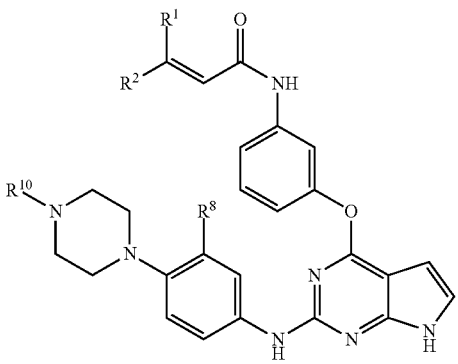

wherein
$R^1$ and $R^2$ are each independently hydrogen, halo, $C_{1-6}$alkyl, or $C_{1-6}$haloalkyl;
$R^8$ is halo, $C_{1-6}$alkyl, $C_{1-6}$haloalkyl, $C_{1-6}$alkoxy, $C_{1-6}$haloalkoxy, hydroxyl, cyano, or nitro; and
$R^{10}$ is $C_{1-6}$alkyl;
or a pharmaceutically acceptable salt thereof.

The methods of making compounds of Formula (III) comprise one or more of steps (a)-(f), where $R^1$, $R^2$, $R^8$, Q, and $R^{10}$ are each defined consistently with Formula (III) or the embodiments of Formula (III) described herein. Said methods further optionally comprise converting a compound of Formula (III) into a pharmaceutically acceptable salt thereof as described herein.

In some embodiments are methods of making a compound shown in Table 1, or a pharmaceutically acceptable salt thereof.

In some embodiments are methods of making a compound of the following structure:

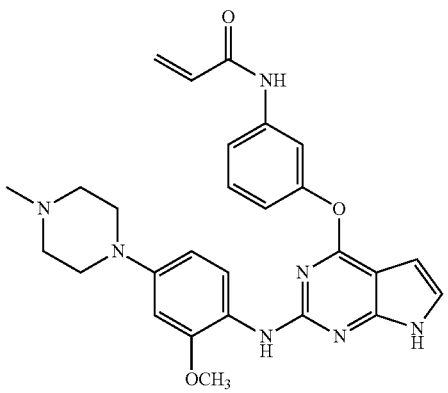 [SMILES: C=CC(=O)Nc1cccc(Oc2nc(Nc3ccc(N4CCN(C)CC4)cc3OC)nc3[nH]ccc23)c1]

or a pharmaceutically acceptable salt thereof, using one or more of steps (a)-(f) as described herein.

In certain embodiments, the present disclosure is directed to methods of making N-(3-((2-((3-fluoro-4-(4-methylpiperazin-1-yl)phenyl)amino)-7H-pyrrolo[2,3-d]pyrimidin-4-yl)oxy)phenyl)acrylamide:

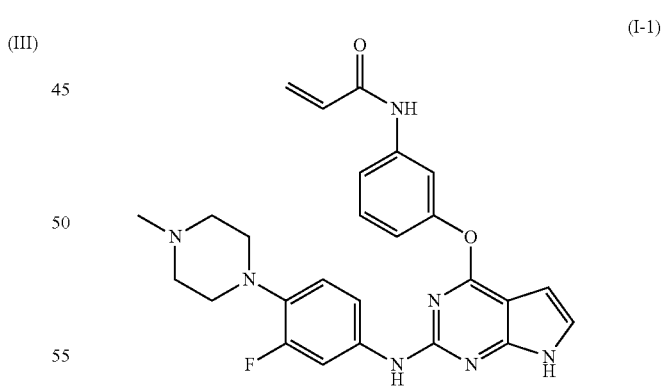

or a pharmaceutically acceptable salt thereof. In certain embodiments are methods of making the maleate salt of N-(3-((2-((3-fluoro-4-(4-methylpiperazin-1-yl)phenyl)amino)-7H-pyrrolo[2,3-d]pyrimidin-4-yl)oxy)phenyl)acrylamide. In certain embodiments are methods of making the hydrochloride salt of N-(3-((2-((3-fluoro-4-(4-methylpiperazin-1-yl)phenyl)amino)-7H-pyrrolo[2,3-d]pyrimidin-4-yl)oxy)phenyl)acrylamide. Said methods comprise one or more of the following steps:

(a) reacting a compound of Formula (X-1):

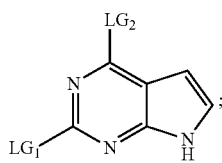
(X-1)

wherein LG₁ and LG₂ are each a leaving group as defined herein; or LG₁ and LG₂ are each chloro;
with chloromethyl pivalate to form a compound of Formula (XI-1);

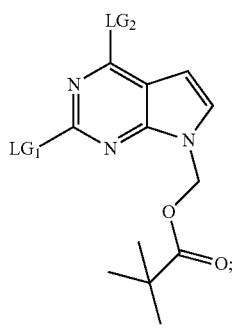
(XI-1)

(b) reacting a compound of Formula (XI-1) with a compound of Formula (XII-1):

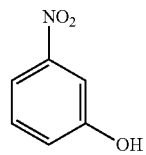
(XII-1)

to form a compound of Formula (XIII-1):

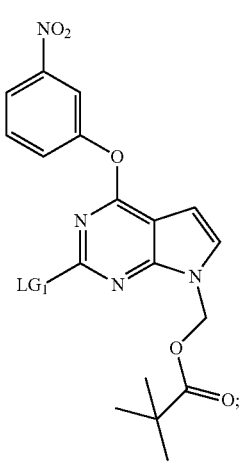
(XIII-1)

(c) coupling a compound of Formula (XIII-1) with a compound of Formula (XIV-1):

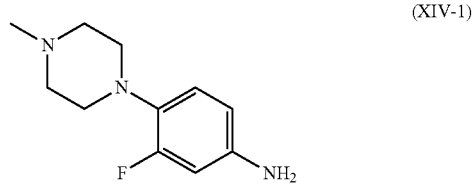
(XIV-1)

to form a compound of Formula (XV-1):

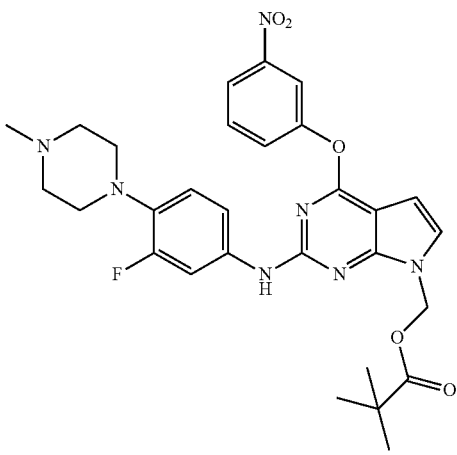
(XV-1)

(d) deprotecting the compound of Formula (XV-1) to form a compound of Formula (XVI-1):

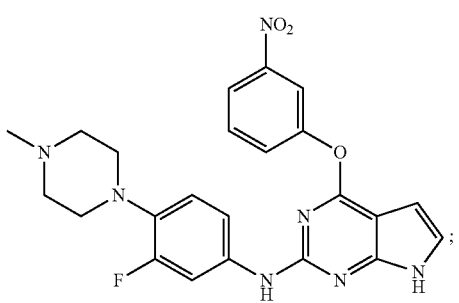
(XVI-1)

(e) reducing the compound of Formula (XVI-1) to form a compound of Formula (XVII-1):

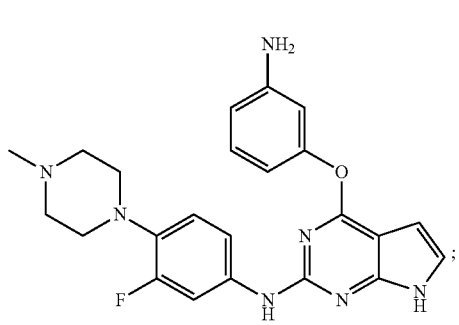

(XVII-1)

(f) reacting the compound of Formula (XVII-1) with acryloyl chloride to form N-(3-((2-((3-fluoro-4-(4-methylpiperazin-1-yl)phenyl)amino)-7H-pyrrolo[2,3-d]pyrimidin-4-yl)oxy)phenyl)acrylamide. In some embodiments, reactions are run at a temperature from about −10° C. to about 100° C.

In other embodiments, the method of making comprises treating N-(3-((2-((3-fluoro-4-(4-methylpiperazin-1-yl)phenyl)amino)-7H-pyrrolo[2,3-d]pyrimidin-4-yl)oxy)phenyl)acrylamide with a pharmaceutically acceptable acid to form a pharmaceutically acceptable salt. In some embodiments, the acid is maleic acid, HCl, or HBr. In other embodiments, the acid is maleic acid. In other embodiments, the acid is HCl. In some embodiments, the salt thereof is the maleate, HCl, or HBr salt. In other embodiments, the salt thereof is a tosylate, mesylate, fumarate, or malate salt.

The present disclosure also contemplates certain polymorphs or amorphous forms of compounds of Formulae (I), (II), or (III), or pharmaceutically acceptable salts thereof, or of Compound 1, or a pharmaceutically acceptable salt thereof. In some embodiments are polymorphs or amorphous forms of a pharmaceutically acceptable salt of Compound 1. In some embodiments, the salt is a maleate salt, an HCl salt, an HBr salt, a sulfate salt, a malate salt, a fumarate salt, a mesylate salt, or a tosylate salt. In some embodiments, the pharmaceutically acceptable salts are optionally solvates. In some embodiments is a crystalline polymorph of a pharmaceutically acceptable salt of Compound 1. In some embodiments, the polymorph is Form I (maleate salt), or is Form II (maleate salt), or is Form III (maleate salt), or is Form IV (HCl salt), or is Form V (fumarate salt), or is Form VI (malate salt), or is Form VII (HBr salt), each having the characteristics discussed herein. In some embodiments, the compound is in amorphous form. In some embodiments, the amorphous form is a maleate, sulfate, mesylate, tosylate, or HBr salt of Compound 1.

In some embodiments, the maleate salt of Compound 1 is Form I. In some embodiments, Form I is characterized by an XRPD spectrum comprising one or more peaks at 2Θ values (within the error range of the experiment) selected from the group consisting of: 22.14, 21.90, 12.40, 25.52, 26.12, 14.10, 11.60, 26.52, and 17.00. In some embodiments, Form I is characterized by one, two, three, four, five, six, seven, eight, nine, or 10, or more peaks within the error range of those shown in the XRPD spectrum in FIG. 1, or in FIG. 4, or in FIG. 5, or in FIG. 21. The error range may be ±0.2 2Θ, ±0.1 2Θ, ±0.05 2Θ, or another suitable range. In some embodiments, Form I of the maleate salt of Compound 1 is crystallized from ethyl acetate or from an ethanol/water mixture. In some embodiments, Form I is crystallized from ethanol/water. In some embodiments, Form I is crystallized from ethanol/water at a ratio of 1:1 to 1:19 (v/v). In some embodiments, the ethanol/water ratio is 1:1, or is 3:7, or is 1:19.

In some embodiments, the maleate salt of Compound 1 is in crystalline polymorph Form II. In some embodiments Form II is characterized by an XRPD spectrum comprising one or more peaks at 2Θ values (within the error range of the experiment) at the positions shown in the XRPD spectrum in FIG. 8 or in FIG. 9. The error range may be ±0.2 2Θ, ±0.1 2Θ, ±0.05 2Θ, or another suitable range. In some embodiments, Form II of the maleate salt of Compound 1 is crystallized from methanol or ethanol.

In some embodiments, the maleate salt of Compound 1 is in crystalline polymorph Form III. In some embodiments Form III is characterized by an XRPD spectrum comprising one or more peaks at 2Θ values (within the error range of the experiment) at the positions shown in the XRPD spectrum in FIG. 12. The error range may be ±0.2 2Θ, ±0.1 2Θ, ±0.05 2Θ, or another suitable range. In some embodiments, Form III of the maleate salt of Compound 1 is crystallized from tetrahydrofuran.

In some embodiments, the maleate salt of Compound 1 is in amorphous form. In some embodiments, the amorphous form is prepared by crystallization from acetone or acetonitrile.

In some embodiments, the hydrochloride salt of Compound 1 is crystalline Form IV. In some embodiments, Form IV is characterized by an XRPD spectrum comprising one or more peaks at 2Θ values (within the error range of the experiment) at the positions shown in the XRPD spectrum in FIG. 22, or in FIG. 25, or in FIG. 28, or in FIG. 31, or in FIG. 34, or in FIG. 37. The error range may be ±0.2 2Θ, ±0.1 2Θ, ±0.05 2Θ, or another suitable range. In some embodiments, Form IV of the hydrochloride salt of Compound 1 is crystallized from water or from an ethanol/water mixture. In some embodiments, Form IV is crystallized from an ethanol/water mixture in a ration of from 3:1 to 5:7 (v/v). In other embodiments, the ethanol/water ratio is 3:1, 1:1, 5:7, 3:2, or 7:3.

In some embodiments, the fumarate salt of Compound 1 is crystalline Form V. In some embodiments, Form V is characterized by an XRPD spectrum comprising one or more peaks at 2Θ values (within the error range of the experiment) at the positions shown in the XRPD spectrum in FIG. 40. The error range may be ±0.2 2Θ, ±0.1 2Θ, ±0.05 2Θ, or another suitable range. In some embodiments, Form V is crystallized from an ethanol/water mixture, optionally 5% aqueous ethanol.

In some embodiments, the malate salt of Compound 1 is crystalline Form VI. In some embodiments, Form VI is characterized by an XRPD spectrum comprising one or more peaks at 2Θ values (within the error range of the experiment) at the positions shown in the XRPD spectrum in FIG. 43. The error range may be ±0.2 2Θ, ±0.1 2Θ, ±0.05 2Θ, or another suitable range. In some embodiments, Form VI is crystallized from an ethanol/water mixture, optionally 10% aqueous ethanol.

In some embodiments, the hydrobromide salt of Compound 1 is crystalline Form VII. In some embodiments, Form VII is characterized by an XRPD spectrum comprising one or more peaks at 2Θ values (within the error range of the experiment) at the positions shown in the XRPD spectrum in FIG. 54. The error range may be ±0.2 2Θ, ±0.1 2Θ, ±0.05 2Θ, or another suitable range. In some embodiments, Form VII is crystallized from an ethanol/water mixture.

In some embodiments, the pharmaceutically acceptable salt of Compound 1 is in an amorphous form. In some embodiments, the amorphous form is a sulfate salt, optionally prepared by crystallization from water, a mesylate salt, optionally prepared by crystallization from ethanol, a tosylate salt, optionally prepared by crystallization from an ethanol/water mixture, or a hydrobromide salt, optionally prepared by crystallization from water.

Pharmaceutical Compositions

Aside from the pharmacological activity of an active pharmaceutical ingredient (API), there are a variety of physical or physicochemical characteristics of the active substance that are relevant for the preparation of solid oral dosage forms (including oral powders, granules, pellets, tablets, capsules, chewable tablets, dispersible tables, troches or lozenges). To achieve adequate formulation characteristics, such as correct assay, content, and mass uniformity, chemical and physical stability of the drug product, and a proper dissolution rate, the characteristics of the drug product intermediates also have to support a robust manufacturing process.

Therefore, in some aspects, how to achieve suitable adequate formulation characteristics depends on making and manufacturing process for stabilized pharmaceutical compositions containing a compound of Formula (I), or a pharmaceutically acceptable salt thereof, or Compound 1, or a pharmaceutically acceptable salt thereof.

While not wishing to be bound by any particular theory, in some instances, the degradation of a compound of Formula (I) or Compound 1 is considered to occur through a pathway involving dimerization of the compound. For example, two molecules of a compound of Formula I could condense under acidic conditions (e.g., during or after salt formation with an acid) to form a dimer. In some embodiments, an amino group on one molecule reacts with the acrylamide group of a second molecule. In some embodiments, the —NR$^{10}$ or N—R$^{15}$ amino group of one molecule reacts with the acrylamide group in a second molecule to form a 3-amino-substituted amido group. In some embodiments, Compound 1 dimerizes. In some embodiments, a dimer of Compound 1 may have the structure Dimer 1 as shown below:

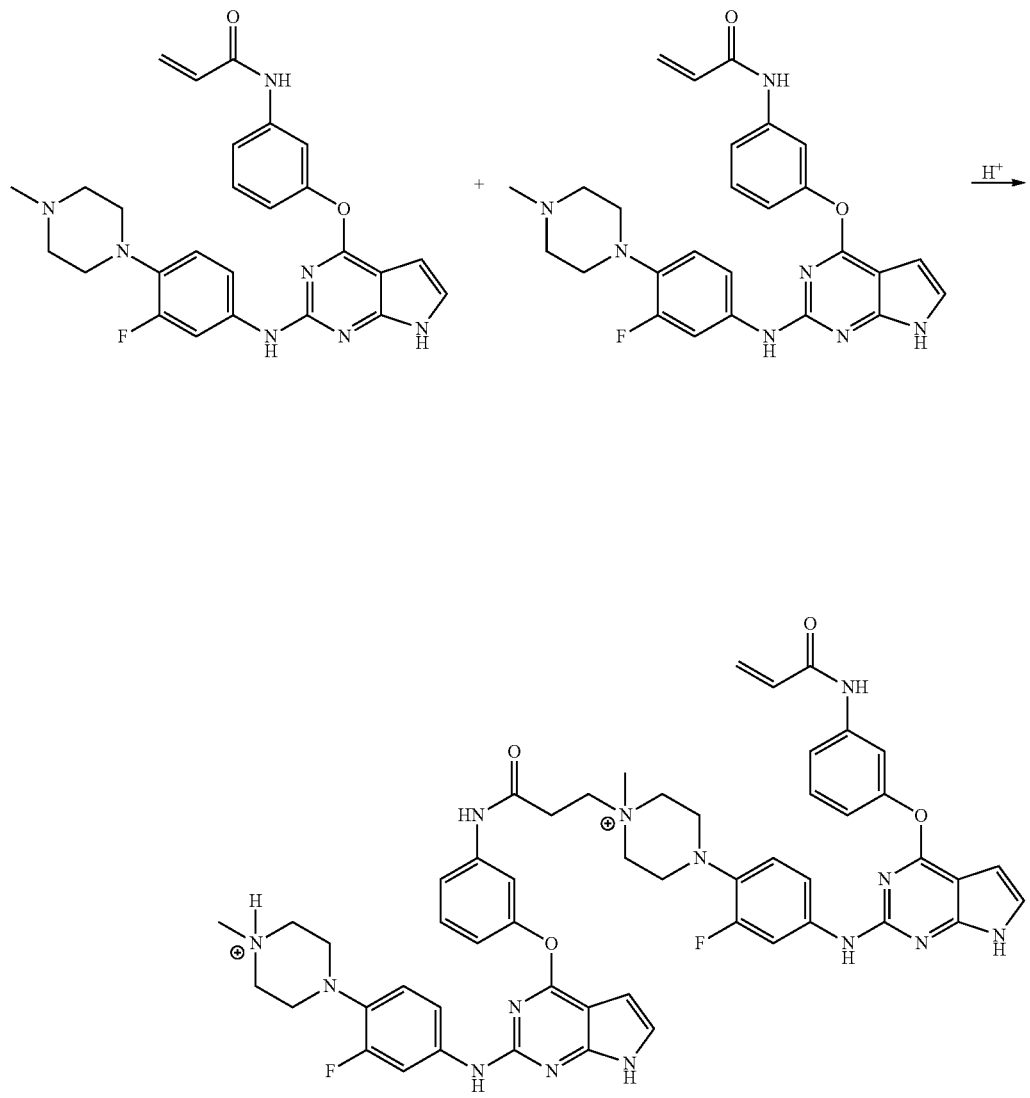

Dimer 1 (plus counterion)

In situations where the compound or salt thereof dimerizes during the formulation process, the dimer may have one or more acid counterions as appropriate for the acid used, e.g., maleate (one molecule, as the dicarboxylate), two bromide counterions, two mesylate counterions, and the like. In some embodiments, the dimer may form as shown below:

adsorbing agent, prior to formulation into a dosage form, lowers dimerization rate of the compound. While not wishing to be bound by any particular theory, it is considered that the adsorbing agent(s) is able to protect the compound of Formula I or Compound 1, or a pharmaceutically acceptable salt thereof, from physical and environmental stress that,

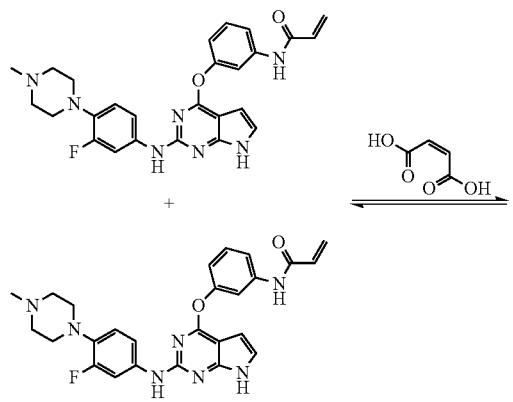 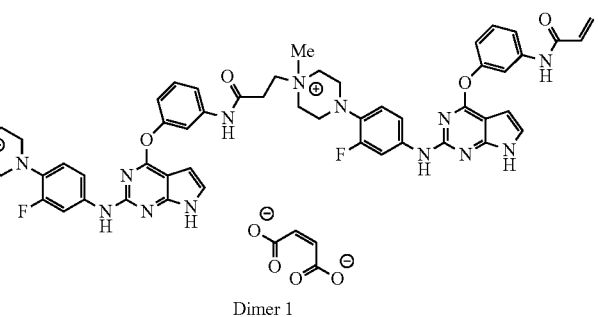

Dimer 1

Undesired dimerization may be promoted by exposure of the drug substance to heat, air, moisture, stress, compaction, or other interactions or events during the manufacturing process. This dimerization can affect particle size of the drug substance, and thus solubility, stability, and bioavailability of the resulting drug product.

Attempts to reduce dimer-based degradation in active pharmaceutical ingredients (API) have been reported in WO2004/045624 A1 (PCT/JP2003/014504) and Chinese Pat. Publ. No. CN104306348 A (Appln. No. CN20141514067). WO 2004/045624 A1 describes a physical method to control dimer formation for an API by using a coating process, which increases the cost and complexity of the manufacturing process. CN104306348 A describes reducing dimer formation through the addition of various chemical additives (butylated hydroxyanisole, BHA). However, use of such chemicals may be limited due to undesired interactions with other components of the drug product, or regulatory approval considerations.

Therefore, there is a need for stabilized pharmaceutical compositions and the manufacturing process thereof that does not require the addition of restricted chemicals or excipients. There is also a need for manufacturing process for making the stabilized pharmaceutical compositions into suitable pharmaceutical dosage forms, e.g., solid oral formulation, without resorting to a more complex manufacturing process.

In some embodiments are methods of making stabilized pharmaceutical compositions comprising a compound of Formula (I) or Compound 1, or a pharmaceutically acceptable salt thereof, comprising pre-blending a suitable adsorbing agent with the therapeutic agent, and then re-blending manufacturing excipients during manufacture of the solid oral formulation, e.g., capsules or tablets. In some embodiments, the pharmaceutical compositions comprise an effective amount of a compound of Formula (I) or Compound 1, or a pharmaceutically acceptable salt thereof.

In some embodiments, it is discovered, surprisingly, that combining a compound of Formula (I) or Compound 1, or a pharmaceutically acceptable salt thereof, with a suitable under unprotected conditions, lead to the formation of degradation products such as a dimers, e.g., a dimer having the structure of Dimer 1.

In some embodiments, it is demonstrated that by utilizing one or more suitable adsorbing agent(s) as a blending agent, the formation of degradation products such as a dimer of the compound of Formula I or Compound 1, or a pharmaceutically acceptable salt thereof, e.g., a dimer having the structure of Dimer 1, is significantly reduced. Indeed, it is demonstrated that a dimer of the compound of Formula (I) or Compound 1, or a pharmaceutically acceptable salt thereof, e.g., a dimer having the structure of Dimer 1, can be reduced to or maintained at a level that is less than any one of 2.0%, or less than 1.0%, or less than 0.75%, or less than 0.5%, or less than 0.25% of the total weight of the compound of Formula I or Compound 1, or a pharmaceutically acceptable salt thereof, upon completion of formulation, or upon storage for a time point that is at least 3 months, or at least 6 months, or at least 12 months, or at least 18 months, or at least 24 months or at least 36 months from the date when the pharmaceutical compositions are first formulated. In some embodiments, the dimer or other impurity is detected by HPLC methods known to one of skill in the art.

In some embodiments, the pharmaceutical composition contains from about 0.001% (w/w) to about 1% (w/w) of a dimer of Compound 1, or a pharmaceutically acceptable salt thereof, after a stability test for about 10 days, or about 1 month, or about 2 months, or about 3 months, or about 6 months, or about 12 months, or about 18 months, or about 24 months. In some embodiments, the stability test is conducted at ambient temperature, or at a temperature greater than or equal to about 25° C., or at a temperature of about 25° C., or about 50° C., or about 60° C., or between about 50° C. to about 70° C., and/or under relative humidity conditions of about 50%, or about 60%, or about 70%, or greater than about 70%, and/or under exposure to light, e.g., visible light.

In some embodiments, the pharmaceutical compositions described herein demonstrate improved stability of the compound of Formula I or Compound 1, or a pharmaceutically acceptable salt thereof, (active agent) upon storage or under stability testing conditions relative to substantially the same formulation without the adsorbing agent. In some embodiments, the storage time and stability testing conditions are those described herein.

In some embodiments, the present invention also relates to methods of making the pharmaceutical compositions. Such methods may comprise first pre-blending or re-blending a compound of Formula I or Compound 1, or a pharmaceutically acceptable salt thereof, with a suitable adsorbing agent. The present methods may also comprise first pre-blending a compound of Formula I or Compound 1, or a pharmaceutically acceptable salt thereof, with a suitable adsorbing agent prior to formulation into a dosage form.

An "adsorbing agent" is an inactive pharmaceutical ingredient that performs a minor adsorbing function and that otherwise serves as a binder or filler.

Any suitable adsorbing agent(s) can be used. In particular embodiments, the adsorbing agent is a porous solid powder. In some embodiments, the active ingredient may be adsorbed into the pores of the adsorbing agent. Exemplary adsorbing agents include, but are not limited to, acacia, bentonite, alginic acid, cellulose derivatives, croscarmellose, gelatin, gelatin hydrolysate, mannitol, maltose, fructose, Plasdone, povidone, sodium starch glycolate, sorbitol, sucrose, lactose, microcrystalline cellulose, silicified microcrystalline cellulose, croscarmellose sodium, dicalcium phosphate, carboxymethyl cellulose, hydroxypropyl cellulose, and polyethylene glycol (particularly in spray dried formulations). In certain embodiments, adsorbing agent(s) are suitable excipients to be used in spray drying processes. In certain embodiments, adsorbing agent(s) are silicified microcrystalline celluloses. In some embodiments, the silicified microcrystalline cellulose (SMCC) is Prosolv® SMCC 50, Prosolv® SMCC 50 LD, Prosolv® SMCC 90, Prosolv® SMCC HD 90, or Prosolv® SMCC 90 LM. In other embodiments, the silicified microcrystalline cellulose is Prosolv® SMCC 50 or Prosolv® SMCC 90. In some embodiments, the SMCC is a blend of microcrystalline cellulose and colloidal silicon dioxide. In some embodiments, the SMCC has a particle size range of about 10 to 100 μm, or about 30 to 90 μm, or about 45 to 80 μm. In some embodiments, the SMCC has an average particle size by laser diffraction of about 50 urn, or about 60 μm, or about 65 μm, or about 70 μm. In some embodiments, the SMCC has average particle size by laser diffraction of 125 μm, or has a range of about 70 to about 200 μm, or about 80 to about 180 μm, or about 90 to 160 μm. In some embodiments, the SMCC has a bulk density of between about 0.20 and about 0.50 g/mL, or between about 0.20 and 0.30 g/mL, or between about 0.25 and about 0.37 g/mL, or between about 0.38 and about 0.50 g/mL, or between about 0.27 to about 0.39 g/mL.

In some embodiments, the pharmaceutical composition comprises from about 1% (w/w) to about 90% (w/w), or about 15% (w/w) to about 85% (w/w), or about 35% (w/w) to about 75% (w/w), of the adsorbing agent. In other embodiments, the pharmaceutical composition comprises at least two different kinds of adsorbing agents. In some embodiments, the pharmaceutical composition comprises at least two different kinds of silicified microcrystalline cellulose. In some embodiments, the pharmaceutical composition comprises from about 1% (w/w) to about 30% (w/w) of Prosolv® SMCC 50, and from about 30% (w/w) to about 70% (w/w) of Prosolv® SMCC 90.

In some embodiments, the present pharmaceutical compositions may also include pharmaceutically acceptable additive(s) into any suitable type of unit dosage form. Thus, in some embodiments, the pharmaceutical composition further comprises at least one pharmaceutically acceptable additive. Suitable additives include, but are not limited to, diluents, binders, vehicles, carriers, excipients, binders, disintegrating agents, lubricants, swelling agents, solubilizing agents, wicking agents, cooling agents, preservatives, stabilizers, sweeteners, flavors, and polymers. While any pharmaceutically acceptable additive is contemplated by the present disclosure, it should be understood that the additives selected for compounding with coated particles of a compound of Formula (I) or Compound 1, or a pharmaceutically acceptable salt thereof, should not defeat the stability objectives of the present disclosure. Even though some pharmaceutically acceptable additives may cause degradation of a compound of Formula (I) or Compound 1, or a pharmaceutically acceptable salt thereof, such additives may be suitable for the pharmaceutical compositions described herein as long as such additives do not increase dimer formation (relative to the formulation without the further additive) as it is combined with a blending agent, or upon storage, or in vivo.

Examples of disintegrating agents include, but are not limited to, cross-linked sodium carboxymethylcellulose, croscarmellose sodium (e.g., VIVASOL®), crospovidone, and their mixtures. In some embodiments, the pharmaceutical composition comprises from about 0.1% (w/w) to about 10% (w/w), or about 5% (w/w), of croscarmellose sodium (e.g., VIVASOL®).

Examples of lubricating agents include, but are not limited to, magnesium stearate, stearic acid or a pharmaceutically acceptable alkali metal salt thereof, sodium stearyl fumarate, polyethylene glycol (such as Macrogol 6000) (particularly in granule or flake formulations to reduce friction with the mold), glyceryl behenate, talc, colloidal or fumed silicon dioxide and silica derivatives (such as Cab-O-Sil, Syloid® products, and the like), calcium stearate, sodium stearate, sodium lauryl sulfate, sodium chloride, magnesium lauryl sulfate, talc, and their mixtures. A portion of the lubricant may be used as an internal solid lubricant which is blended and granulated with other components of the granulation. Another portion of the lubricant may be added into the final blended material just before compression or encapsulation that coats the outside of the granules in the final formulation. In some embodiments, the pharmaceutical composition further comprises a disintegrating agent and a lubricant. In some embodiments, the lubricant is sodium stearyl fumarate. In some embodiments, the pharmaceutical composition comprises from about 0.05% (w/w) to about 5% (w/w) of sodium stearyl fumarate.

Oral pharmaceutical compositions as described herein can generally be in the form of individualized or multi-unit doses, such as tablets, caplets, powders, suspension tablets, chewable tablets, rapid melt tablets, capsules, e.g., a single- or double-shell gelatin capsule, tablet-filled capsules, effervescent powders, effervescent tablets, pellets, granules, liquids, solutions, or suspensions, respectively. In some embodiments, the pharmaceutical composition is formulated as an oral dosage form, or as a solid oral dosage form. In some embodiments, the oral dosage form is an oral powder, a granule, a pellet, a tablet, a capsule, a troch or a lozenge. In some embodiments, the tablet is a chewable tablet, a dispersible tablet, or a troch. In some embodiments, the pharmaceutical composition is formulated to contain a single dose or multiple doses. In some embodiments, each pharmaceutical composition dosage form (e.g., each tablet or capsule) comprises 25 mg, or 50 mg, or 100 mg, or 150 mg, or 200 mg free base equivalent of the compound of Formula I or Compound 1. In some embodiments, the active ingredient (e.g., compound of Formula I or Compound 1 or a pharmaceutically acceptable salt thereof) is present in the pharmaceutical composition at a concentration of about 15 to about 40% (w/w), or about 25 to about 35% (w/w), or about 25% (w/w), or about 30% (w/w), or about 35% (w/w). For salt forms, the concentration is stated as the free base equivalent of the salt form.

Also contemplated are methods of making pharmaceutical compositions with improved stability, bioavailability, and shelf-life. The following exemplary methods of making pharmaceutical compositions in accordance with the presently described processes can be used with any suitable drug. Specifically, the methods described herein are directed to making pharmaceutical compositions comprising any suitable drug that is susceptible to degradation when exposed to the environment or exposed to physical stresses during the manufacturing process.

The pharmaceutical compositions described herein can be made by first combining a drug substance with a suitable adsorbing agent before being processed into capsules or tablets. Combining the drug substance with the adsorbing agent can be accomplished by any suitable methods, e.g., blending, mixing, milling or co-milling, compressing, granulating, dissolving, or precipitating the drug and the adsorbing agent together.

In some embodiments, the combined drug and adsorbing agent are suitable for use in preparing dosage forms by processes including, but not limited to, dry blending, direct compression formulations, and roller compaction formulations.

In some embodiments is a pharmaceutical composition comprising: (a) a compound of Formula (I), or Compound 1:

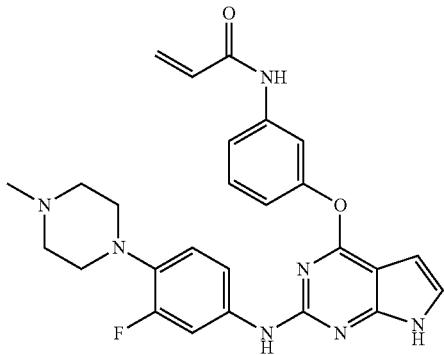

(Compound 1)

or a pharmaceutically acceptable salt thereof; and (b) an adsorbing agent that reduces or eliminates formation of a dimer of Compound 1, or a pharmaceutically acceptable salt thereof. In some embodiments, the reduction or elimination of dimer formation is upon storage or stability testing, and in other embodiments, the reduction or elimination is in vivo, e.g., after administration of the pharmaceutical composition. In some embodiments, the reduction or elimination is relative to substantially the same formulation, without the adsorbing agent, under the same conditions.

In some embodiments, the pharmaceutical composition comprises Compound 1. In other embodiments, the pharmaceutical composition comprises a pharmaceutically acceptable salt of Compound 1. In some embodiments, the pharmaceutically acceptable salt is selected from the group consisting of a maleate salt, a hydrochloride salt, a fumarate salt, a malate salt, a sulfate salt, a mesylate salt, a tosylate salt, and a hydrobromide salt.

In some embodiments, the maleate salt has polymorph Form I. In some embodiments, the maleate salt polymorph Form I is formed by crystallization from an aqueous solution comprising from about 1% (v/v) to about 90% (v/v) of ethanol, or about 100% (v/v) of ethyl acetate. In some embodiments, the maleate salt polymorph Form I is formed by crystallization from an aqueous solution comprising about 50% (v/v) of ethanol. In some embodiments, the maleate salt has polymorph Form II. In some embodiments, the maleate salt polymorph Form II is formed by crystallization from about 100% (v/v) of methanol or ethanol. In some embodiments, the maleate salt has polymorph Form III. In some embodiments, the maleate salt polymorph Form III is formed by crystallization from about 100% (v/v) tetrahydrofuran. In some embodiments, the maleate salt has an amorphous form. In some embodiments, the maleate salt amorphous form is prepared by drying or crystallizing from about 100% (v/v) of acetone or acetonitrile.

In some embodiments, the pharmaceutically acceptable salt of Compound 1 is the hydrochloride salt. In some embodiments, the hydrochloride salt has polymorph Form IV. In some embodiments, the hydrochloride salt polymorph Form IV is formed by crystallization from an aqueous solution comprising from about 0% (v/v) to about 60% (v/v) of ethanol.

In some embodiments, the pharmaceutically acceptable salt of Compound I is the fumarate salt. In some embodiments, the fumarate salt has polymorph Form V. In some embodiments, the fumarate salt polymorph Form V is formed by crystallization from an aqueous solution comprising from about 0% (v/v) to about 60% (v/v) of ethanol.

In some embodiments, the pharmaceutically acceptable salt of Compound I is the malate salt. In some embodiments, the malate salt has polymorph Form VI. In some embodiment, the malate salt polymorph Form VI is formed by crystallization from an aqueous solution comprising from about 0% (v/v) to about 60% (v/v) of ethanol.

In some embodiments, the pharmaceutically acceptable salt of Compound 1 is the sulfate salt, the mesylate salt, the tosylate salt, or the hydrobromide salt. In some embodiments, the sulfate salt, the mesylate salt, the tosylate salt, or the hydrobromide salt is in amorphous form.

In some embodiments, the adsorbing agent reduces the formation of a dimer of Compound 1, or a pharmaceutically acceptable salt thereof. In some embodiments, the dimer level in the pharmaceutical composition is below the limits of quantitation of the detection method. In other embodiments, no dimer formation is detected in the pharmaceutical composition.

Also described herein are processes for preparing a pharmaceutical composition as discussed herein, wherein said method comprises: 1) combining a compound of Formula I, or Compound 1, or a pharmaceutically acceptable salt thereof, with an adsorbing agent to form a first mixture; and 2) formulating the first mixture into a dosage form. In some embodiments, the compound or pharmaceutically acceptable salt thereof and the adsorbing agent are combined in a single step to form the first mixture. In some embodiments, the compound or salt and the adsorbing agent are combined in multiple steps to form the first mixture. In some embodiments, the adsorbing agent is a single adsorbing agent. In some embodiments, the adsorbing agent is multiple adsorbing agents. In some embodiments, the multiple adsorbing agents comprise at least two different kinds of silicified microcrystalline cellulose. In some embodiments, the at least two different kinds of silicified microcrystalline cellulose comprise Prosolv® SMCC 50 and Prosolv® SMCC 90. In some embodiments, the compound or a pharmaceutically acceptable salt thereof is combined with multiple different adsorbing agents sequentially, in some cases in one or more blending steps. In some embodiments, the compound or pharmaceutically acceptable salt thereof is combined with Prosolv® SMCC 50 in a first step, and then combined with Prosolv® SMCC 90 in a second step.

In some embodiments, the process further comprises formulating the first mixture into a dosage form in the presence of a pharmaceutically acceptable additive. In some embodiments, the additive comprises a disintegrating agent and/or a lubricant. In some embodiments, the additive comprises a disintegrating agent and a lubricant. In some embodiments, the disintegrating agent is cross-linked sodium carboxymethylcellulose or croscarmellose sodium (e.g., VIVASOL®), and the lubricant is sodium stearyl fumarate.

In some embodiments, the first mixture is formulated into an oral dosage form, e.g., a solid oral dosage form. In some embodiments, the formulating step comprises a dry blend process, a roller compaction process, or a direct compression process. In some embodiments, the dry blend process comprises a pre-blending step to combine the compound of Formula I, or Compound 1, or a pharmaceutically acceptable salt thereof, with a first microcrystalline cellulose, e.g., Prosolv® SMCC 50, to form a pre-mixture, and a re-blending step to combine the pre-mixture and a second microcrystalline cellulose, e.g., Prosolv® SMCC 90, to form the first mixture, and filling the first mixture with a disintegrating agent, e.g., croscarmellose sodium (VIVASOL®) and a lubricant, e.g., sodium stearyl fumarate, into a capsule.

In some embodiments, the roller compaction process comprises a pre-blending roller compaction step to combine Compound 1, or a pharmaceutically acceptable salt thereof, with a first microcrystalline cellulose, e.g., Prosolv® SMCC 50, to form a pre-mixture, and a re-blending step to combine the pre-mixture and a second microcrystalline cellulose, e.g., Prosolv® SMCC 90, to form the first mixture, and filling the first mixture with a disintegrating agent, e.g., croscarmellose sodium (VIVASOL®) and a lubricant, e.g., sodium stearyl fumarate, into a capsule. In some embodiments, the roller compaction process comprises a pre-blending roller compaction step to combine Compound 1, or a pharmaceutically acceptable salt thereof, with a first microcrystalline cellulose, e.g., Prosolv® SMCC 50, to form a pre-mixture, and a re-blending step to combine the pre-mixture and a second microcrystalline cellulose, e.g., Prosolv® SMCC 90, to form the first mixture, and mixing the first mixture with a disintegrating agent, e.g., croscarmellose sodium (VIVASOL®) and a lubricant, e.g., sodium stearyl fumarate, to form a tablet.

In some embodiments, the direct compression process comprises a pre-blending step to combine Compound 1, or a pharmaceutically acceptable salt thereof, with a first microcrystalline cellulose, e.g., Prosolv® SMCC 50, to form a pre-mixture, and a re-blending step to combine the pre-mixture and a second microcrystalline cellulose, e.g., Prosolv® SMCC 90, to form the first mixture, and mixing the first mixture with a disintegrating agent, e.g., croscarmellose sodium (VIVASOL®) and a lubricant, e.g., sodium stearyl fumarate, to form a tablet.

In certain instances, the processes for preparing pharmaceutical compositions further comprise one or more steps as described herein for preparation of a compound of Formula (I) or Compound 1, or of a pharmaceutically acceptable salt thereof. Embodiments are directed to the other processes described herein; and to the product prepared by any of the processes described herein.

EXAMPLES

Exemplary chemical entities, pharmaceutical compositions, and methods of making such compounds and compositions will now be described by reference to the specific examples that follow. Artisans will recognize that, for the chemical syntheses, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the examples below may be performed in any order that is compatible with the functionality of the particular pendant groups. Each of the reactions depicted in the general schemes is preferably run at a temperature from about 0° C. to the reflux temperature of the organic solvent used. Some of the reactions described in the examples provided below are run at a temperature from about −10° C. to about 100° C. With respect to the pharmaceutical composition examples, one of ordinary skill in the art will recognize that variations of the examples that follow may be appropriate.

The examples described herein are provided solely to illustrate representative embodiments of the invention. Accordingly, it should be understood, that the invention is not to be limited to the specific conditions or details described in these or any other example discussed herein, and that such examples are not to be construed as limiting the scope of the invention in any way. Throughout the specification, any and all references are specifically incorporated herein by reference in their entireties.

The following abbreviations have been used in the specification and examples: DCM=dichloromethane; DIEA=DIPEA=N,N-diisopropylethylamine; DMF=N,N-dimethylformamide; EtOH=ethanol; EtOAc=ethyl acetate; MeOH=methanol; t-BuOH=tert-butyl alcohol; and THF=tetrahydrofuran.

All solvents and reagents obtained from commercial sources were used without further purification. Both $^1$H NMR and $^{13}$C spectra were performed on a Bruker Avance III 500 MHz spectrometer. The mass spectra (MS) were obtained on a LC-MS PE SCIEX API 150EX using 0.05% HCOOH (aq.)/acetonitrile as the mobile phase.

Compounds of Examples 3-7 were also synthesized as shown in the following scheme:
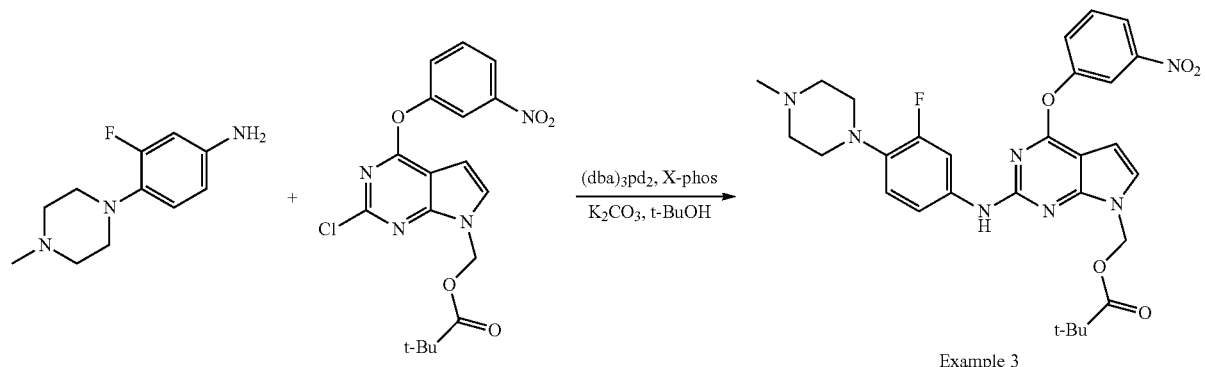
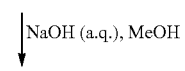
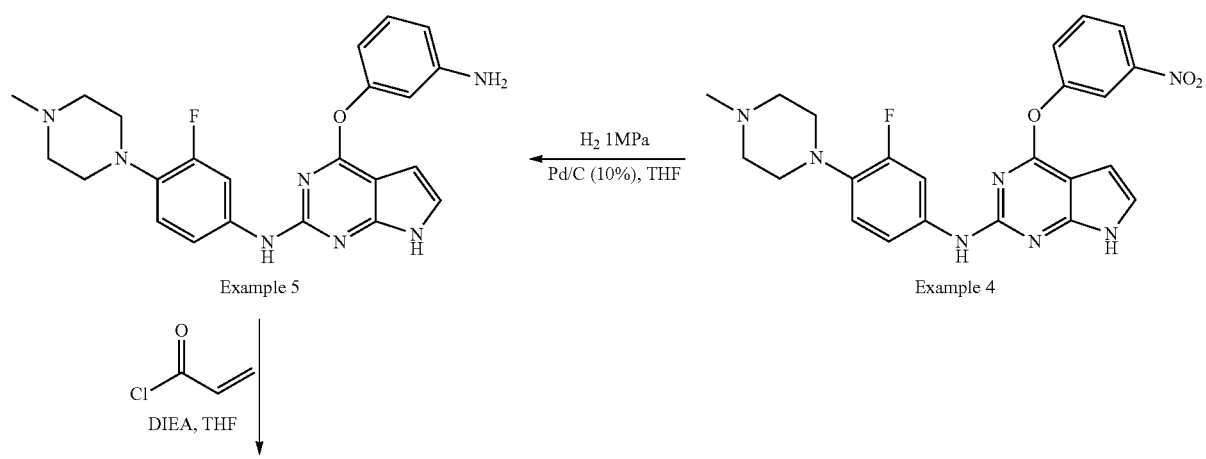
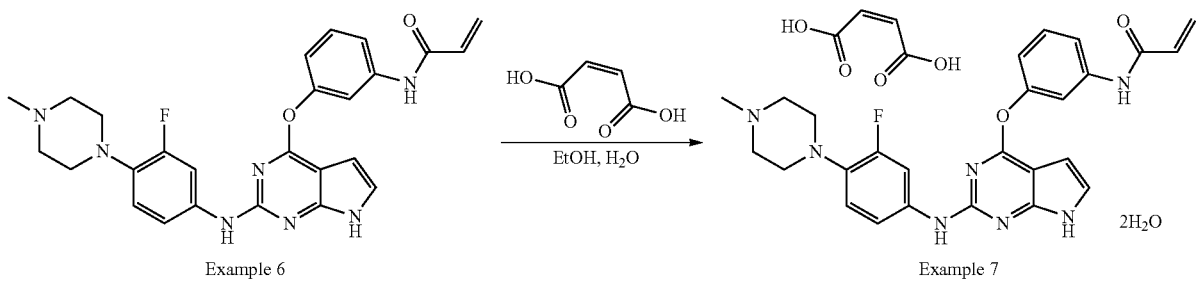

The following examples are offered to illustrate but not to limit the invention.

Example 1. Synthesis of (2,4-dichloro-7H-pyrrolo[2,3-d]pyrimidin-7-yl)methyl pivalate

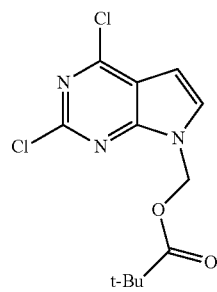 [SMILES: CC(C)(C)C(=O)OCn1ccc2c(Cl)nc(Cl)nc21]

To a 500 L reactor was sequentially added 2,4-dichloro-7H-pyrrolo[2,3-d]pyrimidine (31.5 kg), tetrahydrofuran (THF; 280 kg), chloromethyl pivalate (POMCl; 27.5 kg), $K_2CO_3$ (70 kg), and water (30 kg). The mixture was stirred for 12 h while the reaction temperature was kept between 35±5° C. The reaction mixture was filtered, and the residue was washed with THF until compound 2b was not detected in the filtrate (by thin layer chromatography (TLC)). The filtrate was combined and concentrated under reduced pressure. The residue was then re-dissolved in ethyl acetate (300 kg) and was washed with water until a neutral pH was reached. The organic layer was separated, dried over $Na_2SO_4$, and concentrated under reduced pressure to afford the title compound, which was used directly for next step without further purification. LC-MS: m/z 302.1 [M+H]$^+$.

Example 2. Synthesis of (2-chloro-4-(3-nitrophenoxy)-7H-pyrrolo[2,3-d]pyrimidin-7-yl)methyl pivalate

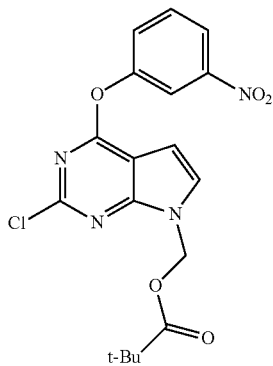 [SMILES: CC(C)(C)C(=O)OCn1ccc2c(Oc3cccc([N+](=O)[O-])c3)nc(Cl)nc21]

The product of Example 1 was combined with DMF (300 kg), 3-nitrophenol (24 kg), and $K_2CO_3$ (70 kg). The mixture was stirred for 48 h while the reaction temperature was kept between 35±5° C. The reaction mixture was filtered, and the collected solid was washed with ethyl acetate until no product was detected in the eluting filtrate (by TLC). Approximately one third of the filtrate was diluted with ethyl acetate (180 kg) and water (300 kg). The mixture was stirred for 2 h and the aqueous layer was separated. The upper layer was washed with water (3×300 kg), resulting in a pH neutral solution. The aqueous layers were combined and extracted with ethyl acetate until no product was detected in the aqueous layer by TLC. All the organic layers were combined, dried over $Na_2SO_4$, and filtered. The filtrate was concentrated under reduced pressure to a volume of ~400 L, which was de-colored with activated carbon and then filtered. The filtrate was concentrated under reduced pressure. The residue was re-dissolved in ethyl acetate (25 kg) and petroleum ether (150 kg) and stirred at reflux temperature. The resulting clear solution was allowed to cool to room temperature. The precipitate was collected and dried to afford the title compound. The same procedures were performed on the two remaining portions of the filtrate. The three portions of product were combined and suspended in petroleum ether (300 kg). The suspension was vigorously stirred at reflux for 3 h, and then was allowed to cool to room temperature. The resulting solid was collected and dried to afford the title compound (42.5 kg, 63% over two steps) as a white solid. LC-MS: m/z 405.2 [M+H]$^+$. $^1$H NMR (500 MHz, CDCl$_3$) δ 8.17-8.14 (m, 1H), 8.14-8.13 (m, 1H), 7.63-7.62 (m, 2H), 7.37 (d, J=3.7 Hz, 1H), 6.62 (d, J=3.7 Hz, 1H), 6.18 (s, 2H), 1.17 (s, 9H). $^{13}$C NMR (125 MHz, CDCl$_3$) δ 178.4, 161.6, 154.6, 152.7, 152.5, 149.1, 130.3, 128.6, 128.2, 120.8, 117.4, 104.8, 100.3, 65.9, 39.0, 27.0 (*3).

Example 3. Synthesis of (2-(3-fluoro-4-(4-methylpiperazin-1-yl)phenylamino)-4-(3-nitrophenoxy)-7H-pyrrolo[2,3-d]pyrimidin-7-yl)methyl pivalate

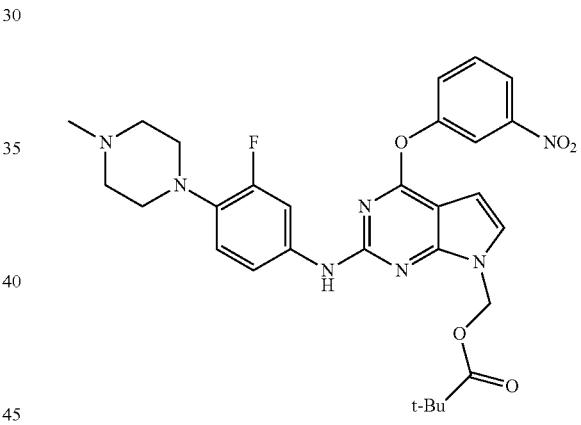

A 500-L, glass-lined reactor was put under an inert atmosphere with nitrogen gas, then was charged with t-butanol (147 kg) under vacuum. Agitation was initiated, and the reactor was heated to 40±5° C. and nitrogen gas was again introduced. To the reactor was added (2-chloro-4-(3-nitrophenoxy)-7H-pyrrolo[2,3-d]pyrimidin-7-yl)methyl pivalate (19.10 kg), anhydrous $K_2CO_3$ (32.02 kg), tris(dibenzylideneacetone)dipalladium (Pd$_2$(dba)3; 0.88 kg), dicyclohexyl (2',4',6'-triisopropylbiphenyl-2-yl)phosphine (XPhos; 0.90 kg), and 3-fluoro-4-(4-methylpiperazin-1-yl) aniline (9.70 kg). The resulting mixture was heated at 85±5° C. for 6 h. The mixture was cooled to 60±5° C. and then filtered through a pad of diatomaceous earth (4.9 kg) at 50° C. The reactor was washed with ethyl acetate (36 kg). The diatomaceous earth pad was slurried with ethyl acetate for 30 min at 50° C. (two times) and then was filtered.

The above procedure was repeated and the filtrates were all combined to afford 351 kg of ethyl acetate solution (assay amount 50.36 kg of title compound). The ethyl acetate solution was concentrated to dryness. Ethyl acetate (281 kg) was added and the mixture was stirred for 30 min to dissolve the residue. Silica gel (37 kg) was then added and the resulting mixture was stirred for 1 h. The mixture was filtered and the resulting filtrate was charged into a 1000-L glass-lined reactor. The solution was washed with purified water (125 kg×2) and then brine (125 kg). The organic layer was concentrated to dryness at 45±5° C. at a vacuum pressure below ~0.02 MPa. Ethanol (124 kg) was added to the residue and the resulting mixture was heated at 85±5° C. for 1 h. Heptane (70 kg) was added and the resulting mixture was heated at 85±5° C. and stirred for 1 h. The mixture was cooled to 5±5° C. at a rate of 20° C./h and then was stirred for 5 h. The resulting precipitate was centrifuged. The solid was washed with heptane (20 kg) and dried at 50±5° C. at a pressure below ~0.02 MPa for 16 h to give the title compound (46.46 kg, 86.4%, 99.21% HPLC purity) as an orange solid. LC-MS: m/z 578.5 [M+H]$^+$. $^1$H NMR (500 MHz, CD$_3$OD) δ 8.17-8.14 (m, 2H), 7.69-7.64 (m, 2H), 7.41 (d, J=15.1 Hz, 1H), 7.13 (d, J=3.7 Hz, 1H), 7.00 (d, J=8.0 Hz, 1H), 6.77 (t, J=9.2 Hz, 1H), 6.49 (d, J=3.6 Hz, 1H), 6.10 (s, 2H), 2.97 (s, 4H), 2.59 (s, 4H), 2.32 (s, 3H), 1.14 (s, 9H); $^{13}$C NMR (125 MHz, CD$_3$OD) δ 179.32, 163.26, 157.81, 156.67, 155.88, 154.79, 150.34, 138.03 (d, J=10 Hz), 134.50 (d, J=10 Hz), 131.60, 129.92, 126.31, 121.34, 120.12 (d, J=3.75 Hz), 119.02, 115.29, 107.96 (d, J=26.25 Hz), 100.72, 100.39, 67.88, 56.05 (*2), 51.69 (d, J=2.5 Hz, *2), 46.12, 39.84, 27.32 (*3).

Example 3A. Alternative Synthesis of (2-(3-fluoro-4-(4-methylpiperazin-1-yl)phenylamino)-4-(3-nitrophenoxy)-7H-pyrrolo[2,3-d]pyrimidin-7-yl)methyl pivalate To a 5 L round bottom flask was added t-BuOH (2.5 L), (2-chloro-4-(3-nitrophenoxy)-7H-pyrrolo[2,3-d]pyrimidin-7-yl)methyl pivalate (300 g, 0.74 mol), and 3-fluoro-4-(4-methylpiperazin-1-yl)aniline (154 g, 0.74 mol). The reaction mixture was stirred at a speed of 360 rpm for 5-10 min. Potassium carbonate (220 g, 1.59 mol), tris(dibenzylideneacetone)dipalladium (14 g, 0.0153 mol), dicyclohexyl (2',4',6'-triisopropylbiphenyl-2-yl)phosphine (14 g, 0.0294 mol) and another portion of t-BuOH (0.5 L) were then added. The flask was placed in an oil bath (110-120° C.), and the reaction mixture was stirred at reflux under N$_2$ at the speed of 320 rpm. After stirring for 3-3.5 h, the mixture was allowed to cool to 40-50° C., filtered through diatomaceous earth, and washed with ethyl acetate (300 mL). The combined filtrate was concentrated under reduced pressure to afford the crude product.

The crude material was re-dissolved in ethyl acetate (2.5 L), and silica gel (300 g) was added (for de-colorization). After the mixture was stirred for 15-30 min, the mixture was filtered and washed with ethyl acetate (2 L). The combined filtrate was washed with water (1 L×2) and brine (1 L), and concentrated under reduced pressure to give a second crude product, which was then re-dissolved in hot EtOH (1 L, ~75° C.) with stirring. The solution was allowed to cool to room temperature. The resulting crystals were collected and washed with n-hexane (200 mL) and dried at 45° C. for 4 h to afford the title compound as a light brown solid (280 g, 96.26% purity by HPLC, 65% yield). mp: 99.5-101.5° C.; [M+H]$^+$: m/z 578.5; $^1$H NMR and $^{13}$C NMR spectral data for (2-(3-fluoro-4-(4-methylpiperazin-1-yl)phenylamino)-4-(3-nitrophenoxy)-7H-pyrrolo[2,3-d]pyrimidin-7-yl)methyl pivalate are consistent with those reported in Example 3.

Example 4. Synthesis of N-(3-fluoro-4-(4-methylpiperazin-1-yl) phenyl)-4-(3-nitrophenoxy)-7H-pyrrolo[2,3-d]pyrimidin-2-amine

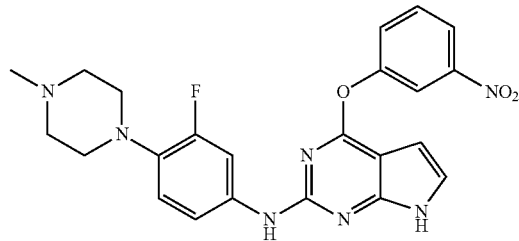 [SMILES: CN1CCN(c2ccc(Nc3nc(Oc4cccc([N+](=O)[O-])c4)c4cc[nH]c4n3)cc2F)CC1]

To a 2000-L glass-lined reactor under vacuum was added methanol (734 kg). Agitation was initiated, and the reactor was charged with (2-(3-fluoro-4-(4-methylpiperazin-1-yl) phenylamino)-4-(3-nitrophenoxy)-7H-pyrrolo[2,3-d]pyrimidin-7-yl)methyl pivalate (46.46 kg). The reaction mixture was cooled to 10±5° C. and was agitated for 1 h. Aqueous NaOH (2.5 M, 66.4 kg (6.40 kg NaOH dissolved in 60 kg purified water)) was added drop-wise to the reactor over 75 min. The resulting mixture was warmed to 15±5° C. and was stirred for 3 h. The reaction mixture was cooled to 10±5° C. and purified water (372 kg) was added over 60 min. The resulting mixture was stirred at 5±5° C. for 3 h. The resulting precipitate was centrifuged and the cake was washed with purified water (48 kg). The wet cake (88.30 kg) and purified water (372 kg) were stirred for 3 h and then filtered by press filtration, washing with purified water (47 kg). The wet cake (100.80 kg) and ethyl acetate (250 kg) were combined, heated to 75±5° C., and stirred for 1 h. The resulting mixture was allowed to stand for 30 min. The aqueous layer was separated while the top organic layer was cooled to 10±5° C. at a rate of 20° C./h, and was stirred for 10 h. The resulting precipitate was centrifuged to provide 28.6 kg of a first wet cake (98.7% purity by HPLC (1.1% of starting material)). The mother liquor was concentrated at 45±5° C. at a vacuum pressure of below 0.02 MPa to about 55-90 L, heated to 75±5° C., and stirred for 1 h. The solution was cooled to 10±5° C. at a rate of 20° C./h, and was stirred for 5 h. The resulting solid was collected by centrifugation to provide a second wet cake (4.94 kg (95.7% purity by HPLC (2.9% of starting material)). The two wet cake portions of product were combined and dried at 50±5° C. under vacuum at below 0.02 MPa for 16 h to give the title compound (28.38 kg, 76.1%) as a yellow solid. LC-MS: m/z 464.1 [M+H]$^+$. $^1$H NMR (500 MHz, CDCl$_3$) δ 9.77 (s, 1H), 8.22-8.10 (m, 2H), 7.66-7.55 (m, 2H), 7.41 (dd, J=14.8, 2.4 Hz, 1H), 6.96 (s, 1H), 6.88-6.82 (m, 2H), 6.77 (t, J=9.1 Hz, 1H), 6.46 (dd, J=3.5, 1.9 Hz, 1H), 3.05 (s, 4H), 2.63 (s, 4H), 2.37 (s, 3H). $^{13}$C NMR (125 MHz, CDCl$_3$) 161.93 (s), 156.52 (s), 155.41 (s), 154.92 (s), 154.57 (s), 153.28 (s), 148.87 (s), 135.13 (d, J=11.0 Hz), 134.56 (d, J=9.7 Hz), 130.04 (s), 128.60 (s), 121.10 (s), 120.29 (s), 119.01 (d, J=4.1 Hz), 117.84 (s), 114.57 (s), 107.77 (d, J=25.9 Hz), 99.38 (d, J=4.4 Hz), 55.13 (s, *2), 50.74 (s, *2), 46.05 (s).

Example 4A. Alternative Synthesis of N-(3-fluoro-4-(4-methylpiperazin-1-yl) phenyl)-4-(3-nitrophenoxy)-7H-pyrrolo[2,3-d]pyrimidin-2-amine To a 50-L jacketed reactor heated using hot water (75° C.) were charged (2-(3-fluoro-4-(4-methylpiperazin-1-yl)phenylamino)-4-(3-nitrophenoxy)-7H-pyrrolo[2,3-d]pyrimidin-7-yl)methyl pivalate (1.5 kg, 2.6 mol) and MeOH (30 L). The mixture was heated at reflux until the (2-(3-fluoro-4-(4-methylpiperazin-1-yl)phenylamino)-4-(3-nitrophenoxy)-7H-pyrrolo[2,3-d]pyrimidin-7-yl)methyl pivalate was completely dissolved and then was stirred for another 30 min at 65° C. At this point, the hot water was removed from jacket, and replaced with cold alcohol (−10~−15° C.) to cool the reactor. When the temperature inside the reactor reached 10-18° C., a NaOH solution (2.5 M, 2.1 L) was added drop-wise into the reaction over a ~1 h period. The temperature was kept below 20° C. during the addition. After the addition was completed, the reaction mixture was stirred between 15-20° C. for another 5 h. At this point, an in-process HPLC analysis indicated that the (2-(3-fluoro-4-(4-methylpiperazin-1-yl)phenylamino)-4-(3-nitrophenoxy)-7H-pyrrolo[2,3-d]pyrimidin-7-yl)methyl pivalate was completely consumed and that there was a partially deprotected intermediate (MW=463.5+30) (less than 10%) in the reaction mixture. The reaction mixture was cooled to 0-5° C., and water (12 L) was added drop-wise into the reactor over 60 min. The temperature was kept below 20° C. during the addition of the water. After the addition of the water, the reaction mixture was stirred for another 15 min. The resulting precipitate (crude product) was collected, washed with water (2 L), and dried under vacuum. The crude material was re-dissolved in ethyl acetate (30 L). The resulting solution was washed with water (10 L ×3) and brine (10 L ×1). The organic layer was passed through a pad of diatomaceous earth to remove the residual insoluble material. The filtrate was concentrated under reduced pressure at 38-42° C. until the volume of the remaining solution was around 5 L. The remaining solution was allowed to cool to 0-5° C. and was stirred overnight. The precipitate was collected and dried under vacuum to afford the title compound (968 g, 89.98% purity by HPLC, 80% yield) as a light yellow powder. mp: 132.5-134.5° C.; [M+H]+: m/z 464.1; $^1$H NMR and $^{13}$C NMR spectral data for N-(3-fluoro-4-(4-methylpiperazin-1-yl) phenyl)-4-(3-nitrophenoxy)-7H-pyrrolo[2,3-d] pyrimidin-2-amine are consistent with those reported in Example 4.

Example 5. Synthesis of 4-(3-aminophenoxy)-N-(3-methyl-4-(4-methylpiperazin-1-yl)phenyl)-7H-pyrrolo[2,3-d]pyrimidin-2-amine

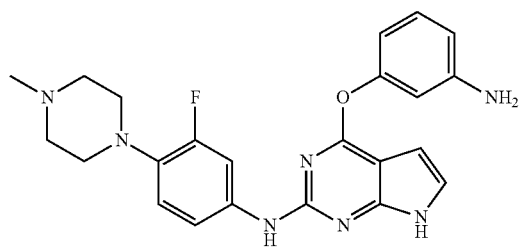

A 500-L pressure reactor was pressurized with N$_2$ to 0.9 MPa for 30 min. The atmosphere in the reactor was exchanged with 0.2 MPa of N$_2$ (5×). The reactor was charged sequentially with THF (204 kg), N-(3-fluoro-4-(4-methylpiperazin-1-yl) phenyl)-4-(3-nitrophenoxy)-7H-pyrrolo[2,3-d]pyrimidin-2-amine (28.38 kg), and Pd/C (1.42 kg). The reactor atmosphere was exchanged with 0.2 MPa of N$_2$ (5×), and then pressurized with N$_2$ to 0.9 MPa for 30 min. The reactor was put under a 0.2 MPa H$_2$ atmosphere (5×), and then was pressurized with H$_2$ to ~0.8-1.0 MPa. The reaction mixture was heated to ~90-100° C. and stirred under a pressure of ~0.8-1.0 MPa for 6 h. The reaction mixture was filtrated through a pad of diatomaceous earth (6.0 kg). The reactor and filter cake were washed with ethyl acetate (14 kg+56 kg). The filtrates were combined and concentrated under vacuum (0.02 MPa) at ~40-50° C. to a residual volume of ~30-50 L. The solution was diluted with ethyl acetate (226 kg) and was stirred for 30 min. The solution was washed with ~20% aq. NaCl (141 kg×2). The organic phase was collected and was filtered through a pad of diatomaceous earth (6.0 kg), washing with ethyl acetate (14 kg+56 kg). The filtrates were combined and concentrated under vacuum (0.02 MPa) at ~40-50° C. to a residual volume of ~30-50 L. A distill and replace operation was then performed using THF (70 kg×2) to achieve 800 ppm H$_2$O by KF analysis (<2000 ppm) and Residual of Solvent (ROS) of 4.5% of ethyl acetate (<10.0%) in the residual THF solution with a volume of ~30-50 L. The solution was diluted with THF (112 kg) and the resulting solution (167 kg, 98.3% purity, 12.9% concentration of title compound by external standard assay, 81.13% assay yield, ~21.54 kg of title compound) was used directly in the next step. LC-MS: m/z 434.4 [M+H]+. $^1$H NMR (500 MHz, CD$_3$OD) δ 7.66 (d, J=15.3 Hz, 1H), 7.14 (t, J=8.0 Hz, 1H), 7.09 (dd, J=9 Hz, 1.5 Hz, 1H), 6.92 (d, J=3.5 Hz, 1H), 6.83 (t, J=9.2 Hz, 1H), 6.63 (d, J=8.1 Hz, 1H), 6.57 (s, 1H), 6.51 (d, J=8.0 Hz, 1H), 6.20 (d, J=3.5 Hz, 1H), 2.99 (s, 4H), 2.58 (s, 4H), 2.31 (s, 3H). $^{13}$C NMR (125 MHz, CD$_3$OD) δ 164.18, 158.03, 156.53 (d, J=18 Hz), 156.10, 155.69, 150.64, 138.59 (d, J=11.1 Hz), 134.17 (d, J=9.6 Hz), 130.94, 122.03, 120.31 (d, J=4.1 Hz), 115.12 (d, J=2.8 Hz), 113.42, 112.12, 109.82, 107.831 (d, J=26.3 Hz), 100.32, 100.00, 56.031 (*2), 51.61 (d, J=2.6 Hz, *2), 46.10.

Example 5A. Alternative Synthesis of 4-(3-aminophenoxy)-N-(3-methyl-4-(4-methylpiperazin-1-yl) phenyl)-7H-pyrrolo[2,3-d]pyrimidin-2-amine Pd/C (10% on activated carbon, 22.58 g, 0.021 mol), THF (1.8 L) and N-(3-fluoro-4-(4-methylpiperazin-1-yl) phenyl)-4-(3-nitrophenoxy)-7H-pyrrolo[2,3-d]pyrimidin-2-amine (447.77 g, 0.97 mol) were charged into a high-pressure hydrogenation reactor. The air in the reactor was removed by nitrogen flow. Then hydrogen was charged into the reactor to replace the nitrogen (repeated 4 times). Hydrogen pressure was applied at 1 MPa, and temperature was set at 90-100° C. The reaction was agitated for approximately 5 h until no more hydrogen was consumed. The reaction mixture was cooled to room temperature, filtered through a pad of diatomaceous earth to remove the catalyst, and washed with ethyl acetate (0.2 L ×3). The combined organic layers were concentrated under reduced pressure at a temperature below 38° C. to afford the crude product. The crude product was re-dissolved in ethyl acetate (5 L) and washed with water (2 L ×2). The organic layer was passed through a pad of diatomaceous earth to remove insolubles and washed with ethyl acetate (0.5 L ×2). The organic solvent was concentrated under reduced pressure (at a temperature below 38° C.) until the remaining solution was around 1.5 L. The remaining solution was allowed to cool to room temperature. The resulting precipitate was collected and dried under vacuum to afford the title compound (360 g, 97.9% purity by HPLC, 86% yield) as an off-white powder. mp: 213.5-215.5° C.; [M+H]+: m/z 434.4; $^1$H NMR and $^{13}$C NMR spectral data for 4-(3-aminophenoxy)-N-(3-methyl-4-(4-methylpiperazin-1-yl)phenyl)-7H-pyrrolo[2,3-d]pyrimidin-2-amine are consistent with those reported in Example 5.

Example 6. Synthesis of N-(3-(2-(3-fluoro-4-(4-methylpiperazin-1-yl)phenylamino)-7H-pyrrolo[2,3-d]pyrimidin-4-yloxy)phenyl)acrylamide

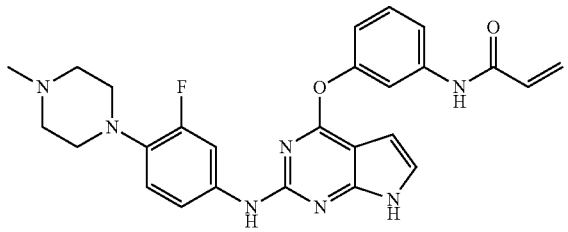 [SMILES: C=CC(=O)Nc1cccc(Oc2nc(Nc3ccc(N4CCN(C)CC4)c(F)c3)nc3[nH]ccc23)c1]

The solution of 4-(3-aminophenoxy)-N-(3-methyl-4-(4-methylpiperazin-1-yl)phenyl)-7H-pyrrolo[2,3-d]pyrimidin-2-amine in THF from Example 5 (166 kg (21.4 kg of starting material)) was agitated under vacuum, and then treated with THF (72 kg) and DIEA (10.8 kg). The reaction mixture was cooled to 5±5° C. Acryloyl chloride (6.70 kg) was diluted with THF (18 kg) and was added drop-wise to the mixture at 5±° C. over 1.5 h. After 3 h, the reaction mixture was warmed to 10±5° C., and 1 N NaOH (150 kg) was added at 10±5° C. over 2 h. The resulting mixture was then warmed to 20±5° C. and stirred for an additional 3 h. The upper THF layer was separated, and was concentrated under vacuum at 45±5° C. to about 40-60 L. A distillation and replacement operation was then performed using ethyl acetate (55 kg) to obtain a residual ethyl acetate solution (~40-60 L). The aqueous layer was extracted with ethyl acetate (100 kg). The ethyl acetate layer was combined with the residual ethyl acetate solution, diluted further with ethyl acetate (210 kg), and stirred for 0.5 h. The solution was washed with 20% brine (110 kg×3) and concentrated under vacuum at 45±5° C. to a volume of ~40-60 L. A distillation and replacement operation was then performed twice using EtOH (44 kg×2) to obtain a residual EtOH solution (40-60 L). The resulting solution was diluted with EtOH (88 kg) at 40±5° C., was treated with purified water (154 kg) slowly at 40±5° C. over 2 h, and then was stirred for 2 h. The mixture was cooled to 15±5° C. and was stirred for another 5 h. The resulting precipitate was centrifuged, and the wet cake was washed with 1:1 EtOH/H$_2$O (22 kg) and then centrifuged again to afford the title compound (22.4 kg) as a pale yellow solid.

The crude material was dissolved in ethyl acetate (75 kg) and EtOH (22 kg), and the resulting solution was added to a silica gel column (88 kg, 200~300 mesh). The title compound was eluted with 4:1 ethyl acetate/EtOH (396 kg/88 kg). Fractions were collected and concentrated under vacuum at 45±5° C. to about 40-50 L. A distill and replace operation was then performed using EtOH (44 kg) to obtain ~40-60 L of a residual ethanol solution. The solution was diluted with EtOH (107 kg) and was heated to 40±5° C. Purified water (39.6 kg) was added over 1 h, and the resulting mixture was stirred for 2 h. A white solid started to precipitate and the suspension was cooled to 15±5° C. and stirred for 5 h. The mixture was centrifuged and the wet cake was washed with H$_2$O:EtOH (8.8 kg: 13.2 kg). The wet cake was dried under vacuum at 50±5° C. for 16 h to afford the title compound (12.24 kg, 99.39% purity, 50.8% assay yield) as a white solid. LC-MS: m/z 488.6 [M+H]+. $^1$H NMR (500 MHz, CD$_3$OD) δ 7.69 (t, J=2.0 Hz, 1H), 7.62-7.55 (m, 2H), 7.41 (t, J=8.1 Hz, 1H), 7.06 (d, J=8.7 Hz, 1H), 7.01-6.99 (m, 2H), 6.80 (t, J=9.2 Hz, 1H), 6.44 (dd, J=17.0, 9.9 Hz, 1H), 6.39-6.32 (m, 2H), 5.77 (dd, J=9.9, 1.9 Hz, 1H), 2.99 (s, 4H), 2.59 (s, 4H), 2.32 (s, 3H). $^{13}$C NMR (125 MHz, CD$_3$OD) δ 164.74, 162.50, 156.58, 155.17 (d, J=3.9 Hz), 154.7, 153.6, 139.7, 137.15 (d, J=11.1 Hz), 132.79 (d, J=9.8 Hz), 131.00, 129.41, 126.71, 120.97, 118.79 (d, J=3.9 Hz), 117.52, 116.51, 113.77 (t, J=2.8 Hz), 106.65, 106.44, 98.97, 98.34, 54.64 (*2), 50.36 (d, J=2.5 Hz, *2), 44.72.

Example 6A. Alternative Synthesis of N-(3-(2-(3-fluoro-4-(4-methylpiperazin-1-yl)phenylamino)-7H-pyrrolo[2,3-d]pyrimidin-4-yloxy)phenyl)acrylamide A reactor (30 L) was charged with 4-(3-aminophenoxy)-N-(3-methyl-4-(4-methylpiperazin-1-yl)phenyl)-7H-pyrrolo[2,3-d]pyrimidin-2-amine (1199 g, 2.77 mol), DIEA (685 g, 5.30 mol) and THF (13 L). When the temperature inside the reactor reached ~3° C., a solution of acryloyl chloride (466.5 g, 5.15 mol) in THF (1 L) was added drop-wise into the reactor over a period of 1 h. The temperature was kept between −5-0° C. during the addition. After stirring for another 30 min, a NaOH solution (1 M, 7.5 L) was added slowly to quench the reaction (the temperature kept between −5-0° C.). The final pH value of the solution was around 9~10. The resulting mixture was stirred for another 3-4 h. The upper THF layer was separated and concentrated under reduced pressure at <40° C. The residue was re-dissolved in ethyl acetate (15 L). The lower aqueous layer was extracted with ethyl acetate (5 L). The residue/ethyl acetate solution was combined with the ethyl acetate layers and all were washed with water (5 L ×3) and concentrated under reduced pressure to give a crude product (~1680 g). The crude material was re-dissolved in EtOH (18 L) at 35-40° C. and water (12 L) was added with stirring. The resulting solution was allowed to cool to room temperature and was stirred overnight (16 h). The resulting precipitate was collected and dried under vacuum to afford a second crude product (1010 g). To further purify this crude product (1010 g), silica gel chromatography (4:1 ethyl acetate/EtOH as mobile phase) and two re-crystallizations from EtOH/water (4:1) were performed to yield the title compound (727 g, 99.2% by HPLC, 54% yield) as off-white powder. mp: 122.0-123.5° C.; [M+H]⁺: m/z 488.6; $^1$H NMR and $^{13}$C NMR spectral data for N-(3-(2-(3-fluoro-4-(4-methylpiperazin-1-yl)phenylamino)-7H-pyrrolo[2,3-d]pyrimidin-4-yloxy)phenyl)acrylamide are consistent with those reported in Example 6.

Example 7. Synthesis of N-(3-(2-(3-fluoro-4-(4-methylpiperazin-1-yl)phenylamino)-7H-pyrrolo[2,3-d]pyrimidin-4-yloxy)phenyl)acrylamide maleate di-hydrate

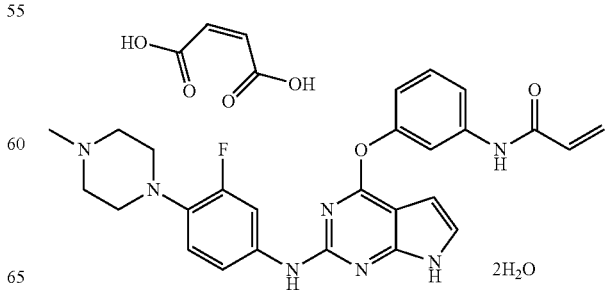

N-(3-(2-(3-Fluoro-4-(4-methylpiperazin-1-yl)phenylamino)-7H-pyrrolo[2,3-d]pyrimidin-4-yloxy)phenyl)acrylamide (12.20 kg) was added to a reactor containing purified water (180 kg) and ethanol (7.54 kg). The mixture was heated to 40±5° C. A solution of maleic acid (3.14 kg) in purified H$_2$O (53.1 kg) and EtOH (2.26 kg) was added to the reactor. The resulting mixture was agitated for 1 h at 40±5° C., then was cooled to 25±5° C. at a rate of 20° C./h and was stirred for another 5 h. The resulting precipitate was centrifuged and the cake was washed with the rest of the H$_2$O/EtOH solution. The wet cake (16.92 kg) was dried for 48 h at 30±5° C. under vacuum to afford the title compound (14.30 kg, 89.3%). LC-MS: m/z 488.6 [M+H]$^+$. $^1$H NMR (500 MHz, DMSO-d$_6$) δ 11.39 (s, 1H), 10.44 (s, 1H), 9.02 (s, 1H), 7.62 (s, 1H), 7.53 (d, J=8.3 Hz, 1H), 7.50 (d, J=15.4 Hz, 1H), 7.42 (t, J=8.2 Hz, 1H), 7.11-7.05 (m, 2H), 6.97 (ddd, J=8.1, 2.3, 0.7 Hz, 1H), 6.82 (t, J=9.4 Hz, 1H), 6.38 (dd, J=16.9, 10.2 Hz, 1H), 6.26 (ddd, J=18.5, 10.2, 1.7 Hz, 2H), 6.14 (s, 2H), 5.76 (dd, J=10.2, 1.5 Hz, 1H), 3.30 (br, 4H), 3.11 (br, 4H), 2.80 (s, 3H). $^{13}$C NMR (125 MHz, DMSO-d$_6$) δ 168.68 (*2), 164.50, 162.36, 156.18, 155.36, 154.97, 154.25, 153.34, 140.30, 137.90 (d, J=11.1 Hz), 136.25 (*2), 131.50, 131.42 (d, J=9.8 Hz), 130.53, 128.52, 122.80, 120.03, 117.70, 116.92, 114.43, 113.47, 106.65 (d, J=26.5 Hz), 98.93 (d, J=23.6 Hz), 53.38 (*2), 48.15 (*2), 42.88.

Example 7A. Alternative Synthesis of N-(3-(2-(3-fluoro-4-(4-methylpiperazin-1-yl)phenylamino)-7H-pyrrolo[2,3-d]pyrimidin-4-yloxy)phenyl)acrylamide maleate di-hydrate In a 30-L reactor, a combination of several batches of N-(3-(2-(3-fluoro-4-(4-methylpiperazin-1-yl)phenylamino)-7H-pyrrolo[2,3-d]pyrimidin-4-yloxy)phenyl)acrylamide (1481 g, ~99.2% HPLC purity) was dissolved in EtOH (15 L) at 36° C. Water (2 L) was added drop-wise at this temperature. The mixture was allowed to cool to room temperature and was stirred overnight. The resulting crystals were collected, washed with a small amount of EtOH, and dried under vacuum at 25° C. overnight to afford the free base of N-(3-(2-(3-fluoro-4-(4-methylpiperazin-1-yl)phenylamino)-7H-pyrrolo[2,3-d]pyrimidin-4-yloxy)phenyl)acrylamide (1255 g, 99.61% HPLC purity) as an off-white powder, which was used in the salt formation step.

A reactor (50 L) was charged with 5% EtOH (20 L) at 40° C. The free base of N-(3-(2-(3-fluoro-4-(4-methylpiperazin-1-yl)phenylamino)-7H-pyrrolo[2,3-d]pyrimidin-4-yloxy)phenyl)acrylamide (1255 g, 2.57 mol, 99.61% HPLC purity) was added with stirring. The resulting suspension was stirred vigorously at 40° C. until a slurry was formed. A solution of maleic acid (325 g, 2.8 mol) in 5% EtOH (2 L) was added drop-wise over 15 min. Once the addition was complete, a clear homogeneous solution was obtained. The solution was allowed to cool to room temperature and was stirred overnight. The resulting crystals were collected, washed with 5% EtOH (0.5 L ×3), and dried under vacuum at 25° C. for 48 h to afford the title compound as a light-yellow powder (1420 g, 99.67% HPLC purity, 86.4% yield). mp: 171.1-173.2° C.; [M+H]+: m/z 488.6; $^1$H NMR and $^{13}$C NMR spectral data for N-(3-(2-(3-fluoro-4-(4-methylpiperazin-1-yl)phenylamino)-7H-pyrrolo[2,3-d]pyrimidin-4-yloxy)phenyl)acrylamide maleate di-hydrate are consistent with those reported in Example 7.

Additional exemplary compounds not shown in these synthetic examples are prepared from appropriate starting materials using methods analogous to those described in the preceding schemes and examples.

Example 8. Synthesis of N-(3-(2-(3-fluoro-4-(4-methylpiperazin-1-yl)phenylamino)-7H-pyrrolo[2,3-d]pyrimidin-4-yloxy)phenyl)acrylamide maleate salt Example 8-1 (Ethanol/Water (1:1))

Figure 2:
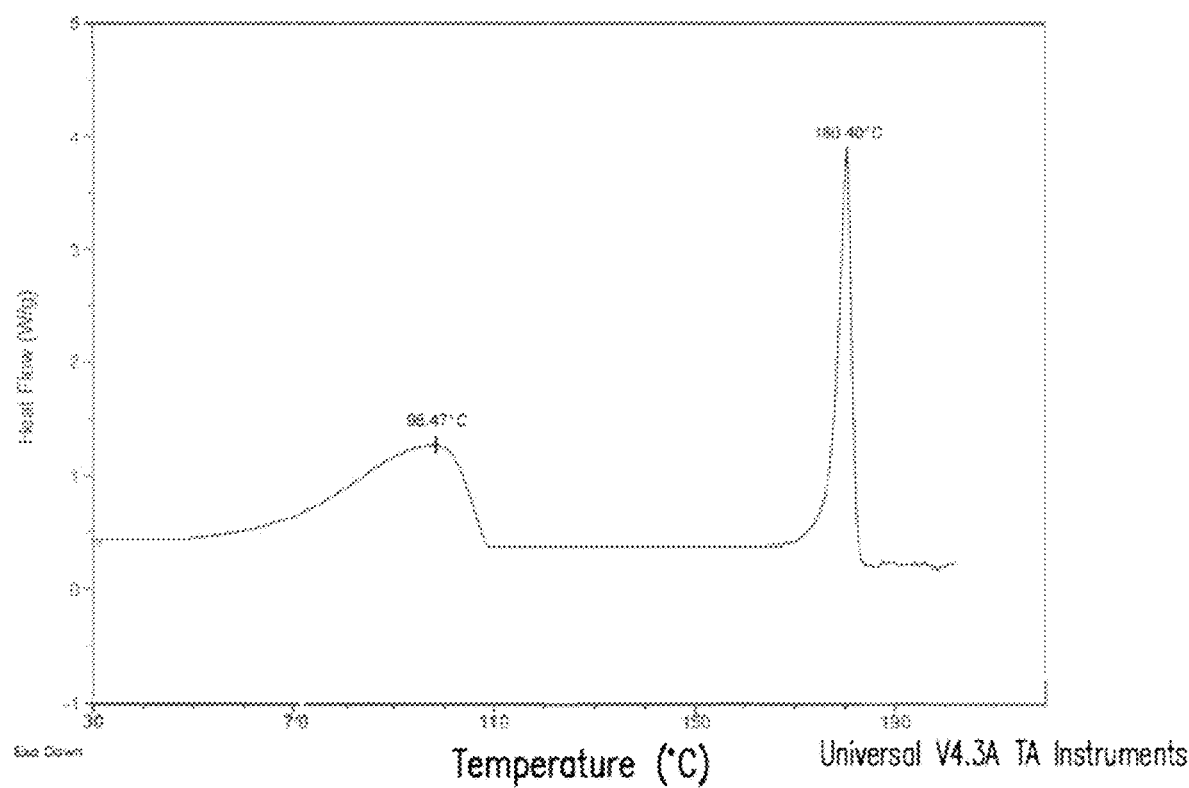
FIG. 2 is a differential scanning calorimetry curve of polymorph Form I maleate salt obtained from 1:1 ethanol/H$_2$O.
Figure 3:
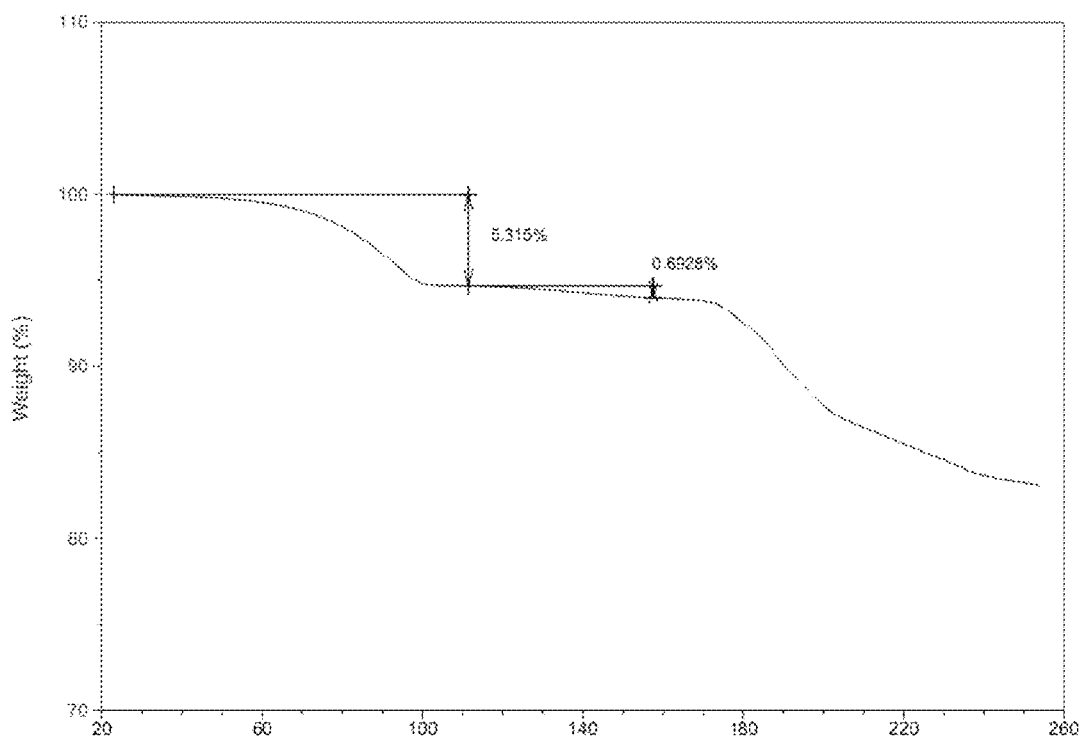
FIG. 3 shows a thermogravimetric analysis of polymorph Form I maleate salt obtained from 1:1 ethanol/H$_2$O.

A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (1 g, 2.05 mmol) in ethanol (5 mL) at 40° C. was treated with a solution of maleic acid (262 mg, 2.26 mmol) in water (5 mL). The solution was cooled to room temperature with stirring. The resulting crystals were collected and dried to yield the title compound (1 g, 76.3% yield) defined as polymorph Form I. Elemental analysis: N: 14.90%; C: 56.54%; H: 5.34%. The XRPD, DSC, and TGA traces for this material are shown in FIGS. 1, 2, and 3, respectively.

Example 8-2 (Ethanol/Water (3:7))

Figure 4:
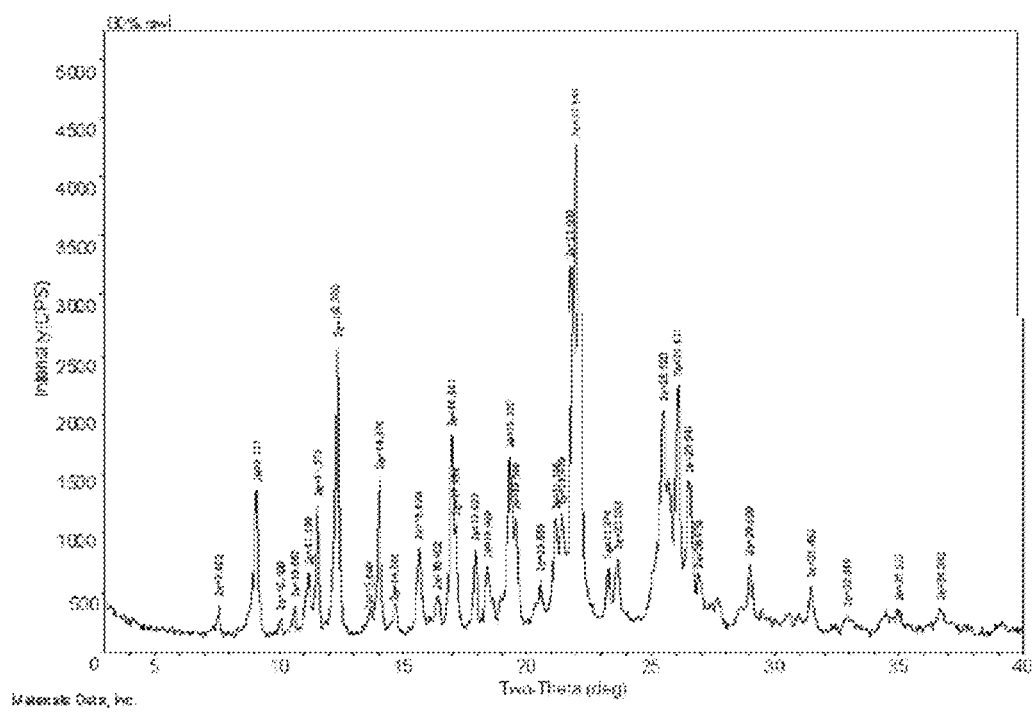
FIG. 4 is an X-ray powder diffractogram of polymorph Form I maleate salt obtained from 3:7 ethanol/H$_2$O.

A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (1 g, 2.05 mmol) in ethanol (4.5 mL) and water (8.5 mL) at 40° C. was treated with 1 M aqueous maleic acid (2 mL). The solution was cooled to room temperature with stirring. The resulting crystals were collected and dried to yield the title compound (0.9 g, 68.7% yield) defined as polymorph Form I. The XRPD trace for this material is shown in FIG. 4.

Example 8-3 (Ethanol/Water (1:19))

Figure 5:
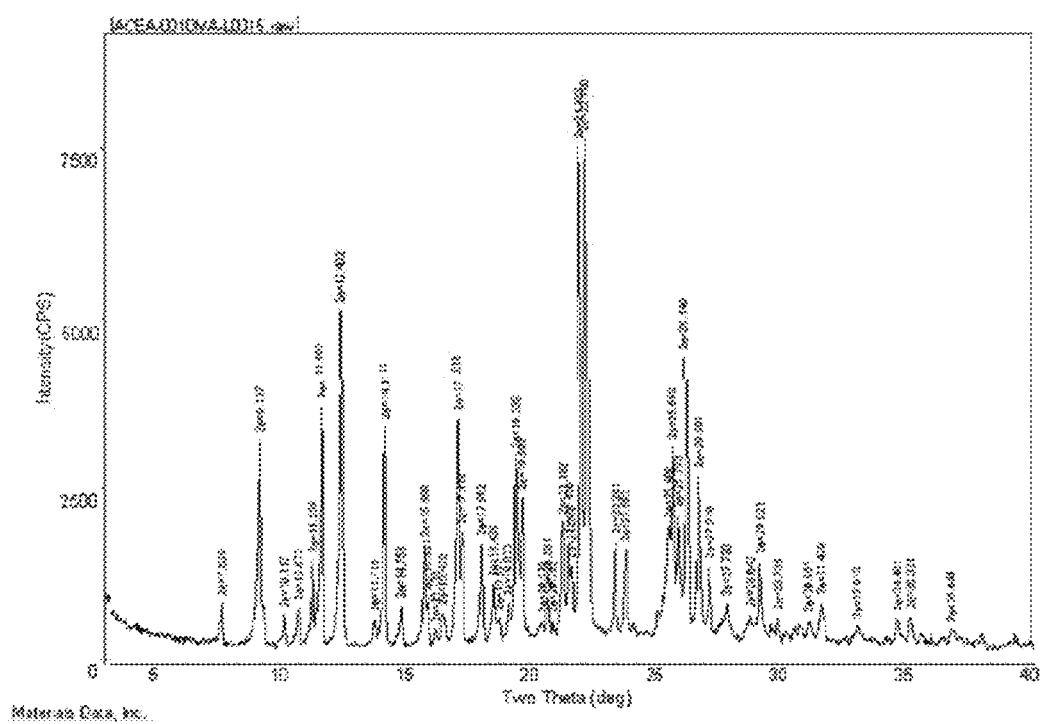
FIG. 5 is an X-ray powder diffractogram of polymorph Form I maleate salt obtained from 1:19 ethanol/H$_2$O.
Figure 6:
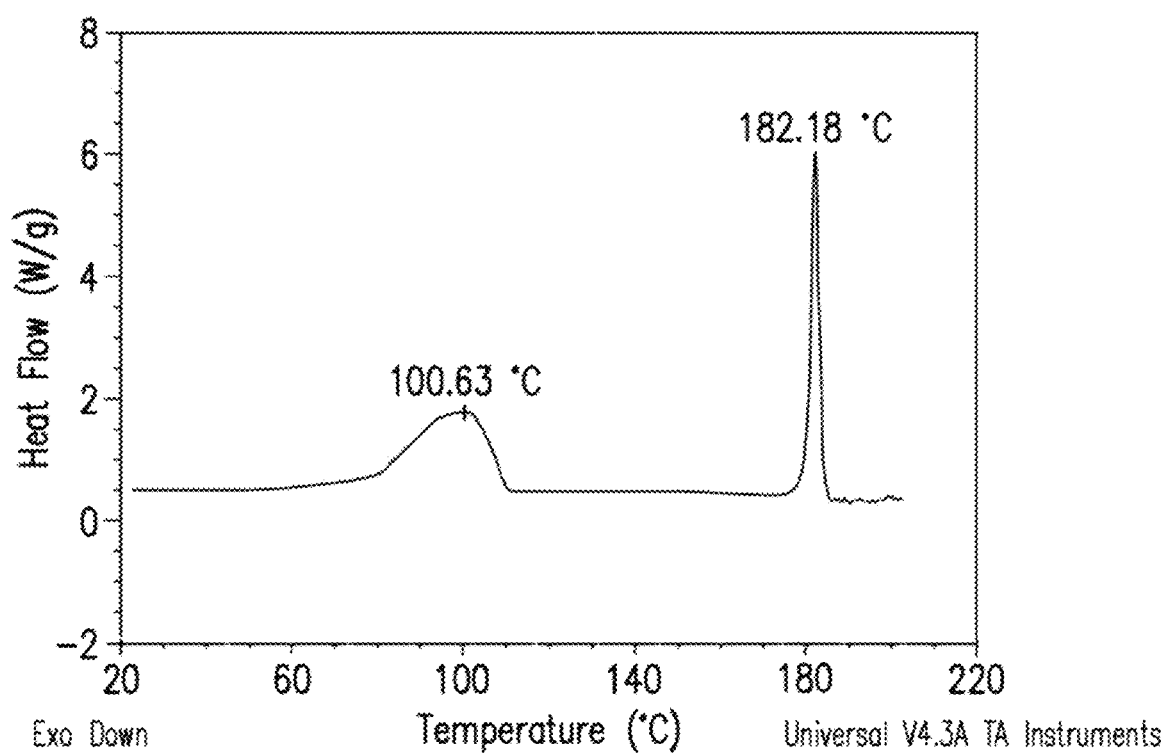
FIG. 6 is a differential scanning calorimetry curve of polymorph Form I maleate salt obtained from 1:19 ethanol/H$_2$O.
Figure 7:
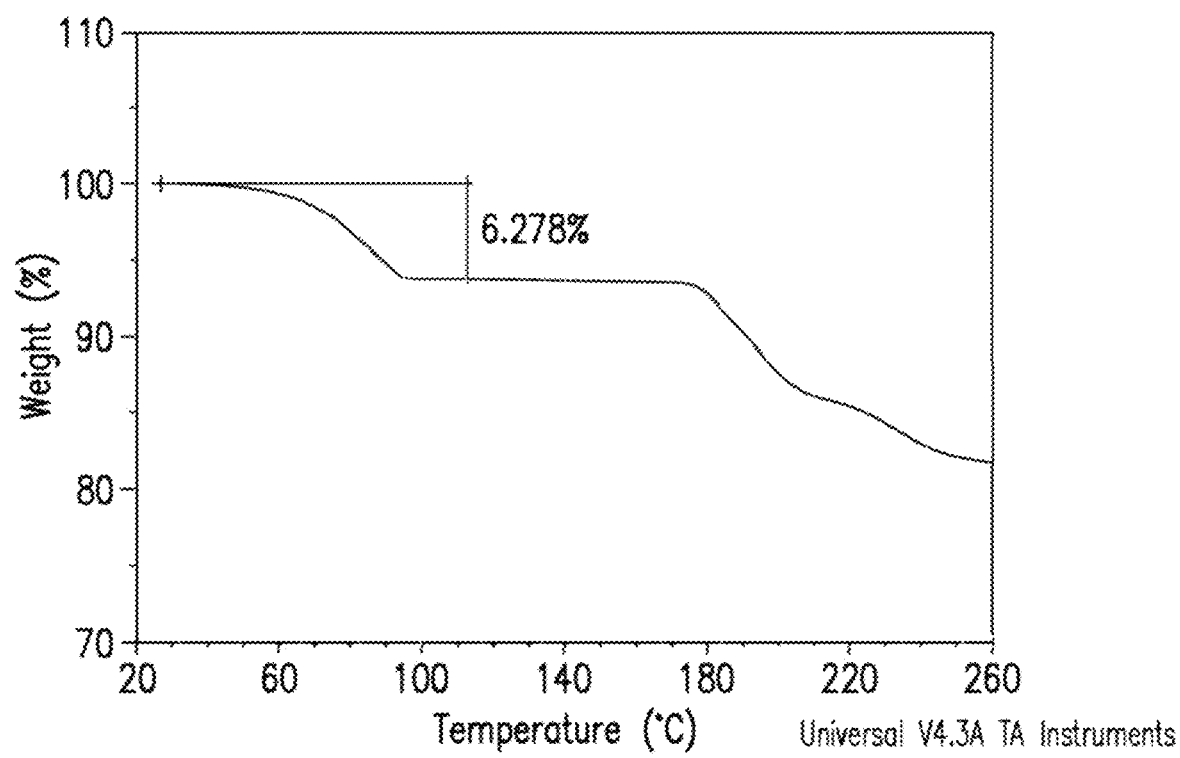
FIG. 7 shows a thermogravimetric analysis of polymorph Form I maleate salt obtained from 1:19 ethanol/H$_2$O.

A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (1255 g, 2.57 mol) in 5% ethanol (20 L) at 40° C. was treated slowly over 15 min with a solution of maleic acid (325 g, 2.8 mol) in 5% ethanol (2 L). The solution was cooled to room temperature and was stirred overnight. The resulting crystals were collected, washed with 5% ethanol (0.5 L ×3), and dried under vacuum at 25° C. for 48 h to yield the title compound (1420 g, 86.4% yield) defined as polymorph Form I. Elemental analysis: N: 14.90%; C: 56.54%; H: 5.34%. The XRPD, DSC, and TGA traces for Form I are shown in FIGS. 5, 6, and 7, respectively. Elemental analysis: N: 14.95%; C: 56.54%; H: 5.40%. The XRPD, DSC, and TGA traces for this material are shown in FIGS. 5, 6, and 7, respectively.

Example 8-4 (Ethanol)

Figure 8:
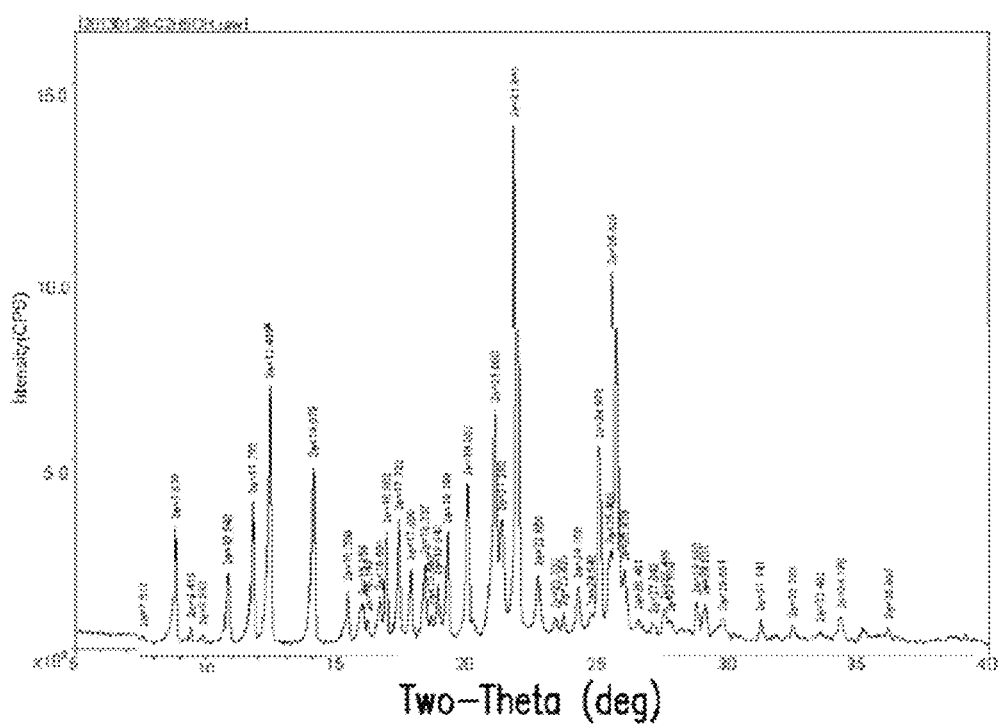
FIG. 8 is an X-ray powder diffractogram of polymorph Form II maleate salt obtained from ethanol.

A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (1 g, 2.05 mmol) in ethanol (9 mL) at 40° C. was treated with maleic acid (262 mg, 2.26 mmol). The solution was cooled to room temperature with stirring. The resulting crystals were collected and dried to yield the title compound (0.8 g, 61.0% yield) defined as polymorph Form II (possible ethanol solvate). Elemental analysis: N: 15.09%; C: 59.08%; H: 5.48%. The XRPD trace for this material is shown in FIG. 8.

Example 8-5 (Methanol)

Figure 9:
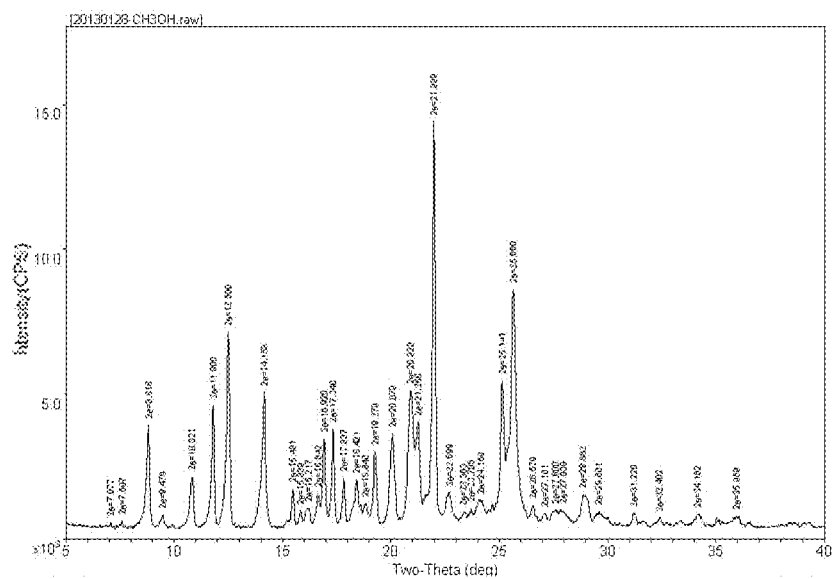
FIG. 9 is an X-ray powder diffractogram of polymorph Form II maleate salt obtained from methanol.
Figure 10:
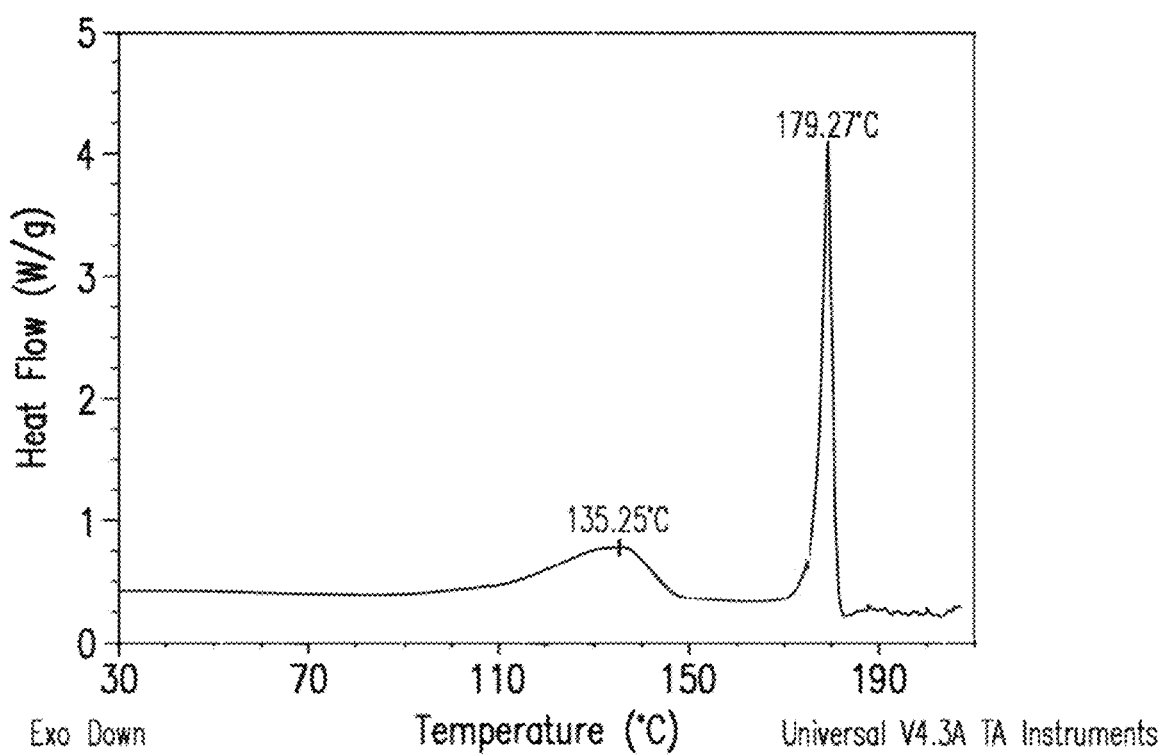
FIG. 10 is a differential scanning calorimetry curve of polymorph Form II maleate salt obtained from methanol.
Figure 11:
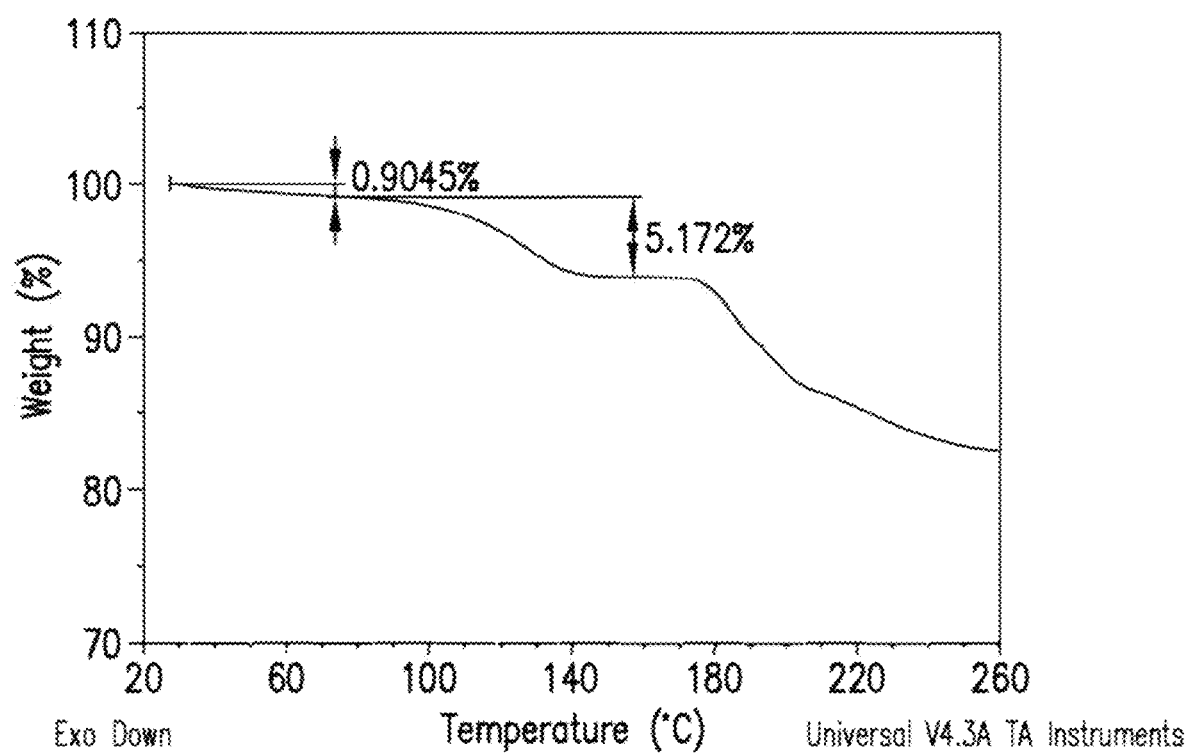
FIG. 11 shows a thermogravimetric analysis of polymorph Form II maleate salt obtained from methanol.

A stirred suspension of N-(3-(2-(3-fluoro-4-(4-methylpiperazin-1-yl)phenylamino)-7H-pyrrolo[2,3-d]pyrimidin-4- yloxy)phenyl)acrylamide (1 g, 2.05 mmol) in methanol (9 mL) at 40° C. was treated with maleic acid (262 mg, 2.26 mmol). The solution was cooled to room temperature with stirring. The resulting crystals were collected and dried to yield the title compound (0.8 g, 61.0% yield) defined as polymorph Form II (possible methanol solvate). Elemental analysis: N: 14.90%; C: 57.76%; H: 5.37%. The XRPD, DSC, and TGA traces for this material are shown in FIGS. 9, 10, and 11, respectively.

Example 8-6 (Tetrahydrofuran)

Figure 12:
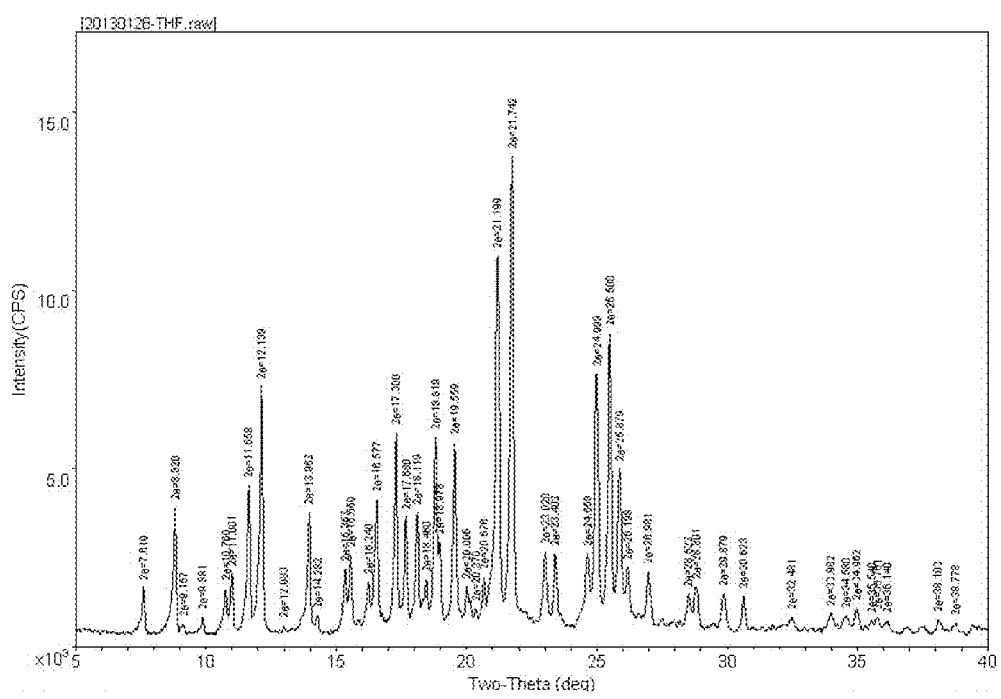
FIG. 12 is an X-ray powder diffractogram of polymorph Form III maleate salt obtained from tetrahydrofuran.
Figure 13:
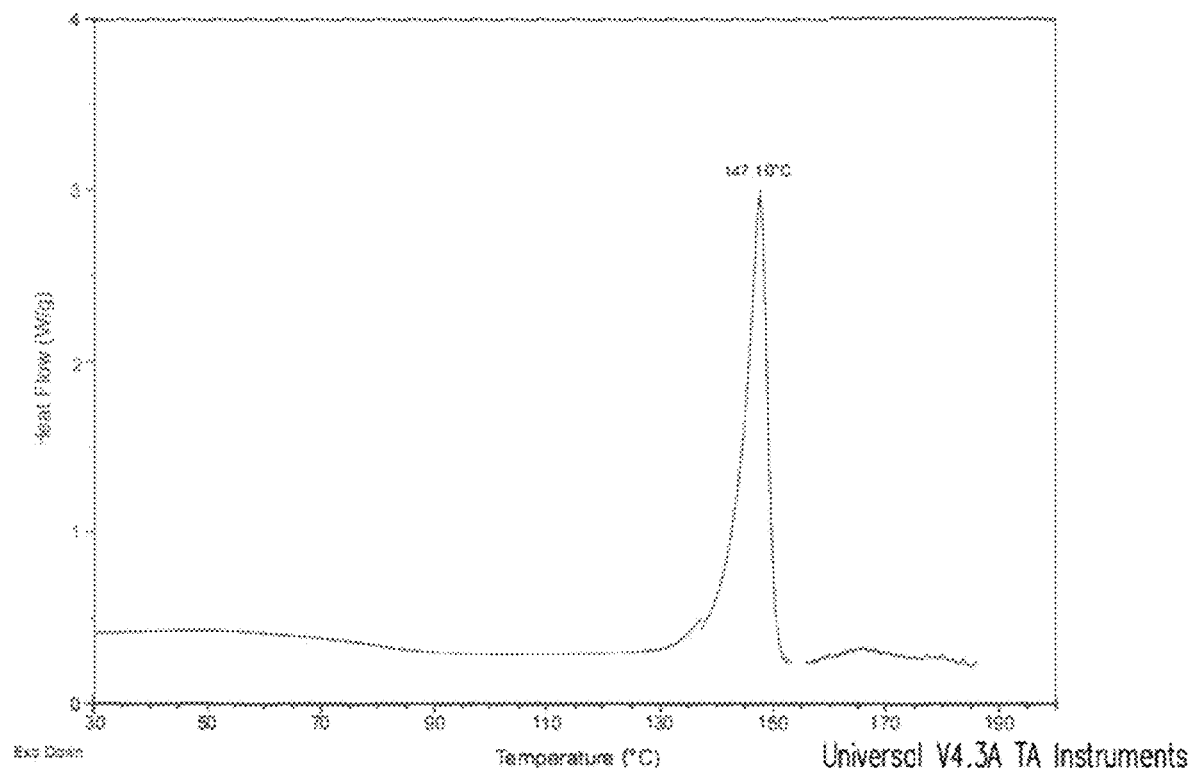
FIG. 13 is a differential scanning calorimetry curve of polymorph Form III maleate salt obtained from tetrahydrofuran.
Figure 14:
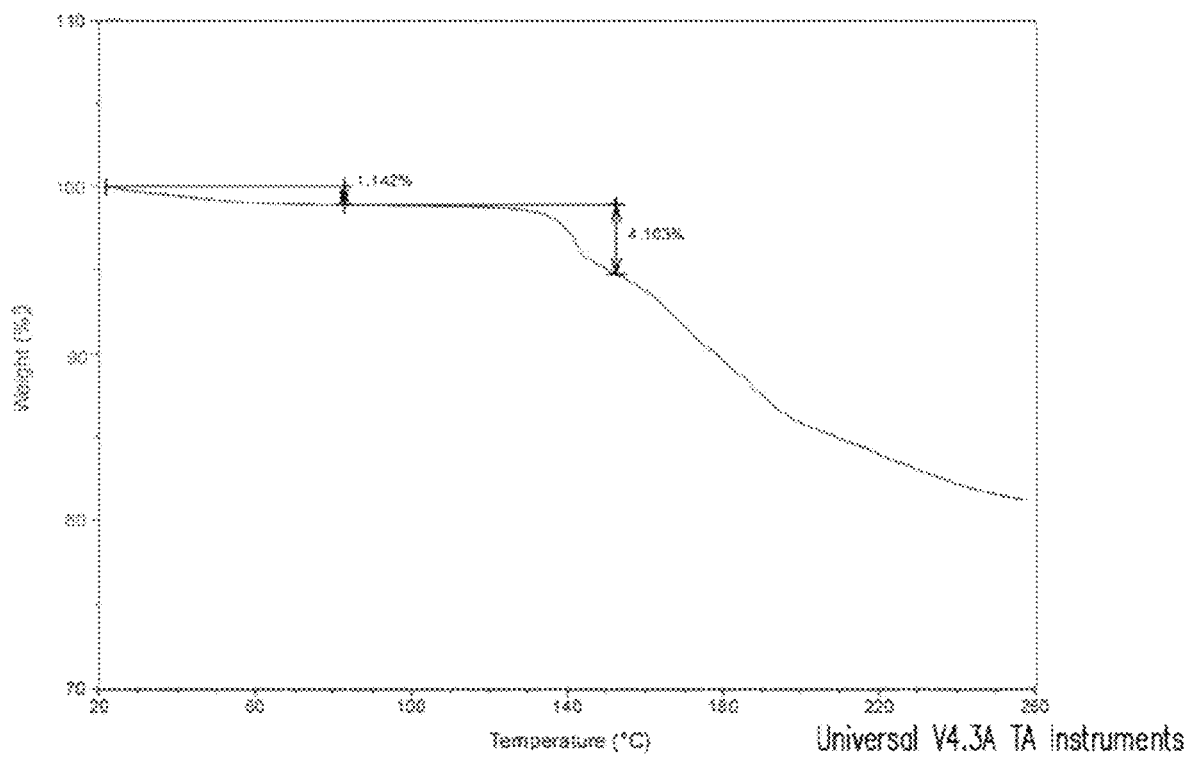
FIG. 14 shows a thermogravimetric analysis of polymorph Form III maleate salt obtained from tetrahydrofuran.

A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (1 g, 2.05 mmol) in THF (8 mL) at 40° C. was treated with maleic acid (262 mg, 2.26 mmol). The solution was cooled to room temperature and was stirred overnight. The resulting crystals were collected and dried to yield the title compound (0.7 g, 53.4% yield) defined as polymorph Form III. Elemental analysis: N: 14.64%; C: 59.02%; H: 5.29%. The XRPD, DSC, and TGA traces for this material are shown in FIGS. 12, 13, and 14, respectively.

Example 8-7 (Acetone)

Figure 15:
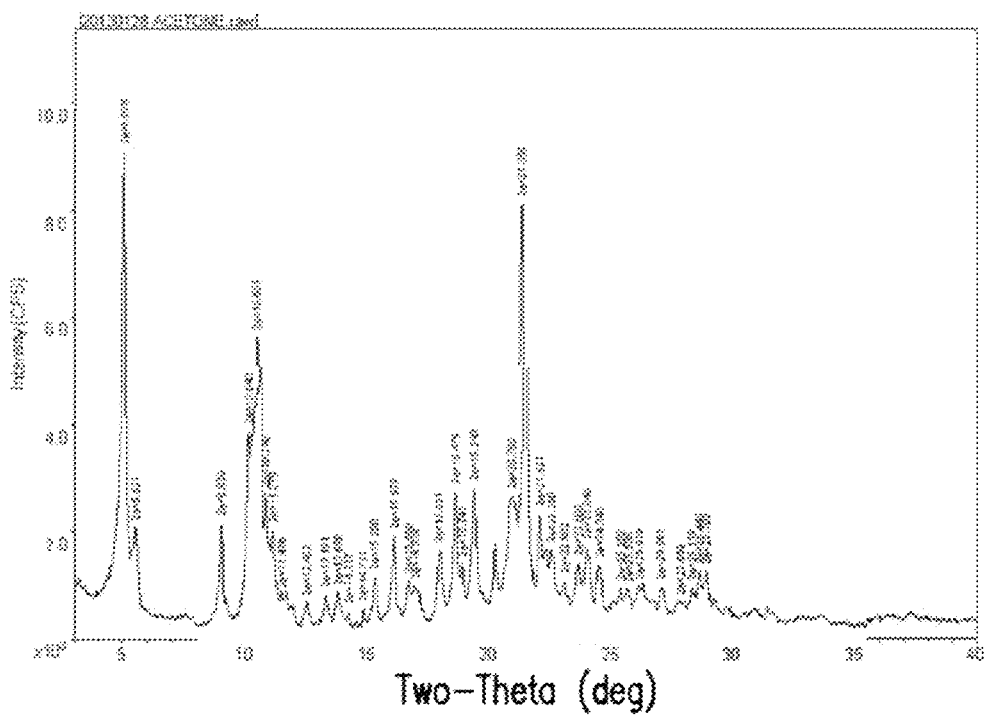
FIG. 15 is an X-ray powder diffractogram of an amorphous form of the maleate salt obtained from acetone.
Figure 16:
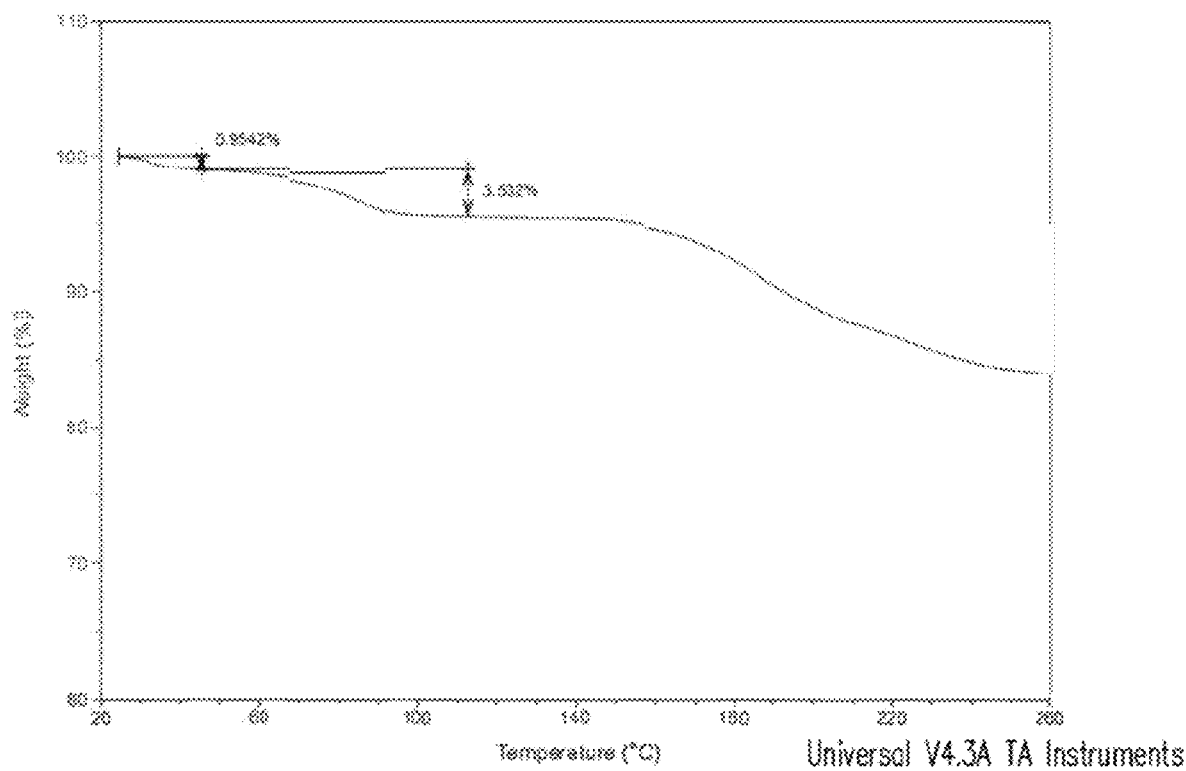
FIG. 16 is a differential scanning calorimetry curve of the amorphous form of the maleate salt obtained from acetone.
Figure 17:
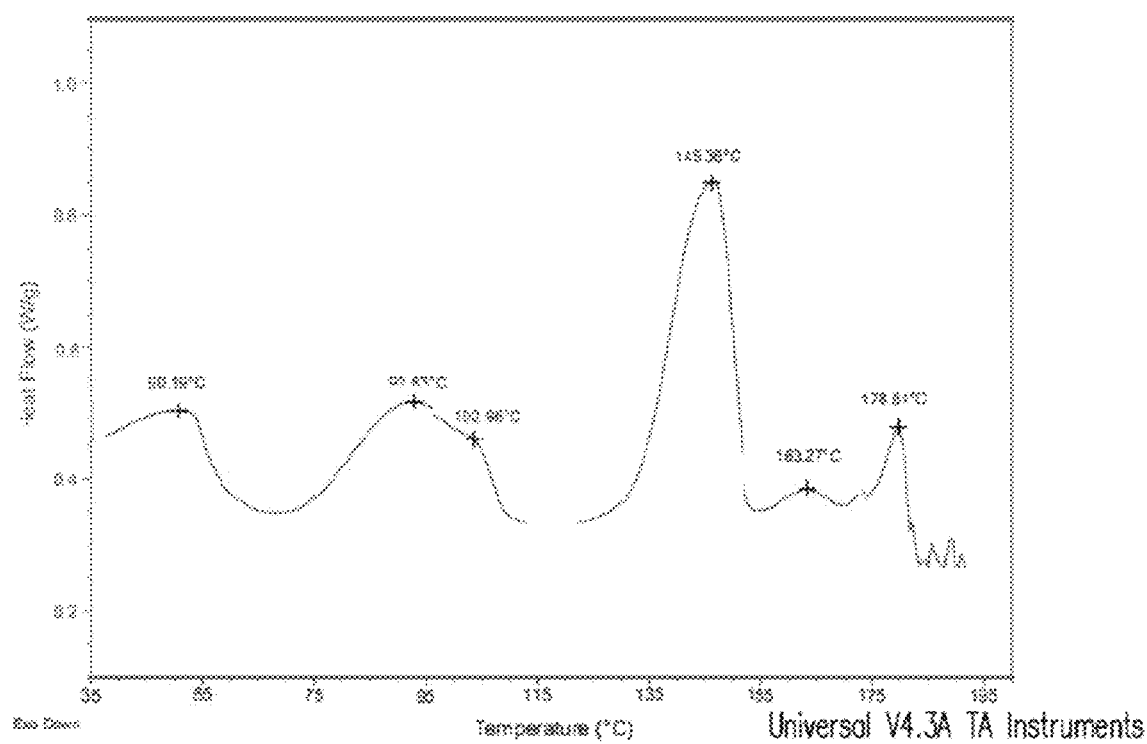
FIG. 17 shows a thermogravimetric analysis of the amorphous form of the maleate salt obtained from acetone.

A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (1 g, 2.05 mmol) in acetone (25 mL) at 40° C. was treated with a solution of maleic acid (262 mg, 2.26 mmol) in acetone (5 mL). The solution was cooled to room temperature and was stirred overnight. The mixture was then exposed to air with stirring for 6 h. The resulting crystals were collected and dried to yield the title compound (0.7 g, 53.4% yield) defined as an amorphous form. Elemental analysis: N: 14.97%; C: 58.37%; H: 5.09%. The XRPD, DSC, and TGA traces for this material are shown in FIGS. 15, 16, and 17, respectively.

Example 8-8 (Acetonitrile)

Figure 18:
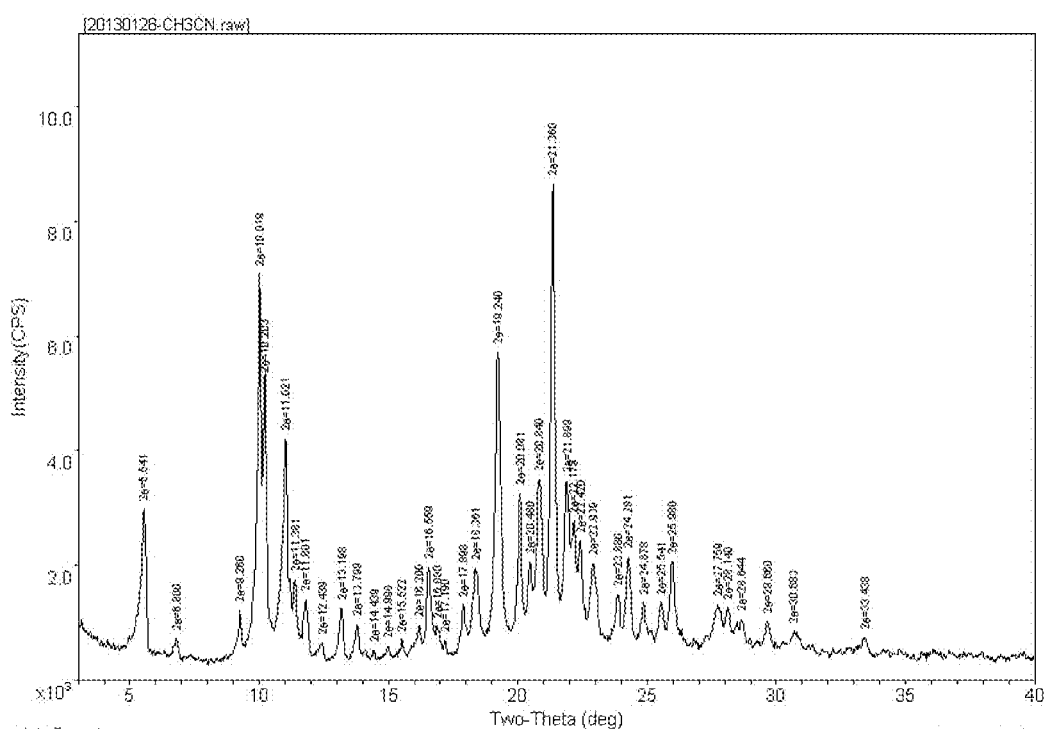
FIG. 18 is an X-ray powder diffractogram of the amorphous form of the maleate salt obtained from acetonitrile.
Figure 19:
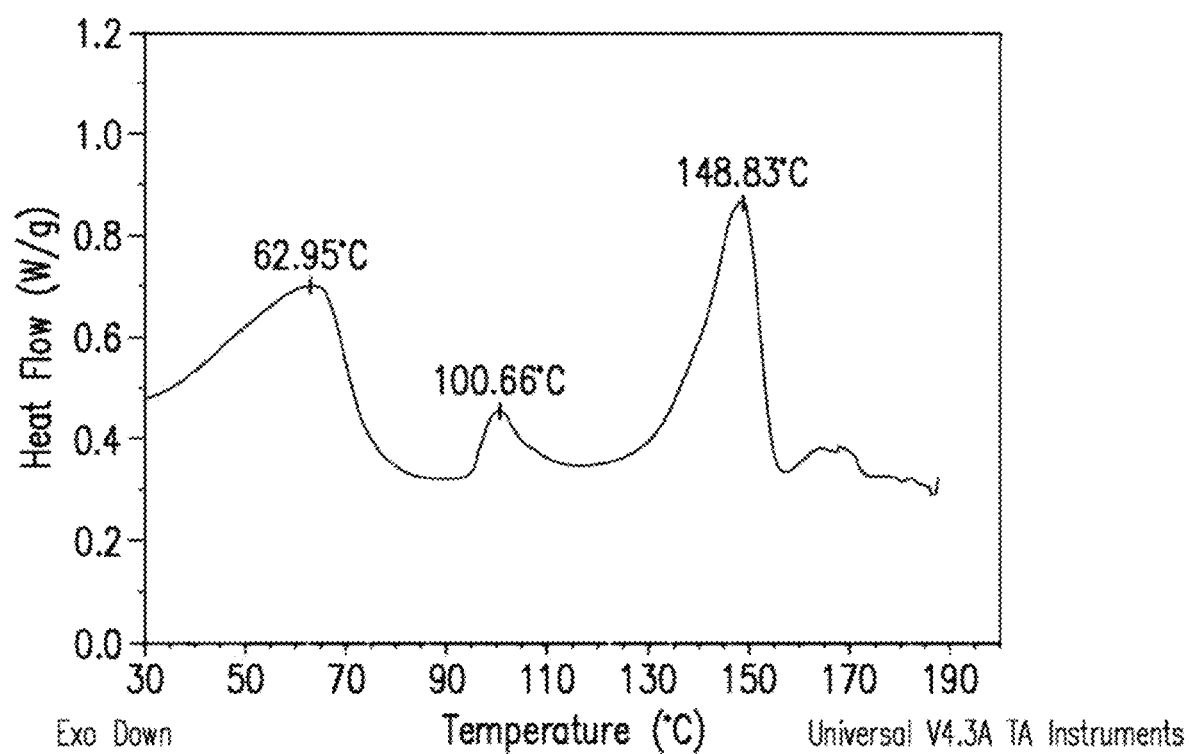
FIG. 19 is a differential scanning calorimetry curve of the amorphous form of the maleate salt obtained from acetonitrile.
Figure 20:
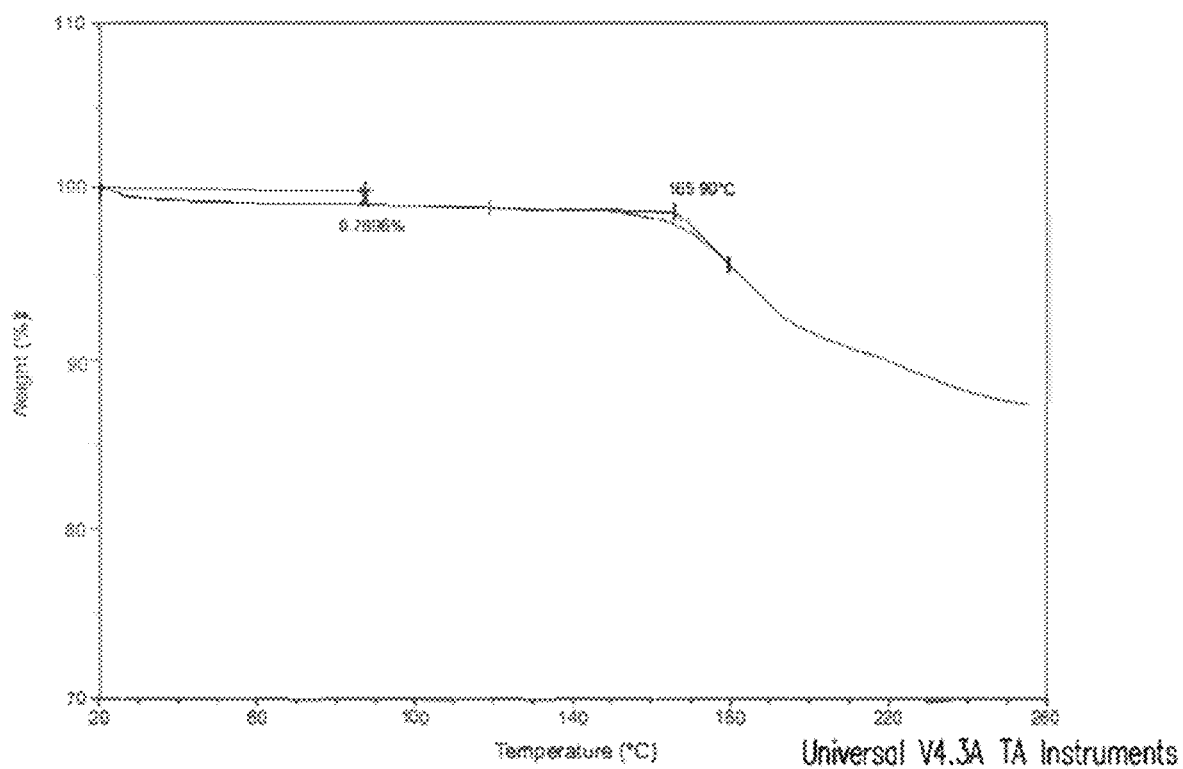
FIG. 20 shows a thermogravimetric analysis of the amorphous form of the maleate salt obtained from acetonitrile.

A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (1 g, 2.05 mmol) in acetonitrile (25 mL) at 40° C. was treated with a solution of maleic acid (262 mg, 2.26 mmol) in acetonitrile (5 mL). The solution was cooled to room temperature and was stirred overnight. The resulting crystals were collected and dried to yield the title compound (1 g, 76.3% yield) defined as an amorphous form. Elemental analysis: N: 15.71%; C: 59.03%; H: 5.06%. The XRPD, DSC, and TGA traces for this material are shown in FIGS. 18, 19, and 20, respectively.

Example 8-9 (Ethyl Acetate)

Figure 21:
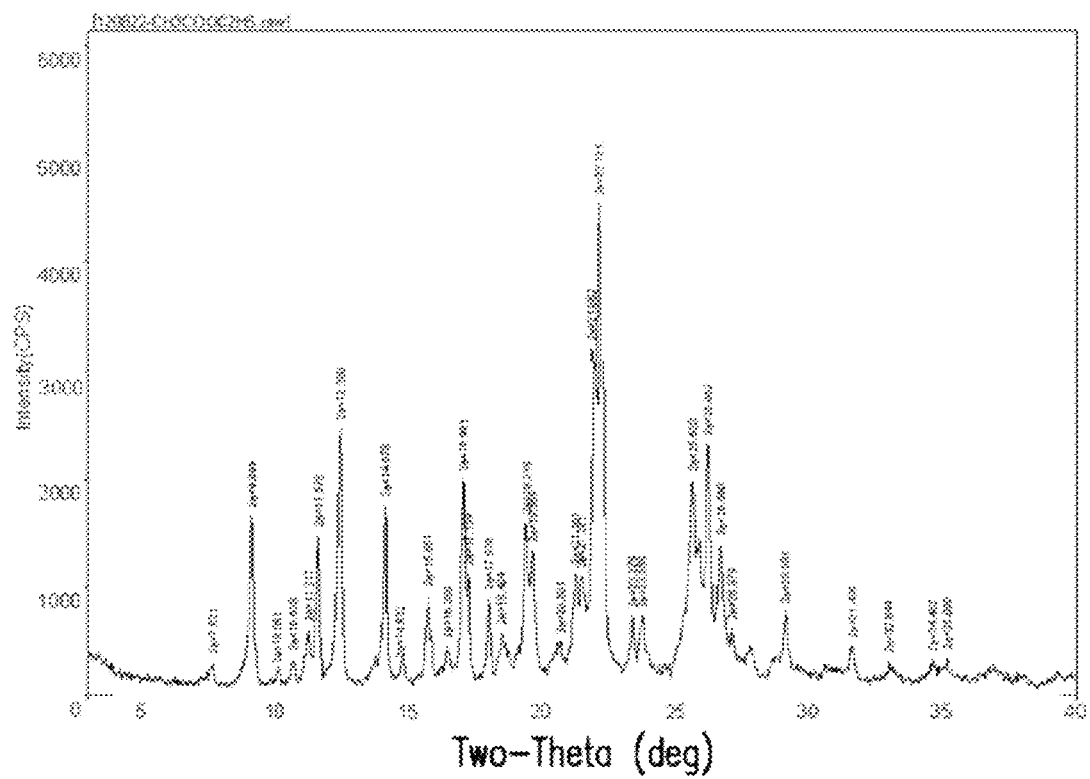
FIG. 21 is an X-ray powder diffractogram of polymorph Form I maleate salt obtained from ethyl acetate.

A sample of N-(3-(2-(3-fluoro-4-(4-methylpiperazin-1-yl)phenylamino)-7H-pyrrolo[2,3-d]pyrimidin-4-yloxy)phenyl)acrylamide maleate salt (0.5 g) was dissolved in ethyl acetate (100 mL) at 40° C. with stirring. The solution was cooled to room temperature and stood overnight without stirring. The resulting crystals were collected and dried to yield the title compound (~50 mg, 10% yield) defined as polymorph Form I. The XRPD trace for this material is shown in FIG. 21.

Example 9. Synthesis of N-(3-(2-(3-fluoro-4-(4-methylpiperazin-1-yl)phenylamino)-7H-pyrrolo[2,3-d]pyrimidin-4-yloxy)phenyl)acrylamide hydrochloride salt Example 9-1 (Water)

Figure 22:
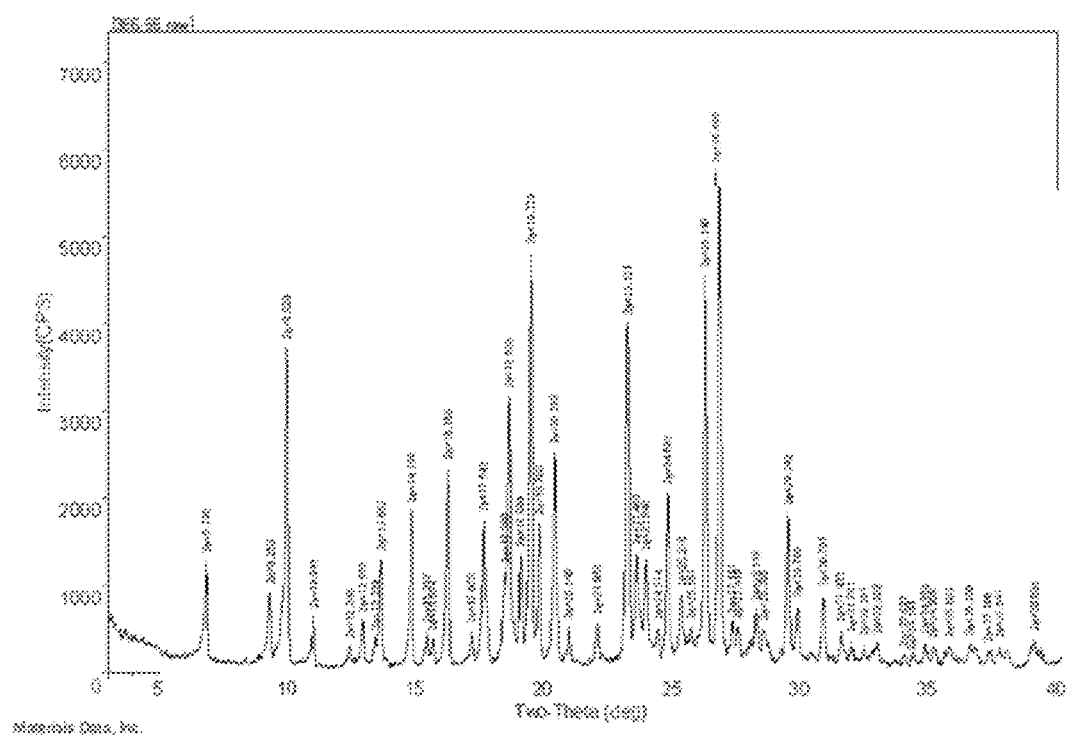
FIG. 22 is an X-ray powder diffractogram of polymorph Form IV hydrochloride salt obtained from water.
Figure 23:
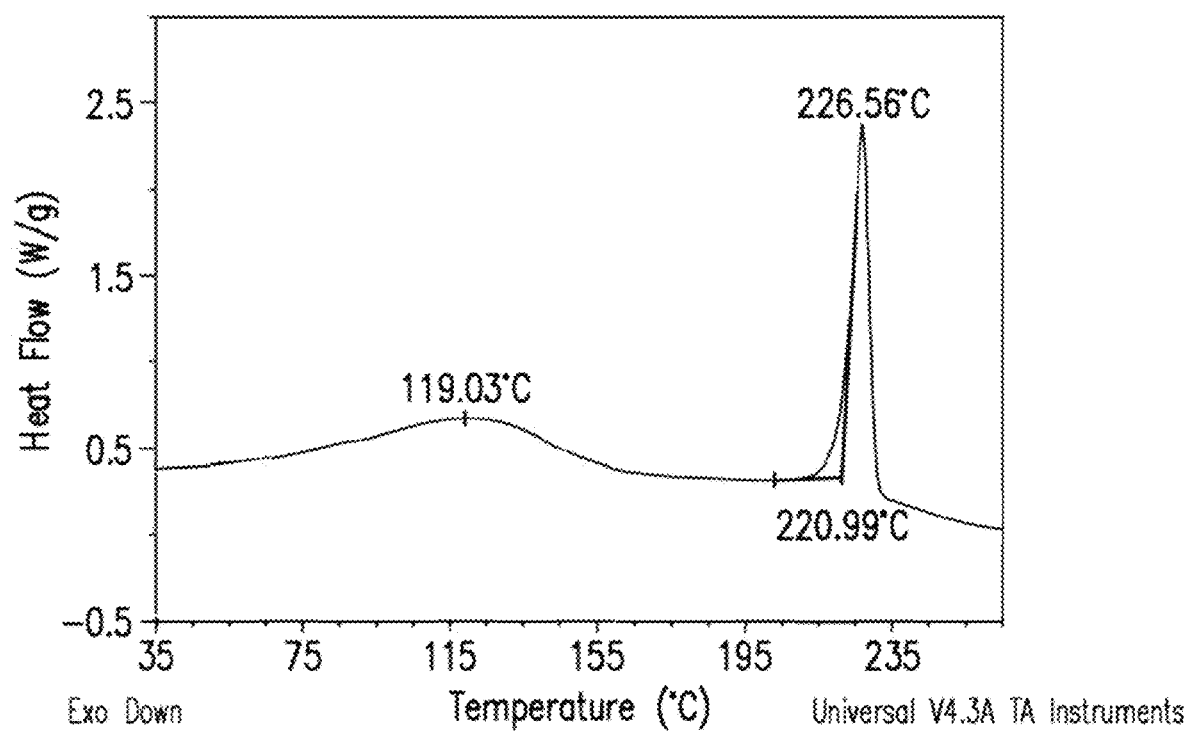
FIG. 23 is a differential scanning calorimetry curve of polymorph Form IV hydrochloride salt obtained from water.
Figure 24:
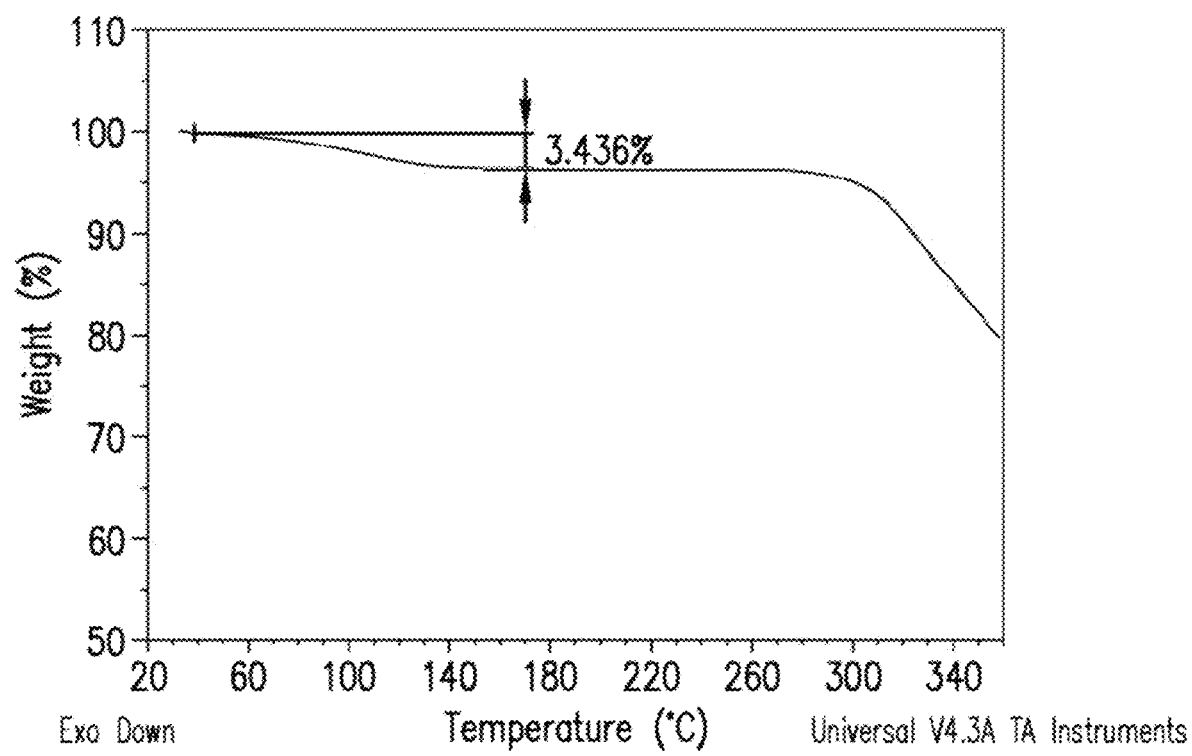
FIG. 24 shows a thermogravimetric analysis of polymorph Form IV hydrochloride salt obtained from water.

To a suspension of N-(3-(2-(3-fluoro-4-(4-methylpiperazin-1-yl)phenylamino)-7H-pyrrolo[2,3-d]pyrimidin-4-yloxy)phenyl)acrylamide (5 g, 10.3 mmol) in water (25 mL) was added aqueous HCl (1 M, 25 mL, 25 mmol). The mixture was stirred at ~40-50° C. until it the starting material dissolved. The solution was cooled to room temperature with stirring. The resulting crystals were collected and dried to yield the title compound (6 g, 95.2% yield), defined as polymorph Form IV. Elemental analysis: N: 17.49%; C: 57.51%; H: 5.32%. The XRPD, DSC, and TGA traces for this material are shown in FIGS. 22, 23, and 24, respectively.

Example 9-2 (Ethanol/Water (3:1))

Figure 25:
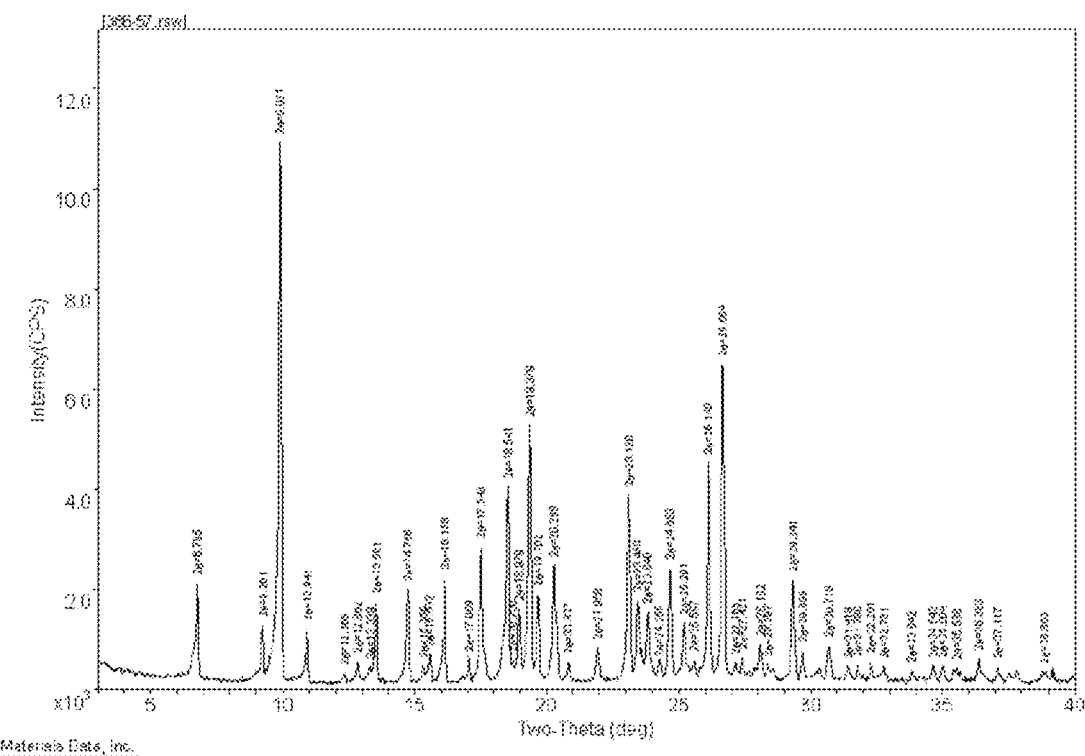
FIG. 25 is an X-ray powder diffractogram of polymorph Form IV hydrochloride salt obtained from 3:1 ethanol/water.
Figure 26:
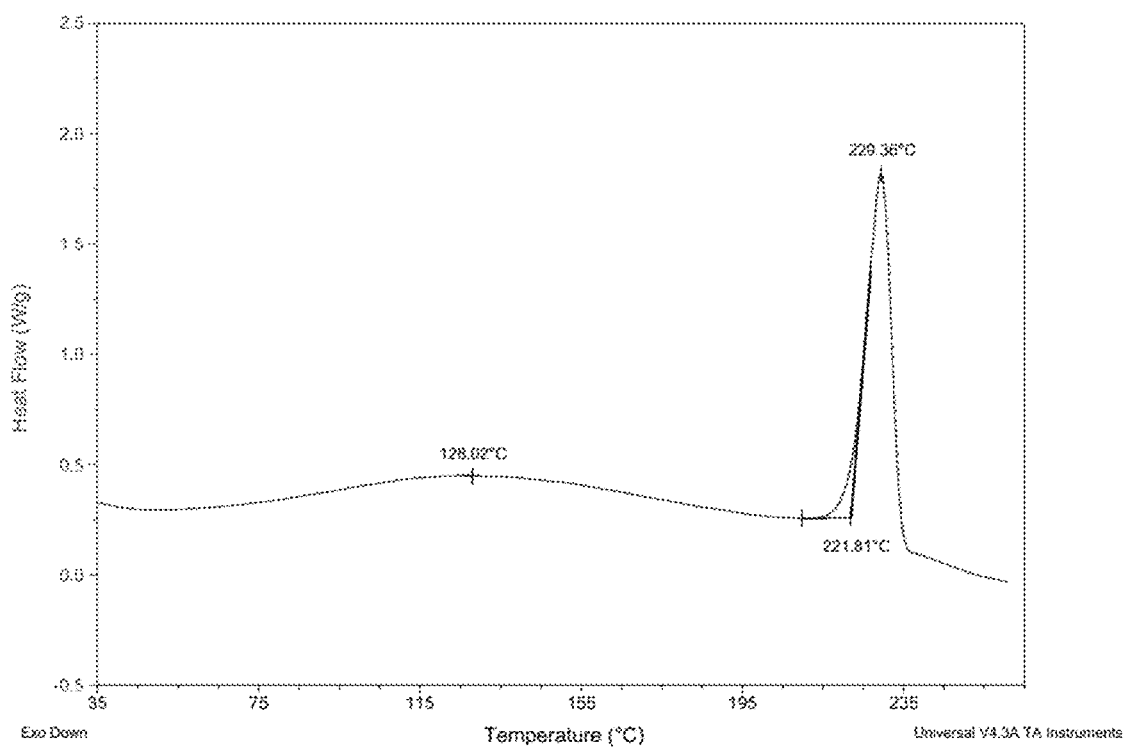
FIG. 26 is a differential scanning calorimetry curve of polymorph Form IV hydrochloride salt obtained from 3:1 ethanol/water.
Figure 27:
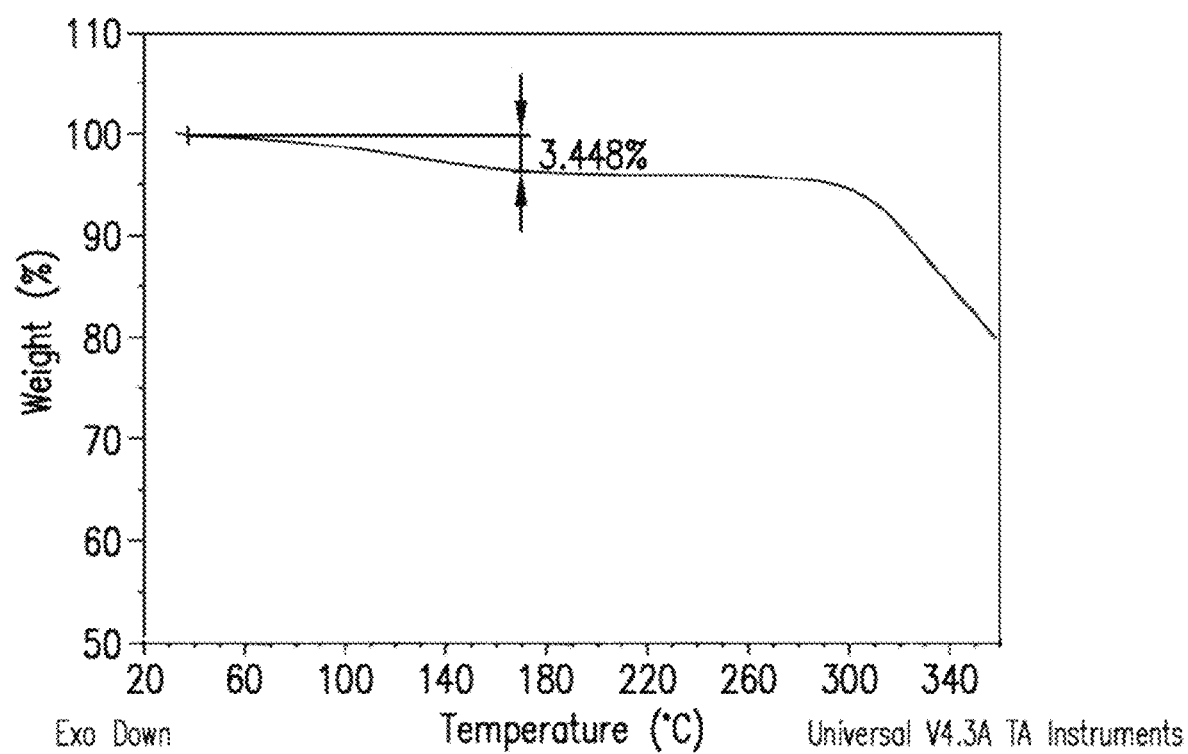
FIG. 27 shows a thermogravimetric analysis of polymorph Form IV hydrochloride salt obtained from 3:1 ethanol/water.

To the salt obtained in Example 9-1 (1.0 g) was added ethanol (15 mL) and water (5 mL). The resulting suspension was stirred at reflux temperature until it became clear and homogeneous. The solution was then allowed to cool to room temperature with stirring. The resulting crystals were collected and dried to yield the title compound (1 g, 100% yield) in a solid form defined as polymorph Form IV. Elemental analysis: N: 17.76%; C: 57.75%; H: 5.37%. The XRPD, DSC, and TGA traces for this material are shown in FIGS. 25, 26, and 27, respectively.

Example 9-3 (Ethanol/Water (1:1))

Figure 28:
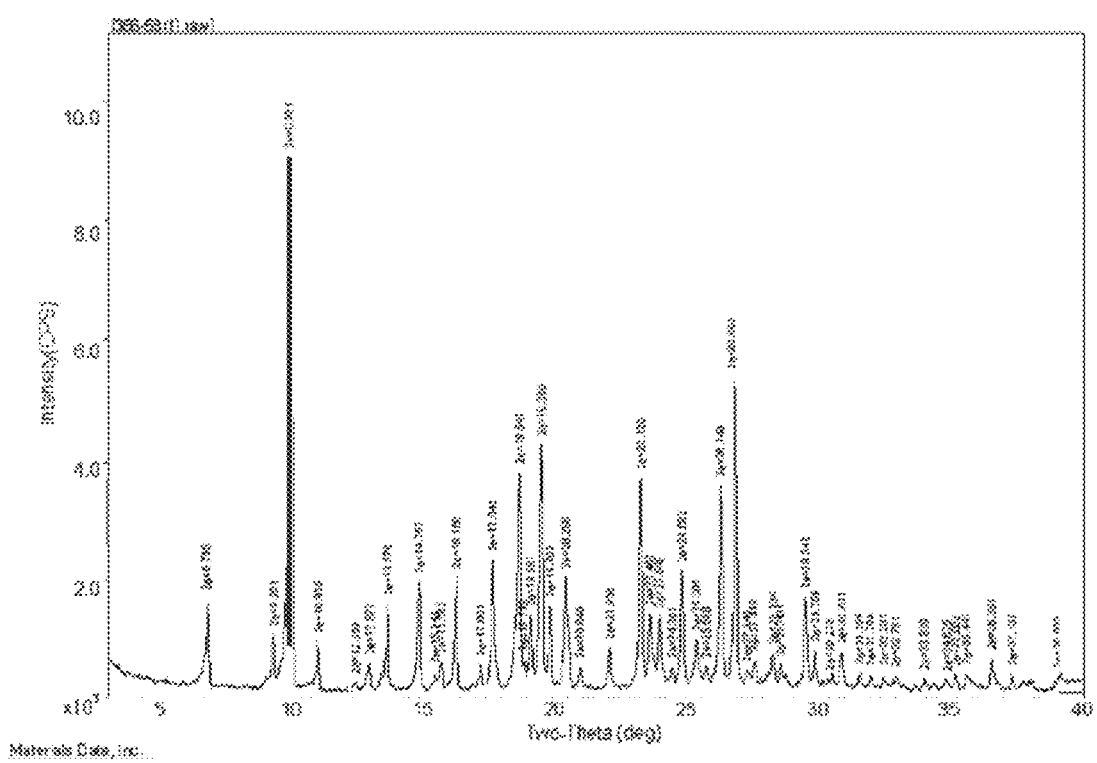
FIG. 28 is an X-ray powder diffractogram of polymorph Form IV hydrochloride salt obtained from 1:1 ethanol/water.
Figure 29:
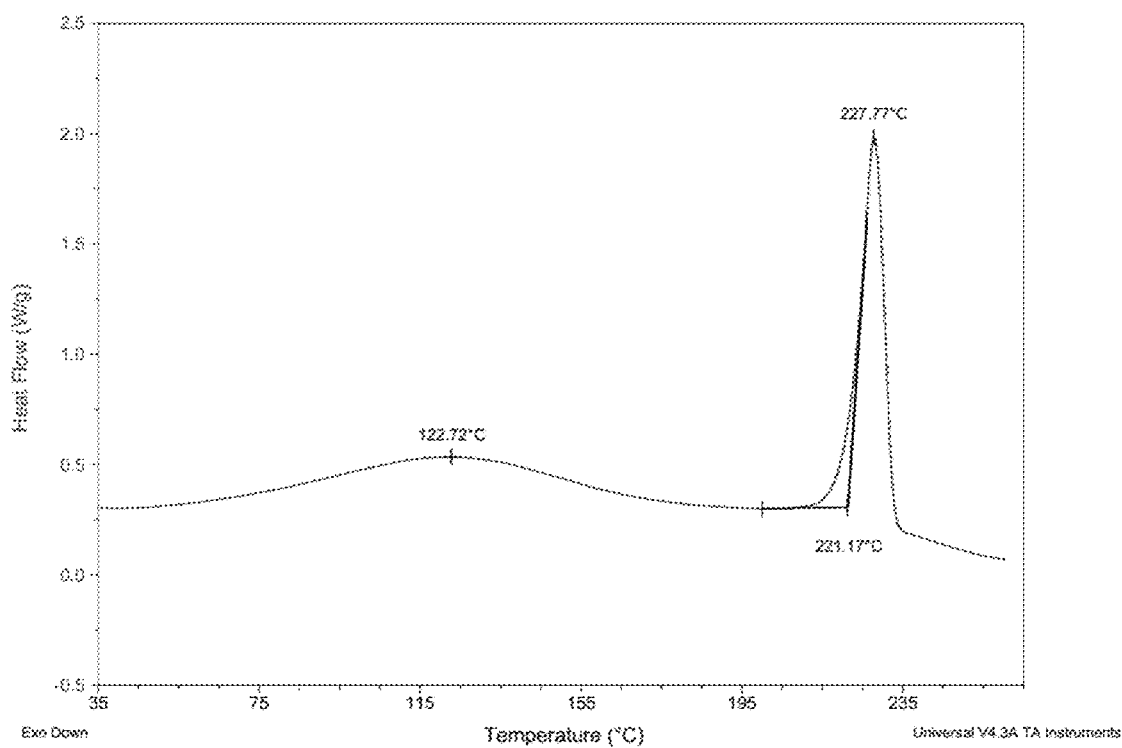
FIG. 29 is a differential scanning calorimetry curve of polymorph Form IV hydrochloride salt obtained from 1:1 ethanol/water.
Figure 30:
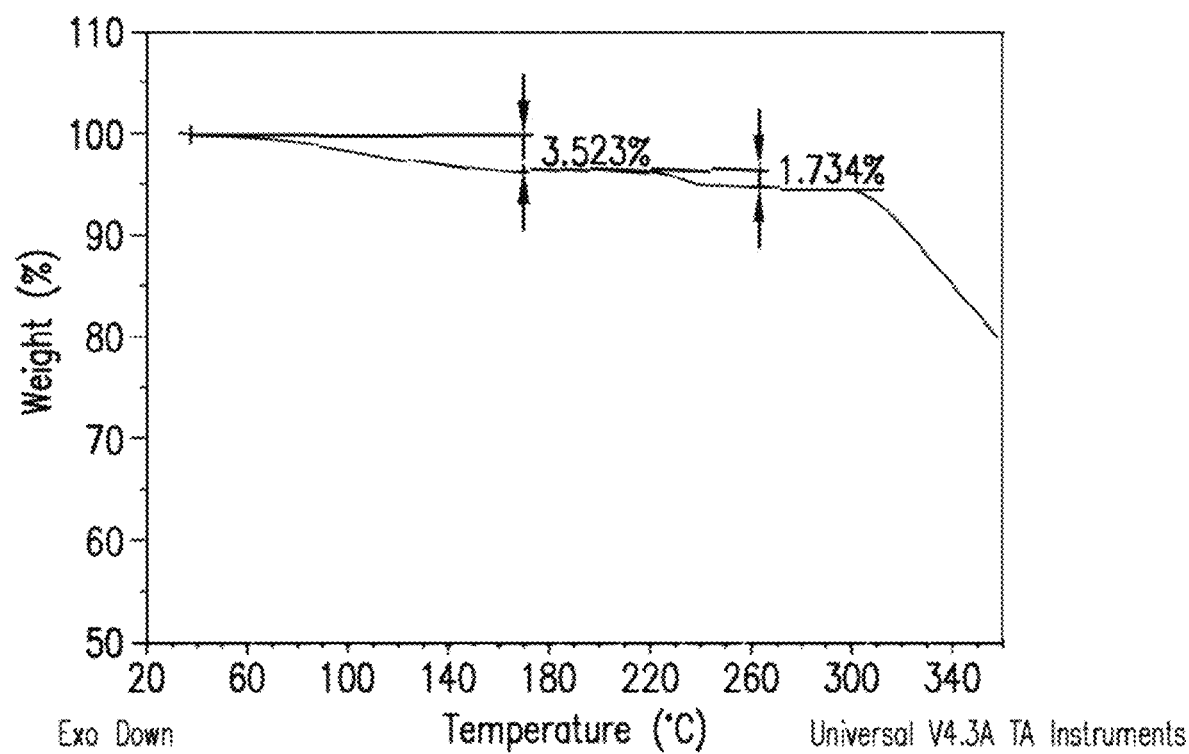
FIG. 30 shows a thermogravimetric analysis of polymorph Form IV hydrochloride salt obtained from 1:1 ethanol/water.

To the above HCl salt as polymorph Form IV (1.0 g) was added 50% aqueous ethanol (10 mL). The resulting suspension was stirred at reflux temperature until it became clear and homogeneous. The solution was then cooled to room temperature with stirring. The resulting crystals were collected and dried to yield the title compound (0.61 g, 61% yield) in a solid form defined as polymorph Form IV. Elemental analysis: N: 17.69%; C: 57.87%; H: 5.40%. The XRPD, DSC, and TGA traces for this material are shown in FIGS. 28, 29, and 30, respectively.

Example 9-4 (Ethanol/Water (5:7))

Figure 31:
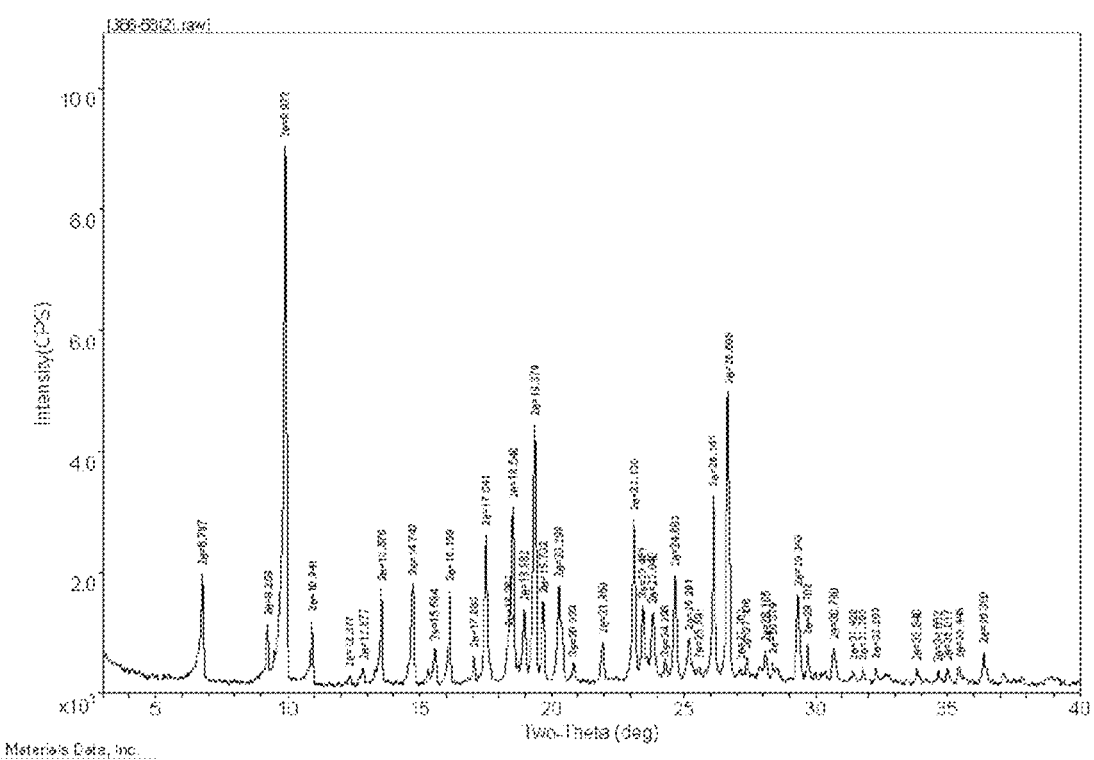
FIG. 31 is an X-ray powder diffractogram of polymorph Form IV hydrochloride salt obtained from 5:7 ethanol/water.
Figure 32:
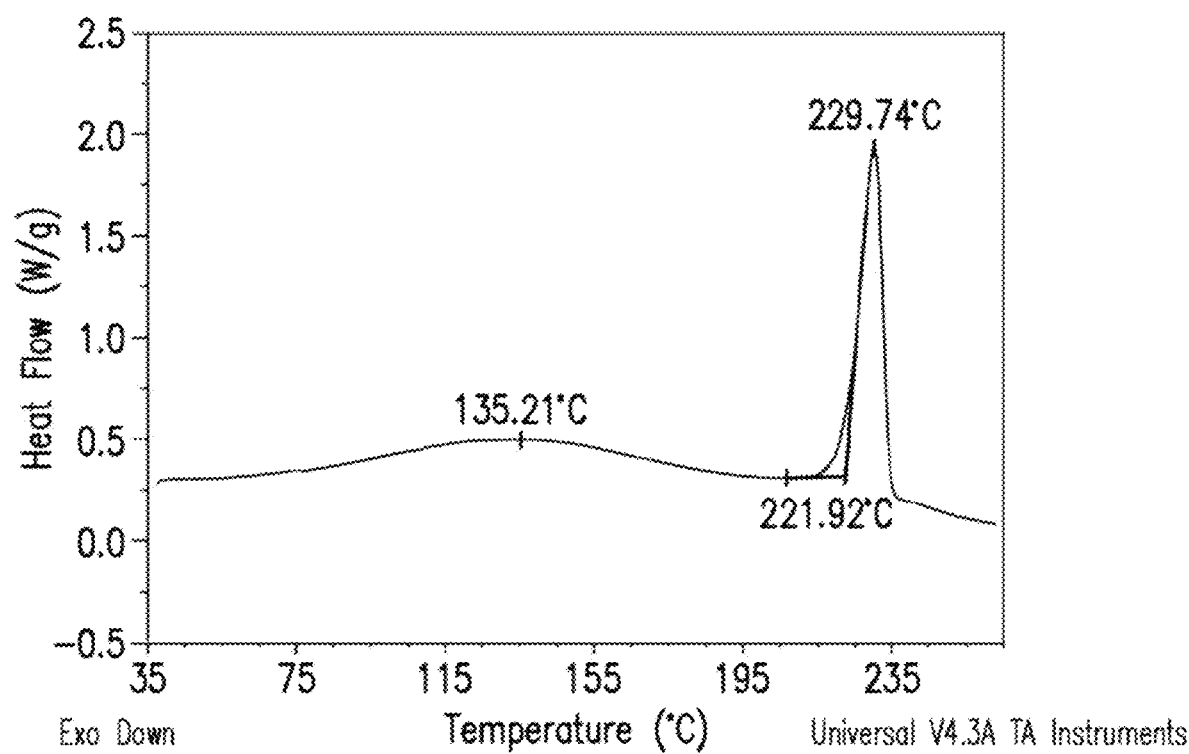
FIG. 32 is a differential scanning calorimetry curve of polymorph Form IV hydrochloride salt obtained from 5:7 ethanol/water.
Figure 33:
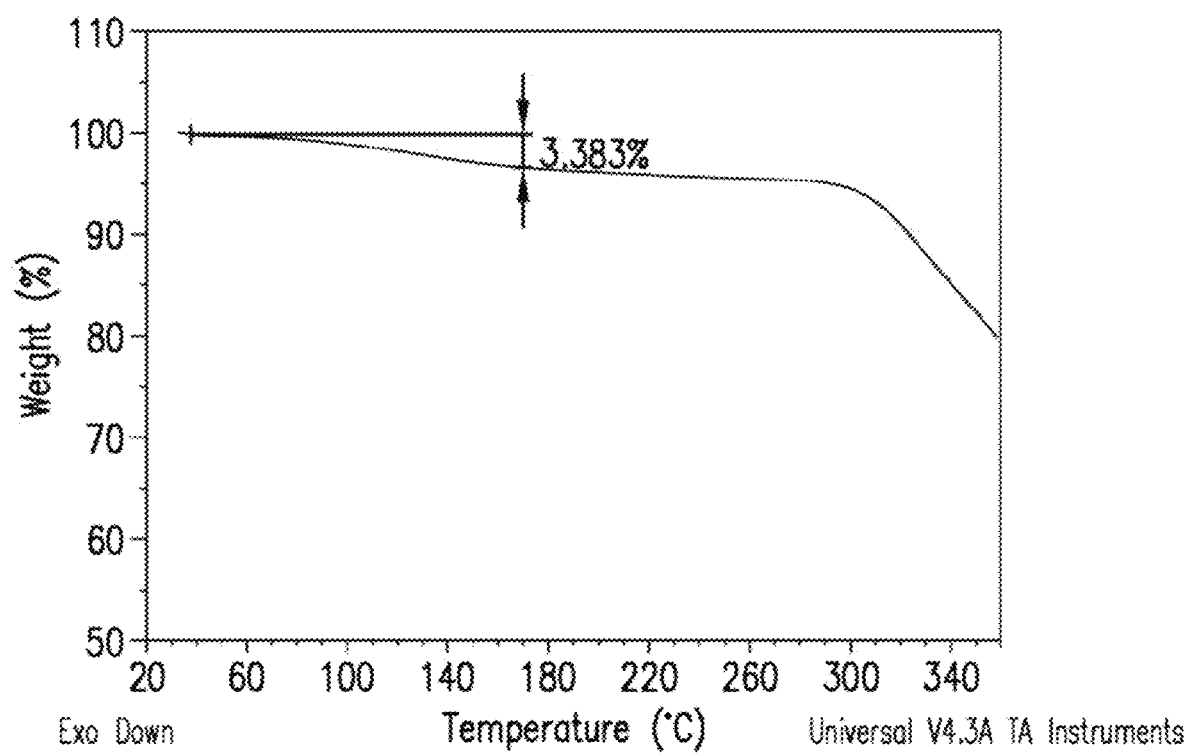
FIG. 33 shows a thermogravimetric analysis of polymorph Form IV hydrochloride salt obtained from 5:7 ethanol/water.

To the HCl salt (1.0 g) was added ethanol (7.5 mL) and water (10.5 mL). The resulting suspension was stirred at reflux temperature until it became clear and homogeneous. The solution was then cooled to room temperature with stirring. The resulting crystals were collected and dried to yield the title compound (0.6 g, 60% yield) in a solid form defined as polymorph Form IV. Elemental analysis: N: 17.79%; C: 57.92%; H: 5.40%. The XRPD, DSC, and TGA traces for this material are shown in FIGS. 31, 32, and 33, respectively.

Example 9-5 (Ethanol/Water (3:2))

Figure 34:
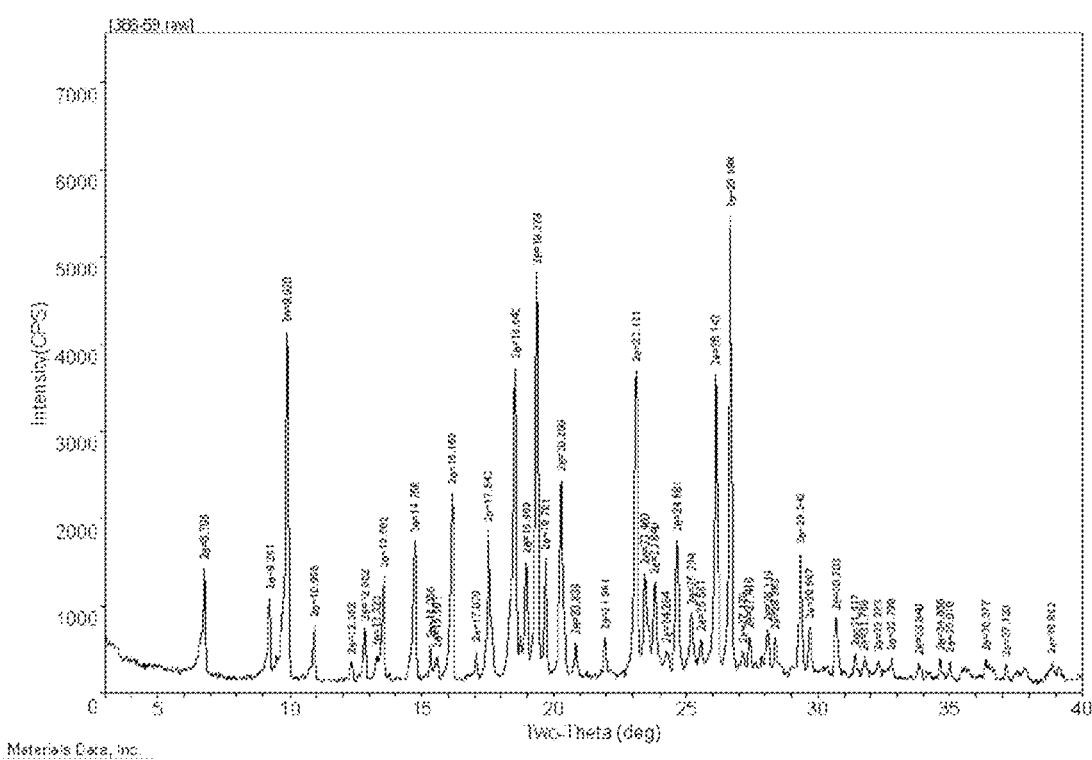
FIG. 34 is an X-ray powder diffractogram of polymorph Form IV hydrochloride salt obtained from 3:2 ethanol/water.
Figure 35:
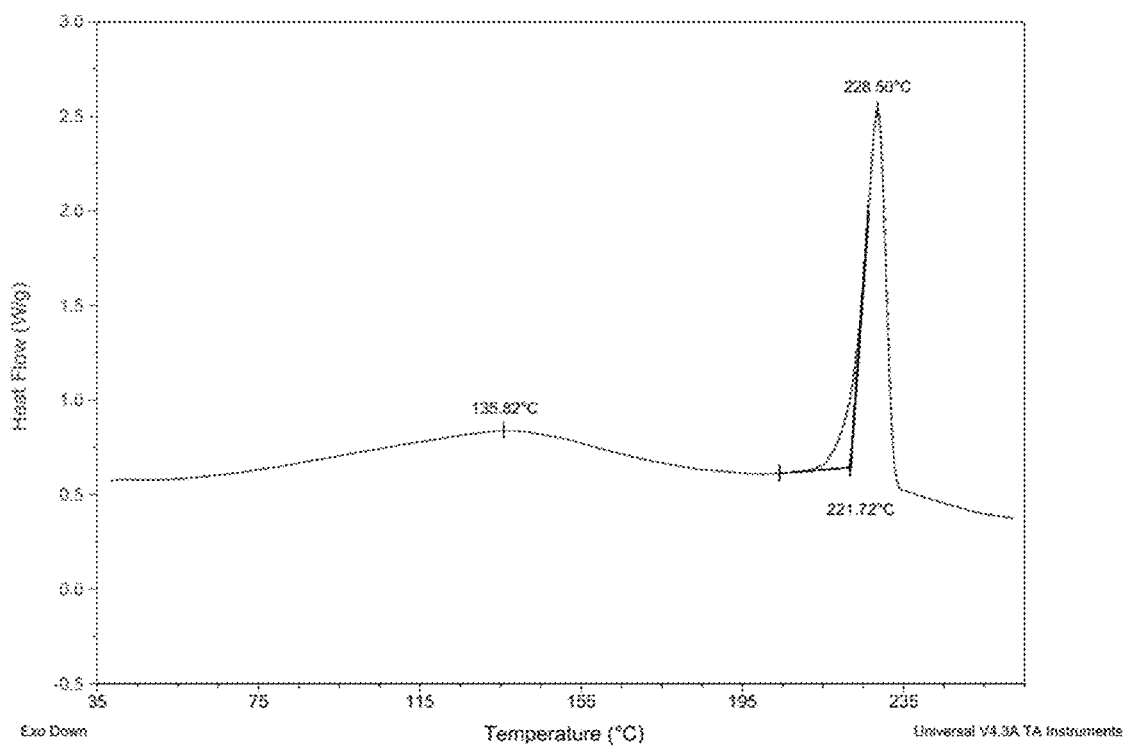
FIG. 35 is a differential scanning calorimetry curve of polymorph Form IV hydrochloride salt obtained from 3:2 ethanol/water.
Figure 36:
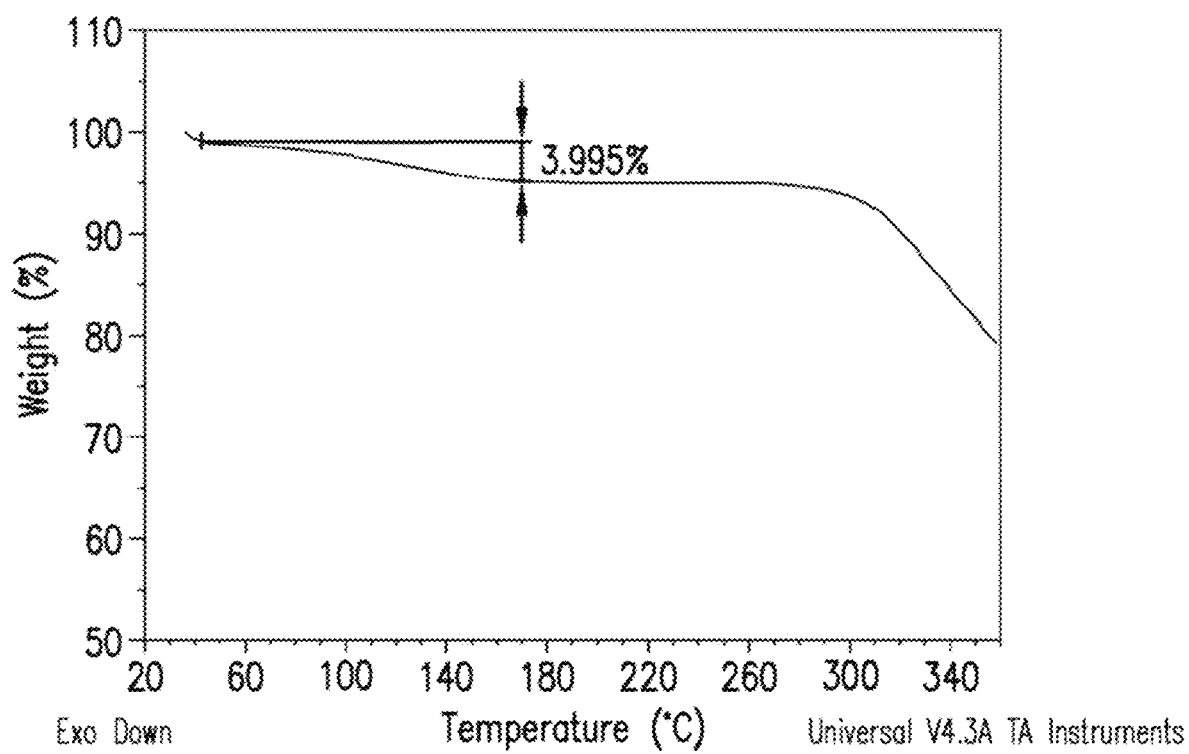
FIG. 36 shows a thermogravimetric analysis of polymorph Form IV hydrochloride salt obtained from 3:2 ethanol/water.

To the HCl salt (1.0 g) was added ethanol (6 mL) and water (4 mL). The resulting suspension was stirred at reflux temperature until it became clear and homogeneous. The solution was then cooled to room temperature with stirring. The resulting crystals were collected and dried to yield the title compound (0.64 g, 64% yield) in a solid form defined as polymorph Form IV. Elemental analysis: N: 17.66%; C: 57.77%; H: 5.42%. The XRPD, DSC, and TGA traces for this material are shown in FIGS. 34, 35, and 36, respectively.

Example 9-6 (Ethanol/Water (7:3))

Figure 37:
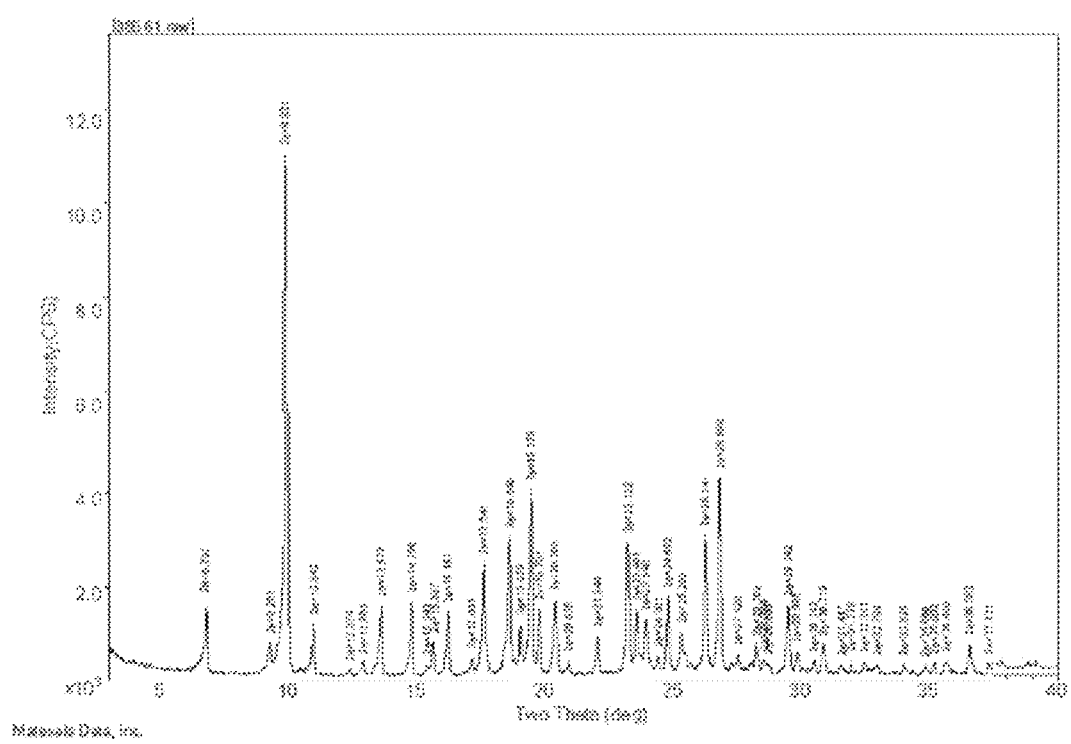
FIG. 37 is an X-ray powder diffractogram of polymorph Form IV hydrochloride salt obtained from 7:3 ethanol/water.
Figure 38:
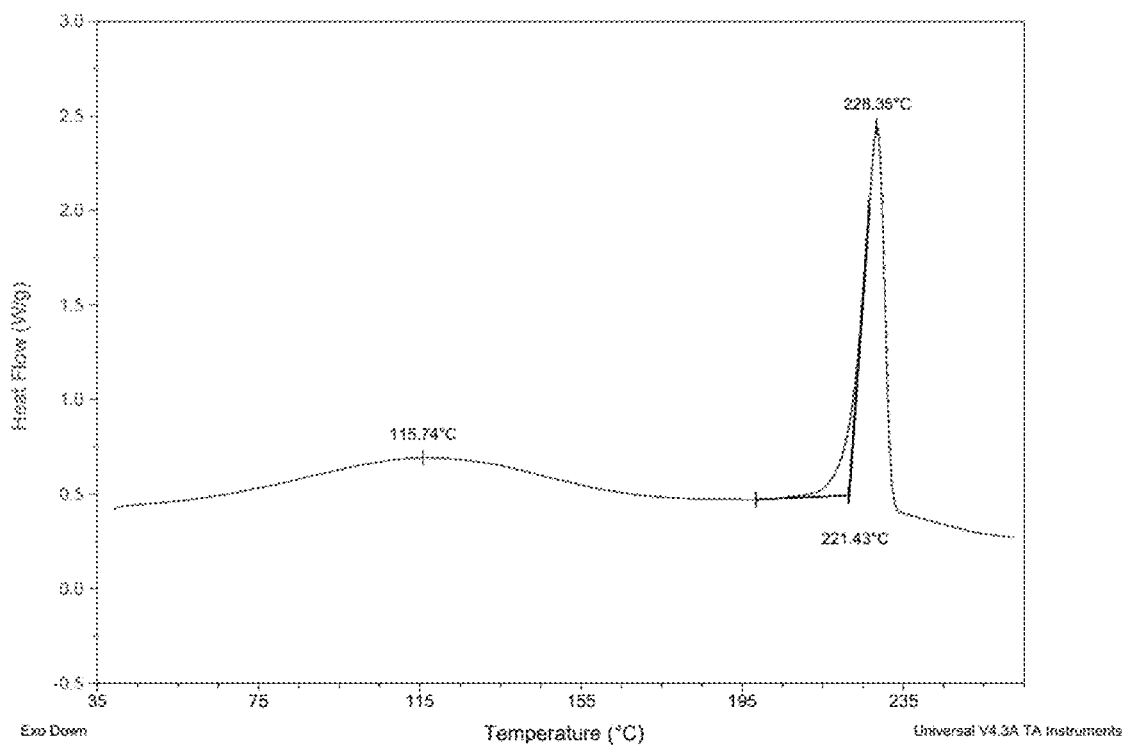
FIG. 38 is a differential scanning calorimetry curve of polymorph Form IV hydrochloride salt obtained from 7:3 ethanol/water.
Figure 39:
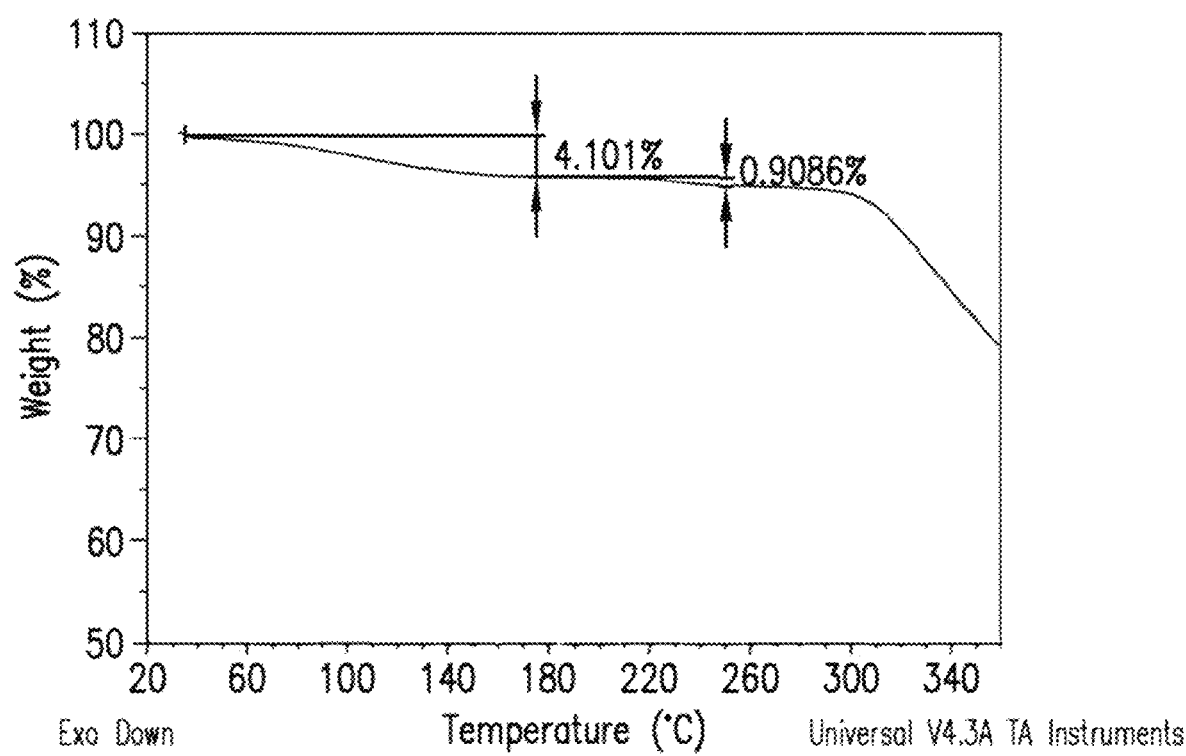
FIG. 39 shows a thermogravimetric analysis of polymorph Form IV hydrochloride salt obtained from 7:3 ethanol/water.

To the HCl salt (1.0 g) was added 70% aqueous ethanol (20 mL). The resulting suspension was stirred at reflux temperature until it became clear and homogeneous. The solution was then cooled to room temperature with stirring. The resulting crystals were collected and dried to yield the title compound (0.7 g, 70% yield) in a solid form defined as polymorph Form IV. Elemental analysis: N: 17.78%; C: 57.76%; H: 5.40%. The XRPD, DSC, and TGA traces for this material are shown in FIGS. 37, 38, and 39, respectively.

Figure 40:
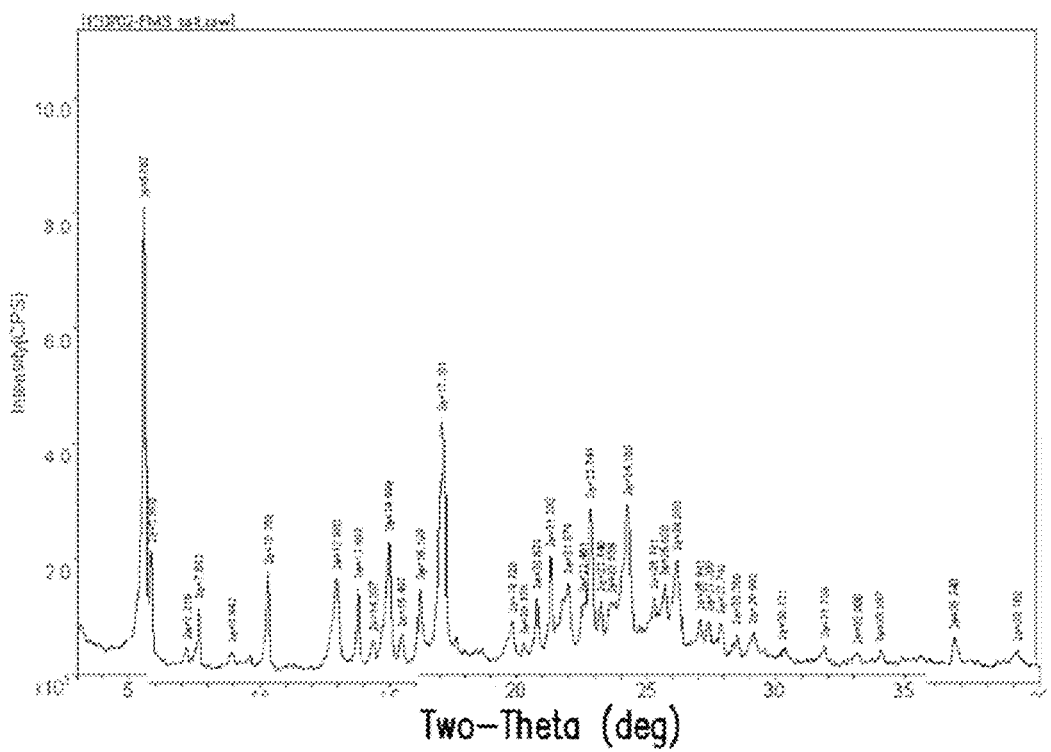
FIG. 40 is an X-ray powder diffractogram of polymorph Form V fumarate salt obtained from 1:19 ethanol/water.
Figure 41:
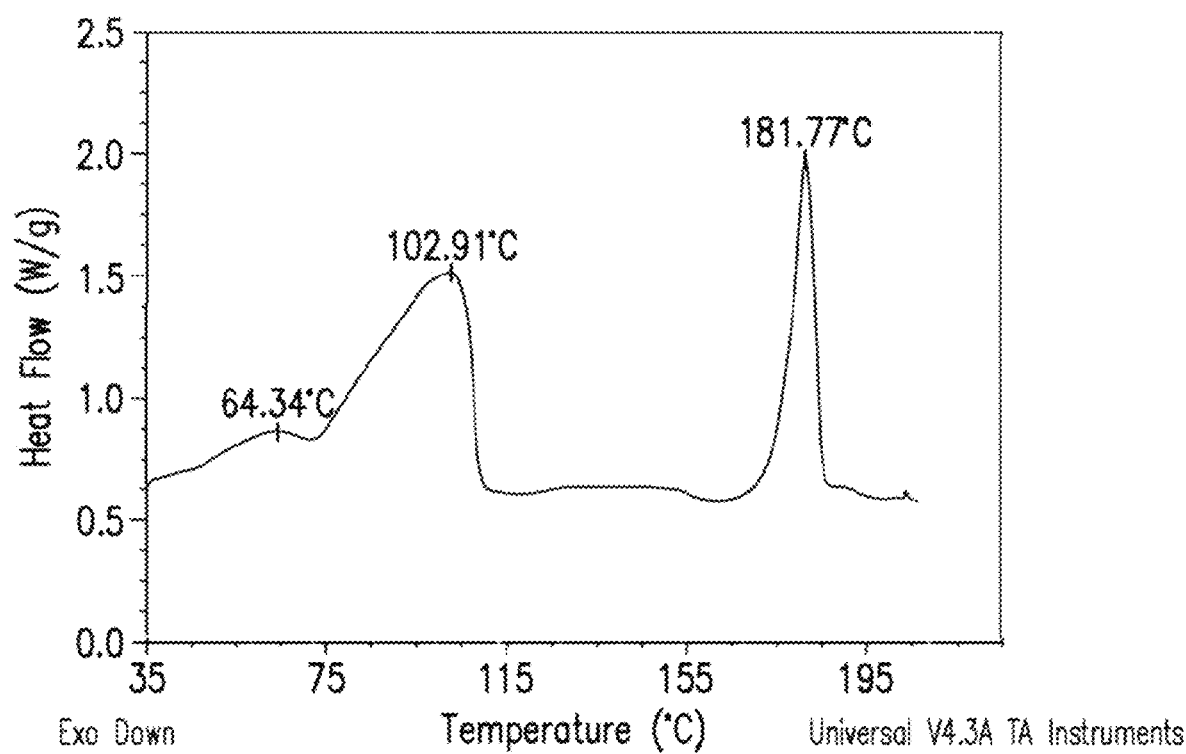
FIG. 41 is a differential scanning calorimetry curve of polymorph Form V fumarate salt obtained from 1:19 ethanol/water.
Figure 42:
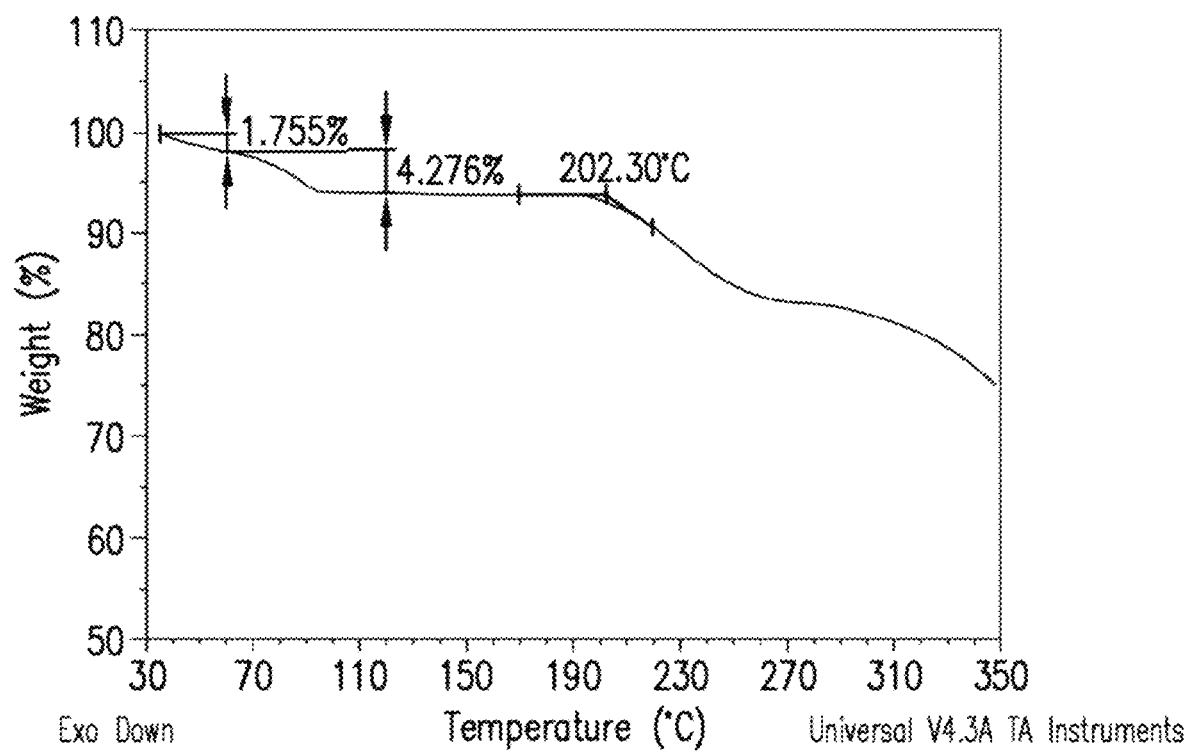
FIG. 42 shows a thermogravimetric analysis of polymorph Form V fumarate salt obtained from 1:19 ethanol/water.

Example 10. Synthesis of N-(3-(2-(3-fluoro-4-(4-methylpiperazin-1-yl)phenylamino)-7H-pyrrolo[2,3-d]pyrimidin-4-yloxy)phenyl)acrylamide fumarate salt A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (5 g, 10.3 mmol) in 5% aq. ethanol (60 mL) at 40° C. was treated with a solution of fumaric acid (1.5 g, 12.9 mmol) in 5% aq. ethanol (15 mL). Crystals formed, which were collected and dried to yield the title compound (5.4 g, 87.2% yield) defined as polymorph Form V. Elemental analysis: N: 15.31%; C: 57.59%; H: 5.38%. The XRPD, DSC, and TGA traces for this material are shown in FIGS. 40, 41, and 42, respectively.

Figure 43:
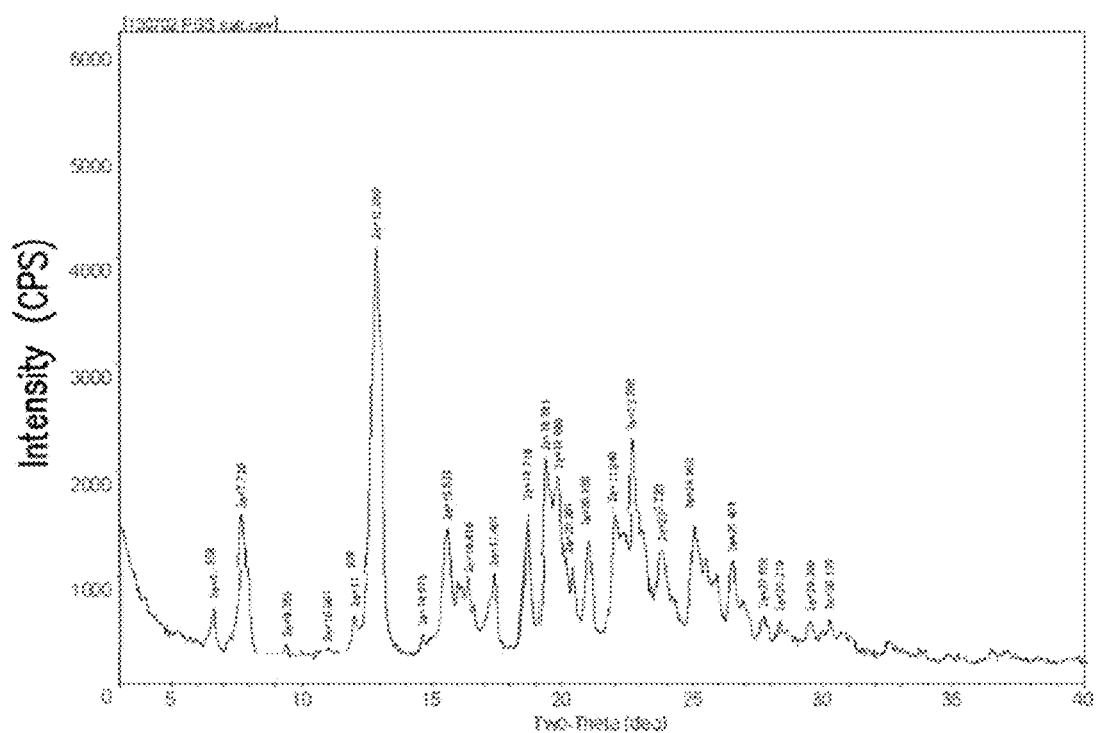
FIG. 43 is an X-ray powder diffractogram of polymorph Form VI malate salt obtained from 1:9 ethanol/water.
Figure 44:
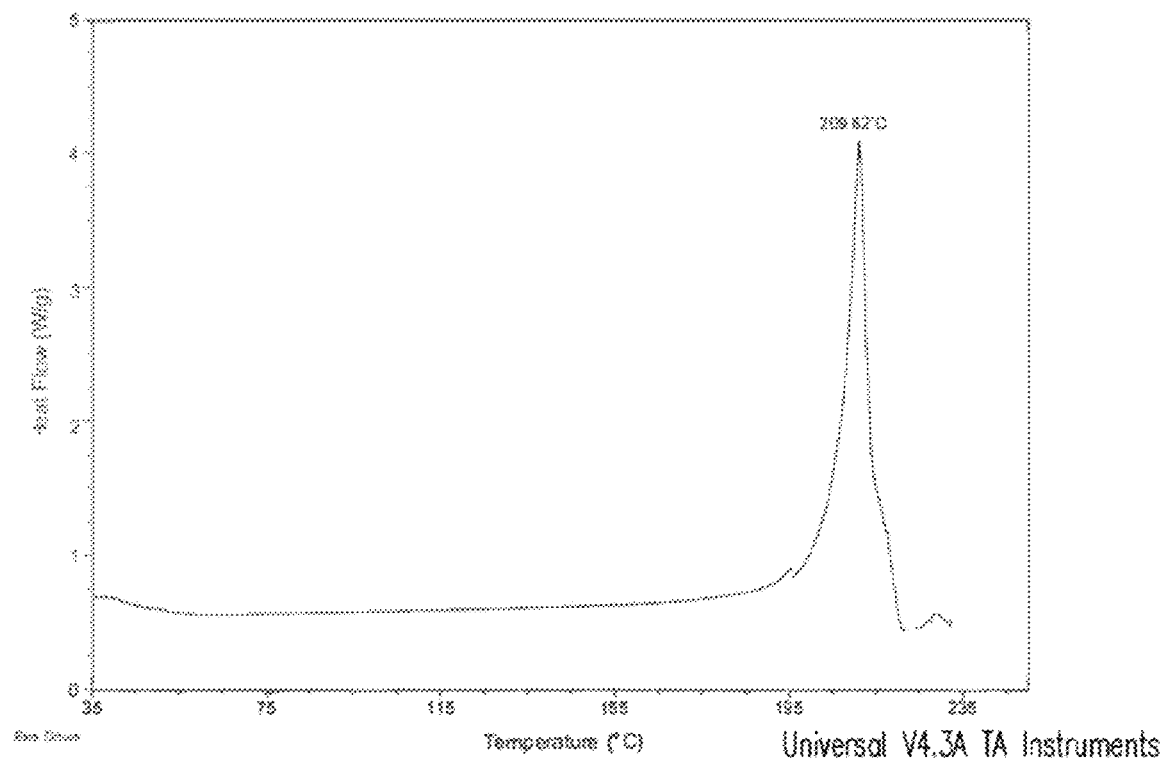
FIG. 44 is a differential scanning calorimetry curve of polymorph Form VI malate salt obtained from 1:9 ethanol/water.
Figure 45:
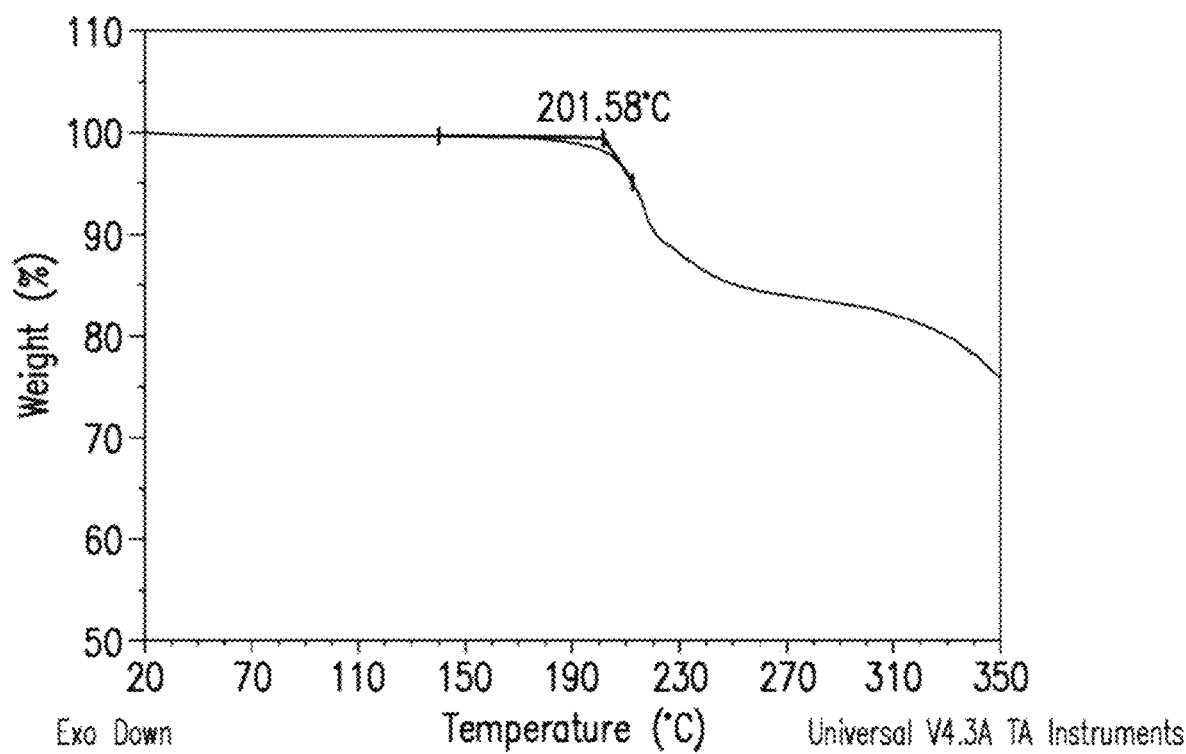
FIG. 45 shows a thermogravimetric analysis of polymorph Form VI malate salt obtained from 1:9 ethanol/water.

Example 11. Synthesis of N-(3-(2-(3-fluoro-4-(4-methylpiperazin-1-yl)phenylamino)-7H-pyrrolo[2,3-d]pyrimidin-4-yloxy)phenyl)acrylamide malate salt A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (2 g, 4.1 mmol) in 10% aq. ethanol (20 mL) at 40° C. was treated with a solution of DL-malic acid (660 mg, 4.93 mmol) in 10% aq. ethanol (5 mL). The solution was cooled to room temperature with stirring. Crystals formed, which were collected and dried to yield the title compound (1.4 g, 55% yield) defined as polymorph Form VI. Elemental analysis: N: 15.17%; C: 57.28%; H: 5.09%. The XRPD, DSC, and TGA traces for this material are shown in FIGS. 43, 44, and 45, respectively.

Figure 46:
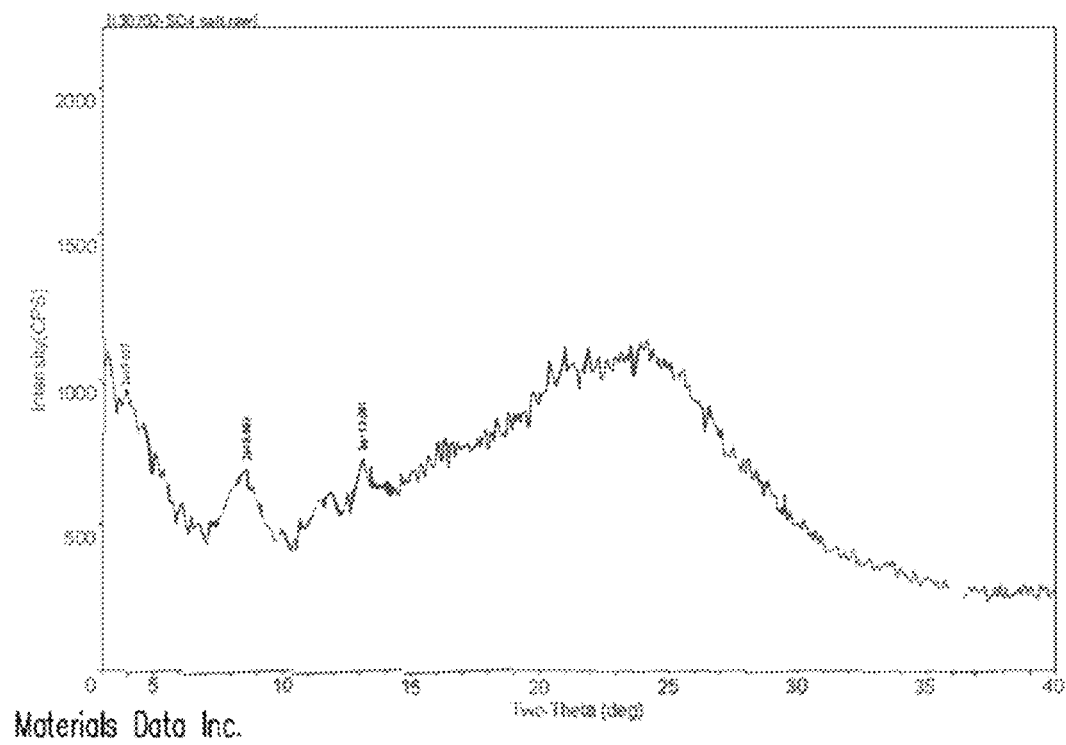
FIG. 46 is an X-ray powder diffractogram of an amorphous form of the sulfate salt obtained from water.
Figure 47:
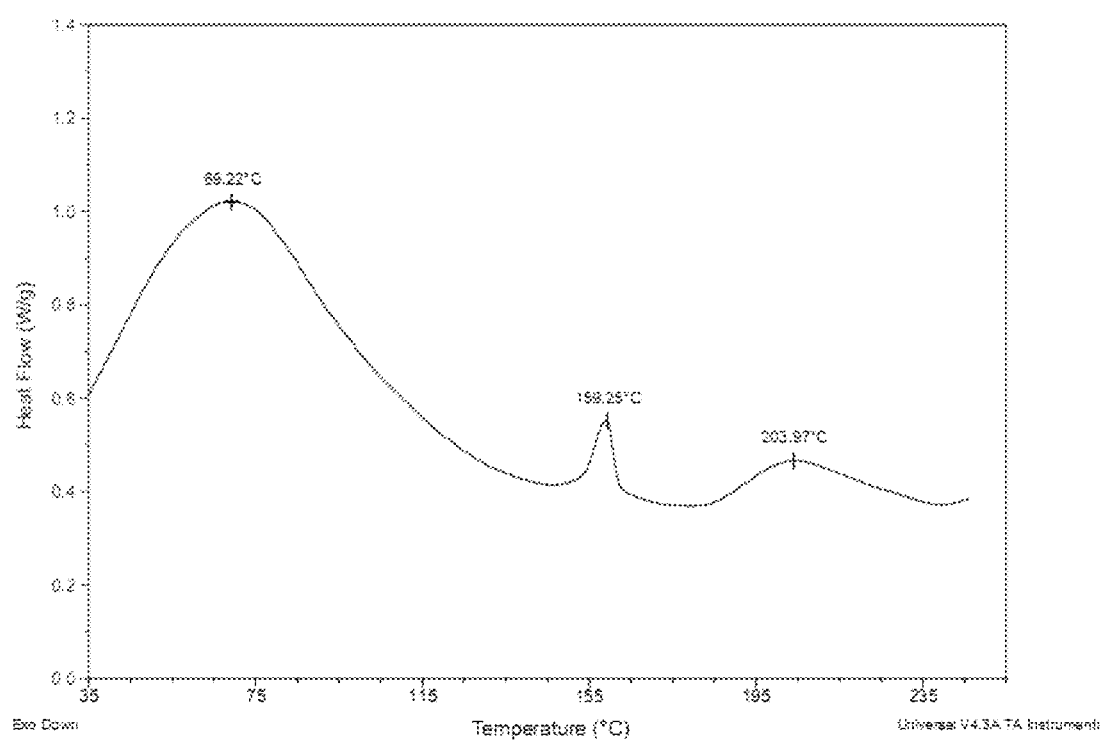
FIG. 47 is a differential scanning calorimetry curve of an amorphous form of the sulfate salt obtained from water.
Figure 48:
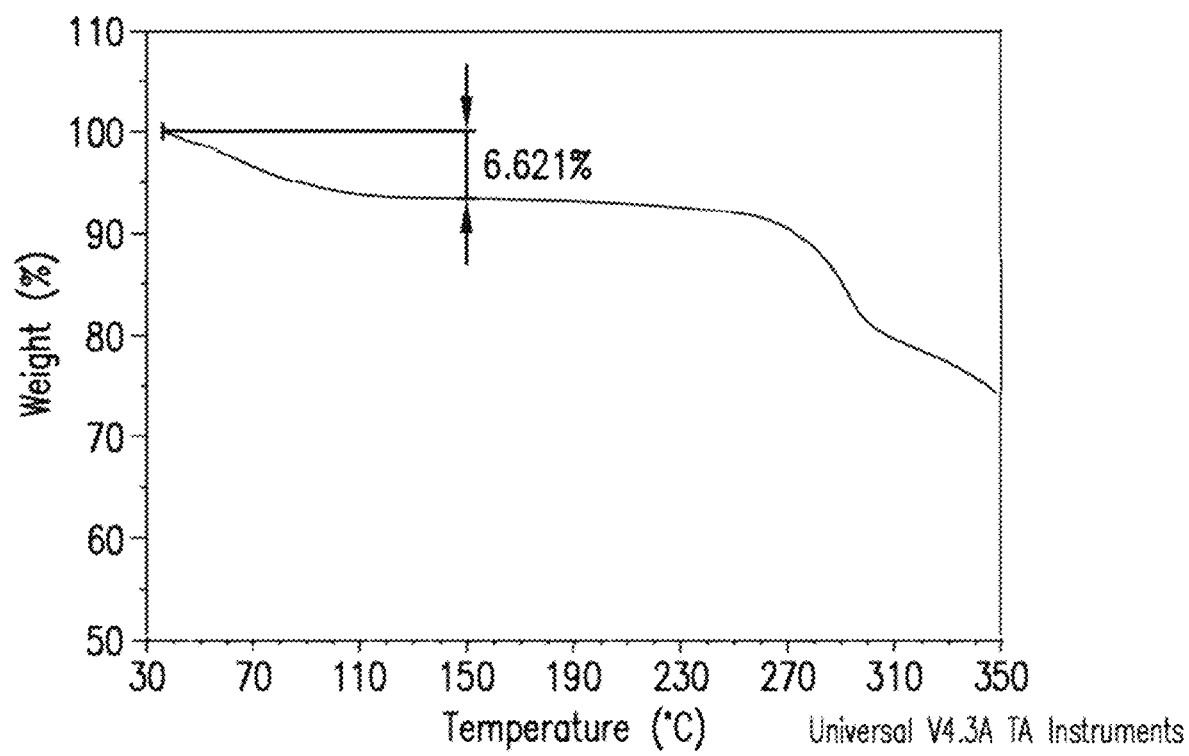
FIG. 48 shows a thermogravimetric analysis of an amorphous form of the sulfate salt obtained from water.

Example 12. Synthesis of N-(3-(2-(3-fluoro-4-(4-methylpiperazin-1-yl)phenylamino)-7H-pyrrolo[2,3-d]pyrimidin-4-yloxy)phenyl)acrylamide sulfate salt A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (2 g, 4.1 mmol) in water (10 mL) at room temperature was treated with 1 M $H_2SO_4$ (5 mL). Crystals formed, which were collected and dried to yield the title compound (1.7 g, 70.8% yield) defined as an amorphous form. Elemental analysis: N: 15.76%; C: 51.15%; H: 5.41%. The XRPD, DSC, and TGA traces for this material are shown in FIGS. 46, 47, and 48, respectively.

Figure 49:
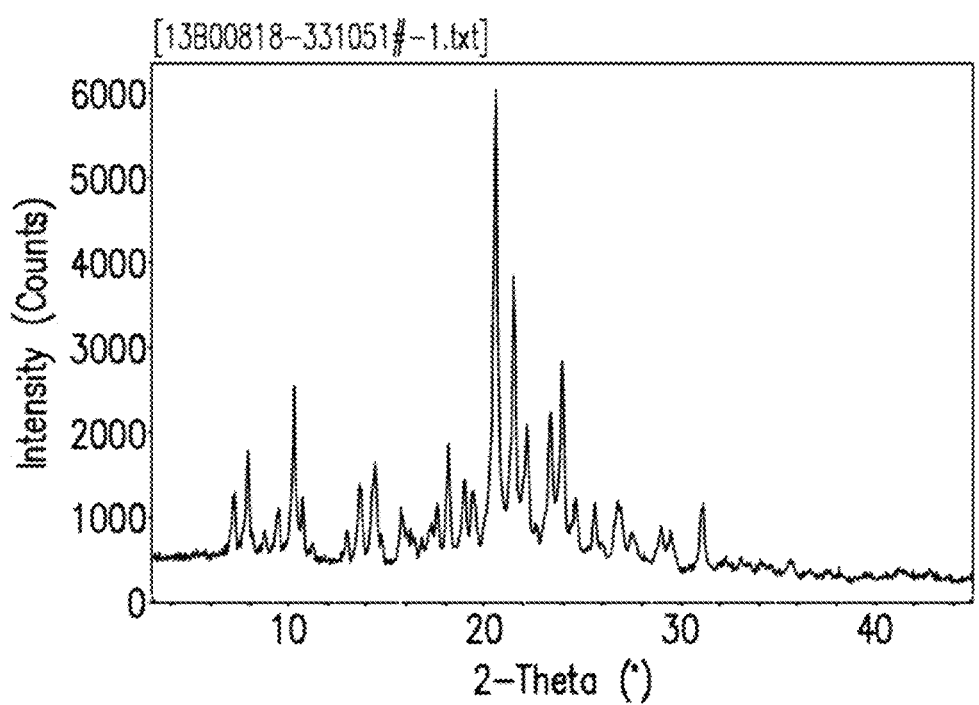
FIG. 49 is an X-ray powder diffractogram of an amorphous form of the mesylate salt obtained from ethanol/ethyl acetate/water.

Example 13. Synthesis of N-(3-(2-(3-fluoro-4-(4-methylpiperazin-1-yl)phenylamino)-7H-pyrrolo[2,3-d]pyrimidin-4-yloxy)phenyl)acrylamide mesylate salt A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (1.3 g, 2.67 mmol) in ethanol (10 mL) at 50° C. was treated with methanesulfonic acid (563 mg, 5.86 mmol). The solution was cooled to –10 C without crystal formation. The mixture was concentrated, and the residue dissolved in a mixture of ethanol (5 mL), ethyl acetate (10 mL), and water (0.5 mL), and was stirred at reflux temperature. The solution was cooled to 35° C. and crystals appeared. The resulting crystals were collected and dried to yield the title compound (1.2 g, 66.3% yield) in a solid form defined as amorphous form. The XRPD trace for this material is shown in FIG. 49.

Figure 50:
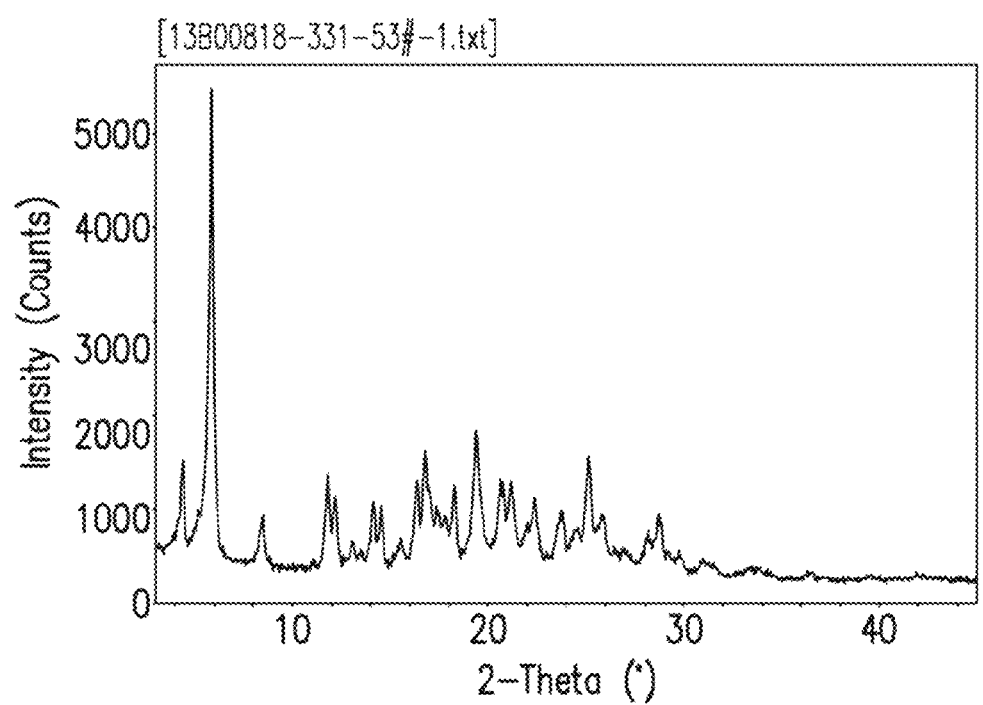
FIG. 50 is an X-ray powder diffractogram of an amorphous form of the tosylate salt obtained from water/ethyl acetate.

Example 14. Synthesis of N-(3-(2-(3-fluoro-4-(4-methylpiperazin-1-yl)phenylamino)-7H-pyrrolo[2,3-d]pyrimidin-4-yloxy)phenyl)acrylamide tosylate salt A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (2.0 g, 4.10 mmol) in ethanol (4 mL) and water (1 mL) at 60° C. was treated with p-toluenesulfonic acid (1.7 g, 9.88 mmol). Ethyl acetate (20 mL) was then added, and the resulting solution was stirred at reflux temperature. The solution was cooled to 0° C. and crystals appeared. The resulting crystals were collected and dried to yield the title compound (2.2 g, 81.5% yield) in a solid form defined as amorphous form. The XRPD trace for this material is shown in FIG. 50.

Example 15. Synthesis of N-(3-(2-(3-fluoro-4-(4-methylpiperazin-1-yl)phenylamino)-7H-pyrrolo[2,3-d]pyrimidin-4-yloxy)phenyl)acrylamide hydrobromide salt Example 15-1 (Water)

Figure 51:
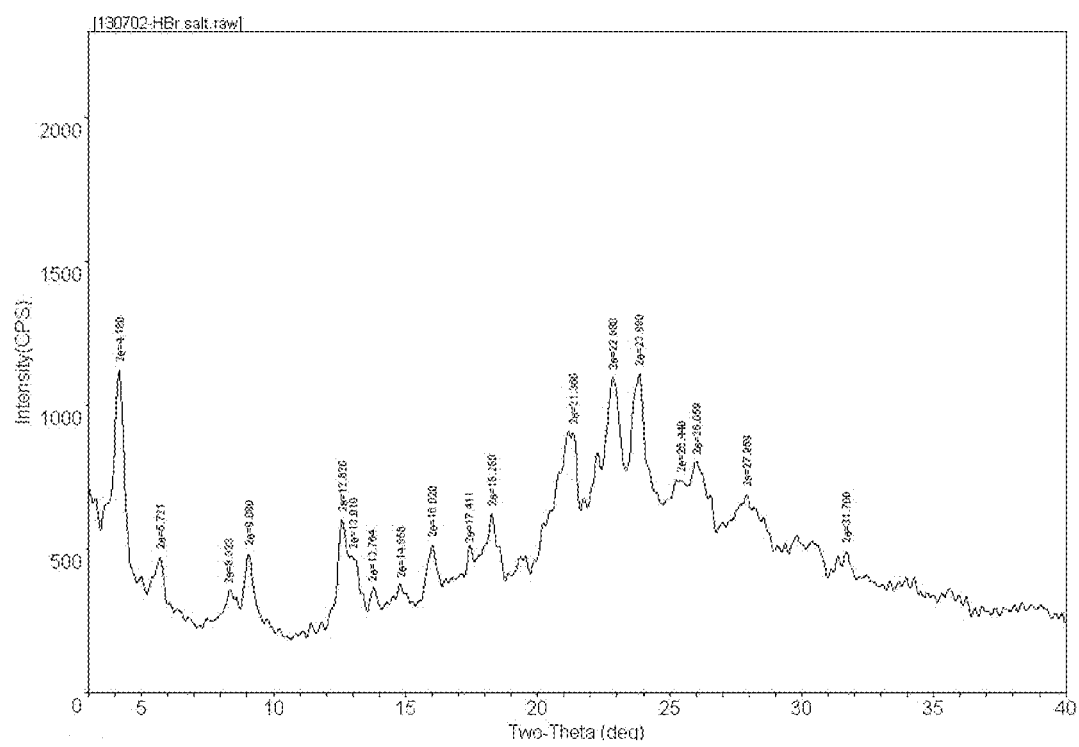
FIG. 51 is an X-ray powder diffractogram of an amorphous form of the hydrobromide salt obtained from water.
Figure 52:
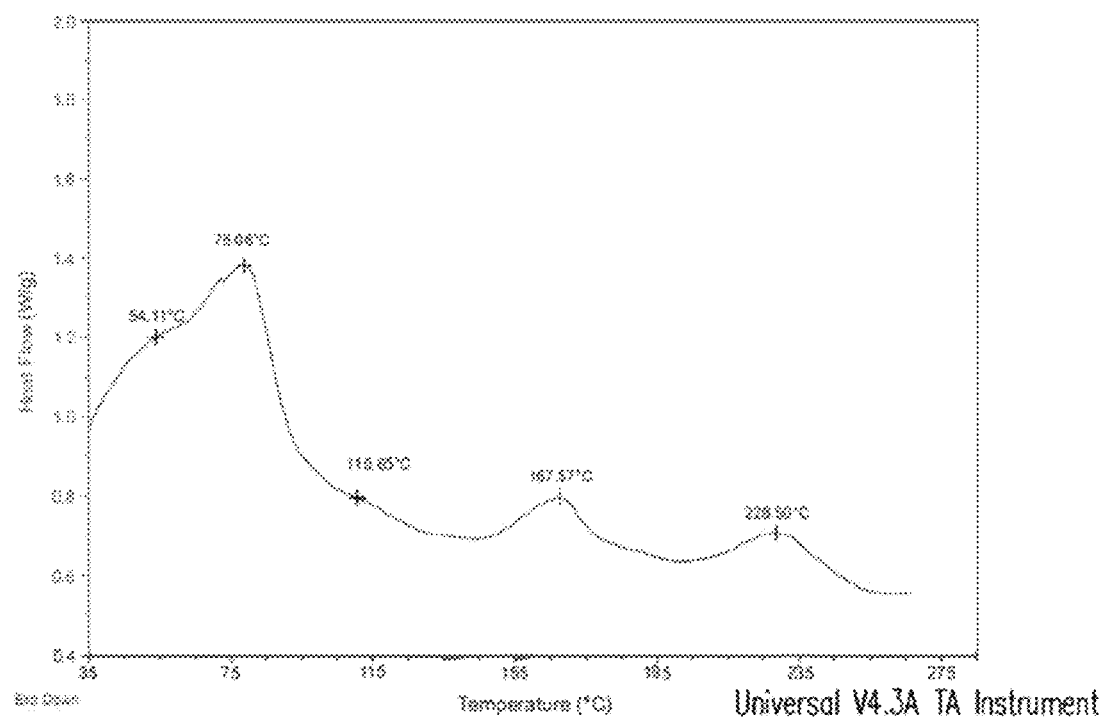
FIG. 52 is a differential scanning calorimetry curve of an amorphous form of the hydrobromide salt obtained from water.
Figure 53:
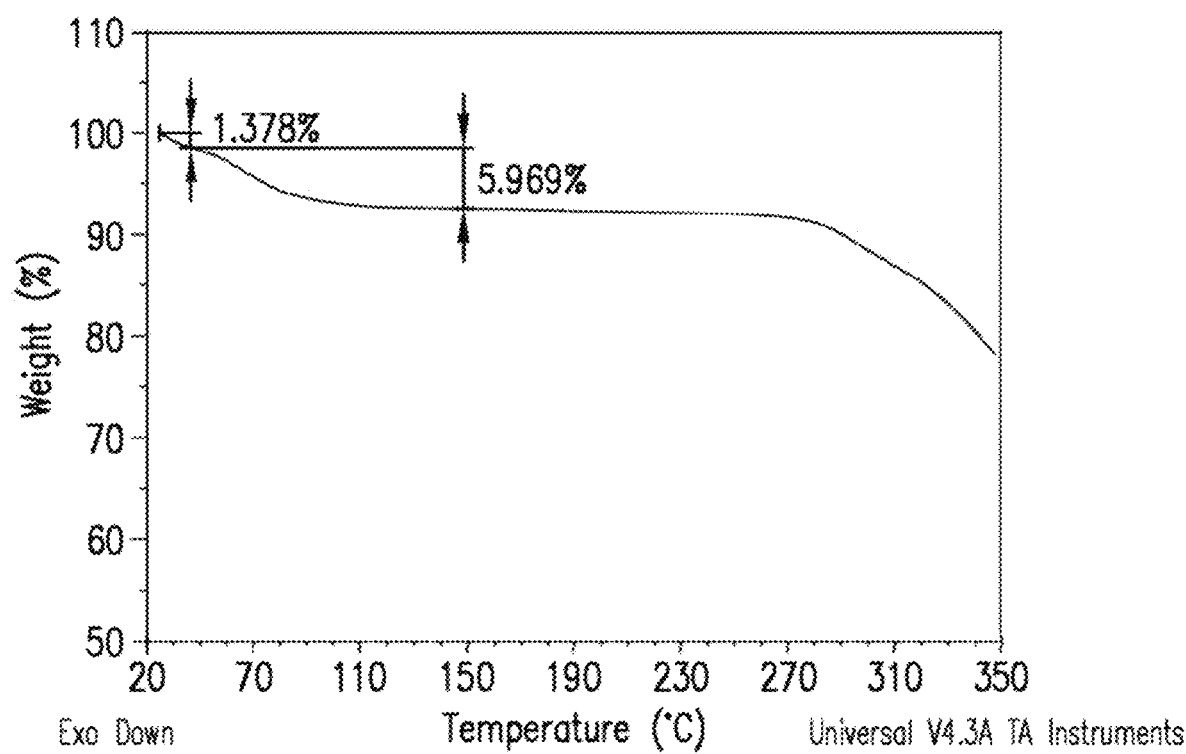
FIG. 53 shows a thermogravimetric analysis of an amorphous form of the hydrobromide salt obtained from water.

A stirred suspension of N-(3-(2-(3-fluoro-4-(4-methylpiperazin-1-yl)phenylamino)-7H-pyrrolo[2,3-d]pyrimidin-4-yloxy)phenyl)acrylamide (2.0 g, 4.10 mmol) in water (10 mL) at room temperature was treated with 1 M HBr (10 mL). The resulting crystals were collected and dried to yield the title compound (1.8 g, 67.7% yield) in a solid form defined as amorphous form. Elemental analysis: N: 14.92%; C: 48.26%; H: 5.02%. The XRPD, DSC, and TGA traces for this material are shown in FIGS. 51, 52, and 53, respectively.

Example 15-2 (Ethanol/Water (1:3))

Figure 54:
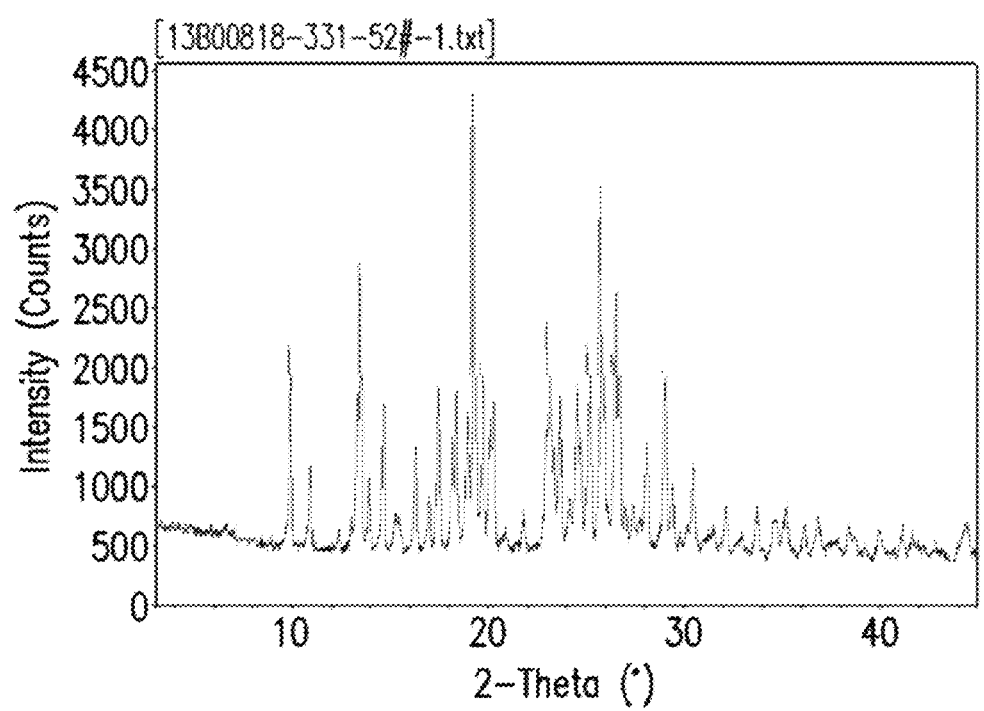
FIG. 54 is an X-ray powder diffractogram of polymorph Form VII hydrobromide salt obtained from 1:3 ethanol/water.

The above amorphous HBr salt form (1 g, 2.05 mmol) was dissolved in ethanol (2 mL) at 50° C. with stirring. Water (6 mL) was then added. The solution was cooled to room temperature with stirring overnight. The resulting crystals were collected and dried to yield the title compound (0.7 g, 70% yield) in a solid form defined as polymorph Form VII. The XRPD trace for this material is shown in FIG. 54.

Formulation Example A: Manufacture of Capsules by Dry Blend Process (Rx1)

Figure 55:
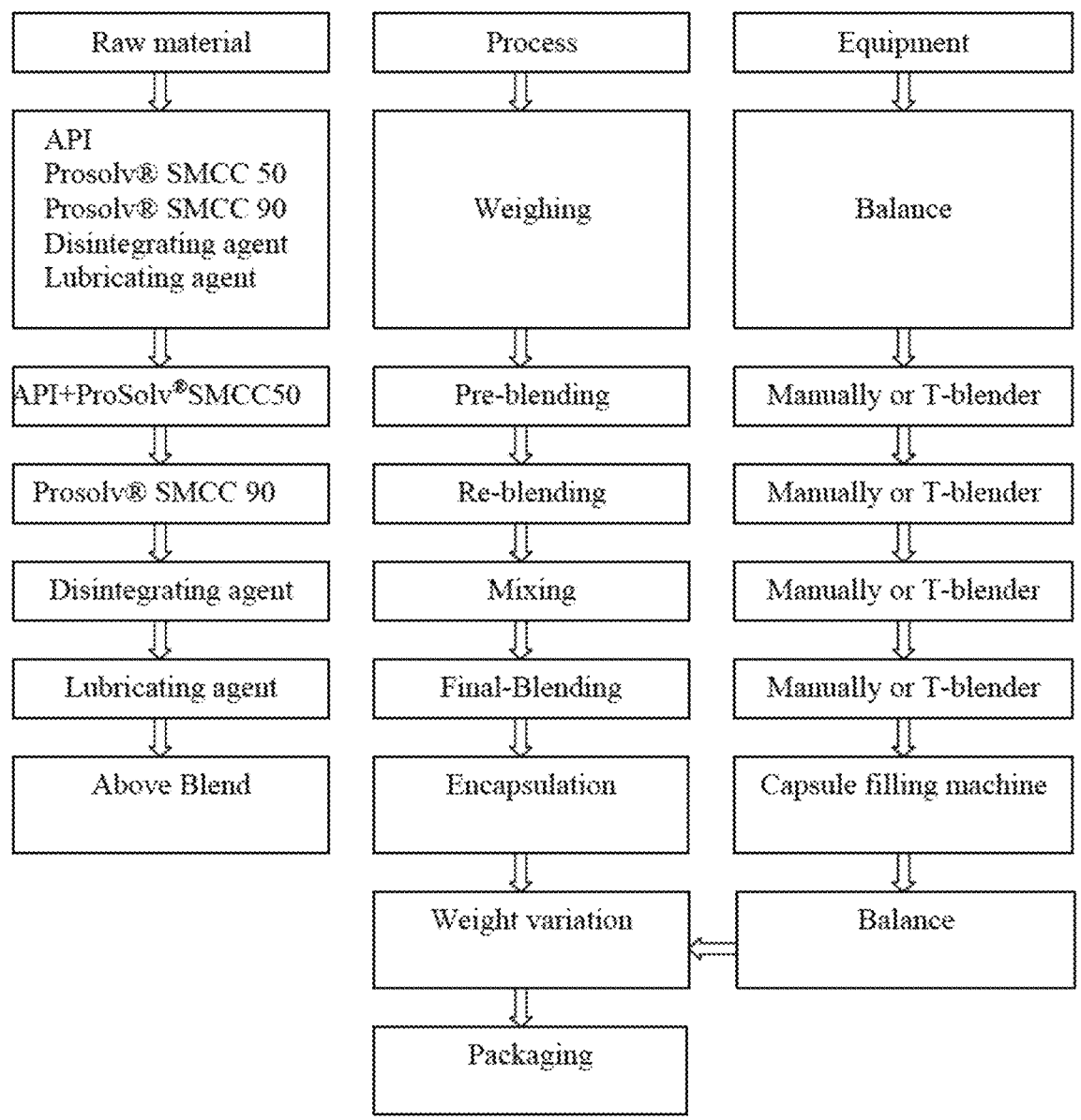
FIG. 55 is a flow diagram for the manufacture of capsules containing Compound 1, maleate salt, by dry blend process.

Capsules containing Compound 1, maleate salt, were prepared by a dry blend process as described below. The final composition of the capsules is shown in Table A1. The flow diagram for the process is shown in FIG. 55 and the process is described in detail below.

TABLE A1

Composition of dry blend capsules (Rx1)

| Ingredient | Rx1 Quantity (per capsule) | Quantity (400 capsules) |
| --- | --- | --- |
| Pre-blending (dry blend) | | |
| API/API Maleate | 25.00 mg/32.80 mg | 13.12 g |
| Prosolv ® SMCC 50 | 22.10 mg | 8.84 g |
| Re-blending | | |
| Prosolv ® SMCC 90 | 71.85 mg | 28.74 g |
| Capsule Preparation | | |
| Vivasol ® sodium croscarmellose | 2.60 mg | 1.04 g |
| sodium stearyl fumarate | 0.65 mg | 0.26 g |
| Capsule weight | 130 mg | — |
| Batch weight | — | 52.0 g |

Preparation of Composition Rx1.

Crystal Form I of N-(3-(2-(3-fluoro-4-(4-methylpiperazin-1-yl)phenylamino)-7H-pyrrolo[2,3-d]pyrimidin-4-yloxy)phenyl)acrylamide, maleate salt (13.12 g; D (v, 0.9) ≤19 μm) and adsorbing agent Prosolv® SMCC 50 (8.84 g) were mixed in a pre-blending process and the resulting mixture was mixed with Prosolv® SMCC 90 (28.74 g) by a re-blending process to obtain Composition A1. Composition A1, Vivasol® croscarmellose sodium (1.04 g), and sodium stearyl fumarate (0.26 g) were mixed and subjected to final blending to form a final powder, which was then filled into hollow gelatin capsules to prepare Composition Rx1. Characterization data for the final powder are shown in Table A2, and results of dissolution and stability studies for Composition Rx1 are reported in Table A3.

TABLE A2

| Final Powder | Characteristics |
| --- | --- |
| Bulk Density | 0.30 g/mL |
| Tapped Density | 0.50 g/mL |
| Carr's index | 34 |
| Angle of repose | 34.6° |

TABLE A3

| Rx1 | Characteristics |
| --- | --- |
| Dissolution (Medium; Method) | 99% (Medium, 0.1N HCl; Basket method, 100 rpm) |
| Heat (60° C.-10 days) | Dimer Formation 0.01% |
| Humidity (75% RH-10 days) | Dimer Formation 0.01% |
| Light (4500 λ ± 500 λ -10 days) | Dimer Formation 0.01% |

Formulation Example B. Manufacture of Capsules by Roller Compaction Process (Rx2)

Figure 56:
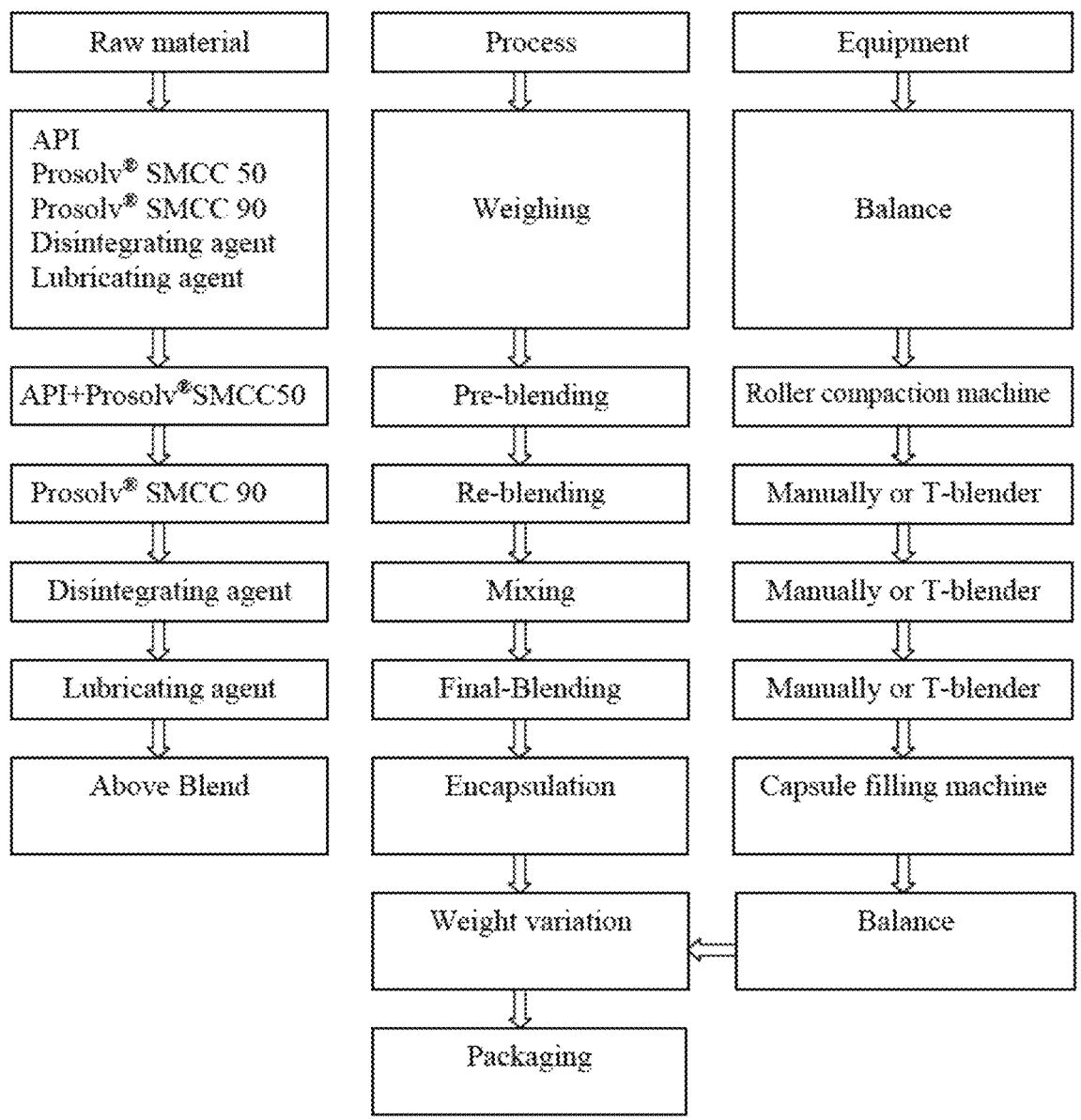
FIG. 56 is a flow diagram for the manufacture of capsules containing Compound 1, maleate salt, by roller compaction process.

Capsules containing Compound 1, maleate salt, were prepared by a roller compaction process. The final composition of the capsules is shown in Table B1. The flow diagram for the process is shown in FIG. 56 and the process is described in detail below.

TABLE B1

Composition of roller compaction capsules (Rx2)

| Ingredient | Rx2 Quantity (per capsule) | Quantity (1000 capsules) |
| --- | --- | --- |
| Pre-blending (roller compaction) | | |
| API/API Maleate | 25.00 mg/32.80 mg | 32.80 g |
| Prosolv ® SMCC 50 | 21.90 mg | 21.90 g |
| Re-blending | | |
| Prosolv ® SMCC90 | 89.30 mg | 89.30 g |
| Capsule Preparation | | |
| Vivasol ® sodium croscarmellose | 3.00 mg | 3.00 g |
| sodium stearyl fumarate | 3.00 mg | 3.00 g |
| Capsule weight | 150 mg | — |
| Batch weight | — | 150.00 g |

Preparation of Composition Rx2.

Crystal Form I of N-(3-(2-(3-fluoro-4-(4-methylpiperazin-1-yl)phenylamino)-7H-pyrrolo[2,3-d]pyrimidin-4-yloxy)phenyl)acrylamide, maleate salt (32.80 g; D (v, 0.9) ≤37 μm) and adsorbing agent Prosolv® SMCC 50 (21.90 g) were mixed in a pre-blending/roller compaction process and the resulting mixture was mixed with Prosolv® SMCC 90 (89.30 g) by a re-blending process to obtain Composition B1. Composition B1, Vivasol® croscarmellose sodium (3.00 g), and sodium stearyl fumarate (3.00 g) were mixed and subjected to final blending to form a final powder, which was then filled into hollow gelatin capsules to prepare Composition Rx2. Characterization of the final powder is shown in Table B2, and the results of dissolution and stability studies of Composition Rx2 are reported in Table B3.

TABLE B2

| Final Powder | Characteristics |
| --- | --- |
| Bulk Density | 0.41 g/mL |
| Tapped Density | 0.58 g/mL |
| Carr's index | 29.3 |
| Angle of repose | 43.6° |

TABLE B3

| Rx2 | Characteristics |
| --- | --- |
| Dissolution (Medium; Method) | 96% (Medium, 0.1N HCl; Basket method, 100 rpm) |
| Heat (60° C.-10 days) | Dimer Formation 0.21% |
| Humidity (75% RH-10 days) | Dimer Formation 0.05% |
| Light (4500 λ ± 500 λ -10 days) | Dimer Formation 0.06% |

Formulation Example C. Manufacture of Tablets by Direct Compression (Rx3)

Figure 57:
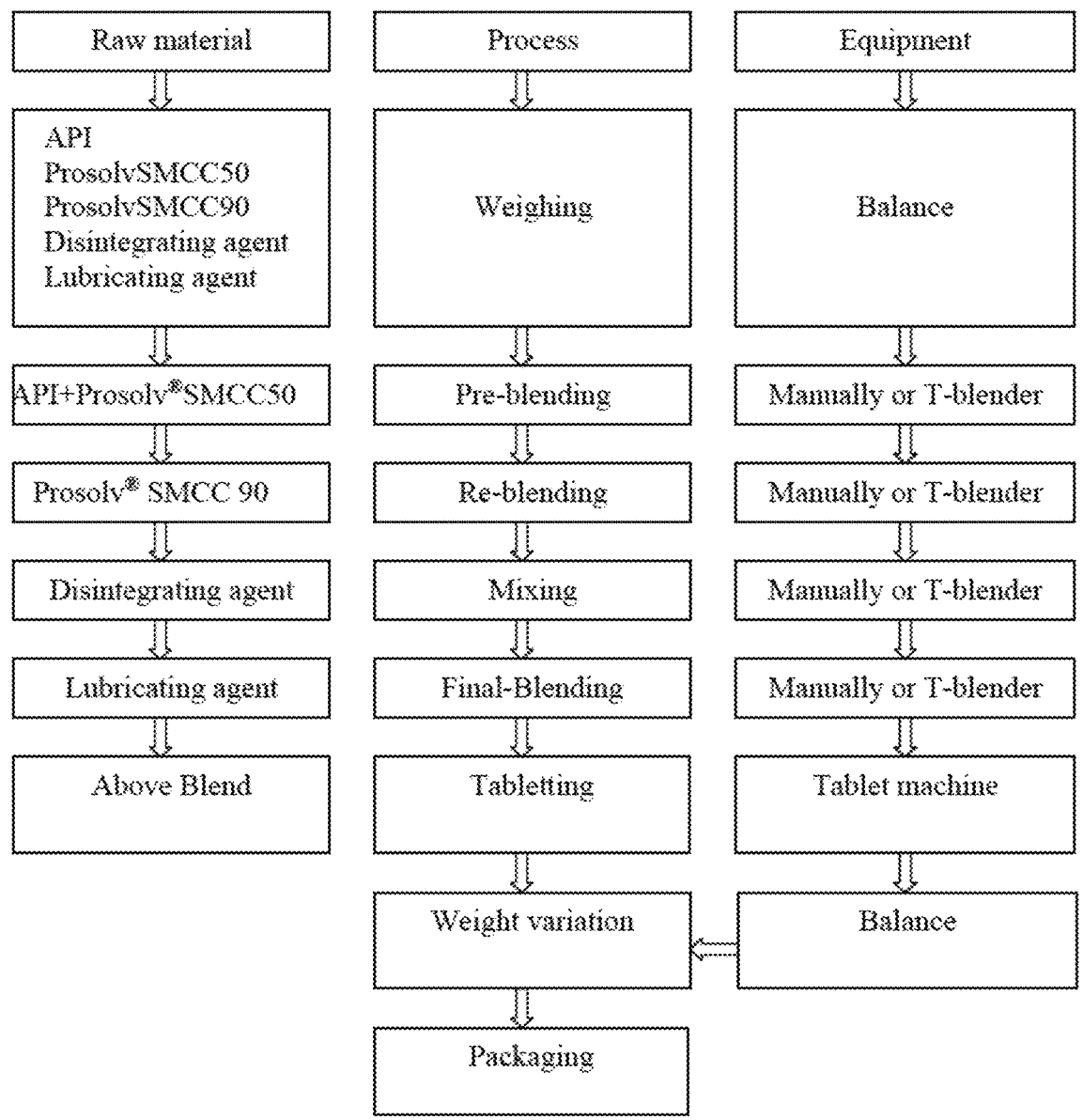
FIG. 57 is a flow diagram for the manufacture of tablets containing Compound 1, maleate salt, by a direct compression process.

Tablets containing Compound 1, maleate salt, were prepared by direct compression. The final composition of the tablets is shown in Table C1. The flow diagram for the process is shown in FIG. 57 and the process is described in detail below.

TABLE C1

Composition of direct compression tables (Rx3)

| | Rx3 | |
|---|---|---|
| Ingredient | Quantity (per tablet) | Quantity (1000 tablets) |
| Pre-blending | | |
| API/API Maleate | 25.00 mg/32.80 mg | 32.80 g |
| Prosolv ® SMCC 50 | 21.90 mg | 21.90 g |
| Re-blending | | |
| Prosolv ® SMCC 90 | 89.30 mg | 89.30 g |
| Tablet formation | | |
| Vivasol ® sodium croscarmellose | 3.00 mg | 3.00 g |
| sodium stearyl fumarate | 3.00 mg | 3.00 g |
| Capsule weight | 150 mg | — |
| Batch weight | — | 150 g |

Preparation of Composition Rx3

Crystal Form I of N-(3-(2-(3-fluoro-4-(4-methylpiperazin-1-yl)phenylamino)-7H-pyrrolo[2,3-d]pyrimidin-4-yloxy)phenyl)acrylamide, maleate salt (21.90 g; D (v, 0.9) ≤150 μm) and adsorbing agent Prosolv® SMCC 50 (21.90 g) were mixed in a pre-blending process and the resulting mixture was mixed with Prosolv® SMCC 90 (89.30 g) by a re-blending process to obtain Composition C1. Composition C1, Vivasol® croscarmellose sodium (3.00 g), and sodium stearyl fumarate (3.00 g) were mixed and subjected to a final blending to form a final powder, which was then directly pressed into tablets of Composition Rx3. Characterization, of the final powder is shown in Table C2, and results of dissolution and stability studies of Composition Rx3 are reported in Table C3.

TABLE C2

| Final Powder | Characteristics |
|---|---|
| Bulk Density | 0.30 g/mL |
| Tapped Density | 0.50 g/mL |
| Carr's index | 34 |
| Angle of repose | 35.6° |

TABLE C3

| Composition Rx3 | Characteristics |
|---|---|
| Dissolution (Medium; Method) | 100% (Medium, 0.1N HCl; Basket method, 100 rpm) |
| Heat (60° C.-10 days) | Dimer Formation 0.10% |
| Humidity (75% RH-10 days) | Dimer Formation 0.01% |
| Light (4500 λ ± 500 λ -10 days) | Dimer Formation 0.01% |

Formulation Example D. Manufacture of Tablets by Roller Compaction Process (Rx4)

Figure 58:
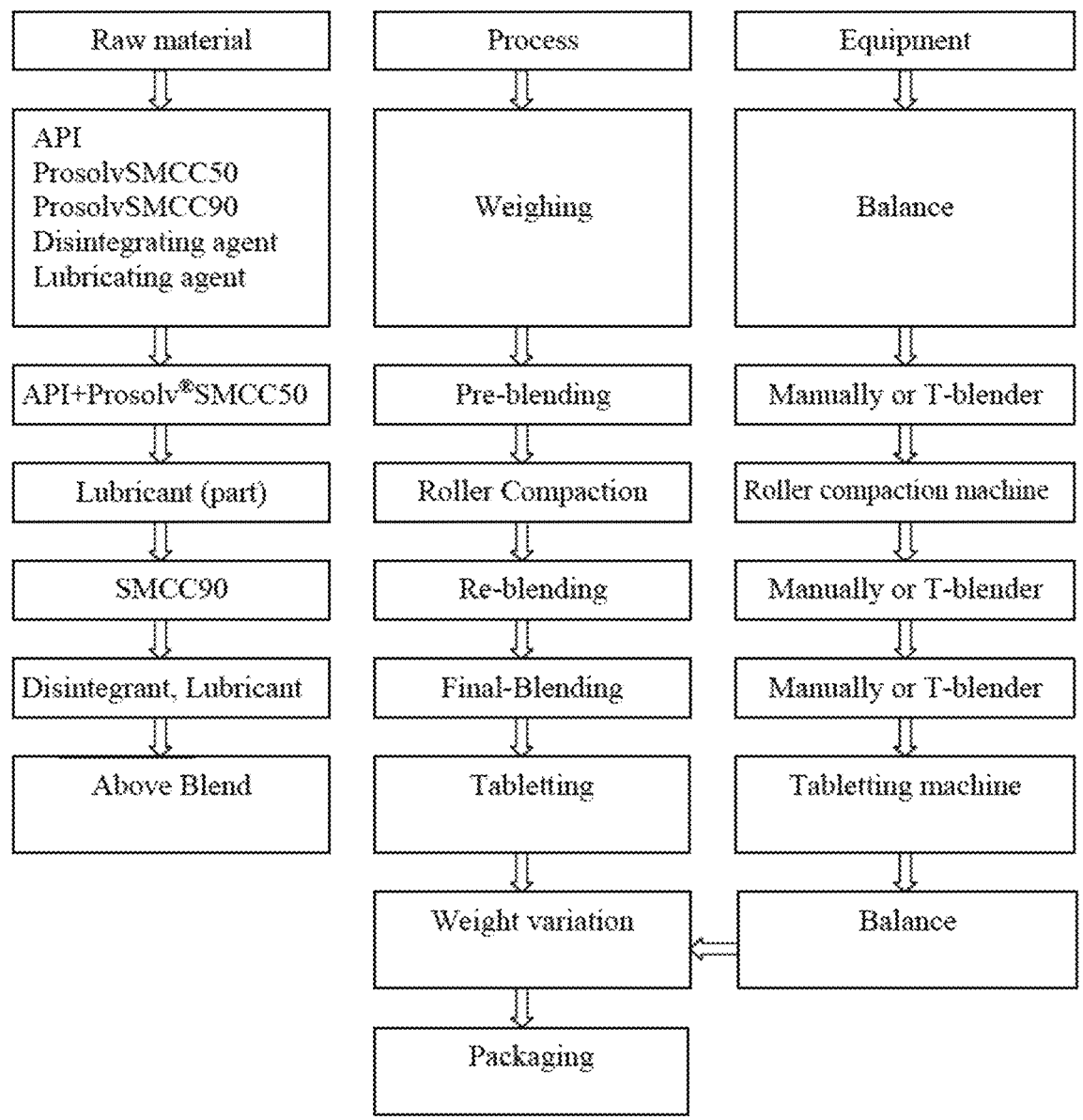
FIG. 58 is a flow diagram for the manufacture of tablets containing Compound 1, maleate salt, by a roller compaction process.

Tablets containing Compound 1, maleate salt, were prepared by a roller compaction process. The final composition of the tablets is shown in Table D1. The flow diagram for the process is shown in FIG. 58 and the process is described in detail below.

TABLE D1

Composition of roller compaction tablets (Rx4)

| | Rx4 | |
|---|---|---|
| Ingredient | Quantity (per Tablet) | Quantity (444 Tablets) |
| Pre-blending (roller compaction) | | |
| API/API Maleate | 25.00 mg/32.80 mg | 14.58 g |
| Prosolv ® SMCC 50 | 21.90 mg | 9.74 g |
| sodium stearyl fumarate | 1.50 mg | 0.67 g |
| Re-blending | | |
| Prosolv ® SMCC 90 | 89.30 mg | 40.2 g |
| Tablet preparation | | |
| Vivasol ® croscarmellose sodium | 3.00 mg | 1.4 g |
| sodium stearyl fumarate | 1.50 mg | 0.7 g |
| Capsule weight | 150 mg | — |
| Batch weight | — | 66.70 g |

Preparation of Composition Rx4.

Crystal Form I of N-(3-(2-(3-fluoro-4-(4-methylpiperazin-1-yl)phenylamino)-7H-pyrrolo[2,3-d]pyrimidin-4-yloxy)phenyl)acrylamide, maleate salt (14.58 g; D (v, 0.9) ≤85 μm) and adsorbing agent Prosolv® SMCC 50 (9.74 g) were mixed in a pre-blending/roller compaction process and the resulting mixture was mixed with Prosolv® SMCC 90 (40.2 g) by a re-blending process to obtain Composition D1. Composition D1, Vivasol® croscarmellose sodium (1.4 g), and sodium stearyl fumarate (0.7 g) were mixed and then subjected to a final blending process to form a final powder, which was used to manufacture tablets (Composition Rx4). Characterization of the final powder is shown in Table D2, and results of dissolution and stability studies of Composition Rx4 are reported in Table D3.

TABLE D2

| Final Powder | Characteristics |
|---|---|
| Bulk Density | 0.38 g/mL |
| Tapped Density | 0.56 g/mL |
| Carr's index | 32.1 |
| Angle of repose | 42.2° |

TABLE D3

| Rx4 | Characteristics |
|---|---|
| Dissolution (Medium; Method) | 97% (Medium, 0.1N HCl; Basket method, 100 rpm) |
| Heat (60° C.-10 days) | Dimer Formation 0.20% |
| Humidity (75% RH-10 days) | Dimer Formation 0.05% |
| Light (4500 λ ± 500 λ -10 days) | Dimer Formation 0.06% |

The pharmaceutical compositions Rx1-Rx4 may be prepared using 25 mg, 50 mg, 100 mg, 150 mg, or 200 mg free base equivalent of the compound of Formula I or Compound 1, and the amounts of the remaining ingredients are adjusted accordingly so they are in the same ratios as in Rx1-Rx4. In other embodiments, the ingredients are the same but the ratios are adjusted as necessary to maintain low dimer formation.

Formulation Example E: Stability Testing

Compositions Rx1-Rx4 were studied in a long-term stability test at 60% (+5%) relative humidity at 25±2° C. for 18 months. Stability testing showed that solid oral formulations manufactured using the methods described herein exhibit limited dimer formation (Table E).

TABLE E

| Composition | Dimer Detected after 18 months |
|---|---|
| Rx1 | 0.02% |
| Rx2 | 0.25% |
| Rx3 | 0.09% |
| Rx4 | 0.24% |

The invention claimed is:

1. A pharmaceutical composition comprising:

(a) a compound of Formula (I):

(I)

wherein $X^1$ is O, NH, or S;

$R^1$ and $R^2$ are each independently hydrogen, halo, $C_{1-6}$alkyl, or $C_{1-6}$haloalkyl;

$R^3$ is halo, hydroxyl, $C_{1-6}$alkyl, $C_{1-6}$alkoxy, cyano, or nitro;

n is 0, 1, 2, 3, or 4;

$R^4$ is hydrogen, $C_{1-6}$alkyl, $C_{3-7}$cycloalkyl, or $-NR^{22}R^{23}$;

wherein the alkyl and cycloalkyl are unsubstituted or substituted with hydroxyl or amino; and $R^{22}$ and $R^{23}$ are each independently hydrogen or $C_{1-6}$alkyl; or $R^{22}$ and $R^{23}$ taken together with the nitrogen to which they are attached form a 3- to 10-membered heterocycloalkyl ring;

$R^5$ is hydrogen or $C_{1-6}$alkyl;

$R^6$ and $R^7$ are each independently hydrogen, halo, $C_{1-6}$alkyl, $C_{1-6}$haloalkyl, $C_{2-6}$alkoxy, $C_{1-6}$haloalkoxy, hydroxyl, cyano, or nitro;

$R^8$ is hydrogen, halo, $C_{1-6}$alkyl, $C_{1-6}$haloalkyl, $C_{1-6}$alkoxy, $C_{1-6}$haloalkoxy, hydroxyl, cyano, or nitro;

$R^{11}$ and $R^{12}$ are each independently hydrogen or $C_{1-6}$alkyl;

Q is $CR^9$ or N;

where $R^9$ is hydrogen, halo, $C_{1-6}$alkyl, $C_{1-6}$haloalkyl, $C_{1-6}$alkoxy, $C_{1-6}$haloalkoxy, hydroxyl, cyano, or nitro;

$-NR^{18}R^{19}$ is:

(a)

where $R^{10}$ is selected from hydrogen and $C_{1-6}$ alkyl;

$R^{15}$ is unsubstituted methyl, or is $C_{2-4}$alkyl unsubstituted or substituted with hydroxy, methoxy, or halo; and m is 1 or 2; or (b) $R^{19}$ and $R^9$ are taken together with the atoms to which they are attached to form a 5- or 6-membered heteroaryl ring optionally substituted with $C_{1-6}$alkyl, wherein the alkyl is unsubstituted or substituted with amino, hydroxyl, halo, or an N-linked heterocycloalkyl; and $R^{18}$ is hydrogen or $C_{1-6}$alkyl, where the alkyl is unsubstituted or substituted with amino, or $R^{18}$ is absent to satisfy valency of the heteroaryl ring;

or Compound 1:

(Compound 1)

or a pharmaceutically acceptable salt of the compound of Formula (I) or Compound 1; and (b) an adsorbing agent that reduces or eliminates formation of a dimer of the compound, or a pharmaceutically acceptable salt thereof;

wherein the pharmaceutical composition contains about 0.001% (w/w) to about 1% (w/w) of the dimer of the compound, or a pharmaceutically acceptable salt thereof, after a stability test for about 10 days to about 24 months.

2. The pharmaceutical composition of claim 1, which comprises Compound 1.

3. The pharmaceutical composition of claim 1, which comprises a pharmaceutically acceptable salt of Compound 1.

4. The pharmaceutical composition of claim 3, wherein the pharmaceutically acceptable salt of Compound 1 is selected from the group consisting of a maleate salt, a hydrochloride salt, a fumarate salt, a malate salt, a sulfate salt, a mesylate salt, a tosylate salt, and a hydrobromide salt.

5. The pharmaceutical composition of claim 4, wherein the pharmaceutically acceptable salt of Compound 1 has a polymorph form selected from Form I, Form II, Form III, Form IV, Form V, and Form VI.

6. The pharmaceutical composition of claim 4, wherein the sulfate salt, mesylate salt, tosylate salt, or hydrobromide salt has an amorphous form.

7. The pharmaceutical composition of claim 1, wherein the adsorbing agent reduces formation a dimer of Compound 1, or a pharmaceutically acceptable salt thereof.

8. The pharmaceutical composition of claim 1, wherein the adsorbing agent is selected from the group consisting of acacia, alginic acid, croscarmellose, gelatin, gelatin hydrolysate, mannitol, maltose, frustose, Plasdone, povidone, sodium starch glycolate, sorbitol, sucrose, lactose, microcrystalline cellulose, silicified microcrystalline cellulose, croscarmellose sodium, dicalcium phosphate, carboxymethyl cellulose, hydroxypropyl cellulose, and polyethylene glycol.

9. The pharmaceutical composition of claim 8, wherein the adsorbing agent comprises silicified microcrystalline cellulose of average particle size 65 μm and density of 0.25-0.37 g/mL, or of average particle size 50 μm and density of 0.20-0.30 g/mL, or of average particle size 125 μm and density 0.25-0.37 g/mL, or of average particle size 125 μm and density 0.38-0.50 g/mL, or of average particle size 125 μm and density 0.27-0.39 g/mL.

10. The pharmaceutical composition of claim 9, which comprises silicified microcrystalline cellulose of average particle size 65 μm and density of 0.25-0.37 g/mL and silicified microcrystalline cellulose of average particle size 125 μm and density of 0.25-0.37 g/mL.

11. The pharmaceutical composition of claim 10, which comprises from about 1% (w/w) to about 30% (w/w) of silicified microcrystalline cellulose of average particle size 65 μm and density of 0.25-0.37 g/mL, and from about 30% (w/w) to about 70% (w/w) of silicified microcrystalline cellulose of average particle size 125 μm and density 0.25-0.37 g/mL.

12. The pharmaceutical composition of claim 1, which further comprises a pharmaceutically acceptable additive selected from the group consisting of a diluent, a binder, a vehicle, a carrier, an excipient, a disintegrating agent, a lubricant, a swelling agent, a solubilizing agent, a wicking agent, a cooling agent, a preservative, a stabilizer, a sweetener, a flavor, and a polymer.

13. The pharmaceutical composition of claim 12, wherein the pharmaceutically acceptable additive comprises a disintegrating agent, and the disintegrating agent is cross-linked sodium carboxymethylcellulose, croscarmellose sodium, crospovidone, or a mixture thereof.

14. The pharmaceutical composition of claim 13, wherein the lubricant is magnesium stearate, stearic acid and its pharmaceutically acceptable alkali metal salt, sodium stearyl fumarate, Macrogol 6000, glyceryl behenate, colloidal silicon dioxide, calcium stearate, sodium stearate, Cab-O-Sil, Syloid, sodium lauryl sulfate, sodium chloride, magnesium lauryl sulfate, talc, or a mixture thereof.

15. The pharmaceutical composition of claim 1, which comprises at least two different kinds of adsorbing agents, and further comprises a disintegrating agent and a lubricant.

16. The pharmaceutical composition of claim 1, which is formulated for an oral dosage form.

17. The pharmaceutical composition of claim 16, wherein the oral dosage form is an oral powder, a granule, a pellet, a tablet, a capsule, a troch, or a lozenge.

18. The pharmaceutical composition of claim 17, wherein the tablet is a chewable tablet, a dispersible tablet, or a troch.

19. A process for preparing a pharmaceutical composition of claim 1, comprising:
  1) combining Compound 1, or a pharmaceutically acceptable salt thereof, with the adsorbing agent to form a first mixture; and
  2) formulating the first mixture into a dosage form.

20. A method of preparing a compound of Formula (I) or Compound 1, or a pharmaceutically acceptable salt thereof, comprising
reacting a compound of Formula (XVII)

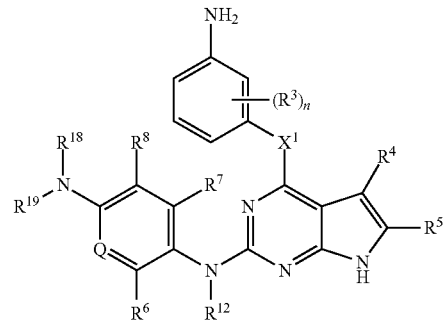

with acryloyl chloride to form the compound of Formula (I);

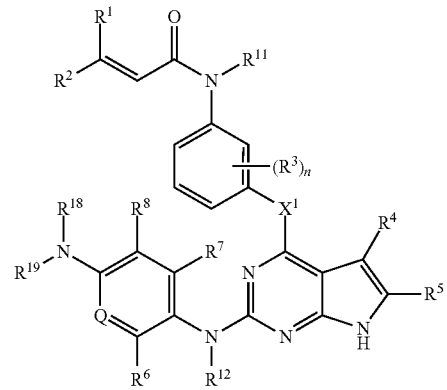

wherein
$X^1$ is O, NH, or S;
$R^1$ and $R^2$ are each independently hydrogen, halo, $C_{1-6}$alkyl, or $C_{1-6}$haloalkyl;
$R^3$ is halo, hydroxyl, $C_{1-6}$alkyl, $C_{1-6}$alkoxy, cyano, or nitro;
n is 0, 1, 2, 3, or 4;
$R^4$ is hydrogen, $C_{1-6}$alkyl, $C_{3-7}$cycloalkyl, or —$NR^{22}R^{23}$;
wherein the alkyl and cycloalkyl are unsubstituted or substituted with hydroxyl or amino; and
$R^{22}$ and $R^{23}$ are each independently hydrogen or $C_{1-6}$alkyl; or $R^{22}$ and $R^{23}$ taken together with the nitrogen to which they are attached form a 3- to 10-membered heterocycloalkyl ring;
$R^5$ is hydrogen or $C_{1-6}$alkyl;
$R^6$ and $R^7$ are each independently hydrogen, halo, $C_{1-6}$alkyl, $C_{1-6}$haloalkyl, $C_{2-6}$alkoxy, $C_{1-6}$haloalkoxy, hydroxyl, cyano, or nitro;
$R^8$ is hydrogen, halo, $C_{1-6}$alkyl, $C_{1-6}$haloalkyl, $C_{1-6}$alkoxy, $C_{1-6}$haloalkoxy, hydroxyl, cyano, or nitro;
$R^{11}$ and $R^{12}$ are each independently hydrogen or $C_{1-6}$alkyl;
Q is $CR^9$ or N;
where $R^9$ is hydrogen, halo, $C_{1-6}$alkyl, $C_{1-6}$haloalkyl, $C_{1-6}$alkoxy, $C_{1-6}$haloalkoxy, hydroxyl, cyano, or nitro;

—NR$^{18}$R$^{19}$ is:

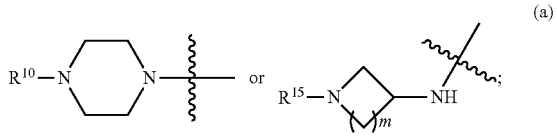

(a)

where R$^{10}$ is selected from hydrogen and C$_{1-6}$ alkyl;
R$^{15}$ is unsubstituted methyl, or is C$_{2-4}$alkyl unsubstituted or substituted with hydroxy, methoxy, or halo; and
m is 1 or 2; or (b) R$^{19}$ and R$^9$ are taken together with the atoms to which they are attached to form a 5- or 6-membered heteroaryl ring optionally substituted with C$_{1-6}$alkyl, wherein the alkyl is unsubstituted or substituted with amino, hydroxyl, halo, or an N-linked heterocycloalkyl; and R$^{18}$ is hydrogen or C$_{1-6}$alkyl, where the alkyl is unsubstituted or substituted with amino, or R$^{18}$ is absent to satisfy valency of the heteroaryl ring.

21. The method of claim 20, wherein the compound of Formula (XVII) is prepared by reducing a compound of Formula (XVI):

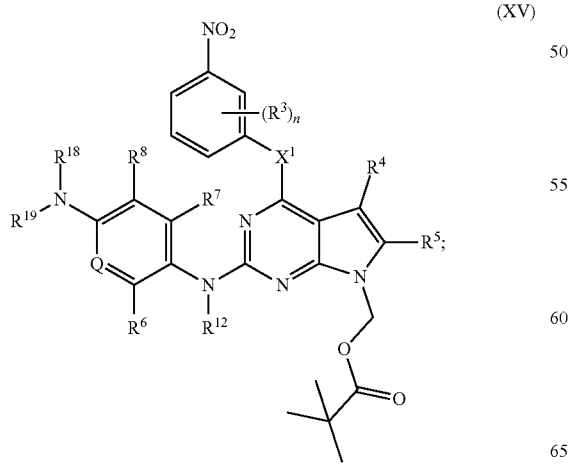

(XVI)

wherein X$^1$, n, R$^3$, R$^4$, R$^5$, R$^6$, R$^7$, R$^8$, R$^{12}$, R$^{18}$, R$^{19}$, and Q are each as defined for Formula (I).

22. The method of claim 21, wherein the compound of Formula (XVI) is prepared by deprotecting a compound of Formula (XV):

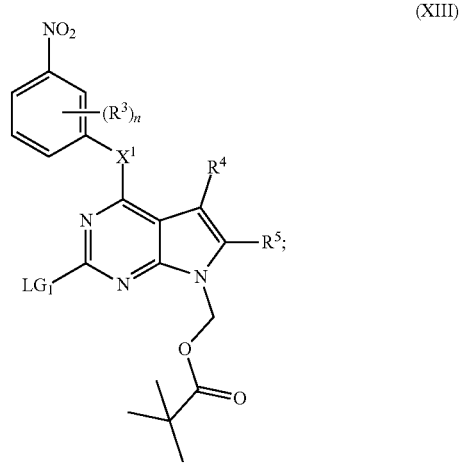

(XV)

wherein X$^1$, n, R$^3$, R$^4$, R$^5$, R$^6$, R$^7$, R$^8$, R$^{12}$, R$^{18}$, R$^{19}$, and Q are each as defined for Formula (I).

23. The method of claim 22, wherein the compound of Formula (XV) is prepared by coupling a compound of Formula (XIII):

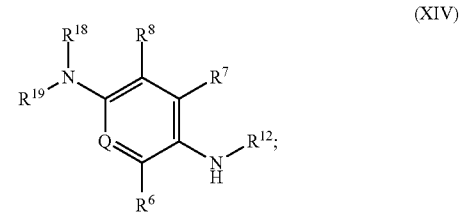

(XIII)

wherein LG$_1$ is a leaving group, and X$^1$, R$^3$, R$^4$, R$^5$, and n are each as defined for Formula (I), with a compound of Formula (XIV):

(XIV)

wherein R$^6$, R$^7$, R$^8$, R$^{12}$, R$^{18}$, R$^{19}$, and Q are each as defined for Formula (I).

24. The method of claim 23, wherein the compound of Formula (XIII) is prepared by reacting a compound of Formula (XI):

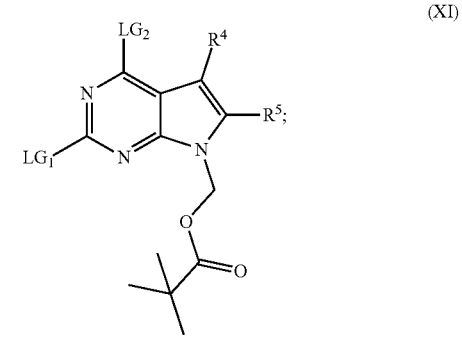

(XI)

wherein LG$_1$ and LG$_2$ are each a leaving group; and R$^4$ and R$^5$ are each as defined for Formula (I), with a compound of Formula (XII):
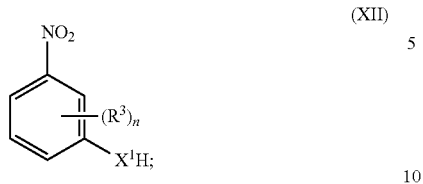
(XII)
wherein $X^1$, n, and $R^3$ are each as defined for Formula (I).
25. The method of claim 24, wherein the compound of Formula (XI) is prepared by reacting a compound of Formula (X):
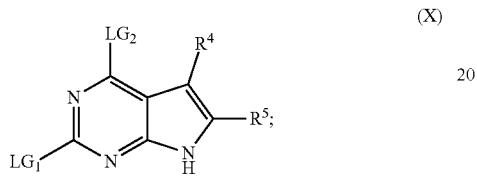
(X)
wherein $LG_1$ and $LG_2$ are each a leaving group; and $R^4$ and $R^5$ are each as defined for Formula (I), with chloromethyl pivalate.
* * * * *